United States Patent
Treon et al.

(10) Patent No.: US 10,597,387 B2
(45) Date of Patent: Mar. 24, 2020

(54) METHODS TO TREAT LYMPHOPLASMACYTIC LYMPHOMA

(71) Applicant: Dana-Farber Cancer Institute, Inc., Boston, MA (US)

(72) Inventors: Steven P. Treon, Jamaica Plain, MA (US); Sara Jean Buhrlage, Somerville, MA (US); Nathanael S. Gray, Boston, MA (US); Li Tan, Shanghai (CN); Guang Yang, Natick, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/904,143

(22) Filed: Feb. 23, 2018

(65) Prior Publication Data

US 2018/0186780 A1    Jul. 5, 2018

Related U.S. Application Data

(63) Continuation of application No. 15/104,005, filed as application No. PCT/US2014/070167 on Dec. 12, 2014, now Pat. No. 9,908,872.
(Continued)

(51) Int. Cl.
  C07D 409/04  (2006.01)
  C07D 413/04  (2006.01)
  (Continued)

(52) U.S. Cl.
  CPC .......... C07D 409/04 (2013.01); A61K 31/44 (2013.01); A61K 31/4436 (2013.01);
  (Continued)

(58) Field of Classification Search
  CPC .. C07D 409/04; C07D 401/04; C07D 413/04; A61K 31/44; A61K 31/4436;
  (Continued)

(56) References Cited

U.S. PATENT DOCUMENTS 6,455,520 B1  9/2002  Brown et al.
7,060,700 B2  6/2006  Brown et al.
(Continued)

FOREIGN PATENT DOCUMENTS

CN  103405429 A  11/2013
JP  2002-522414  7/2002
(Continued)

OTHER PUBLICATIONS

Chio et al. Bioorg. Med. Chem. Lett., (2009), 19, p. 4467-4470.*
(Continued)

*Primary Examiner* — Yong L Chu
(74) *Attorney, Agent, or Firm* — Wolf, Greenfield & Sacks, P.C.

(57) ABSTRACT

The present invention provides compounds of any one of Formulae (I) to (V) (e.g., compounds of any one of Formulae (I-1) to (I-9)), and methods for treating Waldenström's macroglobulinemia (WM) and other B cell neoplams in a subject using the compounds. The methods comprise administering to a subject in need thereof an effective amount of the compounds. Also provided are methods to treat B cell neoplasms using the compounds in combination with inhibitors of Bruton's tyrosine kinase (BTK), interleukin-1 receptor-associated kinase 1 (IRAK1), interleukin-1 receptor-associated kinase 4 (IRAK4), bone marrow on X chromosome kinase (BMX), phosphoinositide 3-kinase (PI3K), transforming growth factor b-activated kinase-1 (TAK1), and/or a Src family kinase.

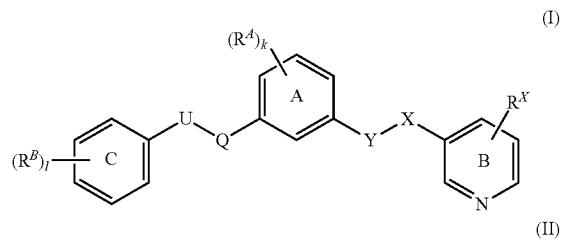

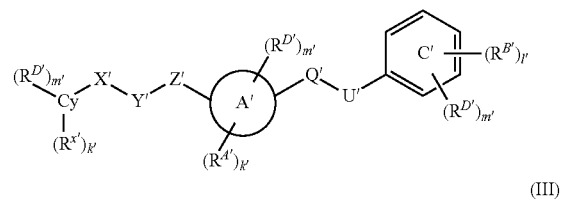

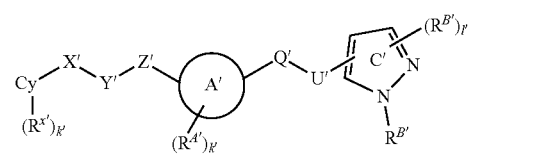

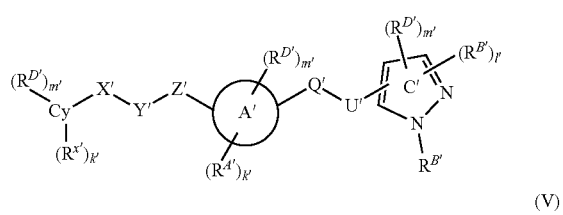

30 Claims, No Drawings
Specification includes a Sequence Listing.

Related U.S. Application Data

(60) Provisional application No. 62/036,917, filed on Aug. 13, 2014, provisional application No. 61/915,684, filed on Dec. 13, 2013.

(51) Int. Cl.

| | | |
|---|---|---|
| *C07D 401/04* | (2006.01) | |
| *C07D 409/14* | (2006.01) | |
| *A61K 31/496* | (2006.01) | |
| *A61K 31/44* | (2006.01) | |
| *A61K 31/4436* | (2006.01) | |
| *A61K 31/4439* | (2006.01) | |
| *A61K 31/4745* | (2006.01) | |
| *A61K 45/06* | (2006.01) | |

(52) U.S. Cl.
CPC ...... *A61K 31/4439* (2013.01); *A61K 31/4745* (2013.01); *A61K 31/496* (2013.01); *A61K 45/06* (2013.01); *C07D 401/04* (2013.01); *C07D 409/14* (2013.01); *C07D 413/04* (2013.01)

(58) Field of Classification Search
CPC ............ A61K 31/4439; A61K 31/4745; A61K 31/496; A61K 45/406; A61K 45/06
See application file for complete search history.

(56) References Cited

U.S. PATENT DOCUMENTS

| | | | |
|---|---|---|---|
| 9,856,223 | B2 | 1/2018 | Treon et al. |
| 9,908,872 | B2 | 3/2018 | Treon et al. |
| 10,112,957 | B2 | 10/2018 | Gray et al. |
| 2004/0106615 | A1 | 6/2004 | Cochran et al. |
| 2007/0060619 | A1 | 3/2007 | Burns et al. |
| 2007/0155746 | A1 | 7/2007 | Lang et al. |
| 2009/0054405 | A1 | 2/2009 | Booker et al. |
| 2009/0118297 | A1 | 5/2009 | Simo et al. |
| 2009/0312396 | A1 | 12/2009 | Byth et al. |
| 2011/0053905 | A1 | 3/2011 | Guo et al. |
| 2012/0108572 | A1 | 5/2012 | Wagner et al. |
| 2013/0040949 | A1 | 2/2013 | Gray et al. |
| 2014/0162983 | A1 | 6/2014 | Hodous et al. |
| 2016/0311807 | A1 | 10/2016 | Treon et al. |
| 2016/0318878 | A1 | 11/2016 | Treon et al. |
| 2017/0233411 | A1 | 8/2017 | Gray et al. |
| 2018/0186780 | A1 | 7/2018 | Treon et al. |
| 2019/0119301 | A1 | 4/2019 | Gray et al. |

FOREIGN PATENT DOCUMENTS

| | | |
|---|---|---|
| JP | 2002-525358 A | 8/2002 |
| JP | 2008-525406 A | 7/2008 |
| JP | 2009-516685 A | 4/2009 |
| JP | 2012-501309 | 1/2012 |
| JP | 2013-503901 | 2/2013 |
| WO | WO 99/054286 A2 | 10/1999 |
| WO | WO 2000/018738 A1 | 4/2000 |
| WO | WO 00/056737 A2 | 9/2000 |
| WO | WO 03/030902 A1 | 4/2003 |
| WO | WO 2006/081172 A2 | 8/2006 |
| WO | WO 2007/019191 A2 | 2/2007 |
| WO | WO 2007/022380 A2 | 2/2007 |
| WO | WO 2007/076474 | 7/2007 |
| WO | WO 2008/144253 A1 | 11/2008 |
| WO | WO 2008/150446 A1 | 12/2008 |
| WO | WO 2009/076373 A1 | 6/2009 |
| WO | WO 2009/137596 A1 | 11/2009 |
| WO | WO 2010/026095 A1 | 3/2010 |
| WO | WO 2010/056875 A1 | 5/2010 |
| WO | WO 2011/028995 A1 | 3/2011 |
| WO | WO 2011/029043 A1 | 3/2011 |
| WO | WO 2011/090738 A2 | 7/2011 |
| WO | WO 2012/007375 A1 | 1/2012 |
| WO | WO 2012/062704 A1 | 5/2012 |
| WO | WO 2012/068096 A2 | 5/2012 |
| WO | WO 2012/161877 A1 | 11/2012 |
| WO | WO 2012/170976 A2 | 12/2012 |
| WO | WO 2013/010380 A1 | 1/2013 |
| WO | WO 2013/050261 A1 | 4/2013 |
| WO | WO 2013/052699 A2 | 4/2013 |
| WO | WO 2013/067277 A1 | 5/2013 |
| WO | WO 2013/074986 A1 | 5/2013 |
| WO | WO 2013/088404 A1 | 6/2013 |
| WO | WO 2015/069287 A1 | 5/2015 |

OTHER PUBLICATIONS

International Search Report and Written Opinion for PCT/US2014/70167, dated Mar. 11, 2015.
International Preliminary Report on Patentability for PCT/US2014/70167, dated Jun. 23, 2016.
International Search Report and Written Opinion for PCT/US2014/70162, dated Mar. 11, 2015.
International Preliminary Report on Patentability for PCT/US2014/70162, dated Jun. 23, 2016.
International Search Report and Written Opinion for PCT/US2015/56899, dated Jan. 29, 2016.
Partial Supplementary European Search Report for EP 15 85 2450, dated Mar. 22, 2018.
International Preliminary Report on Patentability for PCT/US2015/56899, dated May 4, 2017.
Extended European Search Report for EP 14869351.8, dated Jul. 31, 2017.
Extended European Search Report for EP 14869964.8 dated Nov. 16, 2017.
CAS Registry No. 1298854-20-2, STN Entry Date May 22, 2011.
CAS Registry No. 1319879-27-0, STN Entry Date Aug. 19, 2011.
CAS Registry No. 1388492-05-4, STN Entry Date Aug. 9, 2012.
CAS Registry No. 1320831-41-1, STN Entry Date Aug. 21, 2011.
Banker et al., Prodrugs. Modern Pharmaceuticals. 1996;3:596.
Buckley et al., IRAK-4 inhibitors. Part III: A series of imidazo[1,2-a]pyridines, Bioorganic & Medicinal Chemistry Letters, vol. 18, Issue 12, pp. 3656-3660.
Buckley, et al., IRAK-4 inhibitors. Part I: A series of amides, Bioorganic & Medicinal Chemistry Letters, vol. 18, Issue 11, pp. 3211-3214.
Chawla et al., Challenges in polymorphism of pharmaceuticals. CRIPS. 2004;5(1):9-12.
Cheng et al., Binding of Bruton's tyrosine kinase to Fyn, Lyn, or Hck through a Src homology 3 domain-mediated interaction, Proc. Natl. Acad. Sci. USA Aug. 1994; 91:8152-5.
Choi et al., Discovery and structural Bioorg Med Chem. Bioorg Med Chem Lett. Aug. 1, 2009;19(15):4467-70. doi: 10.1016/j.bmcl.2009.05.029. Epub May 13, 2009.
Davis et al., Comprehensive analysis of kinase inhibitor selectivity. Nat. Biotechnol. 2011, 29(11): 1046-1051.
Ding et al., Constitutively activated STAT3 promotes cell proliferation and survival in the activated B-cell subtype of diffuse large B-cell lymphomas. Blood. Feb. 1, 2008; 111(3): 1515-23.
Ditzel et al., Establishment of BVWM.1 cell line for Waldenstrom's macroglobulinemia with productive in vivo engraftment in SCID-hu mice, Experimental Hematology 35 (2007) 1366-1375.
Fabian et al., A small molecule-kinase interaction map for clinical kinase inhibitors. Nat. Biotechnol. 2005, 23(3): 329-336.
Hellwig et al., Small-molecule inhibitors of the c-Fes protein-tyrosine kinase.Chem Biol. Apr. 20, 2012;19(4):529-40. doi: 10.1016/j.chembiol.2012.01.020.
Hodge et al., Establishment and characterization of a novel Waldenstrom macroglobulinemia cell line, MWCL-1, Blood. 2011;117(19):e190-e197, doi:10.1182/blood-2010-12-326868.
Horwood et al., Bruton's tyrosine kinase is required for lipopolysaccharide-induced tumor necrosis factor alpha production, J. Exp. Med., Jun. 16, 2003;197(12):1603-11.
Iwaki et al., Btk Plays a Crucial Role in the Amplification of Fc RI-mediated Mast Cell Activation by Kit, J. Biol. Chem., 2005, 280(48), 40261-40270.

(56) References Cited

OTHER PUBLICATIONS

Jeffries et al., Bruton's Tyrosine Kinase is a Toll/Interleukin-1 Receptor Domain-binding Protein That Participates in Nuclear Factor B Activation by Toll-like Receptor 4, J.Biol. Chem., 2003, 278, 26258-26264.
Koshiol et al., Chronic immune stimulation and subsequent Waldenstrom's macroglobulinemia, Arch Intern Med. Sep. 22, 2008; 168(17): 1903-1909. doi:10.1001/archinternmed.2008.4.
Kurosaki, Functional dissection of BCR signaling pathways, Curr Opin Immunol. Jun. 2000;12(3):276-81.
Kwarcinski et al., Irreversible inhibitors of c-Src kinase that target a nonconserved cysteine. ACS Chem Biol. Nov. 16, 2012;7(11):1910-7. doi: 10.1021/cb300337u. Epub Sep. 5, 2012.
Lam et al., Cooperative signaling through the signal transducer and activator of transcription 3 and nuclear factor-{kappa} B pathways in subtypes of diffuse large B-cell lymphoma. Blood. Apr. 1, 2008; 111(7): 3701-13.
Li et al., Characterization of dasatinib and its structural analogs as CYP3A4 mechanism-based inactivators and the proposed bioactivation pathways. Drug Metab Dispos. Jun. 2009;37(6):1242-50. doi: 10.1124/dmd.108.025932. Epub Mar. 12, 2009.
Li et al., Creating chemical diversity to target protein kinases. Comb Chem High Throughput Screen. Aug. 2004;7(5):453-72.
Lim et al., Oncogenic MYD88 mutants require Toll-like receptors. In: Proceedings of the 104th Annual Meeting of the American Association for Cancer Research; Apr. 6-10, 2013; Washington, DC. Philadelphia: AACR; Cancer Res; (2013) 73(8 Suppl): Abst 2332. 10.1158/1538-7445.AM2013-2332.
Liu et al., Intracellular MHC class II molecules promote TLR-triggered innate immune responses by maintaining activation of the kinase Btk, Nature Immunology 12, 416-424 (2011).doi:10.1038/ni.2015.
Neparidze et al., Waldenstrom's Macroglobulinemia: Recent Advances in Biology and Therapy, Clin Adv Hematol Oncol. Oct. 2009 ; 7(10): 677-690.
Newman et al., Solid-state analysis of the active pharmaceutical ingredient in drug products. Drug Discov Today. Oct. 1, 2003;8(19):898-905.
Ngo et al., Oncogenically active MYD88 mutations in human lymphoma. Nature. Feb. 3, 2011; 470(7332): 115-9.
Patricelli et al., Functional interrogation of the kinome using nucleotide acyl phosphates. Biochemistry, 2007, 46(2): 350-358.
Peng-Cheng et al., Synthesis, molecular docking and evaluation of thiazolyl-pyrazoline derivatives as EGFR TK inhibitors and potential anticancer agents. Bioorg Med Chem Letts. 2011; 21:5374-5377.
Quek et al., A role for Bruton's tyrosine kinase (Btk) in platelet activation by Collagen, Curr. Biol., 1998, 8(20), 1137-1140.
Sawasdikosol et al., HPK1 as a novel target for cancer immunotherapy, Immunol Res (2012) 54:262-265, DOI 10.1007/s12026-012-8319-1.
Schaeffer et al., Tec family kinases in lymphocyte signaling and function, Curr Opin Immunol. Jun. 2000; 12(3): 282-88.
Tan et al., Discovery of type II inhibitors of TGFβ-activated kinase 1 (TAK1) and mitogen-activated protein kinase kinase kinase kinase 2 (MAP4K2). J Med Chem. Jan. 8, 2015;58(1):183-96. doi: 10.1021/jm500480k. Epub Jul. 30, 2014.

Vassilev et al., Bruton's tyrosine kinase as an inhibitor of the Fas/CD95 death-inducing signaling complex, J. Biol. Chem., Jan. 15, 1999, 275(3): 1646-56.
Wang et al., Consequences of the recurrent MYD88(L265P) somatic mutation for B cell tolerance. J Exp Med. Mar. 10, 2014; 211(3): 413-26.
Wang et al., Emerging targets in human lymphoma: targeting the MYD88 mutation. Blood Lymphat Cancer (2013) 2013:53-61.
Wesche et al., MyD88: An Adapter That Recruits IRAK to the IL-1 Receptor Complex, Immunity, 1997, vol. 7, Issue 6, 837-847.
Wolff et al., Some reconsiderations for prodrug design. Burger's Medicinal Chemistry Drug Discovery. 1995;5(1):975-7.
Yang et al., A Mutation in MYD88 (L265P) supports the survival of lymphoplasmacytic cells by activation of Bruton tyrosine kinase in Waldenstrom macroglobulinemia, Blood, Aug. 15, 2013;122(7):1222-32. doi: 10.1182/blood-2012-12-475111. Epub Jul. 8, 2013.
Extended European Search Report for EP 15852450.4, dated Jun. 25, 2018.
CAS Registry No. 1092368-43-8, STN Entry Date: Dec. 31, 2008. 7 pages.
CAS Registry No. 1092368-44-9, STN Entry Date: Dec. 31, 2008. 6 pages.
CAS Registry No. 1240194-14-2, STN Entry Date: Sep. 7, 2010. 1 page.
CAS Registry No. 1348855-14-0, STN Entry Date: Dec. 5, 2011. 1 page.
CAS Registry No. 1359387-63-5, STN Entry Date: Mar. 2, 2012. 1 page.
CAS Registry No. 1359510-63-6, STN Entry Date: Mar. 2, 2012. 1 page.
Drozdowska et al., Semi-Automatic Synthesis of Distamycin Analogues and Their DNA-Binding Properties. Lett Drug Des Discov, 2012; 9:12-16.
Li et al., Synthesis and biological evaluation of 4-[3-chloro-4-(3-fluorobenzyloxy)anilino]-6-(3-substituted-phenoxy)pyrimidines as dual EGFR/ErbB-2 kinase inhibitors. Bioorganic & Medicinal Chemistry Jan. 2012;20(2):877-885.
U.S. Appl. No. 16/169,972, filed Oct. 24, 2018, Gray et al.
U.S. Appl. No. 15/104,005, filed Jun. 13, 2016, Treon et al.
U.S. Appl. No. 15/104,132, filed Jun. 13, 2016, Treon et al.
U.S. Appl. No. 15/847,430, filed Dec. 19, 2017, Treon et al.
U.S. Appl. No. 15/518,541, filed Apr. 12, 2017, Gray et al.
EP 14869351.8, Jul. 31, 2017, Extended European Search Report.
PCT/US2014/070167, Mar. 11, 2015, International Search Report and Written Opinion.
PCT/US2014/070167, Jun. 23, 2016, International Preliminary Report on Patentability.
EP 14869964.8, Nov. 16, 2017, Extended European Search Report.
PCT/US2014/070162, Mar. 11, 2015, International Search Report and Written Opinion.
PCT/US2014/070162, Jun. 23, 2016, International Preliminary Report on Patentability.
EP 15 85 2450, Mar. 22, 2018, Partial Supplementary European Search Report.
PCT/US2015/056899, Jan. 29, 2016, International Search Report and Written Opinion.
PCT/US2015/056899, May 4, 2017, International Preliminary Report on Patentability.

\* cited by examiner

SEQUENCE LISTING

```
<160> NUMBER OF SEQ ID NOS: 116

<210> SEQ ID NO 1
<211> LENGTH: 18
<212> TYPE: PRT
<213> ORGANISM: Homo sapiens

<400> SEQUENCE: 1

Leu Met Thr Gly Asp Thr Tyr Thr Ala His Ala Gly Ala Lys Phe Pro
1               5                   10                  15

Ile Lys

<210> SEQ ID NO 2
<211> LENGTH: 25
<212> TYPE: PRT
<213> ORGANISM: Homo sapiens

<400> SEQUENCE: 2

Thr Val Ser Val Ala Val Lys Cys Leu Lys Pro Asp Val Leu Ser Gln
1               5                   10                  15

Pro Glu Ala Met Asp Asp Phe Ile Arg
            20                  25

<210> SEQ ID NO 3
<211> LENGTH: 8
<212> TYPE: PRT
<213> ORGANISM: Homo sapiens

<400> SEQUENCE: 3

Val Ala Val Lys Ile Leu Asn Arg
1               5

<210> SEQ ID NO 4
<211> LENGTH: 9
<212> TYPE: PRT
<213> ORGANISM: Homo sapiens

<400> SEQUENCE: 4

Phe Tyr Ile Met Met Cys Lys Pro Lys
1               5

<210> SEQ ID NO 5
<211> LENGTH: 16
<212> TYPE: PRT
<213> ORGANISM: Homo sapiens

<400> SEQUENCE: 5

Asp Ile Lys Pro Glu Asn Leu Leu Leu Gly Ser Ala Gly Glu Leu Lys
1               5                   10                  15
```

```
<210> SEQ ID NO 6
<211> LENGTH: 12
<212> TYPE: PRT
<213> ORGANISM: Homo sapiens

<400> SEQUENCE: 6

Ser His Phe Ile Val Ala Leu Lys Val Leu Phe Lys
1               5                   10

<210> SEQ ID NO 7
<211> LENGTH: 16
<212> TYPE: PRT
<213> ORGANISM: Homo sapiens

<400> SEQUENCE: 7

Asp Leu Lys Pro Ala Asn Ile Leu Leu Asp Glu His Gly His Val Arg
1               5                   10                  15

<210> SEQ ID NO 8
<211> LENGTH: 17
<212> TYPE: PRT
<213> ORGANISM: Homo sapiens

<400> SEQUENCE: 8

Ile Ile Asp Ser Glu Tyr Thr Ala Gln Glu Gly Ala Lys Phe Pro Ile
1               5                   10                  15

Lys

<210> SEQ ID NO 9
<211> LENGTH: 16
<212> TYPE: PRT
<213> ORGANISM: Homo sapiens

<400> SEQUENCE: 9

Asp Leu Lys Ser Asn Asn Ile Phe Leu His Glu Asp Leu Thr Val Lys
1               5                   10                  15

<210> SEQ ID NO 10
<211> LENGTH: 11
<212> TYPE: PRT
<213> ORGANISM: Homo sapiens

<400> SEQUENCE: 10

Gly Gln Tyr Asp Val Ala Ile Lys Met Ile Lys
1               5                   10

<210> SEQ ID NO 11
<211> LENGTH: 18
<212> TYPE: PRT
<213> ORGANISM: Homo sapiens

<400> SEQUENCE: 11

Tyr Val Leu Asp Asp Glu Tyr Thr Ser Ser Val Gly Ser Lys Phe Pro
1               5                   10                  15

Val Arg

<210> SEQ ID NO 12
<211> LENGTH: 9
<212> TYPE: PRT
<213> ORGANISM: Homo sapiens

<400> SEQUENCE: 12

Leu Phe Ala Val Lys Cys Ile Pro Lys
```

```
<210> SEQ ID NO 13
<211> LENGTH: 12
<212> TYPE: PRT
<213> ORGANISM: Homo sapiens

<400> SEQUENCE: 13

Asp Leu Lys Pro Glu Asn Leu Leu Ala Ser Lys
1               5                   10

<210> SEQ ID NO 14
<211> LENGTH: 16
<212> TYPE: PRT
<213> ORGANISM: Homo sapiens

<400> SEQUENCE: 14

Ile Pro Thr Gly Gln Glu Tyr Ala Ala Lys Ile Ile Asn Thr Lys Lys
1               5                   10                  15

<210> SEQ ID NO 15
<211> LENGTH: 19
<212> TYPE: PRT
<213> ORGANISM: Homo sapiens

<400> SEQUENCE: 15

Asp Leu Lys Pro Glu Asn Leu Leu Tyr Ala Thr Pro Ala Pro Asp Ala
1               5                   10                  15

Pro Leu Lys

<210> SEQ ID NO 16
<211> LENGTH: 16
<212> TYPE: PRT
<213> ORGANISM: Homo sapiens

<400> SEQUENCE: 16

Asp Leu Lys Pro Gln Asn Leu Leu Ile Asp Asp Lys Gly Thr Ile Lys
1               5                   10                  15

<210> SEQ ID NO 17
<211> LENGTH: 16
<212> TYPE: PRT
<213> ORGANISM: Homo sapiens

<400> SEQUENCE: 17

Asp Leu Lys Pro Ala Asn Ile Leu Val Met Gly Glu Gly Pro Glu Arg
1               5                   10                  15

<210> SEQ ID NO 18
<211> LENGTH: 16
<212> TYPE: PRT
<213> ORGANISM: Homo sapiens

<400> SEQUENCE: 18

Asp Leu Lys Pro Gln Asn Leu Leu Ile Asn Thr Glu Gly Ala Ile Lys
1               5                   10                  15

<210> SEQ ID NO 19
<211> LENGTH: 11
<212> TYPE: PRT
<213> ORGANISM: Homo sapiens

<400> SEQUENCE: 19

Asp Leu Lys Pro Gln Asn Leu Leu Ile Asn Arg
```

```
<210> SEQ ID NO 20
<211> LENGTH: 16
<212> TYPE: PRT
<213> ORGANISM: Homo sapiens

<400> SEQUENCE: 20

Asp Leu Lys Pro Asn Asn Leu Leu Asp Glu Asn Gly Val Leu Lys
1               5                   10                  15

<210> SEQ ID NO 21
<211> LENGTH: 8
<212> TYPE: PRT
<213> ORGANISM: Homo sapiens

<400> SEQUENCE: 21

Val Ala Ile Lys Ile Ile Ser Lys
1               5

<210> SEQ ID NO 22
<211> LENGTH: 13
<212> TYPE: PRT
<213> ORGANISM: Homo sapiens

<400> SEQUENCE: 22

Asp Ile Lys Pro Asp Asn Phe Leu Met Gly Ile Gly Arg
1               5                   10

<210> SEQ ID NO 23
<211> LENGTH: 11
<212> TYPE: PRT
<213> ORGANISM: Homo sapiens

<400> SEQUENCE: 23

Asp Val Lys Pro Glu Asn Phe Leu Ile Gly Arg
1               5                   10

<210> SEQ ID NO 24
<211> LENGTH: 15
<212> TYPE: PRT
<213> ORGANISM: Homo sapiens

<400> SEQUENCE: 24

Asp Val Lys Pro Glu Asn Phe Leu Val Gly Arg Pro Gly Thr Lys
1               5                   10                  15

<210> SEQ ID NO 25
<211> LENGTH: 22
<212> TYPE: PRT
<213> ORGANISM: Homo sapiens

<400> SEQUENCE: 25

Val Ser Asp Phe Gly Leu Thr Lys Glu Ala Ser Ser Thr Gln Asp Thr
1               5                   10                  15

Gly Lys Leu Pro Val Lys
            20

<210> SEQ ID NO 26
<211> LENGTH: 13
<212> TYPE: PRT
<213> ORGANISM: Homo sapiens

<400> SEQUENCE: 26
```

Glu His Pro Phe Leu Val Lys Gly Gly Glu Asp Leu Arg
1               5                   10

<210> SEQ ID NO 27
<211> LENGTH: 12
<212> TYPE: PRT
<213> ORGANISM: Homo sapiens

<400> SEQUENCE: 27

Tyr Ile Lys Tyr Asn Ser Asn Ser Gly Phe Val Arg
1               5                   10

<210> SEQ ID NO 28
<211> LENGTH: 16
<212> TYPE: PRT
<213> ORGANISM: Homo sapiens

<400> SEQUENCE: 28

Asp Leu Lys Pro Ser Asn Leu Leu Ile Asn Thr Thr Cys Asp Leu Lys
1               5                   10                  15

<210> SEQ ID NO 29
<211> LENGTH: 16
<212> TYPE: PRT
<213> ORGANISM: Homo sapiens

<400> SEQUENCE: 29

Asp Leu Lys Pro Ser Asn Leu Leu Leu Asn Thr Thr Cys Asp Leu Lys
1               5                   10                  15

<210> SEQ ID NO 30
<211> LENGTH: 17
<212> TYPE: PRT
<213> ORGANISM: Homo sapiens

<400> SEQUENCE: 30

Thr Ser Val Ala Val Lys Thr Cys Lys Glu Asp Leu Pro Gln Glu Leu
1               5                   10                  15

Lys

<210> SEQ ID NO 31
<211> LENGTH: 18
<212> TYPE: PRT
<213> ORGANISM: Homo sapiens

<400> SEQUENCE: 31

Leu Ile Lys Asp Asp Glu Tyr Asn Pro Cys Gln Gly Ser Lys Phe Pro
1               5                   10                  15

Ile Lys

<210> SEQ ID NO 32
<211> LENGTH: 18
<212> TYPE: PRT
<213> ORGANISM: Homo sapiens

<400> SEQUENCE: 32

Ile Gln Ser Ile Ala Pro Ser Leu Gln Val Ile Thr Ser Lys Gln Arg
1               5                   10                  15

Pro Arg

<210> SEQ ID NO 33
<211> LENGTH: 19
<212> TYPE: PRT

```
<213> ORGANISM: Homo sapiens

<400> SEQUENCE: 33

Gln Gly Ala Lys Phe Pro Ile Lys Trp Thr Ala Pro Glu Ala Ala Leu
1               5                   10                  15

Tyr Gly Arg

<210> SEQ ID NO 34
<211> LENGTH: 16
<212> TYPE: PRT
<213> ORGANISM: Homo sapiens

<400> SEQUENCE: 34

Asp Ile Lys Gly Ala Asn Leu Leu Leu Thr Leu Gln Gly Asp Val Lys
1               5                   10                  15

<210> SEQ ID NO 35
<211> LENGTH: 17
<212> TYPE: PRT
<213> ORGANISM: Homo sapiens

<400> SEQUENCE: 35

Asp Ile Lys Pro Gln Asn Leu Leu Val Asp Pro Asp Thr Ala Val Leu
1               5                   10                  15

Lys

<210> SEQ ID NO 36
<211> LENGTH: 17
<212> TYPE: PRT
<213> ORGANISM: Homo sapiens

<400> SEQUENCE: 36

Asp Ile Lys Pro Gln Asn Leu Leu Leu Asp Pro Asp Thr Ala Val Leu
1               5                   10                  15

Lys

<210> SEQ ID NO 37
<211> LENGTH: 14
<212> TYPE: PRT
<213> ORGANISM: Homo sapiens

<400> SEQUENCE: 37

Asp Lys Val Ser Gly Asp Leu Val Ala Leu Lys Met Val Lys
1               5                   10

<210> SEQ ID NO 38
<211> LENGTH: 19
<212> TYPE: PRT
<213> ORGANISM: Homo sapiens

<400> SEQUENCE: 38

Ser Gly Glu Leu Val Ala Val Lys Val Phe Asn Thr Thr Ser Tyr Leu
1               5                   10                  15

Arg Pro Arg

<210> SEQ ID NO 39
<211> LENGTH: 9
<212> TYPE: PRT
<213> ORGANISM: Homo sapiens

<400> SEQUENCE: 39

Asp Ile Lys Pro Gly Asn Ile Met Arg
```

<210> SEQ ID NO 40
<211> LENGTH: 15
<212> TYPE: PRT
<213> ORGANISM: Homo sapiens

<400> SEQUENCE: 40

Ile Ser Met Ala Asp Val Lys Phe Ser Phe Gln Cys Pro Gly Arg
1               5                   10                  15

<210> SEQ ID NO 41
<211> LENGTH: 16
<212> TYPE: PRT
<213> ORGANISM: Homo sapiens

<400> SEQUENCE: 41

Asp Ile Lys Ser Ala Asn Ile Leu Leu Asp Glu Ala Phe Thr Ala Lys
1               5                   10                  15

<210> SEQ ID NO 42
<211> LENGTH: 28
<212> TYPE: PRT
<213> ORGANISM: Homo sapiens

<400> SEQUENCE: 42

Gln Leu Ala Ser Ala Leu Ser Tyr Leu Glu Lys Asp Leu Val His
1               5                   10                  15

Gly Asn Val Cys Thr Lys Asn Leu Leu Leu Ala Arg
            20                  25

<210> SEQ ID NO 43
<211> LENGTH: 31
<212> TYPE: PRT
<213> ORGANISM: Homo sapiens

<400> SEQUENCE: 43

Tyr Asp Pro Glu Gly Asp Asn Thr Gly Glu Gln Val Ala Val Lys Ser
1               5                   10                  15

Leu Lys Pro Glu Ser Gly Gly Asn His Ile Ala Asp Leu Lys Lys
            20                  25                  30

<210> SEQ ID NO 44
<211> LENGTH: 10
<212> TYPE: PRT
<213> ORGANISM: Homo sapiens

<400> SEQUENCE: 44

Asp Leu Lys Pro Ser Asn Ile Val Val Lys
1               5                   10

<210> SEQ ID NO 45
<211> LENGTH: 14
<212> TYPE: PRT
<213> ORGANISM: Homo sapiens

<400> SEQUENCE: 45

Asn Val His Thr Gly Glu Leu Ala Ala Val Lys Ile Ile Lys
1               5                   10

<210> SEQ ID NO 46
<211> LENGTH: 23
<212> TYPE: PRT
<213> ORGANISM: Homo sapiens

```
<400> SEQUENCE: 46

Glu Gly Ala Lys Phe Pro Ile Lys Trp Thr Ala Pro Glu Ala Ile Asn
1               5                   10                  15

Tyr Gly Thr Phe Thr Ile Lys
            20

<210> SEQ ID NO 47
<211> LENGTH: 16
<212> TYPE: PRT
<213> ORGANISM: Homo sapiens

<400> SEQUENCE: 47

Asp Ile Lys Pro Gly Asn Leu Leu Leu Thr Thr Gly Gly Thr Leu Lys
1               5                   10                  15

<210> SEQ ID NO 48
<211> LENGTH: 16
<212> TYPE: PRT
<213> ORGANISM: Homo sapiens

<400> SEQUENCE: 48

Asp Leu Lys Ala Gly Asn Val Leu Met Thr Leu Glu Gly Asp Ile Arg
1               5                   10                  15

<210> SEQ ID NO 49
<211> LENGTH: 24
<212> TYPE: PRT
<213> ORGANISM: Homo sapiens

<400> SEQUENCE: 49

Val Ala Val Lys Thr Leu Lys Pro Gly Thr Met Ser Val Gln Ala Phe
1               5                   10                  15

Leu Glu Glu Ala Asn Leu Met Lys
            20

<210> SEQ ID NO 50
<211> LENGTH: 23
<212> TYPE: PRT
<213> ORGANISM: Homo sapiens

<400> SEQUENCE: 50

Glu Gly Ala Lys Phe Pro Ile Lys Trp Thr Ala Pro Glu Ala Ile Asn
1               5                   10                  15

Phe Gly Cys Phe Thr Ile Lys
            20

<210> SEQ ID NO 51
<211> LENGTH: 16
<212> TYPE: PRT
<213> ORGANISM: Homo sapiens

<400> SEQUENCE: 51

Ile Met His Arg Asp Val Lys Pro Ser Asn Ile Leu Val Asn Ser Arg
1               5                   10                  15

<210> SEQ ID NO 52
<211> LENGTH: 12
<212> TYPE: PRT
<213> ORGANISM: Homo sapiens

<400> SEQUENCE: 52

Asp Val Lys Pro Ser Asn Ile Leu Val Asn Ser Arg
```

```
1               5                   10
```

<210> SEQ ID NO 53
<211> LENGTH: 11
<212> TYPE: PRT
<213> ORGANISM: Homo sapiens

<400> SEQUENCE: 53

```
Asp Val Lys Pro Ser Asn Val Leu Ile Asn Lys
1               5                   10
```

<210> SEQ ID NO 54
<211> LENGTH: 11
<212> TYPE: PRT
<213> ORGANISM: Homo sapiens

<400> SEQUENCE: 54

```
Asp Ile Lys Pro Ser Asn Ile Leu Leu Asp Arg
1               5                   10
```

<210> SEQ ID NO 55
<211> LENGTH: 12
<212> TYPE: PRT
<213> ORGANISM: Homo sapiens

<400> SEQUENCE: 55

```
Asp Val Lys Pro Ser Asn Met Leu Val Asn Thr Arg
1               5                   10
```

<210> SEQ ID NO 56
<211> LENGTH: 16
<212> TYPE: PRT
<213> ORGANISM: Homo sapiens

<400> SEQUENCE: 56

```
Asp Val Lys Pro Ser Asn Val Leu Ile Asn Ala Leu Gly Gln Val Lys
1               5                   10                  15
```

<210> SEQ ID NO 57
<211> LENGTH: 12
<212> TYPE: PRT
<213> ORGANISM: Homo sapiens

<400> SEQUENCE: 57

```
Asp Val Lys Pro Ser Asn Ile Leu Leu Asp Glu Arg
1               5                   10
```

<210> SEQ ID NO 58
<211> LENGTH: 15
<212> TYPE: PRT
<213> ORGANISM: Homo sapiens

<400> SEQUENCE: 58

```
Asp Val Lys Gly Ala Asn Leu Leu Ile Asp Ser Thr Gly Gln Arg
1               5                   10                  15
```

<210> SEQ ID NO 59
<211> LENGTH: 9
<212> TYPE: PRT
<213> ORGANISM: Homo sapiens

<400> SEQUENCE: 59

```
Asp Ile Lys Gly Ala Asn Ile Leu Arg
1               5
```

```
<210> SEQ ID NO 60
<211> LENGTH: 16
<212> TYPE: PRT
<213> ORGANISM: Homo sapiens

<400> SEQUENCE: 60

Asp Ile Lys Gly Ala Asn Ile Phe Leu Thr Ser Ser Gly Leu Ile Lys
1               5                   10                  15

<210> SEQ ID NO 61
<211> LENGTH: 17
<212> TYPE: PRT
<213> ORGANISM: Homo sapiens

<400> SEQUENCE: 61

Asp Ile Lys Gly Asp Asn Val Leu Ile Asn Thr Tyr Ser Gly Val Leu
1               5                   10                  15

Lys

<210> SEQ ID NO 62
<211> LENGTH: 9
<212> TYPE: PRT
<213> ORGANISM: Homo sapiens

<400> SEQUENCE: 62

Glu Val Ala Val Lys Ile Ile Asp Lys
1               5

<210> SEQ ID NO 63
<211> LENGTH: 16
<212> TYPE: PRT
<213> ORGANISM: Homo sapiens

<400> SEQUENCE: 63

Asp Leu Lys Ala Glu Asn Leu Leu Asp Ala Asp Met Asn Ile Lys
1               5                   10                  15

<210> SEQ ID NO 64
<211> LENGTH: 19
<212> TYPE: PRT
<213> ORGANISM: Homo sapiens

<400> SEQUENCE: 64

Glu Val Ala Ile Lys Ile Ile Asp Lys Thr Gln Leu Asn Pro Thr Ser
1               5                   10                  15

Leu Gln Lys

<210> SEQ ID NO 65
<211> LENGTH: 16
<212> TYPE: PRT
<213> ORGANISM: Homo sapiens

<400> SEQUENCE: 65

Asp Leu Lys Pro Asp Asn Leu Leu Ile Thr Ser Leu Gly His Ile Lys
1               5                   10                  15

<210> SEQ ID NO 66
<211> LENGTH: 8
<212> TYPE: PRT
<213> ORGANISM: Homo sapiens

<400> SEQUENCE: 66

Leu Tyr Ala Val Lys Val Val Lys
```

```
<210> SEQ ID NO 67
<211> LENGTH: 22
<212> TYPE: PRT
<213> ORGANISM: Homo sapiens

<400> SEQUENCE: 67

Glu Thr Gly Gln Ile Val Ala Ile Lys Gln Val Pro Val Glu Ser Asp
1               5                   10                  15

Leu Gln Glu Ile Ile Lys
            20

<210> SEQ ID NO 68
<211> LENGTH: 22
<212> TYPE: PRT
<213> ORGANISM: Homo sapiens

<400> SEQUENCE: 68

Glu Ser Gly Gln Val Val Ala Ile Lys Gln Val Pro Val Glu Ser Asp
1               5                   10                  15

Leu Gln Glu Ile Ile Lys
            20

<210> SEQ ID NO 69
<211> LENGTH: 16
<212> TYPE: PRT
<213> ORGANISM: Homo sapiens

<400> SEQUENCE: 69

Asp Ile Lys Ala Ala Asn Val Leu Leu Ser Glu His Gly Glu Val Lys
1               5                   10                  15

<210> SEQ ID NO 70
<211> LENGTH: 16
<212> TYPE: PRT
<213> ORGANISM: Homo sapiens

<400> SEQUENCE: 70

Asp Ile Lys Ala Ala Asn Val Leu Leu Ser Glu Gln Gly Asp Val Lys
1               5                   10                  15

<210> SEQ ID NO 71
<211> LENGTH: 12
<212> TYPE: PRT
<213> ORGANISM: Homo sapiens

<400> SEQUENCE: 71

Asp Thr Gly His Val Tyr Ala Met Lys Ile Leu Arg
1               5                   10

<210> SEQ ID NO 72
<211> LENGTH: 12
<212> TYPE: PRT
<213> ORGANISM: Homo sapiens

<400> SEQUENCE: 72

Asp Ile Lys Pro Asp Asn Leu Leu Leu Asp Ala Lys
1               5                   10

<210> SEQ ID NO 73
<211> LENGTH: 11
<212> TYPE: PRT
<213> ORGANISM: Homo sapiens
```

<400> SEQUENCE: 73

Ser Lys Asn Ile Phe Leu Thr Gln Asn Gly Lys
1               5                   10

<210> SEQ ID NO 74
<211> LENGTH: 16
<212> TYPE: PRT
<213> ORGANISM: Homo sapiens

<400> SEQUENCE: 74

Asp Ile Lys Pro Ala Asn Val Phe Ile Thr Ala Thr Gly Val Val Lys
1               5                   10                  15

<210> SEQ ID NO 75
<211> LENGTH: 14
<212> TYPE: PRT
<213> ORGANISM: Homo sapiens

<400> SEQUENCE: 75

Ala Ala Cys Leu Leu Asp Gly Val Pro Val Ala Leu Lys Lys
1               5                   10

<210> SEQ ID NO 76
<211> LENGTH: 11
<212> TYPE: PRT
<213> ORGANISM: Homo sapiens

<400> SEQUENCE: 76

Asp Ile Lys Thr Leu Asn Ile Phe Leu Thr Lys
1               5                   10

<210> SEQ ID NO 77
<211> LENGTH: 13
<212> TYPE: PRT
<213> ORGANISM: Homo sapiens

<400> SEQUENCE: 77

Gln Glu Leu Asn Lys Thr Ile Trp Glu Val Pro Glu Arg
1               5                   10

<210> SEQ ID NO 78
<211> LENGTH: 16
<212> TYPE: PRT
<213> ORGANISM: Homo sapiens

<400> SEQUENCE: 78

Asp Leu Lys Pro Gly Asn Leu Ala Val Asn Glu Asp Cys Glu Leu Lys
1               5                   10                  15

<210> SEQ ID NO 79
<211> LENGTH: 16
<212> TYPE: PRT
<213> ORGANISM: Homo sapiens

<400> SEQUENCE: 79

Asp Leu Lys Pro Glu Asn Ile Met Leu Asn His Gln Gly His Val Lys
1               5                   10                  15

<210> SEQ ID NO 80
<211> LENGTH: 8
<212> TYPE: PRT
<213> ORGANISM: Homo sapiens

<400> SEQUENCE: 80

```
Leu Val Ala Leu Lys Val Ile Arg
1               5

<210> SEQ ID NO 81
<211> LENGTH: 14
<212> TYPE: PRT
<213> ORGANISM: Homo sapiens

<400> SEQUENCE: 81

Val Pro His Thr Gln Ala Val Val Leu Asn Ser Lys Asp Lys
1               5                   10

<210> SEQ ID NO 82
<211> LENGTH: 18
<212> TYPE: PRT
<213> ORGANISM: Homo sapiens

<400> SEQUENCE: 82

Thr Glu Asp Gly Gly Lys Tyr Pro Val Ile Phe Lys His Gly Asp Asp
1               5                   10                  15

Leu Arg

<210> SEQ ID NO 83
<211> LENGTH: 18
<212> TYPE: PRT
<213> ORGANISM: Homo sapiens

<400> SEQUENCE: 83

Val Phe Gly Glu Asp Ser Val Gly Val Ile Phe Lys Asn Gly Asp Asp
1               5                   10                  15

Leu Arg

<210> SEQ ID NO 84
<211> LENGTH: 14
<212> TYPE: PRT
<213> ORGANISM: Homo sapiens

<400> SEQUENCE: 84

Val Asn Trp Leu Ala His Asn Val Ser Lys Asp Asn Arg Gln
1               5                   10

<210> SEQ ID NO 85
<211> LENGTH: 18
<212> TYPE: PRT
<213> ORGANISM: Homo sapiens

<400> SEQUENCE: 85

Ala Lys Glu Leu Pro Thr Leu Lys Asp Asn Asp Phe Ile Asn Glu Gly
1               5                   10                  15

Gln Lys

<210> SEQ ID NO 86
<211> LENGTH: 28
<212> TYPE: PRT
<213> ORGANISM: Homo sapiens

<400> SEQUENCE: 86

Thr Leu Val Ile Lys Glu Val Ser Ser Glu Asp Ile Ala Asp Met His
1               5                   10                  15

Ser Asn Leu Ser Asn Tyr His Gln Tyr Ile Val Lys
                20                  25
```

<210> SEQ ID NO 87
<211> LENGTH: 19
<212> TYPE: PRT
<213> ORGANISM: Homo sapiens

<400> SEQUENCE: 87

Gly Gly Lys Ser Gly Ala Ala Phe Tyr Ala Thr Glu Asp Asp Arg Phe
1               5                   10                  15

Ile Leu Lys

<210> SEQ ID NO 88
<211> LENGTH: 16
<212> TYPE: PRT
<213> ORGANISM: Homo sapiens

<400> SEQUENCE: 88

Asp Leu Lys Thr Ser Asn Leu Leu Leu Ser His Ala Gly Ile Leu Lys
1               5                   10                  15

<210> SEQ ID NO 89
<211> LENGTH: 16
<212> TYPE: PRT
<213> ORGANISM: Homo sapiens

<400> SEQUENCE: 89

Asp Leu Lys Leu Asp Asn Val Leu Leu Asp Ser Glu Gly His Ile Lys
1               5                   10                  15

<210> SEQ ID NO 90
<211> LENGTH: 24
<212> TYPE: PRT
<213> ORGANISM: Homo sapiens

<400> SEQUENCE: 90

Asn Ile Val His Cys Asp Leu Lys Pro Glu Asn Val Leu Leu Ala Ser
1               5                   10                  15

Ala Asp Pro Phe Pro Gln Val Lys
            20

<210> SEQ ID NO 91
<211> LENGTH: 9
<212> TYPE: PRT
<213> ORGANISM: Homo sapiens

<400> SEQUENCE: 91

Asp Val Ala Val Lys Val Ile Asp Lys
1               5

<210> SEQ ID NO 92
<211> LENGTH: 24
<212> TYPE: PRT
<213> ORGANISM: Homo sapiens

<400> SEQUENCE: 92

Asn Ile Val His Cys Asp Leu Lys Pro Glu Asn Val Leu Leu Ala Ser
1               5                   10                  15

Ala Glu Pro Phe Pro Gln Val Lys
            20

<210> SEQ ID NO 93
<211> LENGTH: 19
<212> TYPE: PRT
<213> ORGANISM: Homo sapiens

```
<400> SEQUENCE: 93

Val Leu Leu Ser Glu Phe Arg Pro Ser Gly Glu Leu Phe Ala Ile Lys
1               5                   10                  15

Ala Leu Lys

<210> SEQ ID NO 94
<211> LENGTH: 13
<212> TYPE: PRT
<213> ORGANISM: Homo sapiens

<400> SEQUENCE: 94

Asp Leu Lys Pro Ser Asn Ile Phe Leu Val Asp Thr Lys
1               5                   10

<210> SEQ ID NO 95
<211> LENGTH: 20
<212> TYPE: PRT
<213> ORGANISM: Homo sapiens

<400> SEQUENCE: 95

Cys Phe Glu Ile Ser Asp Ala Asp Thr Lys Glu Val Phe Ala Gly Lys
1               5                   10                  15

Ile Val Pro Lys
            20

<210> SEQ ID NO 96
<211> LENGTH: 14
<212> TYPE: PRT
<213> ORGANISM: Homo sapiens

<400> SEQUENCE: 96

Tyr Ile Glu Asp Glu Asp Tyr Tyr Lys Ala Ser Val Thr Arg
1               5                   10

<210> SEQ ID NO 97
<211> LENGTH: 11
<212> TYPE: PRT
<213> ORGANISM: Homo sapiens

<400> SEQUENCE: 97

Asp Val Lys Pro Asp Asn Met Leu Leu Asp Lys
1               5                   10

<210> SEQ ID NO 98
<211> LENGTH: 31
<212> TYPE: PRT
<213> ORGANISM: Homo sapiens

<400> SEQUENCE: 98

Asp Leu Lys Pro Glu Asn Ile Leu Leu Asp Glu Glu Gly His Ile Lys
1               5                   10                  15

Leu Thr Asp Phe Gly Leu Ser Lys Glu Ala Ile Asp His Glu Lys
            20                  25                  30

<210> SEQ ID NO 99
<211> LENGTH: 20
<212> TYPE: PRT
<213> ORGANISM: Homo sapiens

<400> SEQUENCE: 99

Asp Leu Lys Pro Ser Asn Ile Leu Tyr Val Asp Glu Ser Gly Asn Pro
1               5                   10                  15
```

Glu Cys Leu Arg
        20

<210> SEQ ID NO 100
<211> LENGTH: 31
<212> TYPE: PRT
<213> ORGANISM: Homo sapiens

<400> SEQUENCE: 100

Asp Leu Lys Pro Glu Asn Ile Leu Leu Asp Glu Glu Gly His Ile Lys
1               5                   10                  15

Leu Thr Asp Phe Gly Leu Ser Lys Glu Ser Ile Asp His Glu Lys
            20                  25                  30

<210> SEQ ID NO 101
<211> LENGTH: 20
<212> TYPE: PRT
<213> ORGANISM: Homo sapiens

<400> SEQUENCE: 101

Asp Leu Lys Pro Ser Asn Ile Leu Tyr Val Asp Glu Ser Gly Asn Pro
1               5                   10                  15

Glu Ser Ile Arg
        20

<210> SEQ ID NO 102
<211> LENGTH: 9
<212> TYPE: PRT
<213> ORGANISM: Homo sapiens

<400> SEQUENCE: 102

Phe Tyr Ala Val Lys Val Leu Gln Lys
1               5

<210> SEQ ID NO 103
<211> LENGTH: 16
<212> TYPE: PRT
<213> ORGANISM: Homo sapiens

<400> SEQUENCE: 103

Asp Leu Lys Ala Gly Asn Ile Leu Phe Thr Leu Asp Gly Asp Ile Lys
1               5                   10                  15

<210> SEQ ID NO 104
<211> LENGTH: 24
<212> TYPE: PRT
<213> ORGANISM: Homo sapiens

<400> SEQUENCE: 104

Tyr Ser Val Lys Val Leu Pro Trp Leu Ser Pro Glu Val Leu Gln Gln
1               5                   10                  15

Asn Leu Gln Gly Tyr Asp Ala Lys
            20

<210> SEQ ID NO 105
<211> LENGTH: 28
<212> TYPE: PRT
<213> ORGANISM: Homo sapiens

<400> SEQUENCE: 105

Ser Ile Lys Ala Ser His Ile Leu Ile Ser Gly Asp Gly Leu Val Thr
1               5                   10                  15

Leu Ser Gly Leu Ser His Leu His Ser Leu Val Lys
            20                  25

<210> SEQ ID NO 106
<211> LENGTH: 11
<212> TYPE: PRT
<213> ORGANISM: Homo sapiens

<400> SEQUENCE: 106

Ile Ser Asp Phe Gly Leu Ser Lys Ala Leu Arg
1               5                   10

<210> SEQ ID NO 107
<211> LENGTH: 8
<212> TYPE: PRT
<213> ORGANISM: Homo sapiens

<400> SEQUENCE: 107

Thr Val Ala Val Lys Ile Leu Lys
1               5

<210> SEQ ID NO 108
<211> LENGTH: 16
<212> TYPE: PRT
<213> ORGANISM: Homo sapiens

<400> SEQUENCE: 108

Asp Ile Lys Ala Gly Asn Ile Leu Leu Thr Glu Pro Gly Gln Val Lys
1               5                   10                  15

<210> SEQ ID NO 109
<211> LENGTH: 16
<212> TYPE: PRT
<213> ORGANISM: Homo sapiens

<400> SEQUENCE: 109

Asp Val Lys Ala Gly Asn Ile Leu Leu Ser Glu Pro Gly Leu Val Lys
1               5                   10                  15

<210> SEQ ID NO 110
<211> LENGTH: 18
<212> TYPE: PRT
<213> ORGANISM: Homo sapiens

<400> SEQUENCE: 110

Tyr Val Leu Asp Asp Gln Tyr Thr Ser Ser Gly Ala Lys Phe Pro
1               5                   10                  15

Val Lys

<210> SEQ ID NO 111
<211> LENGTH: 31
<212> TYPE: PRT
<213> ORGANISM: Homo sapiens

<400> SEQUENCE: 111

Tyr Leu Asn Glu Ile Lys Pro Pro Ile Ile His Tyr Asp Leu Lys Pro
1               5                   10                  15

Gly Asn Ile Leu Leu Val Asp Gly Thr Ala Cys Gly Glu Ile Lys
            20                  25                  30

<210> SEQ ID NO 112
<211> LENGTH: 31
<212> TYPE: PRT
<213> ORGANISM: Homo sapiens

```
<400> SEQUENCE: 112

Tyr Leu Asn Glu Ile Lys Pro Pro Ile Ile His Tyr Asp Leu Lys Pro
1               5                   10                  15

Gly Asn Ile Leu Leu Val Asn Gly Thr Ala Cys Gly Glu Ile Lys
            20                  25                  30

<210> SEQ ID NO 113
<211> LENGTH: 10
<212> TYPE: PRT
<213> ORGANISM: Homo sapiens

<400> SEQUENCE: 113

Glu Val Val Ala Ile Lys Cys Val Ala Lys
1               5                   10

<210> SEQ ID NO 114
<211> LENGTH: 12
<212> TYPE: PRT
<213> ORGANISM: Homo sapiens

<400> SEQUENCE: 114

Trp Ile Ser Gln Asp Lys Glu Val Ala Val Lys Lys
1               5                   10

<210> SEQ ID NO 115
<211> LENGTH: 20
<212> TYPE: PRT
<213> ORGANISM: Homo sapiens

<400> SEQUENCE: 115

Ile Ser Asp Phe Gly Leu Ser Lys Ala Leu Gly Ala Asp Asp Ser Tyr
1               5                   10                  15

Tyr Thr Ala Arg
            20

<210> SEQ ID NO 116
<211> LENGTH: 16
<212> TYPE: PRT
<213> ORGANISM: Homo sapiens

<400> SEQUENCE: 116

Asp Ile Lys Gly Gln Asn Val Leu Leu Thr Glu Asn Ala Glu Val Lys
1               5                   10                  15
```

METHODS TO TREAT LYMPHOPLASMACYTIC LYMPHOMA

RELATED APPLICATIONS

The present application is a continuation of and claims priority under 35 U.S.C. § 120 to U.S. Application, U.S. Ser. No. 15/104,005, filed Jun. 13, 2016 and issued as U.S. Pat. No. 9,908,872, which is a national stage filing under 35 U.S.C. § 371 of international PCT application, PCT/US2014/070167, filed Dec. 12, 2014, which claims priority under 35 U.S.C. § 119(e) to U.S. provisional patent applications, U.S. Ser. No. 62/036,917, filed Aug. 13, 2014, and U.S. Ser. No. 61/915,684, filed Dec. 13, 2013, each of which is incorporated herein by reference.

GOVERNMENT SUPPORT

This invention was made with government support under grant number P50 CA100707 awarded by the National Institutes of Heath. The government has certain rights in the invention.

BACKGROUND OF THE INVENTION

Waldenström's macroglobulinemia (WM) is a distinct clinicopathological entity resulting from the accumulation, predominantly in the bone marrow, of clonally related lymphoplasmacytic cells which secrete a monoclonal IgM protein. This condition is considered to correspond to lymphoplasmacytic lymphoma (LPL) as defined by the World Health Organization classification system. WM is a rare disorder, with fewer than 1,500 cases occurring in the United States annually. There is a 2- to 3-fold risk increase of developing WM in people with a personal history of autoimmune diseases with autoantibodies and particularly elevated risks associated with hepatitis, human immunodeficiency virus, and rickettsiosis (*Arch. Intern. Med.*, 2008, 168(17), 1903-9). There is no single accepted treatment for WM, and there can be a marked variation in clinical outcome. Objective response rates are high (>80%) but complete response rates are low (0-15%) (*Clin. Adv. Hematol. Oncol.*, 2009, 7(10), 677-81, 687-90). Thus, there is a need for effective treatment of WM.

SUMMARY OF THE INVENTION

The present invention is based, at least in part, on the discovery of compounds of the Formula (I):

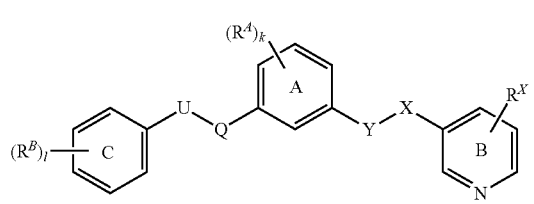

or a pharmaceutically acceptable salt thereof, wherein X, Y, Q, U, $R^A$, $R^B$, $R^X$, k, and l are defined herein, for the treatment of Waldenström's macroglobulinemia. The activity of these compounds was established by in vitro screening against several kinases (e.g., BTK, HCK, TAK1, HPK1).

In certain embodiments, compounds of Formula (I) are of the formula:

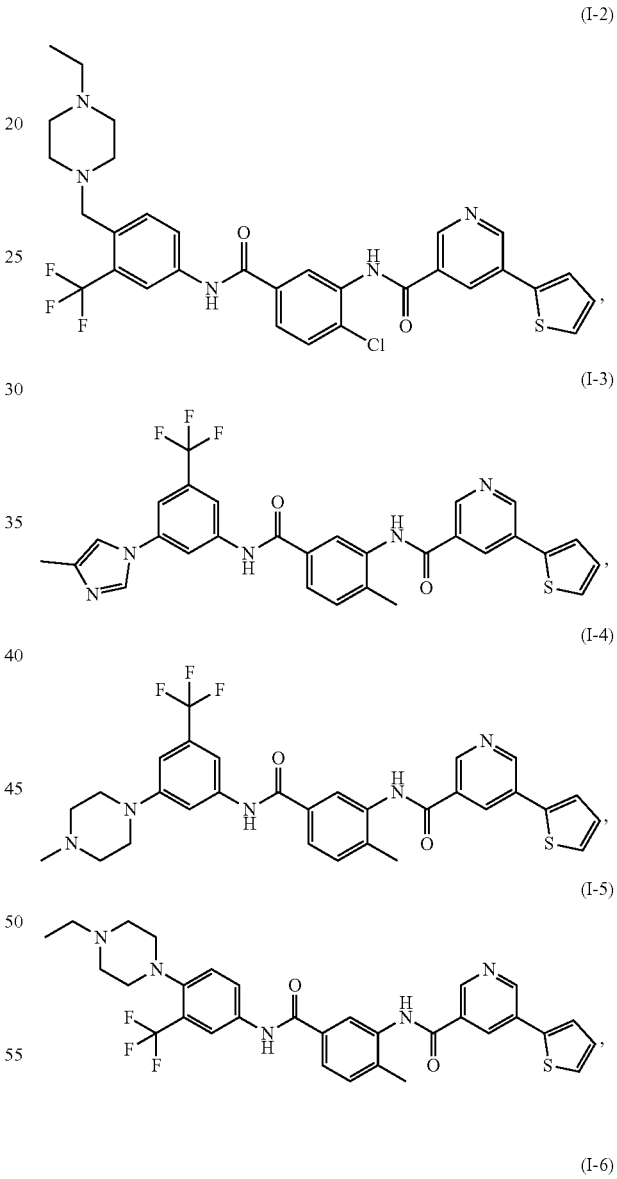

-continued (I-7)

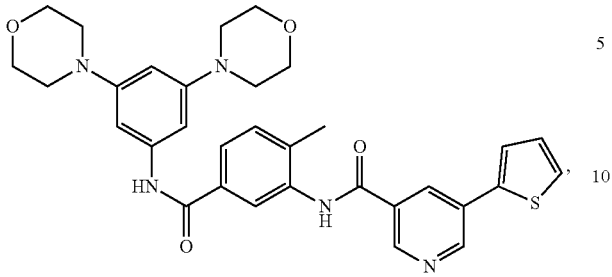

(I-8)

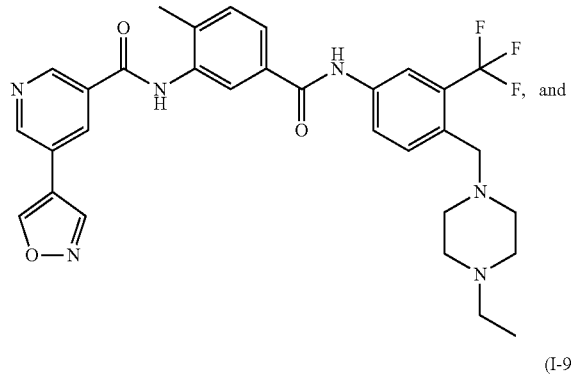

(I-9)

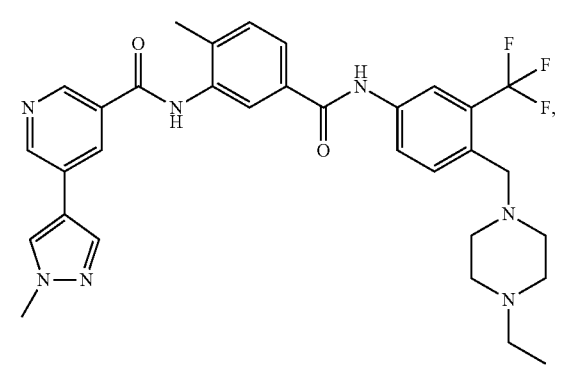

and pharmaceutically acceptable salts thereof.

The present invention also provides compounds of any one of Formulae (II) to (V):

(II)

$$(R^{D'})_{m'} \underset{(R^{x'})_{k'}}{\overset{}{\text{Cy}}} - X' - Y' - Z' - \underset{(R^{A'})_{k'}}{\overset{(R^{D'})_{m'}}{A'}} - Q' - U' - \underset{}{\overset{(R^{B'})_{r'}}{C'}} - (R^{D'})_{m'}$$

(III)

$$\text{Cy} \underset{(R^{x'})_{k'}}{\overset{}{|}} - X' - Y' - Z' - \underset{(R^{A'})_{k'}}{\overset{}{A'}} - Q' - U' - \underset{R^{B'}}{\overset{(R^{B'})_{r'}}{C'}}$$

(IV)

$$(R^{D'})_{m'} \underset{(R^{x'})_{k'}}{\overset{}{\text{Cy}}} - X' - Y' - Z' - \underset{(R^{A'})_{k'}}{\overset{(R^{D'})_{m'}}{A'}} - Q' - U' - \underset{R^{B'}}{\overset{(R^{D'})_{m'} (R^{B'})_{r'}}{C'}}$$

(V)

$$\text{Cy} \underset{(R^{x'})_{k'}}{\overset{}{|}} - X' - Y' - Z' - \underset{(R^{A'})_{k'}}{\overset{}{A'}} - Q' - U' - \underset{}{\overset{}{C'}} - (R^{B'})_{r'}$$

and pharmaceutically acceptable salts thereof, wherein Ring A', Ring C', Cy, X', Y', Z', Q', U', $R^{A'}$, $R^{B'}$, $R^{D'}$, $R^{X'}$, k', l', and m' are as defined herein.

The present invention is also based, at least in part, on the discovery that Waldenström's macroglobulinemia may be treated by administration of a compound of the invention to a subject in need thereof. The activity of these compounds was established by in vitro screening against several kinases (e.g., BTK, HCK, TAK1, HPK1) that are involved in the regulation of aberrant cell growth, as well as cell-based screening against several cell lines (e.g., BCWM.1, MWCL-1) that are disease state models of Waldenström's macroglobulinemia (Ditzel et al. *Exp Hematol.* 2007 September; 35(9):1366-75; Hodge et al. *Blood.* 2011 May 12; 117 (19)).

The methods of treatment utilizing a compound of the invention also apply to B cell neoplasms of the group consisting of Hodgkin's lymphomas and most non-Hodgkin's lymphomas, such as diffuse large B cell lymphoma, Follicular lymphoma, mucosa-associated lymphatic tissue lymphoma (MALT), small cell lymphocytic lymphoma (overlaps with chronic lymphocytic leukemia), mantle cell lymphoma (MCL), Burkitt lymphoma, mediastinal large B cell lymphoma, nodal marginal zone B cell lymphoma (NMZL), splenic marginal zone lymphoma (SMZL), Intravascular large B-cell lymphoma, Primary effusion lymphoma, and Lymphomatoid granulomatosis.

The present invention is also based, at least in part, on pharmaceutical compositions comprising a compound of the invention and a pharmaceutically acceptable excipient. In certain embodiments, the pharmaceutical composition may be useful for modulating the activity of a kinase in vitro or in a subject in need thereof, and/or for treating and/or preventing in a subject in need thereof a condition associated with aberrant activity of a kinase (e.g., a proliferative disease). In certain embodiments, the pharmaceutical composition may be useful for treatment of Waldenström's macroglobulinemia in a subject in need thereof.

The present invention also provides kits comprising a container with a compound of the invention, or a pharmaceutical composition thereof. The kits may include a single dose or multiple doses of a compound described herein or a pharmaceutical composition thereof. The kits may be useful for modulating the activity of a kinase in a subject in need thereof. The kits may also be useful for treating and/or preventing in a subject in need thereof a condition associated with aberrant activity of a kinase. In certain embodiments, the kits further include instructions for using the kit (e.g., for administering a compound described herein, or a pharmaceutical composition thereof).

The details of particular embodiments of the invention are set forth herein. Other features, objects, and advantages of the invention will be apparent from the Detailed Description, the Examples, and the Claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In certain embodiments, the haloalkyl moiety has 1 to 8 carbon atoms ("$C_{1-8}$ haloalkyl"). In certain embodiments, the haloalkyl moiety has 1 to 6 carbon atoms ("$C_{1-6}$ haloalkyl"). In certain embodiments, the haloalkyl moiety has 1 to 4 carbon atoms ("$C_{1-4}$ haloalkyl"). In certain embodiments, the haloalkyl moiety has 1 to 3 carbon atoms ("$C_{1-3}$ haloalkyl"). In certain embodiments, the haloalkyl moiety has 1 to 2 carbon atoms ("$C_{1-2}$ haloalkyl"). In certain embodiments, all of the haloalkyl hydrogen atoms are replaced with fluoro to provide a perfluoroalkyl group. In certain embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In certain embodiments, a heteroalkyl group is a saturated group having 1 to 9 carbon atoms and 1 or more heteroatoms within the parent chain ("heteroC$_{1-9}$ alkyl"). In certain embodiments, a heteroalkyl group is a saturated group having 1 to 8 carbon atoms and 1 or more heteroatoms within the parent chain ("heteroC$_{1-8}$ alkyl"). In certain embodiments, a heteroalkyl group is a saturated group having 1 to 7 carbon atoms and 1 or more heteroatoms within the parent chain ("heteroC$_{1-7}$ alkyl"). In certain embodiments, a heteroalkyl group is a saturated group having 1 to 6 carbon atoms and 1 or more heteroatoms within the parent chain ("heteroC$_{1-6}$ alkyl"). In certain embodiments, a heteroalkyl group is a saturated group having 1 to 5 carbon atoms and 1 or 2 heteroatoms within the parent chain ("heteroC$_{1-5}$ alkyl"). In certain embodiments, a heteroalkyl group is a saturated group having 1 to 4 carbon atoms and 1 or 2 heteroatoms within the parent chain ("heteroC$_{1-4}$ alkyl"). In certain embodiments, a heteroalkyl group is a saturated group having 1 to 3 carbon atoms and 1 heteroatom within the parent chain ("heteroC$_{1-3}$ alkyl"). In certain embodiments, a heteroalkyl group is a saturated group having 1 to 2 carbon atoms and 1 heteroatom within the parent chain ("heteroC$_{1-2}$ alkyl"). In certain embodiments, a heteroalkyl group is a saturated group having 1 carbon atom and 1 heteroatom ("heteroC$_1$ alkyl"). In certain embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In certain embodiments, an alkenyl group has 2 to 9 carbon atoms ("C$_{2-9}$ alkenyl"). In certain embodiments, an alkenyl group has 2 to 8 carbon atoms ("C$_{2-8}$ alkenyl"). In certain embodiments, an alkenyl group has 2 to 7 carbon atoms ("C$_{2-7}$ alkenyl"). In certain embodiments, an alkenyl group has 2 to 6 carbon atoms ("C$_{2-6}$ alkenyl"). In certain embodiments, an alkenyl group has 2 to 5 carbon atoms ("C$_{2-5}$ alkenyl"). In certain embodiments, an alkenyl group has 2 to 4 carbon atoms ("C$_{2-4}$ alkenyl"). In certain embodiments, an alkenyl group has 2 to 3 carbon atoms ("C$_{2-3}$ alkenyl"). In certain embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In certain embodiments, a heteroalkenyl group has 2 to 9 carbon atoms at least one double bond, and 1 or more heteroatoms within the parent chain ("heteroC$_{2-9}$ alkenyl"). In certain embodiments, a heteroalkenyl group has 2 to 8 carbon atoms, at least one double bond, and 1 or more heteroatoms within the parent chain ("heteroC$_{2-8}$ alkenyl"). In certain embodiments, a heteroalkenyl group has 2 to 7 carbon atoms, at least one double bond, and 1 or more heteroatoms within the parent chain ("heteroC$_{2-7}$ alkenyl"). In certain embodiments, a heteroalkenyl group has 2 to 6 carbon atoms, at least one double bond, and 1 or more heteroatoms within the parent chain ("heteroC$_{2-6}$ alkenyl"). In certain embodiments, a heteroalkenyl group has 2 to 5 carbon atoms, at least one double bond, and 1 or 2 heteroatoms within the parent chain ("heteroC$_{2-5}$ alkenyl"). In certain embodiments, a heteroalkenyl group has 2 to 4 carbon atoms, at least one double bond, and 1 or 2 heteroatoms within the parent chain ("heteroC$_{2-4}$ alkenyl"). In certain embodiments, a heteroalkenyl group has 2 to 3 carbon atoms, at least one double bond, and 1 heteroatom within the parent chain ("heteroC$_{2-3}$ alkenyl"). In certain embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl. In an alkenyl group, a C=C double bond for which the stereochemistry is not specified (e.g., —CH=CHCH$_3$ or

)

may be an (E)- or (Z)-double bond.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In certain embodiments, an alkynyl group has 2 to 9 carbon atoms ("C$_{2-9}$ alkynyl"). In certain embodiments, an alkynyl group has 2 to 8 carbon atoms ("C$_{2-8}$ alkynyl"). In certain embodiments, an alkynyl group has 2 to 7 carbon atoms ("C$_{2-7}$ alkynyl"). In certain embodiments, an alkynyl group has 2 to 6 carbon atoms ("C$_{2-6}$ alkynyl"). In certain embodiments, an alkynyl group has 2 to 5 carbon atoms ("C$_{2-5}$ alkynyl"). In certain embodiments, an alkynyl group has 2 to 4 carbon atoms ("C$_{2-4}$ alkynyl"). In certain embodiments, an alkynyl group has 2 to 3 carbon atoms ("C$_{2-3}$ alkynyl"). In certain embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In certain embodiments, a heteroalkynyl group has 2 to 9 carbon atoms, at least one triple bond, and 1 or more heteroatoms within the parent chain ("heteroC$_{2-9}$ alkynyl"). In certain embodiments, a heteroalkynyl group has 2 to 8 carbon atoms, at least one triple bond, and 1 or more heteroatoms within the parent chain ("heteroC$_{2-8}$ alkynyl"). In certain embodiments, a heteroalkynyl group has 2 to 7 carbon atoms, at least one triple bond, and 1 or more heteroatoms within the parent chain ("heteroC$_{2-7}$ alkynyl"). In certain embodiments, a heteroalkynyl group has 2 to 6 carbon atoms, at least one triple bond, and 1 or more heteroatoms within the parent chain ("heteroC$_{2-6}$ alkynyl"). In certain embodiments, a heteroalkynyl group has 2 to 5 carbon atoms, at least one triple bond, and 1 or 2 heteroatoms within the parent chain ("heteroC$_{2-5}$ alkynyl"). In certain embodiments, a heteroalkynyl group has 2 to 4 carbon atoms, at least one triple bond, and 1 or 2 heteroatoms within the parent chain ("heteroC$_{2-4}$ alkynyl"). In certain embodiments, a heteroalkynyl group has 2 to 3 carbon atoms, at least one triple bond, and 1 heteroatom within the parent chain ("heteroC$_{2-3}$ alkynyl"). In certain embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In certain embodiments, a carbocyclyl group has 3 to 10 ring carbon atoms ("C$_{3-10}$ carbocyclyl"). In certain embodiments, a carbocyclyl group has 3 to 8 ring carbon atoms ("C$_{3-8}$ carbocyclyl"). In certain embodiments, a carbocyclyl group has 3 to 7 ring carbon atoms ("C$_{3-7}$ carbocyclyl"). In certain embodiments, a carbocyclyl group has 3 to 6 ring carbon atoms ("C$_{3-6}$ carbocyclyl"). In certain embodiments, a carbocyclyl group has 4 to 6 ring carbon atoms ("C$_{4-6}$ carbocyclyl"). In certain embodiments, a carbocyclyl group has 5 to 6 ring carbon atoms ("C$_{5-6}$ carbocyclyl"). In certain embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl. In certain embodiments, "carbocyclyl" is a monocyclic, saturated carbocyclyl group having from 3 to 14 ring carbon atoms ("C$_{3-14}$ cycloalkyl"). In certain embodiments, a cycloalkyl group has 3 to 10 ring carbon atoms ("C$_{3-10}$ cycloalkyl"). In certain embodiments, a cycloalkyl group has 3 to 8 ring carbon atoms ("C$_{3-8}$ cycloalkyl"). In certain embodiments, a cycloalkyl group has 3 to 6 ring carbon atoms ("C$_{3-6}$ cycloalkyl"). In certain embodiments, a cycloalkyl group has 4 to 6 ring carbon atoms ("C$_{4-6}$ cycloalkyl"). In certain embodiments, a cycloalkyl group has 5 to 6 ring carbon atoms ("C$_{5-6}$ cycloalkyl"). In certain embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In certain embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In certain embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In certain embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In certain embodiments, the 5-6 membered heterocyclyl has 1-3 ring heteroatoms selected from nitrogen, oxygen, and sulfur. In certain embodiments, the 5-6 membered heterocyclyl has 1-2 ring heteroatoms selected from nitrogen, oxygen, and sulfur. In certain embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetra-hydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In certain embodiments, an aryl group has 6 ring carbon atoms ("$C_6$ aryl"; e.g., phenyl). In certain embodiments, an aryl group has 10 ring carbon atoms ("$C_{10}$ aryl"; e.g., naphthyl such as 1-naphthyl and 2-naphthyl). In certain embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In certain embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In certain embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In certain embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In certain embodiments, the 5-6 membered heteroaryl has 1-3 ring heteroatoms selected from nitrogen, oxygen, and sulfur. In certain embodiments, the 5-6 membered heteroaryl has 1-2 ring heteroatoms selected from nitrogen, oxygen, and sulfur. In certain embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP($R^{cc}$)$_3$, —B($R^{aa}$)$_2$, —B(O$R^{cc}$)$_2$, —B$R^{aa}$(O$R^{cc}$), $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+$X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2$$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S) NH$_2$, —C(=O)S(C$_{1-6}$ alkyl), —C(=S)SC$_{1-6}$ alkyl, —SC (=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-4}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., alkyl, aralkyl, heteroaralkyl), $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as described herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$$R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —N($R^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as described herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, o-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as described herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, a "leaving group", or "LG", is a term understood in the art to referred to a molecular fragment that departs with a pair of electrons upon heterolytic bond cleavage, wherein the molecular fragment is an anion or neutral molecule. See, for example, Smith, March *Advanced Organic Chemistry* 6th ed. (501-502). Examples of suitable leaving groups include, but are not limited to, halides (such as chloride, bromide, or iodide), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, haloformates, —NO$_2$, trialkylammonium, and aryliodonium salts. In certain embodiments, the leaving group is a sulfonic acid ester. In certain embodiments, the sulfonic acid ester comprises the formula —OSO$_2$R$^{LG1}$ wherein R$^{LG1}$ is selected from the group consisting alkyl optionally, alkenyl optionally substituted, heteroalkyl optionally substituted, aryl optionally substituted, heteroaryl optionally substituted, arylalkyl optionally substituted, and heterarylalkyl optionally substituted. In certain embodiments, R$^{LG1}$ is substituted or unsubstituted C$_1$-C$_6$ alkyl. In certain embodiments, R$^{LG1}$ is methyl. In certain embodiments, R$^{LG1}$ is —CF$_3$. In certain embodiments, R$^{LG1}$ is substituted or unsubstituted aryl. In certain embodiments, R$^{LG1}$ is substituted or unsubstituted phenyl. In certain embodiments R$^{LG1}$ is:

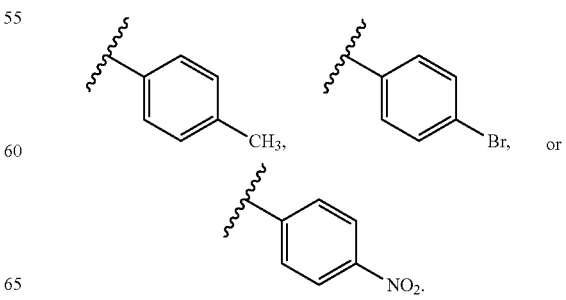

In some cases, the leaving group is toluenesulfonate (tosylate, Ts), methanesulfonate (mesylate, Ms), p-bromobenzenesulfonyl (brosylate, Bs), or trifluoromethanesulfonate (triflate, Tf). In some cases, the leaving group is a brosylate (p-bromobenzenesulfonyl). In some cases, the leaving group is a nosylate (2-nitrobenzenesulfonyl). In certain embodiments, the leaving group is a sulfonate-containing group. In certain embodiments, the leaving group is a tosylate group. The leaving group may also be a phosphineoxide (e.g., formed during a Mitsunobu reaction) or an internal leaving group such as an epoxide or cyclic sulfate.

These and other exemplary substituents are described in more detail in the Detailed Description, Examples, and Claims. The invention is not intended to be limited in any manner by the above exemplary listing of substituents.

Other Definitions

The following definitions are more general terms used throughout the present application.

As used herein, the term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ \text{alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. Compounds of the invention may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R.0.5\ H_2O$)), and polyhydrates (x is a number greater than 1, e.g., dihydrates ($R.2\ H_2O$) and hexahydrates ($R.6\ H_2O$)).

The term "tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds of the invention, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention (e.g., the compounds of Formula (I) and compounds of any one of Formulae (II) to (V)).

DETAILED DESCRIPTION OF THE INVENTION

In an effort to identify novel treatments for Waldenström's macroglobulinemia, in vitro screens were carried out against several kinases (e.g., BTK, HCK, TAK1). These kinases are involved in the regulation of aberrant cell growth associated with this condition. Cell-based screening was also carried out in several disease state model lines of Waldenström's macroglobulinemia (e.g., BCWM. 1, MWCL-1). Based on these screening efforts and subsequent lead optimization, compounds of the invention were identified.

In one aspect, the present invention provides compounds of Formula (I):

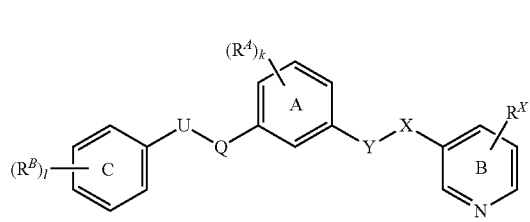

(I)

and pharmaceutically acceptable salts, solvates, hydrates, polymorphs, co-crystals, tautomers, stereoisomers, isotopically labeled derivatives, and prodrugs thereof;
wherein:
each instance of $R^A$ is independently selected from the group consisting of hydrogen, halogen, optionally substituted alkyl, optionally substituted carbocyclyl, —$OR^{A1}$, —$N(R^{A1})_2$, —CN, —C(=O)$R^{A1}$, —C(=O)$OR^{A1}$, —C(=O)N($R^{A1}$)$_2$, —$NO_2$, —$NR^{A1}$C(=O)$R^{A1}$, —$NR^{A1}$C(=O)$OR^{A1}$, —$NR^{A1}$S(=O)$_2$$R^{A1}$, —S(=O)$_2$$R^{A1}$, or —S(=O)$_2$N($R^{A1}$)$_2$;
each instance of $R^B$ is independently selected from the group consisting of hydrogen, halogen, optionally substituted alkyl, optionally substituted carbocyclyl, optionally substituted heterocyclyl, optionally substituted aryl, optionally substituted heteroaryl, —$OR^{A1}$, —$N(R^{A1})_2$, —CN, —C(=O)$R^{A1}$, —C(=O)$OR^{A1}$, —C(=O)N($R^{A1}$)$_2$, —$NO_2$, —$NR^{A1}$C(=O)$R^{A1}$, —$NR^{A1}$C(=O)$OR^{A1}$, —$NR^{A1}$S(=O)$_2$$R^{A1}$, —S(=O)$_2$$R^{A1}$, or —S(=O)$_2$N($R^{A1}$)$_2$;
each instance of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A1}$ groups are joined to form an optionally substituted heterocyclic ring;
$R^X$ is $R^D$ or is selected from the group consisting of optionally substituted carbocyclyl, optionally substituted heterocyclyl, optionally substituted aryl, optionally substituted heteroaryl, and —N($R^{A1}$)($R^{Xa}$);
each instance of $R^{Xa}$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{A1}$, —C(=O)$OR^{A1}$, —C(=O)N($R^{A1}$)$_2$, —S(=O)$R^{A1}$, —S(=O)N($R^{A1}$)$_2$, —S(=O)$_2$$R^{A1}$, —S(=O)$_2$ $OR^{A1}$, —S(=O)$_2$N($R^{A1}$)$_2$, and a nitrogen protecting group;
k is 0, 1, 2, 3, or 4;
l is 1, 2, 3, 4, or 5;
X and Y are taken together to be —$NR^A$(C=O)— or —(C=O)$NR^A$;
Q and U are taken together to be —$NR^A$(C=O)— or —(C=O)$NR^A$—; and
$R^D$ is an electrophilic moiety as described herein.

In certain embodiments, the present invention provides compounds from the group consisting of:

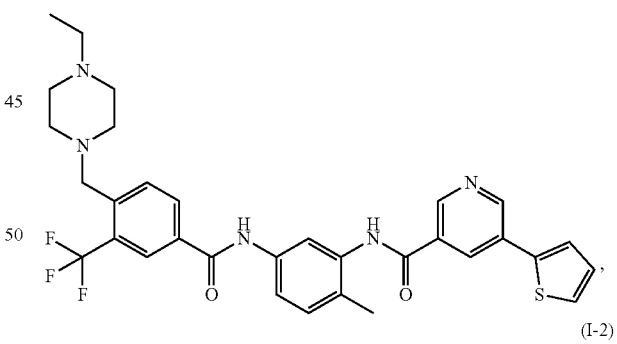

(I-1)

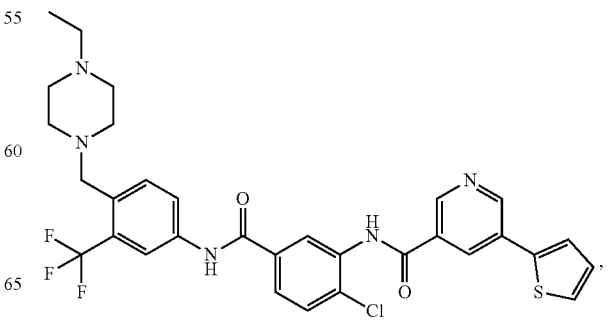

(I-2)

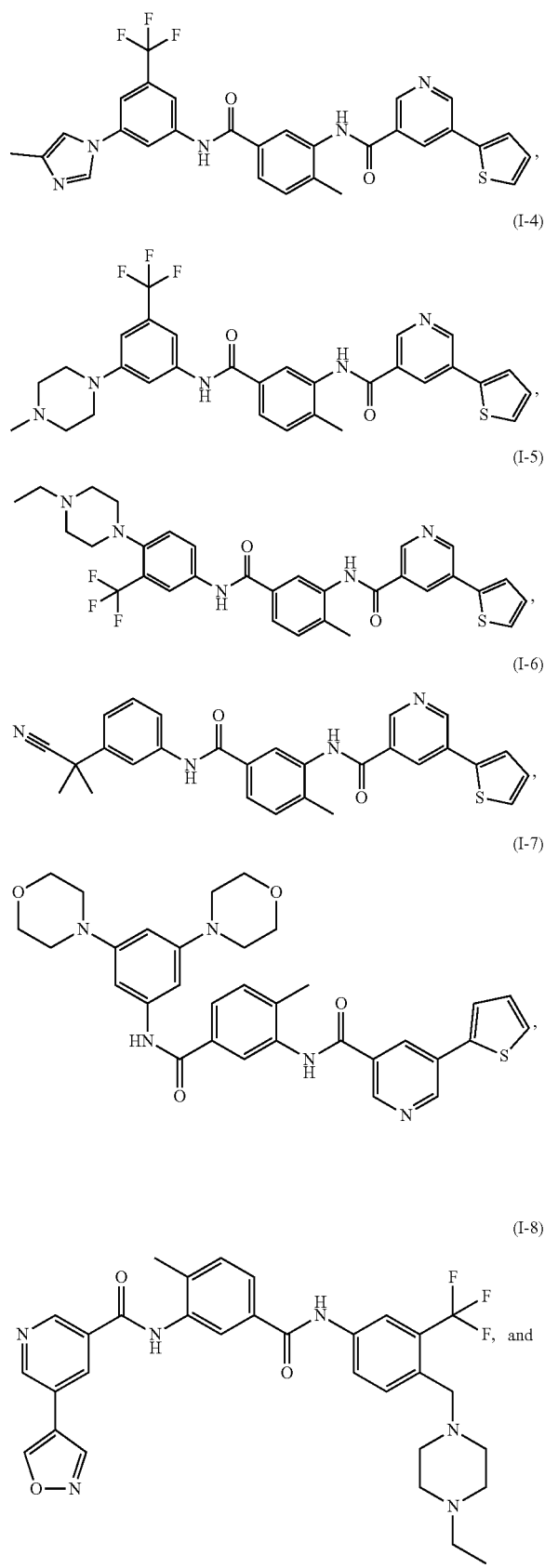

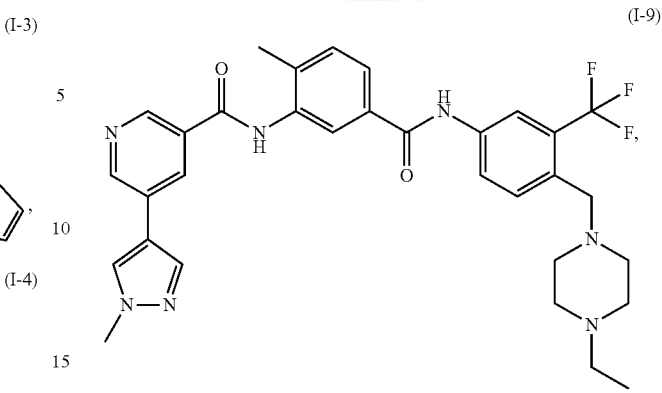

and pharmaceutically acceptable salts thereof.

In another aspect, the present invention provides methods for treating Waldenström's macroglobulinemia (WM) in a subject using compounds of the invention. The methods comprise administering to a subject in need thereof an effective amount of a compound of the invention. Also provided are methods to treat other B cell neoplasms using compounds of the invention in combination with inhibitors of Bruton's tyrosine kinase (BTK), interleukin-1 receptor-associated kinase 1 (IRAK1), interleukin-1 receptor-associated kinase 4 (IRAK4), bone marrow on X chromosome kinase (BMX), phosphoinositide 3-kinase (PI3K), transforming growth factor b-activated kinase-1 (TAK1), and/or a Src family kinase. In certain embodiments, one or more compounds of the invention are used in combination with an inhibitor of the phosphoinositide 3-kinase delta isoform (PI3Kδ). In certain embodiments, combinations of 2, 3, 4, 5, 6, 7, 8, 9, 10, or more of the agents described herein are used for treating WM. In certain embodiments, the agents described herein are used in combination with kinase inhibitors such as inhibitors of Bruton's tyrosine kinase (BTK), interleukin-1 receptor-associated kinase 1 (IRAK1), interleukin-1 receptor-associated kinase 4 (IRAK4), bone marrow on X chromosome kinase (BMX), phosphoinositide 3-kinase (PI3K), and/or transforming growth factor b-activated kinase-1 (TAK1), and/or a Src family kinase.

Waldenstrom's macroglobulinemia (WM) is a distinct clinicopathological entity resulting from the accumulation, predominantly in the bone marrow, of clonally related lymphoplasmacytic cells which secrete a monoclonal IgM protein. This condition is considered to correspond to lymphoplasmacytic lymphoma (LPL) as defined by the World Health Organization classification system. Genetic factors play an important role in the pathogenesis of WM, with 25% of patients demonstrating a family history. IgM monoclonal gammopathy of unknown significance (MGUS) often precedes the development of WM.

As used herein, a B cell neoplasm includes both Hodgkin's lymphoma and non-Hodgkin's lymphomas. Classical Hodgkin's lymphoma (HL) includes various subtypes such as Nodular sclerosing HL, Mixed-cellularity subtype, Lymphocyte-rich or Lymphocytic predominance and Lymphocyte depleted. Examples of B cell non-Hodgkin's lymphomas include, but are not limited to, Waldenström's macroglobulinemia, diffuse large B cell lymphoma, follicular lymphoma, mucosa-associated lymphatic tissue lymphoma (MALT), small cell lymphocytic lymphoma (overlaps with chronic lymphocytic leukemia), mantle cell lymphoma (MCL), Burkitt lymphoma, mediastinal large B cell lymphoma, nodal marginal zone B cell lymphoma (NMZL), splenic marginal zone lymphoma (SMZL), intravascular large B-cell lymphoma, primary effusion lymphoma, and lymphomatoid granulomatosis.

In certain embodiments, the subject is administered a compound of Formula (I):

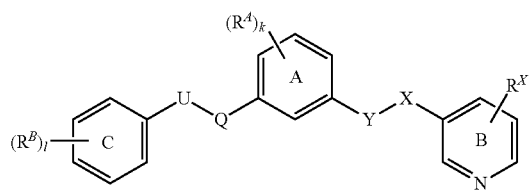

(I)

and pharmaceutically acceptable salts, solvates, hydrates, polymorphs, co-crystals, tautomers, stereoisomers, isotopically labeled derivatives, and prodrugs thereof;
wherein:
each instance of $R^A$ is independently selected from the group consisting of hydrogen, halogen, optionally substituted alkyl, optionally substituted carbocyclyl, —$OR^{A1}$, —$N(R^{A1})_2$, —CN, —C(=O)$R^{A1}$, —C(=O)$OR^{A1}$, —C(=O)N($R^{A1}$)$_2$, —NO$_2$, —$NR^{A1}$C(=O)$R^{A1}$, —$NR^{A1}$C(=O)$OR^{A1}$, —$NR^{A1}$S(=O)$_2R^{A1}$, —S(=O)$_2R^{A1}$, or —S(=O)$_2$N($R^{A1}$)$_2$;

each instance of $R^B$ is independently selected from the group consisting of hydrogen, halogen, optionally substituted alkyl, optionally substituted carbocyclyl, optionally substituted heterocyclyl, optionally substituted aryl, optionally substituted heteroaryl, —$OR^{A1}$, —$N(R^{A1})_2$, —CN, —C(=O)$R^{A1}$, —C(=O)$OR^{A1}$, —C(=O)N($R^{A1}$)$_2$, —NO$_2$, —$NR^{A1}$C(=O)$R^{A1}$, —$NR^{A1}$C(=O)$OR^{A1}$, —$NR^{A1}$S(=O)$_2$$R^{A1}$, —S(=O)$_2R^{A1}$, or —S(=O)$_2$N($R^{A1}$)$_2$;

each instance of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A1}$ groups are joined to form an optionally substituted heterocyclic ring;

$R^X$ is $R^D$ or is selected from the group consisting of optionally substituted carbocyclyl, optionally substituted heterocyclyl, optionally substituted aryl, optionally substituted heteroaryl, and —N($R^{A1}$)($R^{Xa}$);

each instance of $R^{Xa}$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{A1}$, —C(=O)$OR^{A1}$, —C(=O)N($R^{A1}$)$_2$, —S(=O)$R^{A1}$, —S(=O)N($R^{A1}$)$_2$, —S(=O)$_2R^{A1}$, —S(=O)$_2$ $OR^{A1}$, —S(=O)$_2$N($R^{A1}$)$_2$, and a nitrogen protecting group;

k is 0, 1, 2, 3, or 4;
l is 1, 2, 3, 4, or 5;
X and Y are taken together to be —$NR^A$(C=O)— or —(C=O)$NR^A$—;
Q and U are taken together to be —$NR^A$(C=O)— or —(C=O)$NR^A$—; and
$R^D$ is an electrophilic moiety as described herein.

In certain embodiments, the subject is administered a compound (I-1):

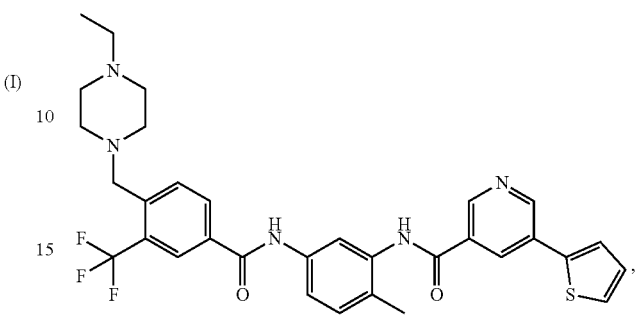

(I-1)

or a pharmaceutically acceptable salt thereof.

In certain embodiments, the subject is administered a compound (I-2):

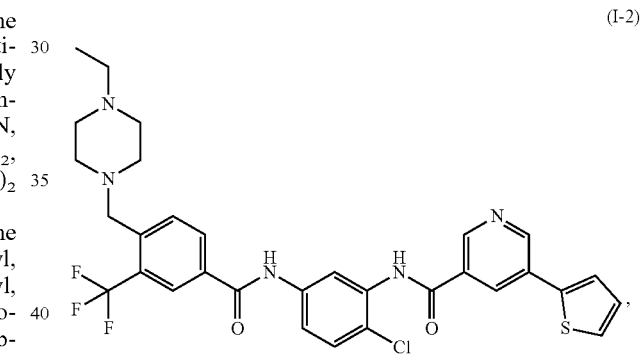

(I-2)

or a pharmaceutically acceptable salt thereof.

In certain embodiments, the subject is administered a compound (I-3):

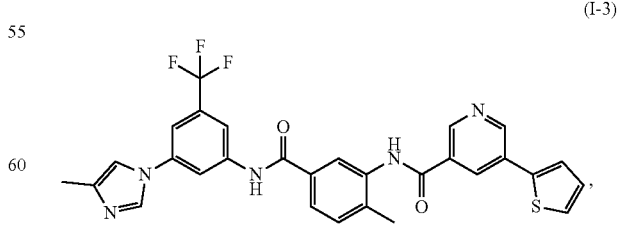

(I-3)

or a pharmaceutically acceptable salt thereof.

In certain embodiments, the subject is administered a compound (I-4):

(I-4)

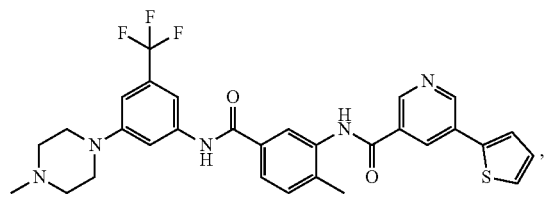

or a pharmaceutically acceptable salt thereof.

In certain embodiments, the subject is adminstered a compound (I-5):

(I-5)

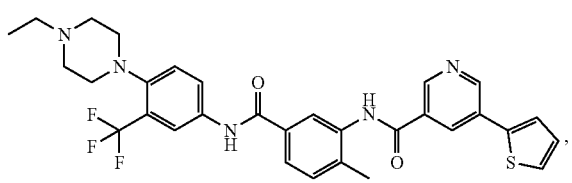

or a pharmaceutically acceptable salt thereof.

In certain embodiments, the subject is adminstered a compound (I-6):

(I-6)

or a pharmaceutically acceptable salt thereof.

In certain embodiments, the subject is adminstered a compound (I-7):

(I-7)

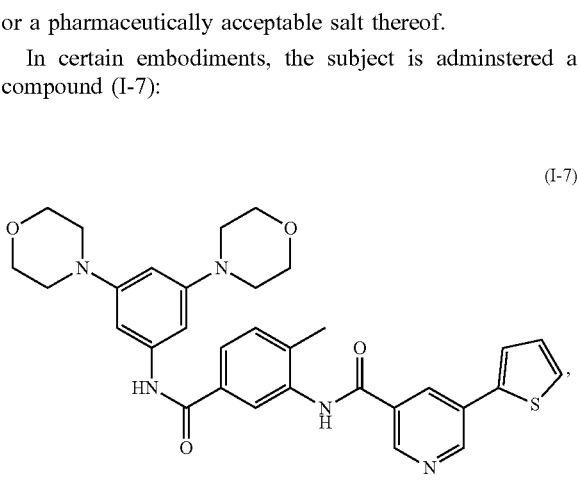

or a pharmaceutically acceptable salt thereof.

In certain embodiments, the subject is adminstered a compound (I-8):

(I-8)

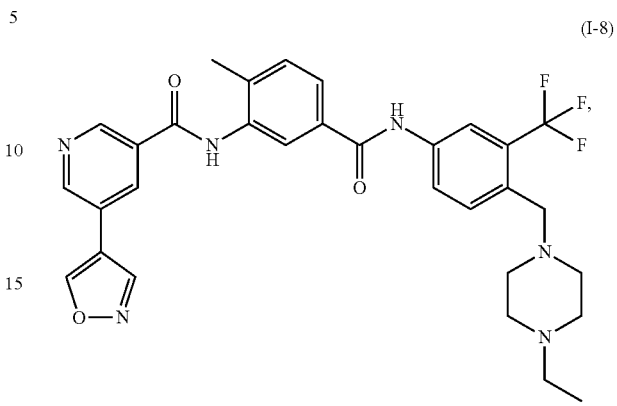

or a pharmaceutically acceptable salt thereof.

In certain embodiments, the subject is adminstered a compound (I-9):

(I-9)

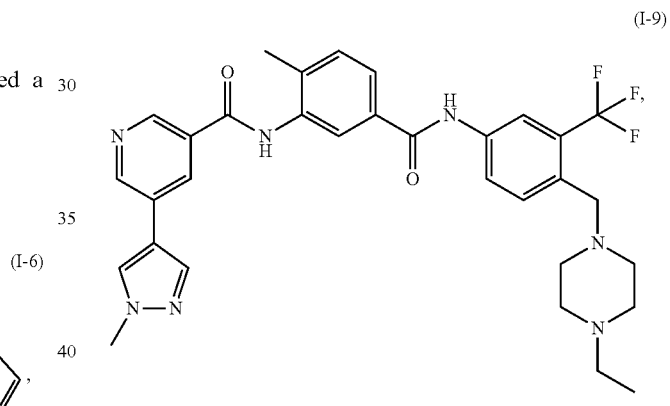

or a pharmaceutically acceptable salt thereof.

Compounds of Formula (I) include a phenyl Ring A optionally substituted with one or more $R^4$ groups. In certain embodiments, k is 0. In certain embodiments, Ring A is of the formula:

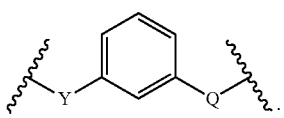

In certain embodiments, Ring A is of the formula:

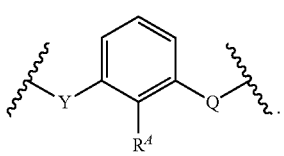

In certain embodiments, Ring A is of the formula:

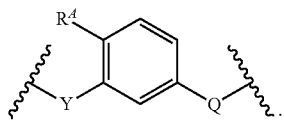

In certain embodiments, Ring A is of the formula:

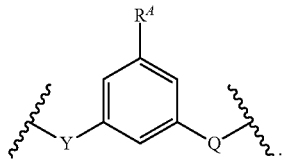

In certain embodiments, Ring A is of the formula:

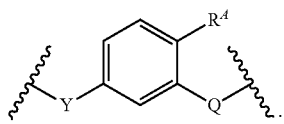

In certain embodiments, k is 2. In certain embodiments, Ring A is of the formula:

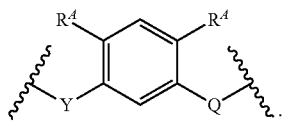

In certain embodiments, Ring A is of the formula:

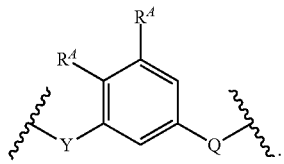

In certain embodiments, Ring A is of the formula:

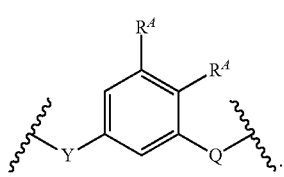

In certain embodiments, Ring is of the formula:

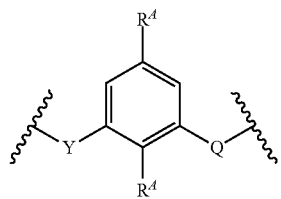

In certain embodiments, Ring A is of the formula

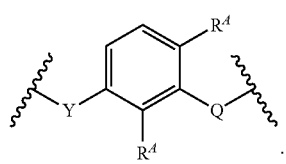

In certain embodiments, Ring A is of the formula:

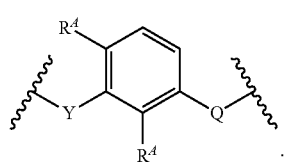

In certain embodiments, k is 3. In certain embodiments, Ring A is of the formula:

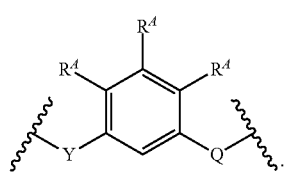

In certain embodiments, Ring A is of the formula:

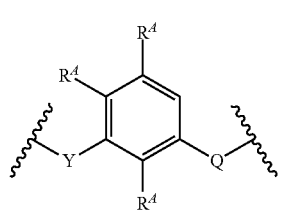

In certain embodiments, Ring A is of the formula:

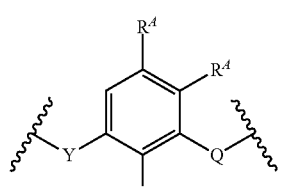

In certain embodiments, k is 4. In certain embodiments, Ring A is of the formula:

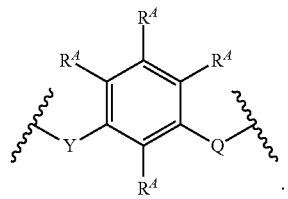

In compounds of Formula (I), Ring A may be substituted with one or more $R^4$ groups. In certain embodiments, at least one $R^4$ is H. In certain embodiments, at least two $R^4$ groups are H. In certain embodiments, at least three $R^4$ groups are H. In certain embodiments, at least four $R^4$ groups are H. In certain embodiments, at least one $R^4$ is not H. In certain embodiments, at least two $R^4$ groups are not H. In certain embodiments, at least three $R^4$ groups are not H. In certain embodiments, at least one $R^4$ is halogen. In certain embodiments, at least one $R^4$ is F. In certain embodiments, at least one $R^4$ is Cl. In certain embodiments, at least one $R^4$ is Br. In certain embodiments, at least one $R^4$ is I (iodine). In certain embodiments, one $R^4$ is F. In certain embodiments, one $R^4$ is Cl. In certain embodiments, at least one $R^4$ is substituted alkyl. In certain embodiments, at least one $R^4$ is unsubstituted alkyl. In certain embodiments, at least one $R^4$ is substituted $C_{1-6}$ alkyl. In certain embodiments, at least one $R^4$ is unsubstituted $C_{1-6}$ alkyl. In certain embodiments, at least one $R^4$ is methyl. In certain embodiments, at least one $R^4$ is ethyl. In certain embodiments, at least one $R^4$ is propyl. In certain embodiments, at least one $R^4$ is butyl. In certain embodiments, at least one $R^4$ is substituted carbocyclyl. In certain embodiments, at least one $R^4$ is unsubstituted carbocyclyl. In certain embodiments, at least one $R^4$ is $-OR^{41}$. In certain embodiments, at least one $R^4$ is $-O(C_{1-6}$ alkyl) where the alkyl is substituted or unsubstituted. In certain embodiments, at least one $R^4$ is $-OMe$. In certain embodiments, at least one $R^4$ is $-OH$. In certain embodiments, at least one $R^4$ is $-N(R^{41})_2$. In certain embodiments, at least one $R^4$ is $-NH_2$. In certain embodiments, at least one $R^4$ is $-CN$. In certain embodiments, at least one $R^4$ is $-C(=O)R^{41}$. In certain embodiments, at least one $R^4$ is acetyl. In certain embodiments, at least one $R^4$ is $-C(=O)OR^{41}$. In certain embodiments, at least one $R^4$ is $-C(=O)N(R^{41})_2$. In certain embodiments, at least one $R^4$ is $-C(=O)NHR^{41}$. In certain embodiments, at least one $R^4$ is $-C(=O)NH(C_{1-6}$ alkyl) where the alkyl is substituted or unsubstituted. In certain embodiments, at least one $R^4$ is $-C(=O)NHMe$. In certain embodiments, at least one $R^4$ is $-C(=O)NH_2$. In certain embodiments, at least one $R^4$ is $-NO_2$. In certain embodiments, at least one $R^4$ is $-NR^{41}C(=O)R^{41}$. In certain embodiments, at least one $R^4$ is $-NR^{41}C(=O)OR^{41}$. In certain embodiments, at least one $R^4$ is $-NR^{41}S(=O)_2R^{41}$. In certain embodiments, at least one $R^4$ is $-NHS(=O)_2R^{41}$. In certain embodiments, at least one $R^4$ is $-NHS(=O)_2(C_{1-6}$ alkyl) where the alkyl is substituted or unsubstituted. In certain embodiments, at least one $R^4$ is $-NHS(=O)_2Me$. In certain embodiments, at least one $R^4$ is $-S(=O)_{2R}{}^{41}$. In certain embodiments, at least one $R^4$ is $-S(=O)_2N(R^{41})_2$. In certain embodiments, at least one $R^4$ is $-S(=O)_2N(R^{41})_2$. In certain embodiments, at least one $R^4$ is $-S(=O)_2N(C_{1-6}$ alkyl)$_2$. In certain embodiments, at least one $R^4$ is $-S(=O)_2NH(C_{1-6}$ alkyl). In certain embodiments, at least one $R^4$ is $-S(=O)_2NH(t-Bu)$. In certain embodiments, at least one $R^4$ is $-S(=O)_2NH_2$.

In certain embodiments, $R^4$ is $-OR^{41}$; and k is 1. In certain embodiments, $R^4$ is $-O(C_{1-6}$ alkyl); and k is 1. In certain embodiments, $R^4$ is $-OMe$; and k is 1. In certain embodiments, $R^4$ is $-OH$; and k is 1.

In certain embodiments, $R^4$ is substituted $C_{1-6}$ alkyl; and k is 1. In certain embodiments, $R^4$ is unsubstituted $C_{1-6}$ alkyl; and k is 1. In certain embodiments, $R^4$ is methyl; and k is 1. In certain embodiments, $R^4$ is $-CF_3$; and k is 1. In certain embodiments, $R^4$ is ethyl; and k is 1. In certain embodiments, $R^4$ is propyl; and k is 1. In certain embodiments, $R^4$ is butyl; and k is 1. In certain embodiments, $R^4$ is propyl; and k is 1. In certain embodiments, $R^4$ is butyl; and k is 1.

In certain embodiments, $R^4$ is halogen; and k is 1. In certain embodiments, $R^4$ is F; and k is 1. In certain embodiments, $R^4$ is Cl; and k is 1. In certain embodiments, $R^4$ is Br; and k is 1. In certain embodiments, $R^4$ is I (iodine); and k is 1.

In certain embodiments, one instance of $R^4$ is halogen; another instance of $R^4$ is substituted $C_{1-6}$ alkyl; and k is 2. In certain embodiments, one instance of $R^4$ is F; another instance of $R^4$ is substituted $C_{1-6}$ alkyl; and k is 2. In certain embodiments, one instance of $R^4$ is Cl; another instance of $R^4$ is substituted $C_{1-6}$ alkyl; and k is 2. In certain embodiments, one instance of $R^4$ is halogen; another instance of $R^4$ is unsubstituted $C_{1-6}$ alkyl; and k is 2. In certain embodiments, one instance of $R^4$ is F; another instance of $R^4$ is unsubstituted $C_{1-6}$ alkyl; and k is 2. In certain embodiments, one instance of $R^4$ is Cl; another instance of $R^4$ is unsubstituted $C_{1-6}$ alkyl; and k is 2. In certain embodiments, one instance of $R^4$ is halogen; another instance of $R^4$ is methyl; and k is 2. In certain embodiments, one instance of $R^4$ is F; another instance of $R^4$ is methyl; and k is 2. In certain embodiments, one instance of $R^4$ is Cl; another instance of $R^4$ is methyl; and k is 2. In certain embodiments, one instance of $R^4$ is halogen; another instance of $R^4$ is $-CF_3$; and k is 2. In certain embodiments, one instance of $R^4$ is F; another instance of $R^4$ is $-CF_3$; and k is 2. In certain embodiments, one instance of $R^4$ is Cl; another instance of $R^4$ is $-CF_3$; and k is 2.

In certain embodiments, at least one $R^{41}$ is H. In certain embodiments, at least one $R^{41}$ is substituted acyl. In certain embodiments, at least one $R^{41}$ is unsubstituted acyl. In certain embodiments, at least one $R^{41}$ is acetyl. In certain embodiments, at least one $R^{41}$ is substituted alkyl. In certain embodiments, at least one $R^{41}$ is unsubstituted alkyl. In certain embodiments, at least one $R^{41}$ is $C_{1-6}$ alkyl. In certain embodiments, at least one $R^{41}$ is methyl. In certain embodiments, at least one $R^{41}$ is ethyl. In certain embodiments, at least one $R^{41}$ is propyl. In certain embodiments, at least one $R^{41}$ is butyl. In certain embodiments, at least one $R^{41}$ is substituted alkenyl. In certain embodiments, at least one $R^{41}$ is unsubstituted alkenyl. In certain embodiments, at least one $R^{41}$ is substituted alkynyl. In certain embodiments, at least one $R^{41}$ is unsubstituted alkynyl. In certain embodiments, at least one $R^{41}$ is substituted carbocyclyl. In certain embodiments, at least one $R^{41}$ is unsubstituted carbocyclyl. In certain embodiments, at least one $R^{41}$ is substituted heterocyclyl. In certain embodiments, at least one $R^{41}$ is unsubstituted heterocyclyl. In certain embodiments, at least one $R^{41}$ is substituted aryl. In certain embodiments, at least one $R^{41}$ is unsubstituted aryl. In certain embodiments, at least one $R^{41}$ is substituted phenyl. In certain embodiments, at least one $R^{41}$ is unsubstituted phenyl. In certain embodiments, at least one $R^{A1}$ is substituted heteroaryl. In certain embodiments, at least one $R^{A1}$ is unsubstituted heteroaryl. In certain embodiments, at least one $R^{A1}$ is substituted pyridyl. In certain embodiments, at least one $R^{A1}$ is unsubstituted pyridyl. In certain embodiments, at least one $R^{A1}$ is a nitrogen protecting group when attached to a nitrogen atom. In certain embodiments, at least one $R^{A1}$ is Bn, BOC, Cbz, Fmoc, trifluoroacetyl, triphenylmethyl, or Ts when attached to a nitrogen atom. In certain embodiments, $R^{A1}$ is an oxygen protecting group when attached to an oxygen atom. In certain embodiments, $R^{A1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1}$ is a sulfur protecting group when attached to a sulfur atom. In certain embodiments, $R^{A1}$ is acetamidomethyl, t-Bu, 3-nitro-2-pyridine sulfenyl, 2-pyridine-sulfenyl, or triphenylmethyl when attached to a sulfur atom.

In compounds of Formula (I), two $R^{A1}$ groups may be joined to form an optionally substituted carbocyclic, optionally substituted heterocyclic, optionally substituted aryl, or optionally substituted heteroaryl ring. In certain embodiments, two $R^{A1}$ groups are joined to form a substituted carbocyclic ring. In certain embodiments, two $R^{A1}$ groups are joined to form an unsubstituted carbocyclic ring. In certain embodiments, two $R^{A1}$ groups are joined to form a substituted heterocyclic ring. In certain embodiments, two $R^{A1}$ groups are joined to form an unsubstituted heterocyclic ring. In certain embodiments, two $R^{A1}$ groups are joined to form a substituted aryl ring. In certain embodiments, two $R^{A1}$ groups are joined to form an unsubstituted aryl ring. In certain embodiments, two $R^{A1}$ groups are joined to form a substituted phenyl ring. In certain embodiments, two $R^{A1}$ groups are joined to form an unsubstituted phenyl ring. In certain embodiments, two $R^{A1}$ groups are joined to form a substituted heteroaryl ring. In certain embodiments, two $R^{A1}$ groups are joined to form an unsubstituted heteroaryl ring.

Compounds of Formula (I) include a phenyl Ring C optionally substituted with one or more $R^B$ groups. In certain embodiments, l is 1. In certain embodiments, Ring C is of the formula:

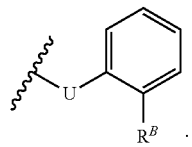

In certain embodiments, Ring C is of the formula:

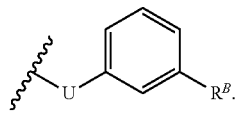

In certain embodiments, Ring C is of the formula:

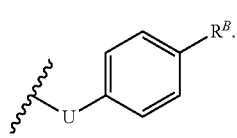

In certain embodiments, l is 2. In certain embodiments, Ring C is of the formula:

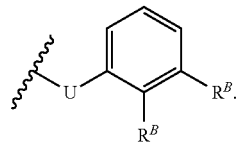

In certain embodiments, l is 2. In certain embodiments, Ring C is of the formula:

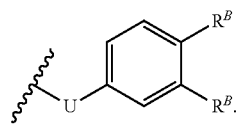

In certain embodiments, Ring C is of the formula:

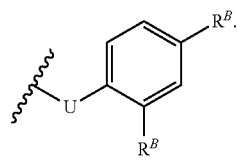

In certain embodiments, Ring C is of the formula:

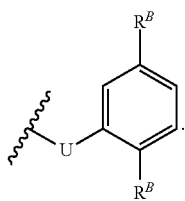

In certain embodiments, Ring C is of the formula:

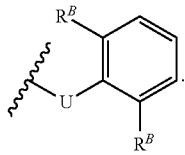

In certain embodiments, Ring C is of the formula:

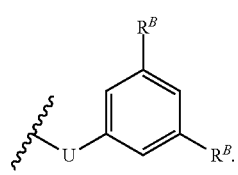

In certain embodiments, l is 3. In certain embodiments, Ring C is of the formula:

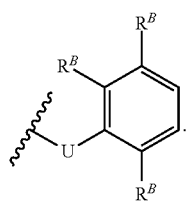

In certain embodiments, Ring C is of the formula:

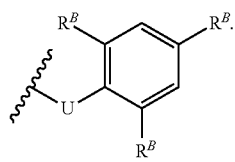

In certain embodiments, Ring C is of the formula:

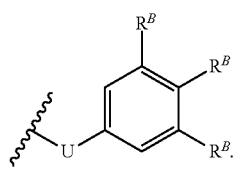

In certain embodiments, Ring C is of the formula:

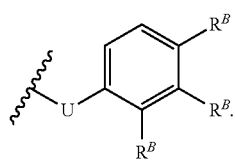

In certain embodiments, l is 4. In certain embodiments, Ring C is of the formula:

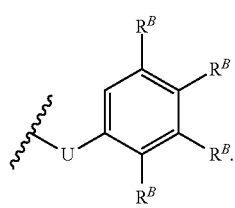

In certain embodiments, Ring C is of the formula:

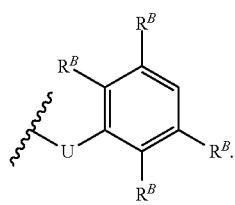

In certain embodiments, Ring C is of the formula:

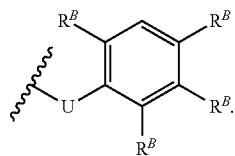

In certain embodiments, l is 5. In certain embodiments, Ring C is of the formula:

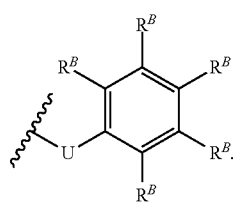

In compounds of Formula (I), Ring C may be substituted with one or more $R^B$ groups. In certain embodiments, at least one $R^B$ is H. In certain embodiments, at least two $R^B$ groups are H. In certain embodiments, at least three $R^B$ groups are H. In certain embodiments, at least four $R^B$ groups are H. In certain embodiments, at least one $R^B$ is not H. In certain embodiments, at least two $R^B$ groups are not H. In certain embodiments, at least three $R^B$ groups are not H. In certain embodiments, at least one $R^B$ is halogen. In certain embodiments, at least one $R^B$ is F. In certain embodiments, at least one $R^B$ is Cl. In certain embodiments, at least one $R^B$ is Br. In certain embodiments, at least one $R^B$ is I (iodine). In certain embodiments, one $R^B$ is F. In certain embodiments, one $R^B$ is Cl. In certain embodiments, at least one $R^B$ is substituted alkyl. In certain embodiments, at least one $R^B$ is unsubstituted alkyl. In certain embodiments, at least one $R^B$ is substituted $C_{1-6}$ alkyl. In certain embodiments, at least one $R^B$ is unsubstituted $C_{1-6}$ alkyl. In certain embodiments, at least one $R^B$ is methyl. In certain embodiments, at least one $R^B$ is ethyl. In certain embodiments, at least one $R^B$ is propyl. In certain embodiments, at least one $R^B$ is

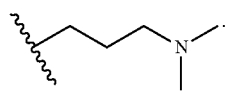 [SMILES: *CCCN(C)C]

In certain embodiments, at least one $R^B$ is

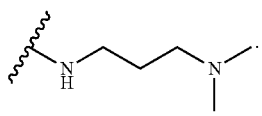 [SMILES: *NCCCN(C)C]

In certain embodiments, at least one $R^B$ is

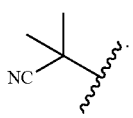

In certain embodiments, at least one $R^B$ is butyl. In certain embodiments, at least one $R^B$ is substituted carbocyclyl. In certain embodiments, at least one $R^B$ is unsubstituted carbocyclyl. In certain embodiments, at least one $R^B$ is substituted heterocyclyl. In certain embodiments, at least one $R^B$ is unsubstituted heterocyclyl. In certain embodiments, at least one $R^B$ is substituted piperidine. In certain embodiments, at least one $R^B$ is unsubstituted piperidine. In certain embodiments, at least one $R^B$ substituted piperizine. In certain embodiments, at least one $R^B$ unsubstituted piperizine. In certain embodiments, at least one $R^B$ substituted pyrrolidine. In certain embodiments, at least one $R^B$ unsubstituted pyrrolidine. In certain embodiments, at least one $R^B$ is substituted morpholine. In certain embodiments, at least one $R^B$ is unsubstituted morpholine. In certain embodiments, at least one $R^B$ is substituted diazapane. In certain embodiments, at least one $R^B$ is unsubstituted diazapane. In certain embodiments, at least one $R^B$ is

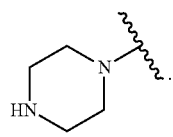

In certain embodiments, at least one $R^B$

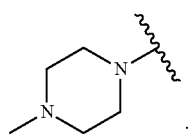 [SMILES: *N1CCN(C)CC1]

In certain embodiments, at least one $R^B$ is

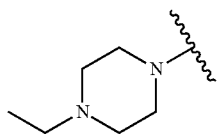

In certain embodiments, at least one $R^B$ is

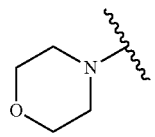

In certain embodiments, at least one $R^B$ is substituted —(CH$_2$)(heterocyclyl). In certain embodiments, at least one $R^B$ is unsubstituted —(CH$_2$)(heterocyclyl). In certain embodiments, at least one $R^B$ is

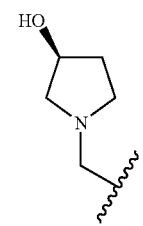

In certain embodiments, at least one $R^B$ is

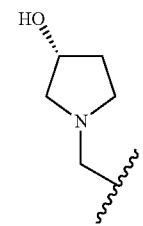

In certain embodiments, at least one $R^B$ is

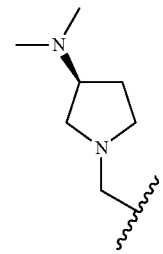

In certain embodiments, at least one $R^B$ is

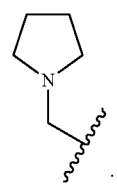 [SMILES: *CN1CCCC1]

In certain embodiments, at least one $R^B$ is

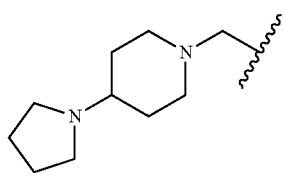

In certain embodiments, at least one $R^B$ is

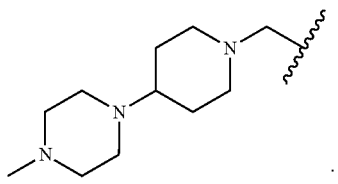 [SMILES: *CN1CCC(N2CCN(C)CC2)CC1]

In certain embodiments, at least one $R^B$ is

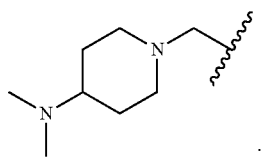 [SMILES: *CN1CCC(N(C)C)CC1]

In certain embodiments, at least one $R^B$ is

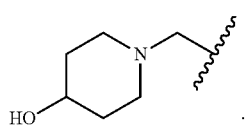 [SMILES: *CN1CCC(O)CC1]

In certain embodiments, at least one $R^B$ is

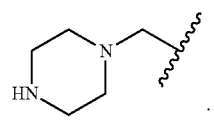

In certain embodiments, at least one $R^B$ is

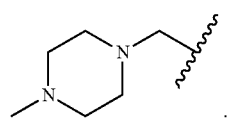

In certain embodiments, at least one $R^B$ is

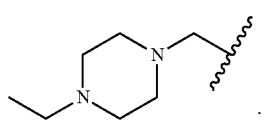 [SMILES: *CN1CCN(CC)CC1]

In certain embodiments, at least one $R^B$ is

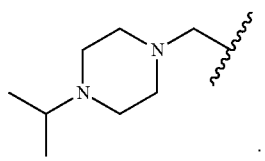 [SMILES: *CN1CCN(C(C)C)CC1]

In certain embodiments, at least one $R^B$ is

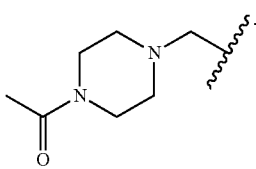 [SMILES: *CN1CCN(C(C)=O)CC1]

In certain embodiments, at least one $R^B$ is

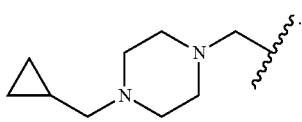 [SMILES: *CN1CCN(CC2CC2)CC1]

In certain embodiments, at least one $R^B$ is

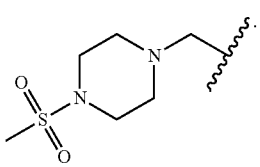 [SMILES: *CN1CCN(S(C)(=O)=O)CC1]

In certain embodiments, at least one $R^B$ is

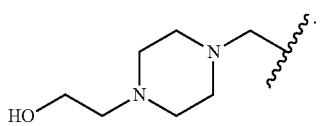 [SMILES: *CN1CCN(CCO)CC1]

In certain embodiments, at least one $R^B$ is

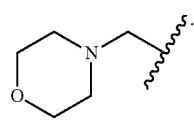 [SMILES: *CN1CCOCC1]

In certain embodiments, at least one $R^B$ is

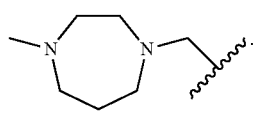 [SMILES: *CN1CCCN(C)CC1]

In certain embodiments, at least one $R^B$ is substituted —(CH$_2$)$_2$(heterocyclyl). In certain embodiments, at least one $R^B$ is unsubstituted —(CH$_2$)$_2$(heterocyclyl). In certain embodiments, at least one $R^B$ is

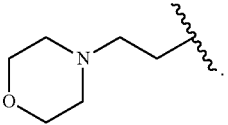 [SMILES: *CCN1CCOCC1]

In certain embodiments, at least one $R^B$ is substituted —(CH$_2$)$_3$(heterocyclyl). In certain embodiments, at least one $R^B$ is unsubstituted —(CH$_2$)$_3$(heterocyclyl). In certain embodiments, at least one $R^B$ is

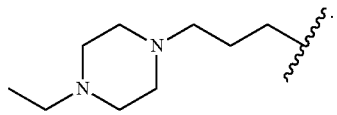 [SMILES: *CCCN1CCN(CC)CC1]

In certain embodiments, at least one $R^B$ is substituted aryl. In certain embodiments, at least one $R^B$ is unsubstituted aryl. In certain embodiments, at least one $R^B$ is substituted phenyl. In certain embodiments, at least one $R^B$ is unsubstituted phenyl. In certain embodiments, at least one $R^B$ is substituted heteroaryl. In certain embodiments, at least one $R^B$ is unsubstituted heteroaryl. In certain embodiments, at least one $R^B$ is substituted pyridyl. In certain embodiments, at least one $R^B$ is unsubstituted pyridyl. In certain embodiments, at least one $R^B$ is substituted imidazole. In certain embodiments, at least one $R^B$ is unsubstituted imidazole. In certain embodiments, at least one $R^B$ is

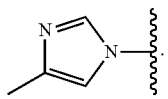 [SMILES: *n1cnc(C)c1]

In certain embodiments, at least one $R^B$ is

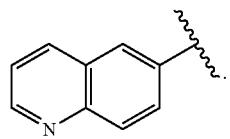 [SMILES: *c1ccc2ncccc2c1]

In certain embodiments, at least one $R^B$ is —OR$^{A1}$. In certain embodiments, at least one $R^B$ is —O(C$_{1-6}$ alkyl) where the alkyl is substituted or unsubstituted. In certain embodiments, at least one $R^B$ is —OMe. In certain embodiments, at least one $R^B$ is —OPh. In certain embodiments, at least one $R^B$ is

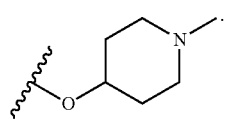 [SMILES: *OC1CCN(C)CC1]

In certain embodiments, at least one $R^B$ is

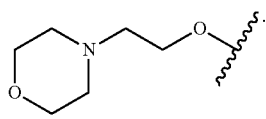 [SMILES: *OCCN1CCOCC1]

In certain embodiments, at least one $R^B$ is —OH. In certain embodiments, at least one $R^B$ is —N(R$^{A1}$)$_2$. In certain embodiments, at least one $R^B$ is —NEt$_2$. In certain embodiments, at least one $R^B$ is —NMe$_2$. In certain embodiments, at least one $R^B$ is —NHtBu. In certain embodiments, at least one $R^B$ is

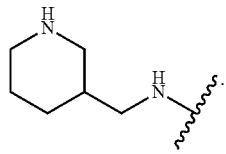 [SMILES: *NCC1CCCNC1]

In certain embodiments, at least one $R^B$ is

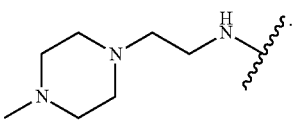 [SMILES: *NCCN1CCN(C)CC1]

In certain embodiments, at least one $R^B$ is —NH$_2$. In certain embodiments, at least one $R^B$ is —CN. In certain embodiments, at least one $R^B$ is —C(=O)R$^{A1}$. In certain embodiments, at least one $R^B$ is acetyl. In certain embodiments, at least one $R^B$ is —C(=O)OR$^{A1}$. In certain embodiments, at least one $R^B$ is —C(=O)N(R$^{A1}$)$_2$. In certain embodiments, at least one $R^B$ is —C(=O)NHR$^{A1}$. In certain embodiments, at least one $R^B$ is —C(=O)NH(C$_{1-6}$ alkyl) where the alkyl is substituted or unsubstituted. In certain embodiments, at least one $R^B$ is —C(=O)NHMe. In certain embodiments, at least one $R^B$ is —C(=O)NH$_2$. In certain embodiments, at least one $R^B$ is

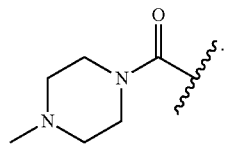 [SMILES: *C(=O)N1CCN(C)CC1]

In certain embodiments, at least one $R^B$ is

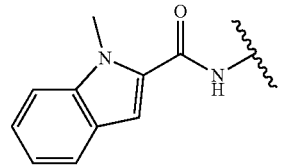

In certain embodiments, at least one $R^B$ is —NO$_2$. In certain embodiments, at least one $R^B$ is —NR$^{A1}$C(=O)R$^{A1}$. In certain embodiments, at least one $R^B$ is —NR$^{A1}$C(=O)OR$^{A1}$. In certain embodiments, at least one $R^B$ is —NR$^{A1}$S(=O)$_2$R$^{A1}$. In certain embodiments, at least one $R^B$ is —NHS(=O)$_2$R$^{A1}$. In certain embodiments, at least one $R^B$ is —NHS(=O)$_2$(C$_{1-6}$ alkyl) where the alkyl is substituted or unsubstituted. In certain embodiments, at least one $R^B$ is —NHS(=O)$_2$Me. In certain embodiments, at least one $R^B$ is —S(=O)$_2$R$^{A1}$. In certain embodiments, at least one $R^B$ is —S(=O)$_2$N(R$^{A1}$)$_2$. In certain embodiments, at least one $R^B$ is —S(=O)$_2$N(R$^{A1}$)$_2$. In certain embodiments, at least one $R^B$ is —S(=O)$_2$N(C$_{1-6}$ alkyl)$_2$. In certain embodiments, at least one $R^B$ is —S(=O)$_2$NH(C$_{1-6}$ alkyl). In certain embodiments, at least one $R^B$ is —S(=O)$_2$NH(t-Bu). In certain embodiments, at least one $R^B$ is —S(=O)$_2$NH$_2$.

In certain embodiments, $R^B$ is substituted or unsubstituted $C_{1-6}$alkyl; and l is 1. In certain embodiments, $R^B$ is substituted or unsubstituted $C_{1-6}$alkyl; l is 1; and $R^B$ is meta to the point of attachment of U. In certain embodiments, $R^B$ is substituted or unsubstituted $C_{1-6}$alkyl; l is 1; and $R^B$ is para to the point of attachment of U. In certain embodiments, $R^B$ is $C_{1-6}$alkyl substituted with one —CN group; and l is 1. In certain embodiments, $R^B$ is $C_{1-6}$alkyl substituted with one —CN group; l is 1; and $R^B$ is meta to the point of attachment of U. In certain embodiments, $R^B$ is $C_{1-6}$alkyl substituted with one —CN group; l is 1; and $R^B$ is para to the point of attachment of U. In certain embodiments, $R^B$ is

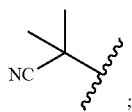

and l is 1. In certain embodiments, $R^B$ is

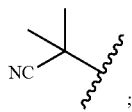

l is 1; and $R^B$ is meta to the point of attachment of U. In certain embodiments, $R^B$ is

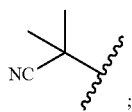 [SMILES: *C(C)(C)C#N]

l is 1; and $R^B$ is para to the point of attachment of U. In certain embodiments, $R^B$ is substituted or unsubstituted —CH$_2$-(piperazinyl); and l is 1. In certain embodiments, $R^B$ is substituted or unsubstituted —CH$_2$-(piperazinyl); l is 1; and $R^B$ is meta to the point of attachment of U. In certain embodiments, $R^B$ is substituted or unsubstituted —CH$_2$-(piperazinyl); l is 1; and $R^B$ is para to the point of attachment of U. In certain embodiments, $R^B$ is

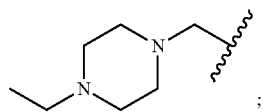 [SMILES: *CN1CCN(CC)CC1]

and l is 1. In certain embodiments, $R^B$ is

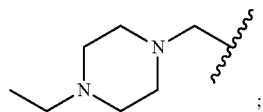 [SMILES: *CN1CCN(CC)CC1]

l is 1; and $R^B$ is meta to the point of attachment of U. In certain embodiments, $R^B$ is

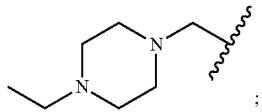

l is 1; and $R^B$ is para to the point of attachment of U. In certain embodiments, $R^B$ is haloalkyl; and l is 1. In certain embodiments, $R^B$ is haloalkyl; l is 1; and $R^B$ is meta to the point of attachment of U. In certain embodiments, $R^B$ is haloalkyl; l is 1; and $R^B$ is para to the point of attachment of U. In certain embodiments, $R^B$ is —CF$_3$; and l is 1. In certain embodiments, $R^B$ is —CF$_3$; l is 1; and $R^B$ is meta to the point of attachment of U. In certain embodiments, $R^B$ is —CF$_3$; l is 1; and $R^B$ is para to the point of attachment of U. In certain embodiments, $R^B$ is substituted or unsubstituted imidazoyl; and l is 1. In certain embodiments, $R^B$ is substituted or unsubstituted imidazoyl; l is 1; and $R^B$ is meta to the point of attachment of U. In certain embodiments, $R^B$ is substituted or unsubstituted imidazoyl; l is 1; and $R^B$ is para to the point of attachment of U. In certain embodiments, $R^B$ is

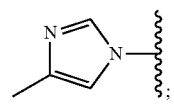

and l is 1. In certain embodiments, $R^B$ is

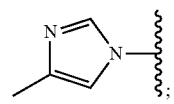

l is 1; and $R^B$ is meta to the point of attachment of U. In certain embodiments, $R^B$ is

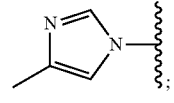

l is 1; and $R^B$ is para to the point of attachment of U. In certain embodiments, $R^B$ is substituted or unsubstituted piperazinyl; and l is 1. In certain embodiments, $R^B$ is substituted or unsubstituted piperazinyl; l is 1; and $R^B$ is meta to the point of attachment of U. In certain embodiments, $R^B$ is substituted or unsubstituted piperazinyl; l is 1; and $R^B$ is para to the point of attachment of U. In certain embodiments, $R^B$ is

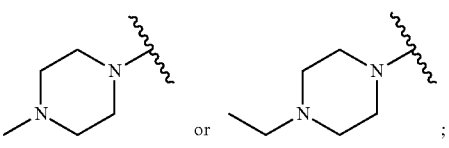 or 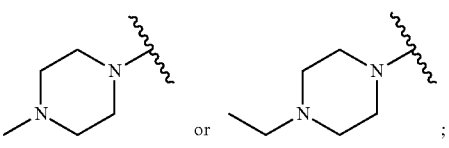;

and l is 1. In certain embodiments, $R^B$ is

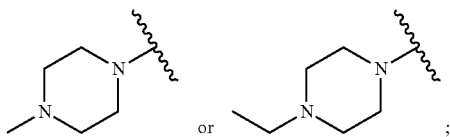

l is 1; and $R^B$ is meta to the point of attachment of U. In certain embodiments, $R^B$ is

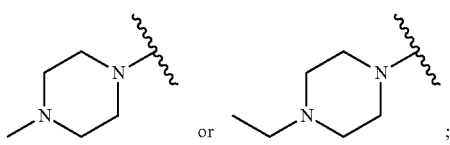

l is 1; and $R^B$ is para to the point of attachment of U. In certain embodiments, $R^B$ is substituted or unsubstituted morpholine; and l is 1. In certain embodiments, $R^B$ is substituted or unsubstituted morpholine; l is 1; and $R^B$ is meta to the point of attachment of U. In certain embodiments, $R^B$ is substituted or unsubstituted morpholine; l is 1; and $R^B$ is para to the point of attachment of U.

In certain embodiments, at least one $R^B$ group is substituted or unsubstituted $C_{1-6}$alkyl; and l is 2. In certain embodiments, at least one $R^B$ group is substituted or unsubstituted $C_{1-6}$alkyl; l is 2; and at least one $R^B$ is meta to the point of attachment of U. In certain embodiments, at least one $R^B$ group is substituted or unsubstituted $C_{1-6}$alkyl; l is 2; and one $R^B$ is para to the point of attachment of U. In certain embodiments, at least one $R^B$ group is $C_{1-6}$alkyl substituted with one —CN group; and l is 2. In certain embodiments, at least one $R^B$ group is $C_{1-6}$alkyl substituted with one —CN group; l is 2; and at least one $R^B$ is meta to the point of attachment of U. In certain embodiments, at least one $R^B$ group is $C_{1-6}$alkyl substituted with one —CN group; l is 2; and one $R^B$ is para to the point of attachment of U. In certain embodiments, at least one $R^B$ group is

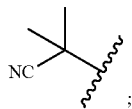 [SMILES: *C(C)(C)C#N]

and l is 2. In certain embodiments at least one $R^B$ group is

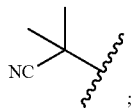 [SMILES: *C(C)(C)C#N]

l is 2; and at least one R is meta to the point of attachment of U. In certain embodiments, at least one $R^B$ group is

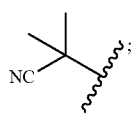 [SMILES: *C(C)(C)C#N]

l is 2; and one $R^B$ is para to the point of attachment of U. In certain embodiments, at least one $R^B$ group is substituted or unsubstituted —CH$_2$-(piperazinyl); and l is 2. In certain embodiments, at least one $R^B$ group is substituted or unsubstituted —CH$_2$-(piperazinyl); l is 2; and at least one $R^B$ is meta to the point of attachment of U. In certain embodiments, at least one $R^B$ group is substituted or unsubstituted —CH$_2$-(piperazinyl); l is 2; and one $R^B$ is para to the point of attachment of U. In certain embodiments, at least one $R^B$ group is

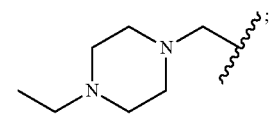 [SMILES: *CN1CCN(CC)CC1]

and l is 2. In certain embodiments, at least one $R^B$ group is

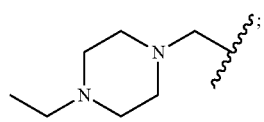

l is 2; and at least one $R^B$ is meta to the point of attachment of U. In certain embodiments, at least one $R^B$ group is

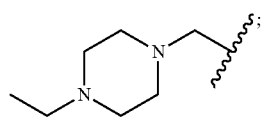 [SMILES: *CN1CCN(CC)CC1]

l is 2; and one $R^B$ is para to the point of attachment of U. In certain embodiments, at least one $R^B$ group is haloalkyl; and l is 2. In certain embodiments, at least one $R^B$ group is haloalkyl; l is 2; and at least one $R^B$ is meta to the point of attachment of U. In certain embodiments, at least one $R^B$ group is haloalkyl; l is 2; and one $R^B$ is para to the point of attachment of U. In certain embodiments, at least one $R^B$ group is —CF$_3$; and l is 2. In certain embodiments, at least one $R^B$ group is —CF$_3$; l is 2; and at least one $R^B$ is meta to the point of attachment of U. In certain embodiments, at least one $R^B$ group is —CF$_3$; l is 2; and one $R^B$ is para to the point of attachment of U. In certain embodiments, at least one $R^B$ group is substituted or unsubstituted imidazoyl; and l is 2. In certain embodiments, at least one $R^B$ group is substituted or unsubstituted imidazoyl; l is 2; and at least one $R^B$ is meta to the point of attachment of U. In certain embodiments, at least one $R^B$ group is substituted or unsubstituted imidazoyl; l is 2; and one $R^B$ is para to the point of attachment of U. In certain embodiments, at least one $R^B$ group is

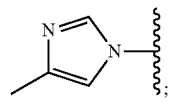

and l is 2. In certain embodiments, at least one $R^B$ group is

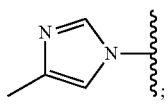

l is 2; and at least one $R^B$ is meta to the point of attachment of U. In certain embodiments, at least one $R^B$ group is

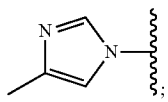 [SMILES: *n1cnc(C)c1]

l is 2; and one $R^B$ is para to the point of attachment of U. In certain embodiments, at least one $R^B$ group is substituted or unsubstituted piperazinyl; and l is 2. In certain embodiments, at least one $R^B$ group is substituted or unsubstituted piperazinyl; l is 2; and at least one $R^B$ is meta to the point of attachment of U. In certain embodiments, at least one $R^B$ group is substituted or unsubstituted piperazinyl; l is 2; and one $R^B$ is para to the point of attachment of U. In certain embodiments, at least one $R^B$ group is

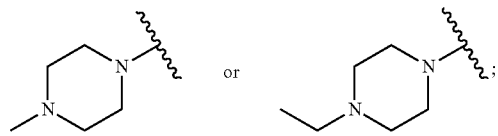

and l is 2. In certain embodiments, at least one $R^B$ group is

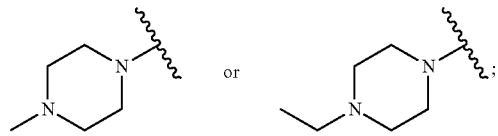

l is 2; and at least one $R^B$ is meta to the point of attachment of U. In certain embodiments, at least one $R^B$ group is

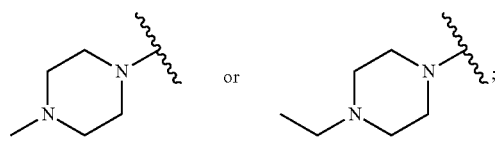

l is 2; and one $R^B$ is para to the point of attachment of U. In certain embodiments, at least one $R^B$ group is substituted or unsubstituted morpholine; and l is 2. In certain embodiments, at least one $R^B$ group is substituted or unsubstituted morpholine; l is 2; and at least one $R^B$ is meta to the point of attachment of U. In certain embodiments, at least one $R^B$ group is substituted or unsubstituted morpholine; l is 2; and one $R^B$ is para to the point of attachment of U. In certain embodiments, two $R^B$ groups are substituted or unsubstituted morpholine; l is 2; and both $R^B$ groups are meta to the point of attachment of U.

In compounds of Formula (I), X and Y are taken together to represent a divalent linker moiety. In certain embodiments, X and Y are taken together to represent

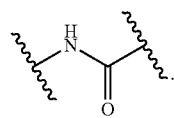

In certain embodiments, X and Y are taken together to represent

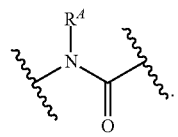

In certain embodiments, X and Y are taken together to represent

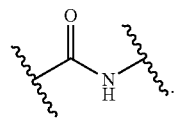

In certain embodiments, X and Y are taken together to represent

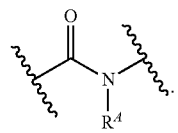

In compounds of Formula (I), Q and U are taken together to represent a divalent linker moiety. In certain embodiments, Q and U are taken together to represent

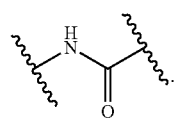

In certain embodiments, Q and U are taken together to represent

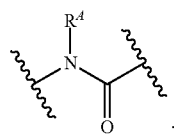

In certain embodiments, Q and U are taken together to represent

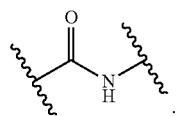

In certain embodiments, Q and U are taken together to represent

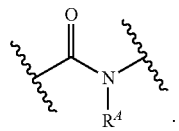

In compounds of Formula (I), the pyridine ring may be substituted with one or more $R^X$ groups. In certain embodiments, at least one $R^X$ is substituted carbocyclyl. In certain embodiments, at least one $R^X$ is unsubstituted carbocyclyl. In certain embodiments, at least one $R^X$ is

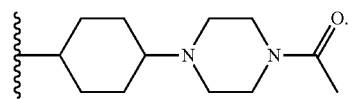

In certain embodiments, at least one $R^X$ is

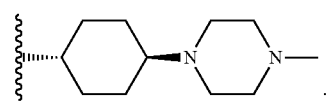 [SMILES: *[C@H]1CC[C@H](N2CCN(C)CC2)CC1]

In certain embodiments, at least one $R^X$ is

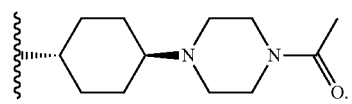 [SMILES: *[C@H]1CC[C@H](N2CCN(C(C)=O)CC2)CC1]

In certain embodiments, at least one $R^X$ is substituted heterocyclyl. In certain embodiments, at least one $R^X$ is unsubstituted heterocyclyl. In certain embodiments, at least one $R^X$ is

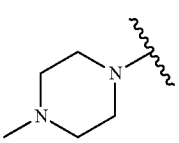

In certain embodiments, at least one $R^X$ is

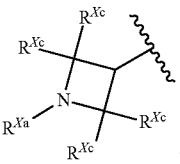

In certain embodiments, at least one $R^X$ is

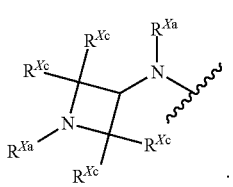

In certain embodiments, at least one $R^X$ is

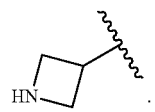

In certain embodiments, at least one $R^X$ is

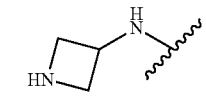

In certain embodiments, at least one $R^X$ is

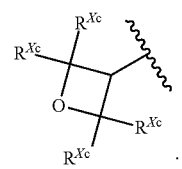

In certain embodiments, at least one $R^X$ is

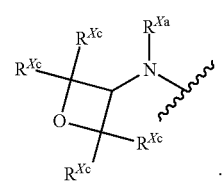

In certain embodiments, at least one $R^X$ is

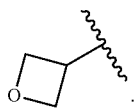

In certain embodiments, at least one $R^X$ is

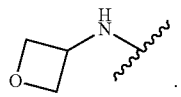

In certain embodiments, at least one $R^X$ is substituted aryl. In certain embodiments, at least one $R^X$ is unsubstituted aryl. In certain embodiments, at least one $R^X$ is substituted phenyl. In certain embodiments, at least one $R^X$ is unsubstituted phenyl. In certain embodiments, at least one $R^X$ is

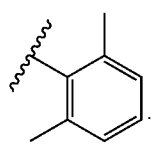

In certain embodiments, at least one $R^X$ is

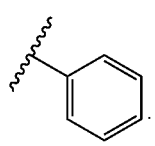

In certain embodiments, at least one $R^X$ is

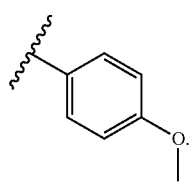 [SMILES: *c1ccc(OC)cc1]

In certain embodiments, at least one $R^X$ is

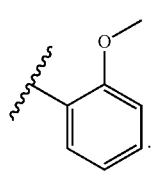

In certain embodiments, at least one $R^X$ is

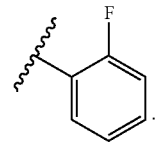

In certain embodiments, at least one $R^X$ is

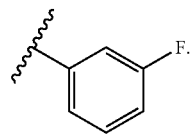 [SMILES: *c1cccc(F)c1]

In certain embodiments, at least one $R^X$ is

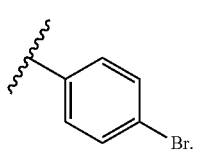 [SMILES: *c1ccc(Br)cc1]

In certain embodiments, at least one $R^X$ is

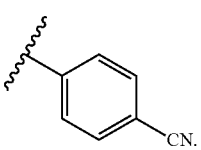 [SMILES: *c1ccc(C#N)cc1]

In certain embodiments, at least one $R^X$ is substituted heteroaryl. In certain embodiments, at least one $R^X$ is unsubstituted heteroaryl. In certain embodiments, at least one $R^X$ is

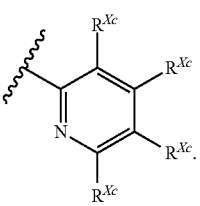

In certain embodiments, at least one $R^X$ is

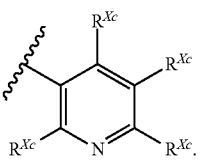

In certain embodiments, at least one R$^X$ is

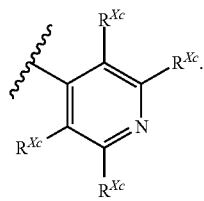

In certain embodiments, at least one R$^X$ is

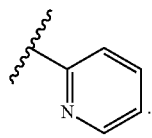

In certain embodiments, at least one R$^X$ is

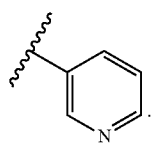

In certain embodiments, at least one R$^X$ is

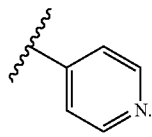

In certain embodiments, at least one R$^X$ is

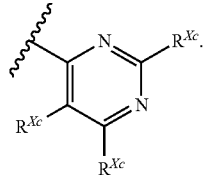

In certain embodiments, at least one R$^X$ is

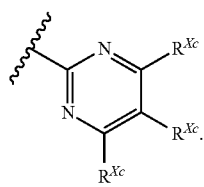

In certain embodiments, at least one R$^X$ is

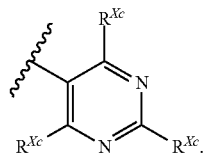

In certain embodiments, at least one R$^X$ is

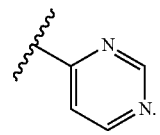 [SMILES: *c1ccncn1]

In certain embodiments, at least one R$^X$ is

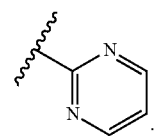 [SMILES: *c1ncccn1]

In certain embodiments, at least one R$^X$ is

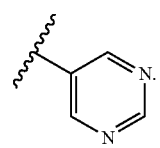 [SMILES: *c1cncnc1]

In certain embodiments, at least one R$^X$ is

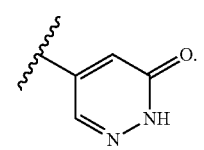 [SMILES: *c1cn[nH]c(=O)c1]

In certain embodiments, at least one R$^X$ is

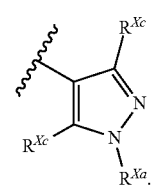

In certain embodiments, at least one $R^X$ is

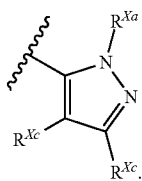

In certain embodiments, at least one $R^X$ is

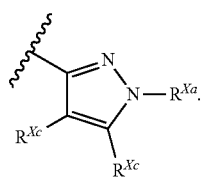

In certain embodiments, at least one $R^X$ is

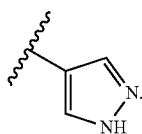

In certain embodiments, at least one $R^X$ is

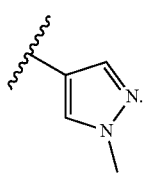

In certain embodiments, at least one $R^X$ is

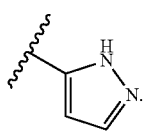

In certain embodiments, at least one $R^X$ is

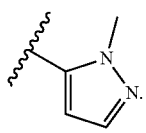

In certain embodiments, at least one $R^X$ is

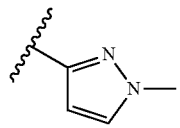

In certain embodiments, at least one $R^X$ is

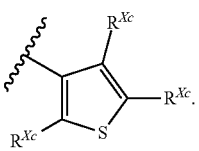

In certain embodiments, at least one $R^X$ is

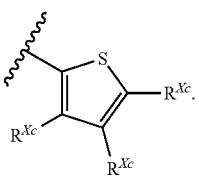

In certain embodiments, at least one $R^X$ is

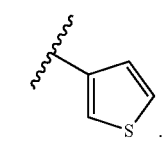 [SMILES: *c1ccsc1]

In certain embodiments, at least one $R^X$ is

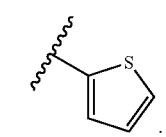

In certain embodiments, at least one $R^X$ is

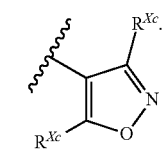

In certain embodiments, at least one $R^X$ is

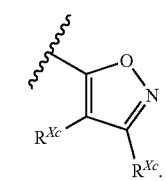

In certain embodiments, at least one $R^X$ is

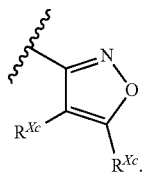

In certain embodiments, at least one $R^X$ is

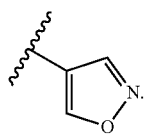

In certain embodiments, at least one $R^X$ is

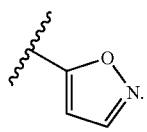

In certain embodiments, at least one $R^X$ is

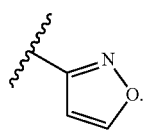 [SMILES: *c1ccon1]

In certain embodiments, at least one $R^X$ is —N($R^{A1}$)($R^{Xa}$). In certain embodiments, at least one $R^X$ is —NH$_2$. In certain embodiments, at least one $R^X$ is

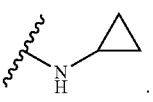 [SMILES: *NC1CC1]

certain embodiments, at least one $R^X$ is

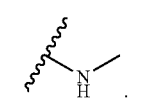

In certain embodiments, at least one $R^X$ is

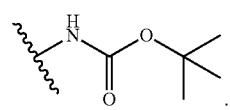 [SMILES: *NC(=O)OC(C)(C)C]

In certain embodiments, at least one $R^X$ is

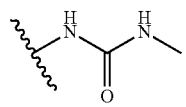

In certain embodiments, at least one $R^X$ is

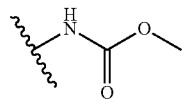

In certain embodiments, at least one $R^X$ is

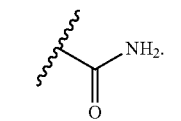

In certain embodiments, at least one $R^X$ is

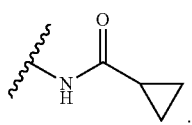 [SMILES: *NC(=O)C1CC1]

In certain embodiments, at least one $R^X$ is

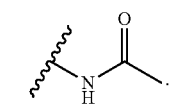

In certain embodiments, at least one $R^X$ is

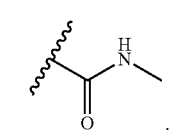 [SMILES: *C(=O)NC]

In certain embodiments, at least one $R^X$ is

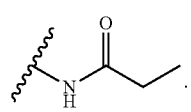 [SMILES: *NC(=O)CC]

61

In certain embodiments, at least one $R^X$ is

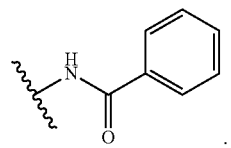

In certain embodiments, at least one $R^X$ is

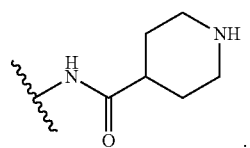 [SMILES: *NC(=O)C1CCNCC1]

In certain embodiments, at least one $R^X$ is

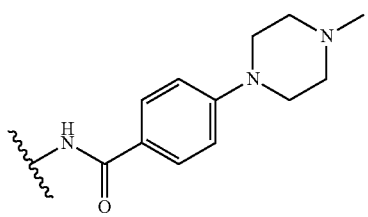

In certain embodiments, at least one $R^X$ is

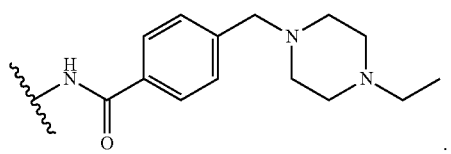 [SMILES: *NC(=O)c1ccc(CN2CCN(CC)CC2)cc1]

In certain embodiments, at least one $R^X$ is

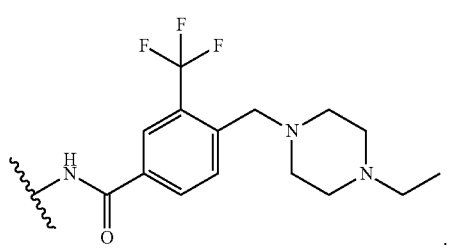 [SMILES: *NC(=O)c1ccc(CN2CCN(CC)CC2)c(C(F)(F)F)c1]

In certain embodiments, at least one $R^X$ is

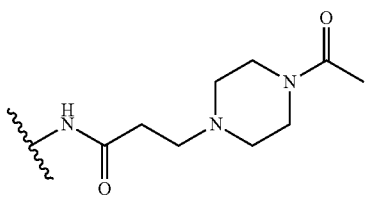

62

In certain embodiments, at least one $R^X$ is

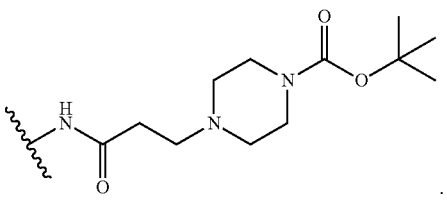 [SMILES: *NC(=O)CCN1CCN(C(=O)OC(C)(C)C)CC1]

In certain embodiments, at least one $R^X$ is

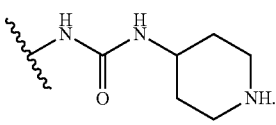 [SMILES: *NC(=O)NC1CCNCC1]

In certain embodiments, at least one $R^X$ is

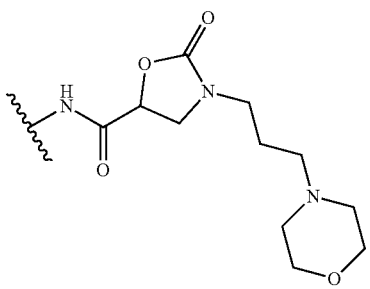

In certain embodiments, at least one $R^X$ is

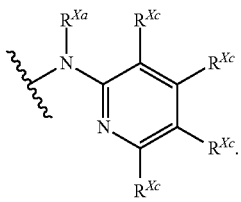

In certain embodiments, at least one $R^X$ is

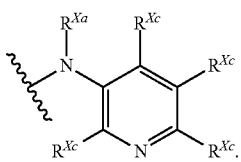

In certain embodiments, at least one $R^X$ is

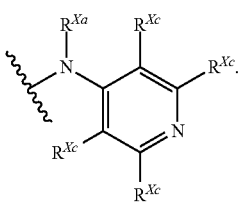

In certain embodiments, at least one $R^X$ is

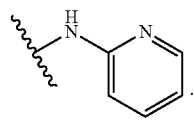

In certain embodiments, at least one $R^X$ is

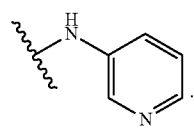

In certain embodiments, at least one $R^X$ is

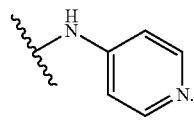

In certain embodiments, at least one $R^X$ is

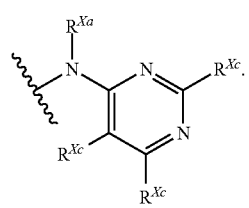

In certain embodiments, at least one $R^X$ is

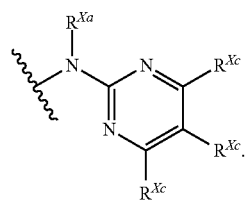

In certain embodiments, at least one $R^X$ is

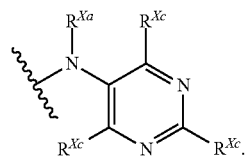

In certain embodiments, at least one $R^X$ is

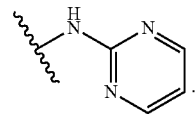

In certain embodiments, at least one $R^X$ is

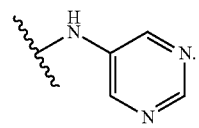 [SMILES: *Nc1cncnc1]

In certain embodiments, at least one $R^X$ is

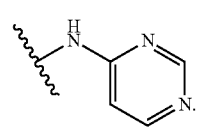

In certain embodiments, at least one $R^X$ is

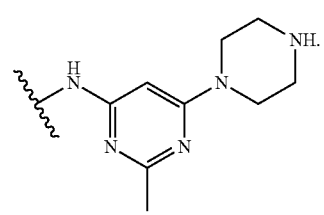 [SMILES: *Nc1cc(N2CCNCC2)nc(C)n1]

In certain embodiments, at least one $R^X$ is

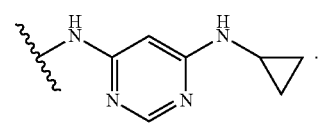 [SMILES: *Nc1cc(NC2CC2)ncn1]

In certain embodiments, at least one $R^X$ is

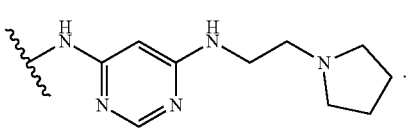 [SMILES: *Nc1cc(NCCN2CCCC2)ncn1]

In certain embodiments, at least one $R^X$ is

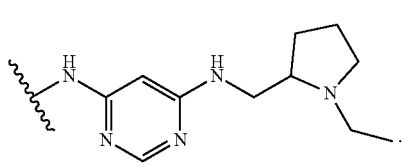 [SMILES: *Nc1cc(NCC2CCCN2CC)ncn1]

In certain embodiments, at least one $R^X$ is

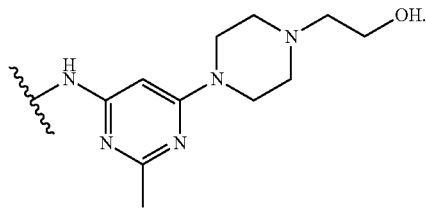 [SMILES: *Nc1cc(N2CCN(CCO)CC2)nc(C)n1]

In certain embodiments, at least one $R^X$ is

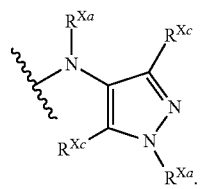

In certain embodiments, at least one $R^X$ is

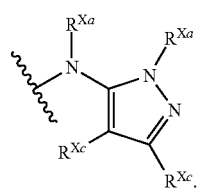

In certain embodiments, at least one $R^X$ is

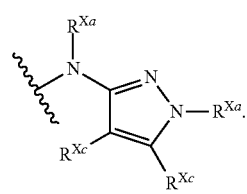

In certain embodiments, at least one $R^X$ is

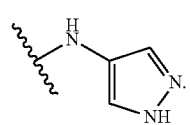 [SMILES: *Nc1cn[nH]c1]

In certain embodiments, at least one $R^X$ is

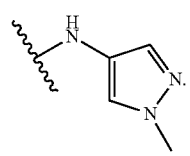 [SMILES: *Nc1cnn(C)c1]

In certain embodiments, at least one $R^X$ is

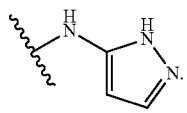

In certain embodiments, at least one $R^X$ is

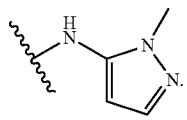 [SMILES: *Nc1ccnn1C]

In certain embodiments, at least one $R^X$ is

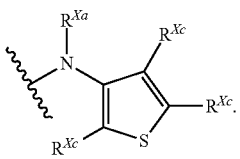

In certain embodiments, at least one $R^X$ is

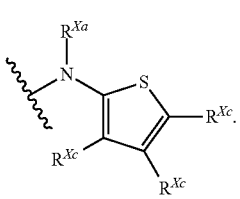

In certain embodiments, at least one $R^X$ is

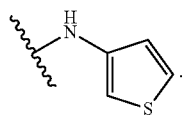 [SMILES: *Nc1ccsc1]

In certain embodiments, at least one $R^X$ is

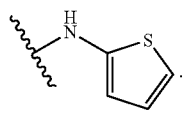 [SMILES: *Nc1cccs1]

In certain embodiments, at least one $R^X$ is

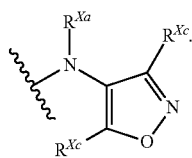

In certain embodiments, at least one $R^X$ is

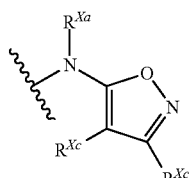

In certain embodiments, at least one $R^X$ is

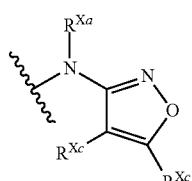

In certain embodiments, at least one $R^X$ is

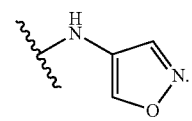 [SMILES: *Nc1cnoc1]

In certain embodiments, at least one $R^X$ is

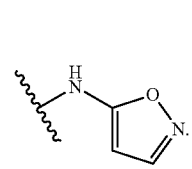

In certain embodiments, at least one $R^X$ is

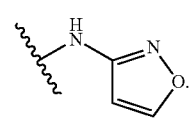

In certain embodiments, at least one $R^X$ is

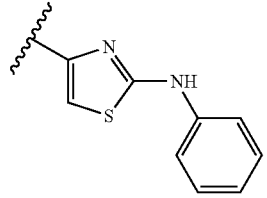

In certain embodiments, at least one $R^X$ is

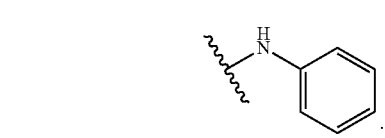

In certain embodiments, at least one $R^X$ is

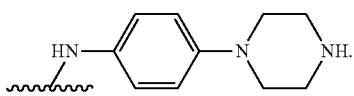

In certain embodiments, at least one $R^X$ is

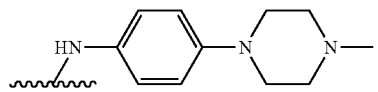

In certain embodiments, at least one $R^X$ is

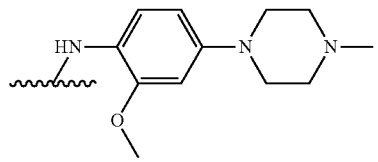

In certain embodiments, at least one $R^X$ is

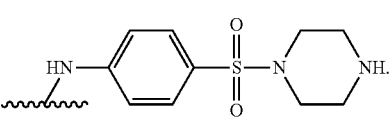

In compounds of Formula (I), $R^X$ may be substituted with one or more $R^{Xa}$ groups. Each instance of $R^{Xa}$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{41}$, —C(=O)O$R^{41}$, —C(=O)N($R^{41}$)$_2$, —S(=O)$R^{41}$, —S(=O)N($R^{41}$)$_2$, —S(=O)$_2R^{41}$, —S(=O)$_2$O$R^4$, —S(=O)$_2$N($R^{41}$)$_2$, and a nitrogen protecting group; wherein each occurrence of $R^{41}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A1}$ groups are joined to form an optionally substituted heterocyclic ring.

In certain embodiments, at least one $R^{Xa}$ is H. In certain embodiments, all $R^{Xa}$ groups are H. In certain embodiments, at least one $R^{Xa}$ is substituted alkyl. In certain embodiments, at least one $R^{Xa}$ is substituted $C_{1-6}$ alkyl. In certain embodiments, at least one $R^{Xa}$ is substituted methyl. In certain embodiments, at least one $R^{Xa}$ is unsubstituted alkyl. In certain embodiments, at least one $R^{Xa}$ is unsubstituted $C_{1-6}$ alkyl. In certain embodiments, at least one $R^{X}a$ is methyl. In certain embodiments, at least one $R^{Xa}$ is ethyl. In certain embodiments, at least one $R^{Xa}$ is propyl. In certain embodiments, at least one $R^{Xa}$ is butyl. In certain embodiments, at least one $R^{Xa}$ is substituted alkenyl. In certain embodiments, at least one $R^{X}a$ is unsubstituted alkenyl. In certain embodiments, at least one $R^{Xa}$ is substituted alkynyl. In certain embodiments, at least one $R^{Xa}$ is unsubstituted alkynyl. In certain embodiments, at least one $R^{Xa}$ is substituted carbocyclyl. In certain embodiments, at least one $R^{Xa}$ is unsubstituted carbocyclyl. In certain embodiments, at least one $R^{Xa}$ is substituted heterocyclyl. In certain embodiments, at least one $R^{Xa}$ is unsubstituted heterocyclyl. In certain embodiments, at least one $R^{Xa}$ is substituted aryl. In certain embodiments, at least one $R^{Xa}$ is unsubstituted aryl. In certain embodiments, at least one $R^{Xa}$ is substituted phenyl. In certain embodiments, at least one $R^{Xa}$ is unsubstituted phenyl. In certain embodiments, at least one $R^{Xa}$ is substituted heteroaryl. In certain embodiments, at least one $R^{Xa}$ is unsubstituted heteroaryl. In certain embodiments, at least one $R^{Xa}$ is —C(=O)$R^{A1}$. In certain embodiments, at least one $R^{Xa}$ is —C(=O)H. In certain embodiments, at least one $R^{Xa}$ is acetyl. In certain embodiments, at least one $R^{Xa}$ is —C(=O)($C_{1-6}$alkyl). In certain embodiments, at least one $R^{Xa}$ is —C(=O)O$R^{A1}$. In certain embodiments, at least one $R^{Xa}$ is —C(=O)OH. In certain embodiments, at least one $R^{Xa}$ is —C(=O)O($C_{1-6}$alkyl). In certain embodiments, at least one $R^{Xa}$ is —C(=O)N($R^{A1}$)$_2$. In certain embodiments, at least one $R^{Xa}$ is —C(=O)NH$R^{A1}$. In certain embodiments, at least one $R^{Xa}$ is —C(=O)N($C_{1-6}$ alkyl)$_2$. In certain embodiments, at least one $R^{Xa}$ is —C(=O)NH($C_{1-6}$ alkyl). In certain embodiments, at least one $R^{Xa}$ is —C(=O)NH$_2$. In certain embodiments, at least one $R^{Xa}$ is —S(=O)$R^{A1}$. In certain embodiments, at least one $R^{Xa}$ is —S(=O)($C_{1-6}$alkyl). In certain embodiments, at least one $R^{Xa}$ is —S(=O)N($R^{A1}$)$_2$. In certain embodiments, at least one $R^{X}a$ is —S(=O)NH($R^{A1}$). In certain embodiments, at least one $R^{Xa}$ is —S(=O)NH$_2$. In certain embodiments, at least one $R^{Xa}$ is —S(=O)N($C_{1-6}$alkyl)$_2$. In certain embodiments, at least one $R^{Xa}$ is —S(=O)NH($C_{1-6}$alkyl). In certain embodiments, at least one $R^{Xa}$ is —S(=O)$_2$$R^{A1}$. In certain embodiments, at least one $R^{Xa}$ is —S(=O)$_2$($C_{1-6}$alkyl). In certain embodiments, at least one $R^{Xa}$ is —S(=O)$_2$O$R^{A1}$. In certain embodiments, at least one $R^{Xa}$ is —S(=O)$_2$OH. In certain embodiments, at least one $R^{Xa}$ is —S(=O)$_2$N($R^{A1}$)$_2$. In certain embodiments, at least one $R^{Xa}$ is —S(=O)$_2$NH($R^{A1}$). In certain embodiments, at least one $R^{Xa}$ is —S(=O)$_2$NH$_2$. In certain embodiments, at least one $R^{Xa}$ is —S(=O)$_2$N($C_{1-6}$alkyl)$_2$. In certain embodiments, at least one $R^{Xa}$ is —S(=O)$_2$NH($C_{1-6}$alkyl).

In compounds of Formula (I), $R^X$ may be substituted with one or more $R^{Xc}$ groups. Each instance of $R^{Xc}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —O$R^{A1}$, —N($R^{A1}$)$_2$, —S$R^{A1}$, —CN, —C(=O)$R^{A1}$, —C(=O)O$R^{A1}$, —C(=O)N($R^{A1}$)$_2$, —NO$_2$, —N$_3$, —$NR^{A1}$C(=O)$R^{A1}$, —$NR^{A1}$C(=O)O$R^{A1}$, —$NR^{A1}$C(=O)N($R^{A1}$)$_2$, —$NR^{A1}$S(=O)$_2$$R^{A1}$, —$NR^{A1}$S(=O)$R^{A1}$, —OC(=O)$R^{A1}$, —OC(=O)O$R^{A1}$, —OC(=O)N($R^{A1}$)$_2$, —S(=O)$R^{A1}$, —S(=O)N($R^{A1}$)$_2$, —S(=O)$_2$$R^{A1}$, —S(=O)$_2$N($R^{A1}$)$_2$; wherein each occurrence of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A1}$ groups are joined to form an optionally substituted heterocyclic ring.

In certain embodiments, at least one $R^{Xc}$ is H. In certain embodiments, all $R^{Xc}$ groups are H. In certain embodiments, at least one $R^{Xc}$ is substituted alkyl. In certain embodiments, at least one $R^{Xc}$ is substituted $C_{1-6}$ alkyl. In certain embodiments, at least one $R^{Xc}$ is substituted methyl. In certain embodiments, at least one $R^{Xc}$ is unsubstituted alkyl. In certain embodiments, at least one $R^{Xc}$ is unsubstituted $C_{1-6}$ alkyl. In certain embodiments, at least one $R^{Xc}$ is methyl. In certain embodiments, at least one $R^{Xc}$ is ethyl. In certain embodiments, at least one $R^{Xc}$ is propyl. In certain embodiments, at least one $R^{Xc}$ is butyl. In certain embodiments, at least one $R^{Xc}$ is substituted alkenyl. In certain embodiments, at least one $R^{Xc}$ is unsubstituted alkenyl. In certain embodiments, at least one $R^{Xc}$ is substituted alkynyl. In certain embodiments, at least one $R^{Xc}$ is unsubstituted alkynyl. In certain embodiments, at least one $R^{Xc}$ is substituted carbocyclyl. In certain embodiments, at least one $R^{Xc}$ is unsubstituted carbocyclyl. In certain embodiments, at least one $R^{Xc}$ is substituted heterocyclyl. In certain embodiments, at least one $R^{Xc}$ is unsubstituted heterocyclyl. In certain embodiments, at least one $R^{Xc}$ is substituted aryl. In certain embodiments, at least one $R^{Xc}$ is unsubstituted aryl. In certain embodiments, at least one $R^{Xc}$ is substituted phenyl. In certain embodiments, at least one $R^{Xc}$ is unsubstituted phenyl. In certain embodiments, at least one $R^{Xc}$ is substituted heteroaryl. In certain embodiments, at least one $R^{Xc}$ is unsubstituted heteroaryl. In certain embodiments, at least one $R^{Xc}$ is —O$R^{A1}$. In certain embodiments, at least one $R^{Xc}$ is —OH. In certain embodiments, at least one $R^{Xc}$ is —O($C_{1-6}$alkyl). In certain embodiments, at least one $R^{Xc}$ is —N($R^{A1}$)$_2$. In certain embodiments, at least one $R^{Xc}$ is —NH($R^{A1}$). In certain embodiments, at least one $R^{Xc}$ is —N($C_{1-6}$alkyl)$_2$. In certain embodiments, at least one $R^{Xc}$ is —NH($C_{1-6}$alkyl). In certain embodiments, at least one $R^{Xc}$ is —NH$_2$. In certain embodiments, at least one $R^{Xc}$ is —S$R^{A1}$. In certain embodiments, at least one $R^{Xc}$ is —SH. In certain embodiments, at least one $R^{Xc}$ is —S($C_{1-6}$alkyl). In certain embodiments, at least one $R^{Xc}$ is —CN. In certain embodiments, at least one $R^{Xc}$ is —NO$_2$. In certain embodiments, at least one $R^{Xc}$ is —N$_3$. In certain embodiments, at least one $R^{Xc}$ is —$NR^{A1}$C(=O)$R^{A1}$. In certain embodiments, at least one $R^{Xc}$ is —NHC(=O)$R^{A1}$. In certain embodiments, at least one $R^{Xc}$ is —NHC(=O)($C_{1-6}$alkyl). In certain embodiments, at least one $R^{Xc}$ is —$NR^{A1}$C(=O)O$R^{A1}$ In certain embodiments, at least one $R^{Xc}$ is —NHC (=O)OR$^{A1}$. In certain embodiments, at least one R$^{Xc}$ is —NR$^{A1}$C(=O)O(C$_{1-6}$alkyl). In certain embodiments, at least one R$^{Xc}$ is —NR$^{A1}$C(=O)N(R$^{A1}$)$_2$. In certain embodiments, at least one R$^{Xc}$ is —NHC(=O)N(C$_{1-6}$alkyl)$_2$. In certain embodiments, at least one R$^{Xc}$ is —NHC(=O)NH$_2$. In certain embodiments, at least one R$^{Xc}$ is —NR$^{A1}$S(=O)$_2$R$^{A1}$. In certain embodiments, at least one R$^{Xc}$ is —NHS(=O)$_2$R$^{A1}$. In certain embodiments, at least one R$^{Xc}$ is —NHS(=O)$_2$(C$_{1-6}$alkyl). In certain embodiments, at least one R$^{Xc}$ is —NR$^{A1}$S(=O)R$^{A1}$. In certain embodiments, at least one R$^{Xc}$ is —NR$^{A1}$S(=O)(C$_{1-6}$alkyl). In certain embodiments, at least one R$^{Xc}$ is —NHS(=O)(C$_{1-6}$alkyl). In certain embodiments, at least one R$^{Xc}$ is —OC(=O)R$^{A1}$. In certain embodiments, at least one R$^{Xc}$ is —OC(=O)(C$_{1-6}$alkyl). In certain embodiments, at least one R$^{Xc}$ is —OC(=O)OR$^{A1}$. In certain embodiments, at least one R$^{Xc}$ is —OC(=O)O(C$_{1-6}$alkyl). In certain embodiments, at least one R$^{Xc}$ is —OC(=O)N(R$^{A1}$)$_2$. In certain embodiments, at least one R$^{Xc}$ is —OC(=O)NH(R$^{A1}$). In certain embodiments, at least one R$^{Xc}$ is —OC(=O)N(C$_{1-6}$alkyl)$_2$. In certain embodiments, at least one R$^{Xc}$ is —C(=O)R$^{A1}$. In certain embodiments, at least one R$^{Xc}$ is —C(=O)H. In certain embodiments, at least one R$^{Xc}$ is acetyl. In certain embodiments, at least one R$^{Xc}$ is —C(=O)(C$_{1-6}$alkyl). In certain embodiments, at least one R$^{Xc}$ is —C(=O)OR$^{A1}$. In certain embodiments, at least one R$^{Xc}$ is —C(=O)OH. In certain embodiments, at least one R$^{Xc}$ is —C(=O)O(C$_{1-6}$alkyl). In certain embodiments, at least one R$^{Xc}$ is —C(=O)N(R$^{A1}$)$_2$. In certain embodiments, at least one R$^{Xc}$ is —C(=O)NHR$^{A1}$. In certain embodiments, at least one R$^{Xc}$ is —C(=O)N(C$_{1-6}$ alkyl)$_2$. In certain embodiments, at least one R$^{Xc}$ is —C(=O)NH(C$_{1-6}$ alkyl). In certain embodiments, at least one R$^{Xc}$ is —C(=O)NH$_2$. In certain embodiments, at least one R$^{Xc}$ is —S(=O)R$^{A1}$. In certain embodiments, at least one R$^{Xc}$ is —S(=O)(C$_{1-6}$alkyl). In certain embodiments, at least one R$^{Xc}$ is —S(=O)N(R$^{A1}$)$_2$. In certain embodiments, at least one R$^{Xc}$ is —S(=O)NH(R$^{A1}$). In certain embodiments, at least one R$^{Xc}$ is —S(=O)NH$_2$. In certain embodiments, at least one R$^{Xc}$ is —S(=O)N(C$_{1-6}$alkyl)$_2$. In certain embodiments, at least one R$^{Xc}$ is —S(=O)NH(C$_{1-6}$alkyl). In certain embodiments, at least one R$^{Xc}$ is —S(=O)$_2$R$^{A1}$. In certain embodiments, at least one R$^{Xc}$ is —S(=O)$_2$(C$_{1-6}$alkyl). In certain embodiments, at least one R$^{Xc}$ is —S(=O)$_2$OR$^{A1}$. In certain embodiments, at least one R$^{Xc}$ is —S(=O)$_2$OH. In certain embodiments, at least one R$^{Xc}$ is —S(=O)$_2$N(R$^{A1}$)$_2$. In certain embodiments, at least one R$^{Xc}$ is —S(=O)$_2$NH(R$^{A1}$). In certain embodiments, at least one R$^{Xc}$ is —S(=O)$_2$NH$_2$. In certain embodiments, at least one R$^{Xc}$ is —S(=O)$_2$N(C$_{1-6}$alkyl)$_2$. In certain embodiments, at least one R$^{Xc}$ is —S(=O)$_2$NH(C$_{1-6}$alkyl).

In compounds of Formula (I), R$^D$ is an optional electrophilic moiety that is attached to the pyridyl ring. In certain embodiments, R$^D$ is any one of Formulae (i-1)-(i-18):

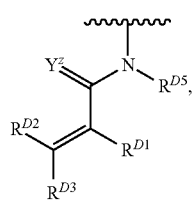
(i-1)

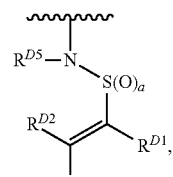
(i-2)

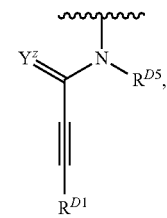
(i-3)

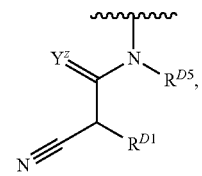
(i-4)

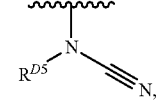
(i-5)

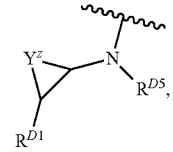
(i-6)

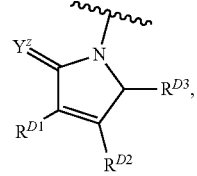
(i-7)

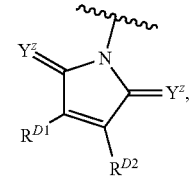
(i-8)

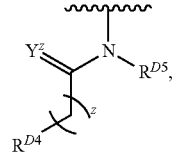
(i-9)

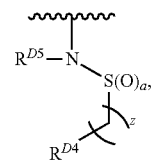
(i-10)

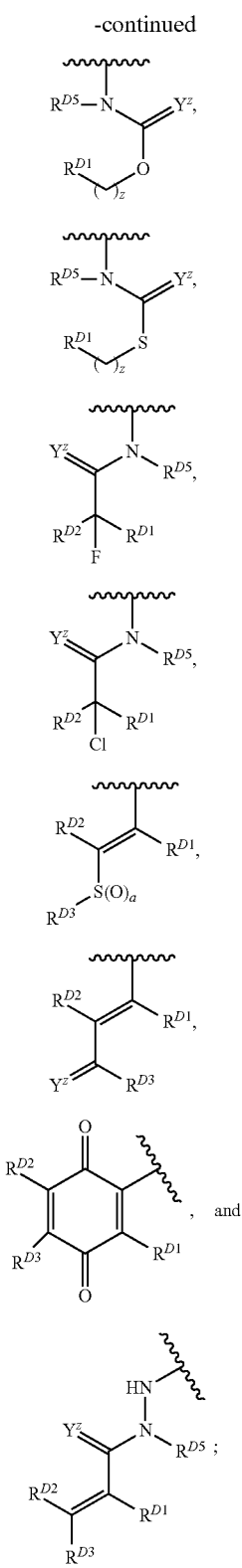

$R^{D1}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, —C(=S)R$^{D1a}$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)SR$^{D1a}$, and —C(=NR$^{D1a}$)N(R$^{D1a}$)$_2$, wherein each occurrence of R$^{D1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D1a}$ groups are joined to form an optionally substituted heterocyclic ring;

R$^{D2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D2a}$, —N(R$^{D2a}$)$_2$, —SR$^{D2a}$, —CH$_2$OR$^{D2a}$, —CH$_2$N(R$^{D2a}$)$_2$, —CH$_2$SR$^{D2a}$, —C(=O)R$^{D2a}$, —C(=O)OR$^{D2a}$, —C(=O)SR$^{D2a}$, —C(=O)N(R$^{D2a}$)$_2$, —C(=S)R$^{D2a}$, —C(=S)OR$^{D2a}$, —C(=S)SR$^{D2a}$, —C(=S)N(R$^{D2a}$)$_2$, —C(=NR$^{D2a}$)R$^{D2a}$, —C(=NR$^{D2a}$)OR$^{D2a}$, —C(=NR$^{D2a}$)SR$^{D2a}$, and —C(=NR$^{D2a}$)N(R$^{D2a}$)$_2$, wherein each occurrence of R$^{D2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D2a}$ groups are joined to form an optionally substituted heterocyclic ring;

R$^{D3}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D3a}$, —N(R$^{D3a}$)$_2$, —SR$^{D3a}$, —CH$_2$OR$^{D3a}$, —CH$_2$N(R$^{D3a}$)$_2$, —CH$_2$SR$^{D3a}$, —C(=O)R$^{D3a}$, —C(=O)OR$^{D3a}$, —C(=O)SR$^{D3a}$, —C(=O)N(R$^{D3a}$)$_2$, —C(=S)R$^{D3a}$, —C(=S)OR$^{D3a}$, —C(=S)SR$^{D3a}$, —C(=S)N(R$^{D3a}$)$_2$, —C(=NR$^{D3a}$)R$^{D3a}$, —C(=NR$^{D3a}$)OR$^{D3a}$, —C(=NR$^{D3a}$)SR$^{D3a}$, and —C(=NR$^{D3a}$)N(R$^{D3a}$)$_2$, wherein each occurrence of R$^{D3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D3a}$ groups are joined to form an optionally substituted heterocyclic ring;

optionally R$^{D1}$ and R$^{D3}$, or R$^{D2}$ and R$^{D3}$, or R$^{D1}$ and R$^{D2}$ are joined to form an optionally substituted carbocyclic or optionally substituted heterocyclic ring;

R$^{D4}$ is a leaving group;

R$^{D5}$ is hydrogen, C$_{1-6}$ alkyl, or a nitrogen protecting group;

Y$^Z$ is —O—, —S—, or —NR$^{D6}$—, wherein R$^{D6}$ is hydrogen, C$_{1-6}$ alkyl, or a nitrogen protecting group;

a is 1 or 2;

z is 0, 1, 2, 3, 4, 5, or 6; and optionally R$^{D5}$ and one R$^C$ are joined to form an optionally substituted heterocyclic ring.

In certain embodiments, R$^D$ comprises a Michael acceptor moiety. This Michael acceptor moiety may react with a cysteine or other nucleophilic residue to allow covalent attachment of the compound to the target. In certain embodiments, the covalent attachment is irreversible. In other embodiments, the covalent attachment is reversible. In certain embodiments, $R^D$ is of Formula (i-1). In certain embodiments, $R^D$ is of Formula (i-2). In certain embodiments, $R^D$ is of Formula (i-3). In certain embodiments, $R^D$ is of Formula (i-4). In certain embodiments, $R^D$ is of Formula (i-5). In certain embodiments, $R^D$ is of Formula (i-6). In certain embodiments, $R^D$ is of Formula (i-7). In certain embodiments, $R^D$ is of Formula (i-8). In certain embodiments, $R^D$ is of Formula (i-9). In certain embodiments, $R^D$ is of Formula (i-10). In certain embodiments, $R^D$ is of Formula (i-1). In certain embodiments, $R^D$ is of Formula (i-12). In certain embodiments, $R^D$ is of Formula (i-13). In certain embodiments, $R^D$ is of Formula (i-14). In certain embodiments, $R^D$ is of Formula (i-15). In certain embodiments, $R^D$ is of Formula (i-16). In certain embodiments, $R^D$ is of Formula (i-17).

In compounds of Formula (I), $R^D$ may include a substituent $R^{D1}$. In certain embodiments, $R^{D1}$ is H. In certain embodiments, $R^{D1}$ is halogen. In certain embodiments, $R^{D1}$ is F. In certain embodiments, $R^{D1}$ is Cl. In certain embodiments, $R^{D1}$ is Br. In certain embodiments, $R^{D1}$ is I (iodine). In certain embodiments, $R^{D1}$ is substituted acyl. In certain embodiments, $R^{D1}$ is unsubstituted acyl. In certain embodiments, $R^{D1}$ is acetyl. In certain embodiments, $R^{D1}$ is substituted alkyl. In certain embodiments, $R^{D1}$ is unsubstituted alkyl. In certain embodiments, $R^{D1}$ is $C_{1-6}$ alkyl. In certain embodiments, $R^{D1}$ is methyl. In certain embodiments, $R^{D1}$ is ethyl. In certain embodiments, $R^{D1}$ is propyl. In certain embodiments, $R^{D1}$ is butyl. In certain embodiments, $R^{D1}$ is substituted alkenyl. In certain embodiments, $R^{D1}$ is unsubstituted alkenyl. In certain embodiments, $R^{D1}$ is substituted alkynyl. In certain embodiments, $R^{D1}$ is unsubstituted alkynyl. In certain embodiments, $R^{D1}$ is substituted carbocyclyl. In certain embodiments, $R^{D1}$ is unsubstituted carbocyclyl. In certain embodiments, $R^{D1}$ is substituted heterocyclyl. In certain embodiments, $R^{D1}$ is unsubstituted heterocyclyl. In certain embodiments, $R^{D1}$ is substituted aryl. In certain embodiments, $R^{D1}$ is unsubstituted aryl. In certain embodiments, $R^{D1}$ is substituted phenyl. In certain embodiments, $R^{D1}$ is unsubstituted phenyl. In certain embodiments, $R^{D1}$ is substituted heteroaryl. In certain embodiments, $R^{D1}$ is unsubstituted heteroaryl. In certain embodiments, $R^{D1}$ is substituted pyridyl. In certain embodiments, $R^{D1}$ is unsubstituted pyridyl. In certain embodiments, $R^{D1}$ is —CN. In certain embodiments, $R^{D1}$ is —NO$_2$. In certain embodiments, $R^{D1}$ is —OR$^{D1a}$. In certain embodiments, $R^{D1}$ is —N(R$^{D1a}$)$_2$. In certain embodiments, $R^{D1}$ is —SR$^{D1a}$. In certain embodiments, $R^{D1}$ is —CH$_2$OR$^{D1a}$. In certain embodiments, $R^{D1}$ is —CH$_2$N(R$^{D1a}$)$_2$. In certain embodiments, $R^{D1}$ is —CH$_2$SR$^{D1a}$.

In certain embodiments, at least one $R^{D1a}$ is H. In certain embodiments, at least one $R^{D1a}$ is substituted acyl. In certain embodiments, at least one $R^{D1a}$ is unsubstituted acyl. In certain embodiments, at least one $R^{D1a}$ is acetyl. In certain embodiments, at least one $R^{D1a}$ is substituted alkyl. In certain embodiments, at least one $R^{D1a}$ is unsubstituted alkyl. In certain embodiments, at least one $R^{D1a}$ is $C_{1-6}$ alkyl. In certain embodiments, at least one $R^{D1a}$ is methyl. In certain embodiments, at least one $R^{D1a}$ is ethyl. In certain embodiments, at least one $R^{D1a}$ is propyl. In certain embodiments, at least one $R^{D1a}$ is butyl. In certain embodiments, at least one $R^{D1a}$ is substituted alkenyl. In certain embodiments, at least one $R^{D1a}$ is unsubstituted alkenyl. In certain embodiments, at least one $R^{D1a}$ is substituted alkynyl. In certain embodiments, at least one $R^{D1a}$ is unsubstituted alkynyl. In certain embodiments, at least one $R^{D1a}$ is substituted carbocyclyl. In certain embodiments, at least one $R^{D1a}$ is unsubstituted carbocyclyl. In certain embodiments, at least one $R^{D1a}$ is substituted heterocyclyl. In certain embodiments, at least one $R^{D1a}$ is unsubstituted heterocyclyl. In certain embodiments, at least one $R^{D1a}$ is substituted aryl. In certain embodiments, at least one $R^{D1a}$ is unsubstituted aryl. In certain embodiments, at least one $R^{D1a}$ is substituted phenyl. In certain embodiments, at least one $R^{D1a}$ is unsubstituted phenyl. In certain embodiments, at least one $R^{D1}$ is substituted heteroaryl. In certain embodiments, at least one $R^{D1a}$ is unsubstituted heteroaryl. In certain embodiments, at least one $R^{D1a}$ is substituted pyridyl. In certain embodiments, at least one $R^{D1a}$ is unsubstituted pyridyl. In certain embodiments, at least one $R^{D1a}$ is a nitrogen protecting group when attached to a nitrogen atom. In certain embodiments, at least one $R^{D1a}$ is Bn, BOC, Cbz, Fmoc, trifluoroacetyl, triphenylmethyl, or Ts when attached to a nitrogen atom. In certain embodiments, $R^{D1a}$ is an oxygen protecting group when attached to an oxygen atom. In certain embodiments, $R^{D1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1a}$ is a sulfur protecting group when attached to a sulfur atom. In certain embodiments, $R^{D1a}$ is acetamidomethyl, t-Bu, 3-nitro-2-pyridine sulfenyl, 2-pyridine-sulfenyl, or triphenylmethyl when attached to a sulfur atom. In certain embodiments, two $R^{D1a}$ groups are joined to form a substituted heterocyclic ring. In certain embodiments, two $R^{D1a}$ groups are joined to form an unsubstituted heterocyclic ring.

In compounds of Formula (I), $R^D$ may include a substituent $R^{D2}$. In certain embodiments, $R^{D2}$ is H. In certain embodiments, $R^{D2}$ is halogen. In certain embodiments, $R^{D2}$ is F. In certain embodiments, $R^{D2}$ is Cl. In certain embodiments, $R^{D2}$ is Br. In certain embodiments, $R^{D2}$ is I (iodine). In certain embodiments, $R^{D2}$ is substituted acyl. In certain embodiments, $R^{D2}$ is unsubstituted acyl. In certain embodiments, $R^{D2}$ is acetyl. In certain embodiments, $R^{D2}$ is substituted alkyl. In certain embodiments, $R^{D2}$ is unsubstituted alkyl. In certain embodiments, $R^{D2}$ is $C_{1-6}$ alkyl. In certain embodiments, $R^{D2}$ is methyl. In certain embodiments, $R^{D2}$ is ethyl. In certain embodiments, $R^{D2}$ is propyl. In certain embodiments, $R^{D2}$ is butyl. In certain embodiments, $R^{D2}$ is substituted alkenyl. In certain embodiments, $R^{D2}$ is unsubstituted alkenyl. In certain embodiments, $R^{D2}$ is substituted alkynyl. In certain embodiments, $R^{D2}$ is unsubstituted alkynyl. In certain embodiments, $R^{D2}$ is substituted carbocyclyl. In certain embodiments, $R^{D2}$ is unsubstituted carbocyclyl. In certain embodiments, $R^{D2}$ is substituted heterocyclyl. In certain embodiments, $R^{D2}$ is unsubstituted heterocyclyl. In certain embodiments, $R^{D2}$ is substituted aryl. In certain embodiments, $R^{D2}$ is unsubstituted aryl. In certain embodiments, $R^{D2}$ is substituted phenyl. In certain embodiments, $R^{D2}$ is unsubstituted phenyl. In certain embodiments, $R^{D2}$ is substituted heteroaryl. In certain embodiments, $R^{D2}$ is unsubstituted heteroaryl. In certain embodiments, $R^{D2}$ is substituted pyridyl. In certain embodiments, $R^{D2}$ is unsubstituted pyridyl. In certain embodiments, $R^{D2}$ is —CN. In certain embodiments, $R^{D2}$ is —NO$_2$. In certain embodiments, $R^{D2}$ is —OR$^{D2a}$. In certain embodiments, $R^{D2}$ is —N(R$^{D2a}$)$_2$. In certain embodiments, $R^{D2}$ is —SR$^{D2a}$. In certain embodiments, $R^{D2}$ is —CH$_2$OR$^{D2a}$. In certain embodiments, $R^{D2}$ is —CH$_2$N(R$^{D2a}$)$_2$. In certain embodiments, $R^{D2}$ is —CH$_2$SR$^{D2a}$.

In certain embodiments, at least one $R^{D2a}$ is H. In certain embodiments, at least one $R^{D2a}$ is substituted acyl. In certain embodiments, at least one $R^{D2a}$ is unsubstituted acyl. In certain embodiments, at least one $R^{D2a}$ is acetyl. In certain embodiments, at least one $R^{D2a}$ is substituted alkyl. In certain embodiments, at least one $R^{D2a}$ is unsubstituted alkyl. In certain embodiments, at least one $R^{D2a}$ is $C_{1-6}$ alkyl. In certain embodiments, at least one $R^{D2a}$ is methyl. In certain embodiments, at least one $R^{D2a}$ is ethyl. In certain embodiments, at least one $R^{D2a}$ is propyl. In certain embodiments, at least one $R^{D2a}$ is butyl. In certain embodiments, at least one $R^{D2a}$ is substituted alkenyl. In certain embodiments, at least one $R^{D2a}$ is unsubstituted alkenyl. In certain embodiments, at least one $R^{D2a}$ is substituted alkynyl. In certain embodiments, at least one $R^{D2a}$ is unsubstituted alkynyl. In certain embodiments, at least one $R^{D2a}$ is substituted carbocyclyl. In certain embodiments, at least one $R^{D2a}$ is unsubstituted carbocyclyl. In certain embodiments, at least one $R^{D2a}$ is substituted heterocyclyl. In certain embodiments, at least one $R^{D2a}$ is unsubstituted heterocyclyl. In certain embodiments, at least one $R^{D2a}$ is substituted aryl. In certain embodiments, at least one $R^{D2a}$ is unsubstituted aryl. In certain embodiments, at least one $R^{D2a}$ is substituted phenyl. In certain embodiments, at least one $R^{D2a}$ is unsubstituted phenyl. In certain embodiments, at least one $R^{D2a}$ is substituted heteroaryl. In certain embodiments, at least one $R^{D2a}$ is unsubstituted heteroaryl. In certain embodiments, at least one $R^{D2a}$ is substituted pyridyl. In certain embodiments, at least one $R^{D2a}$ is unsubstituted pyridyl. In certain embodiments, at least one $R^{D2a}$ is a nitrogen protecting group when attached to a nitrogen atom. In certain embodiments, at least one $R^{D2a}$ is Bn, BOC, Cbz, Fmoc, trifluoroacetyl, triphenylmethyl, or Ts when attached to a nitrogen atom. In certain embodiments, $R^{D2a}$ is an oxygen protecting group when attached to an oxygen atom. In certain embodiments, $R^{D2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D2a}$ is a sulfur protecting group when attached to a sulfur atom. In certain embodiments, $R^{D2a}$ is acetamidomethyl, t-Bu, 3-nitro-2-pyridine sulfenyl, 2-pyridine-sulfenyl, or triphenylmethyl when attached to a sulfur atom. In certain embodiments, two $R^{D2a}$ groups are joined to form a substituted heterocyclic ring. In certain embodiments, two $R^{D2a}$ groups are joined to form an unsubstituted heterocyclic ring.

In compounds of Formula (I), $R^D$ may include a substituent $R^{D3}$. In certain embodiments, $R^{D3}$ is H. In certain embodiments, $R^{D3}$ is halogen. In certain embodiments, $R^{D3}$ is F. In certain embodiments, $R^{D3}$ is C. In certain embodiments, $R^{D3}$ is Br. In certain embodiments, $R^{D3}$ is I (iodine). In certain embodiments, $R^{D3}$ is substituted acyl. In certain embodiments, $R^{D3}$ is unsubstituted acyl. In certain embodiments, $R^{D3}$ is acetyl. In certain embodiments, $R^{D3}$ is substituted alkyl. In certain embodiments, $R^{D3}$ is unsubstituted alkyl. In certain embodiments, $R^{D3}$ is $C_{1-6}$ alkyl. In certain embodiments, $R^{D3}$ is methyl. In certain embodiments, $R^{D3}$ is ethyl. In certain embodiments, $R^{D3}$ is propyl. In certain embodiments, $R^{D3}$ is butyl. In certain embodiments, $R^{D3}$ is substituted alkenyl. In certain embodiments, $R^{D3}$ is unsubstituted alkenyl. In certain embodiments, $R^{D3}$ is substituted alkynyl. In certain embodiments, $R^{D3}$ is unsubstituted alkynyl. In certain embodiments, $R^{D3}$ is substituted carbocyclyl. In certain embodiments, $R^{D3}$ is unsubstituted carbocyclyl. In certain embodiments, $R^{D3}$ is substituted heterocyclyl. In certain embodiments, $R^{D3}$ is unsubstituted heterocyclyl. In certain embodiments, $R^{D3}$ is substituted aryl. In certain embodiments, $R^{D3}$ is unsubstituted aryl. In certain embodiments, $R^{D3}$ is substituted phenyl. In certain embodiments, $R^{D3}$ is unsubstituted phenyl. In certain embodiments, $R^{D3}$ is substituted heteroaryl. In certain embodiments, $R^{D3}$ is unsubstituted heteroaryl. In certain embodiments, $R^{D3}$ is substituted pyridyl. In certain embodiments, $R^{D3}$ is unsubstituted pyridyl. In certain embodiments, $R^{D3}$ is —CN. In certain embodiments, $R^{D3}$ is —$NO_2$. In certain embodiments, $R^{D3}$ is —$OR^{D3a}$. In certain embodiments, $R^{D3}$ is —$N(R^{D3a})_2$. In certain embodiments, $R^{D3}$ is —$SR^{D3a}$. In certain embodiments, $R^D$ is —$CH_2OR^{D3a}$. In certain embodiments, $R^{D3}$ is —$CH_2N(R^{D3a})_2$. In certain embodiments, $R^{D3}$ is —$CH_2SR^{D3a}$.

In certain embodiments, at least one $R^{D1a}$ is H. In certain embodiments, at least one $R^{D3a}$ is substituted acyl. In certain embodiments, at least one $R^{D3a}$ is unsubstituted acyl. In certain embodiments, at least one $R^{D3a}$ is acetyl. In certain embodiments, at least one $R^{D3a}$ is substituted alkyl. In certain embodiments, at least one $R^{D3a}$ is unsubstituted alkyl. In certain embodiments, at least one $R^{D3a}$ is $C_{1-6}$ alkyl. In certain embodiments, at least one $R^{D3a}$ is methyl. In certain embodiments, at least one $R^{D3a}$ is ethyl. In certain embodiments, at least one $R^{D3a}$ is propyl. In certain embodiments, at least one $R^{D3a}$ is butyl. In certain embodiments, at least one $R^{D3a}$ is substituted alkenyl. In certain embodiments, at least one $R^{D3a}$ is unsubstituted alkenyl. In certain embodiments, at least one $R^{D3a}$ is substituted alkynyl. In certain embodiments, at least one $R^{D3a}$ is unsubstituted alkynyl. In certain embodiments, at least one $R^{D3a}$ is substituted carbocyclyl. In certain embodiments, at least one $R^{D3a}$ is unsubstituted carbocyclyl. In certain embodiments, at least one $R^{D3a}$ is substituted heterocyclyl. In certain embodiments, at least one $R^{D3a}$ is unsubstituted heterocyclyl. In certain embodiments, at least one $R^{D3a}$ is substituted aryl. In certain embodiments, at least one $R^{D3a}$ is unsubstituted aryl. In certain embodiments, at least one $R^{D3a}$ is substituted phenyl. In certain embodiments, at least one $R^{D3a}$ is unsubstituted phenyl. In certain embodiments, at least one $R^{D3a}$ is substituted heteroaryl. In certain embodiments, at least one $R^{D3a}$ is unsubstituted heteroaryl. In certain embodiments, at least one $R^{D3a}$ is substituted pyridyl. In certain embodiments, at least one $R^{D3a}$ is unsubstituted pyridyl. In certain embodiments, at least one $R^{D3a}$ is a nitrogen protecting group when attached to a nitrogen atom. In certain embodiments, at least one $R^{D3a}$ is Bn, BOC, Cbz, Fmoc, trifluoroacetyl, triphenylmethyl, or Ts when attached to a nitrogen atom. In certain embodiments, $R^{D3a}$ is an oxygen protecting group when attached to an oxygen atom. In certain embodiments, $R^{D3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D3a}$ is a sulfur protecting group when attached to a sulfur atom. In certain embodiments, $R^{D3a}$ is acetamidomethyl, t-Bu, 3-nitro-2-pyridine sulfenyl, 2-pyridine-sulfenyl, or triphenylmethyl when attached to a sulfur atom. In certain embodiments, two $R^{D3a}$ groups are joined to form a substituted heterocyclic ring. In certain embodiments, two $R^{D3a}$ groups are joined to form an unsubstituted heterocyclic ring.

In compounds of Formula (I), $R^D$ may include a substituent $R^{D4}$. In certain embodiments, $R^{D4}$ is a leaving group. In certain embodiments, $R^{D4}$ is halogen. In certain embodiments, $R^{D4}$ is F. In certain embodiments, $R^{D4}$ is Cl. In certain embodiments, $R^{D4}$ is Br. In certain embodiments, $R^{D4}$ is I (iodine). In certain embodiments, $R^{D4}$ is —$OS(=O)_wR^{D4a}$. In certain embodiments, w is 1. In certain embodiments, w is 2. In certain embodiments, $R^{D4}$ is —OMs. In certain embodiments, $R^{D4}$ is —OTf. In certain embodiments, $R^{D4}$ is —OTs. In certain embodiments, $R^{D4}$ is —OBs. In certain embodiments, $R^{D4}$ is 2-nitrobenzenesulfonyloxy. In certain embodiments, $R^{D4}$ is —$OR^{D4a}$. In certain embodiments, $R^{D4}$ is —OMe. In certain embodiments, $R^{D4}$ is —$OCF_3$. In certain embodiments, $R^{D4}$ is —OPh. In certain embodiments, $R^{D4}$ is —OC(=O)$R^{D4a}$. In certain embodiments, $R^{D4}$ is —OC(=O)Me. In certain embodiments, $R^{D4}$ is —OC(=O)$CF_3$. In certain embodiments, $R^{D4}$ is —OC(=O)Ph. In certain embodiments, $R^{D4}$ is —OC(=O)$C_1$. In certain embodiments, $R^{D4}$ is —OC(=O)$OR^{D4a}$. In certain embodiments, $R^{D4}$ is —OC(=O)OMe. In certain embodiments, $R^{D4}$ is —OC(=O)O(t-Bu).

In certain embodiments, $R^{D4a}$ is substituted alkyl. In certain embodiments, $R^{D4a}$ is unsubstituted alkyl. In certain embodiments, $R^{D4a}$ is $C_{1-6}$ alkyl. In certain embodiments, $R^{D4a}$ is methyl. In certain embodiments, $R^{D4a}$ is ethyl. In certain embodiments, $R^{D4a}$ is propyl. In certain embodiments, $R^{D4a}$ is butyl. In certain embodiments, $R^{D4a}$ is substituted alkenyl. In certain embodiments, $R^{D4a}$ is unsubstituted alkenyl. In certain embodiments, $R^{D4a}$ is vinyl. In certain embodiments, $R^{D4a}$ is substituted alkynyl. In certain embodiments, $R^{D4a}$ is unsubstituted alkynyl. In certain embodiments, $R^{D4a}$ is ethynyl. In certain embodiments, $R^{D4a}$ is substituted carbocyclyl. In certain embodiments, $R^{D4a}$ is unsubstituted carbocyclyl. In certain embodiments, $R^{D4a}$ is substituted heterocyclyl. In certain embodiments, $R^{D4a}$ is unsubstituted heterocyclyl. In certain embodiments, $R^{D4a}$ is substituted aryl. In certain embodiments, $R^{D4a}$ is unsubstituted aryl. In certain embodiments, $R^{D4a}$ is substituted phenyl. In certain embodiments, $R^{D4a}$ is unsubstituted phenyl. In certain embodiments, $R^{D4a}$ is substituted heteroaryl. In certain embodiments, $R^{D4a}$ is unsubstituted heteroaryl. In certain embodiments, $R^{D4a}$ is substituted pyridyl. In certain embodiments, $R^{D4a}$ is unsubstituted pyridyl.

In compounds of Formula (I), $R^D$ may include a substituent $R^{D5}$. In certain embodiments, $R^{D5}$ is H. In certain embodiments, $R^{D5}$ is substituted alkyl. In certain embodiments, $R^{D5}$ is unsubstituted alkyl. In certain embodiments, $R^{D5}$ is $C_{1-6}$ alkyl. In certain embodiments, $R^{D5}$ is methyl. In certain embodiments, $R^{D5}$ is ethyl. In certain embodiments, $R^{D5}$ is propyl. In certain embodiments, $R^{D5}$ is butyl. In certain embodiments, $R^{D5}$ is a nitrogen protecting group. In certain embodiments, $R^{D5}$ is Bn, BOC, Cbz, Fmoc, trifluoroacetyl, triphenylmethyl, or Ts.

In certain embodiments, $R^{D1}$ and $R^{D2}$ are each hydrogen. In certain embodiments, $R^{D1}$ and $R^{D3}$ are each hydrogen. In certain embodiments, $R^{D2}$ and $R^{D3}$ are each hydrogen. In certain embodiments, $R^{D1}$, $R^{D2}$, and $R^{D3}$ are each hydrogen. In certain embodiments, $R^{D1}$, $R^{D2}$, $R^{D3}$, and $R^{D5}$ are each hydrogen.

In certain embodiments, a is 1. In certain embodiments, a is 2.

In certain embodiments, z is 0. In certain embodiments, z is 1. In certain embodiments, z is 2. In certain embodiments, z is 3. In certain embodiments, z is 4. In certain embodiments, z is 5. In certain embodiments, z is 6.

In certain embodiments, Y is —O—. In certain embodiments, Y is —C(=O)—. In certain embodiments, Y is —S—. In certain embodiments, Y is —C(=S)—. In certain embodiments, Y is —$NR^{D6}$—, wherein $R^{D6}$ is hydrogen, $C_{1-6}$ alkyl, or a nitrogen protecting group. In certain embodiments, Y is —NH—. In certain embodiments, Y is —$NCH_3$—. In certain embodiments, Y is —N(BOC)—. In certain embodiments, Y is —N(Fmoc)-. In certain embodiments, Y is —N(Cbz)-. In certain embodiments, Y is —N(Bn)-. In certain embodiments, Y is —C(=$NR^{D6}$)—, wherein $R^{D6}$ is hydrogen, $C_{1-6}$ alkyl, or a nitrogen protecting group. In certain embodiments, Y is —C(=NH)—. In certain embodiments, Y is —C(=$NCH_3$)—. In certain embodiments, Y is —C(=NTs)-. In certain embodiments, Y is —C(=NBn)-. In certain embodiments, Y is —C(=NCH$(Ph)_2$)—.

In certain embodiments, $R^D$ is of the formula:

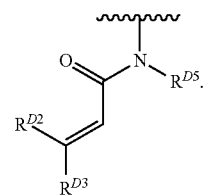

In certain embodiments, $R^D$ is of the formula:

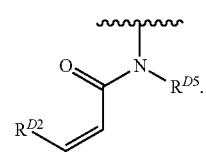

In certain embodiments, $R^D$ is of the formula:

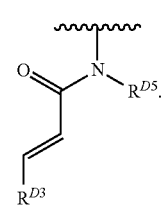

In certain embodiments, $R^D$ is of the formula:

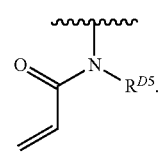

In certain embodiments, $R^D$ is of the formula:

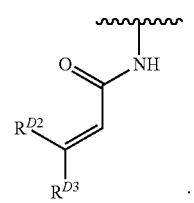

In certain embodiments, $R^D$ is of the formula:

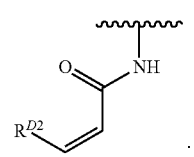

In certain embodiments, $R^D$ is of the formula:

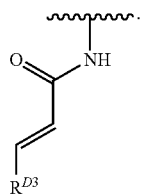

In certain embodiments, $R^D$ is of the formula:

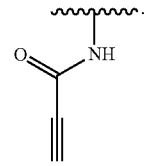

In certain embodiments, $R^D$ is of the formula:

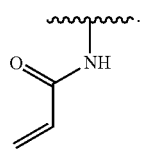

In certain embodiments, $R^D$ is of the formula:

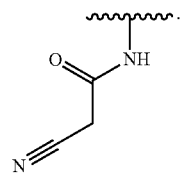

In certain embodiments, $R^D$ is of the formula:

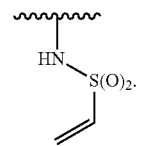

In certain embodiments, $R^D$ is of the formula:

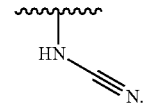

In certain embodiments, $R^D$ is of the formula:

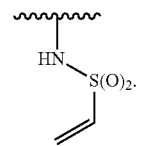

In certain embodiments, $R^D$ is of the formula:

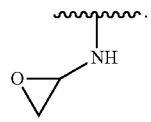

In certain embodiments, $R^D$ is of the formula:

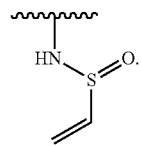 [SMILES: *NS(=O)C=C]

In certain embodiments, $R^D$ is of the formula:

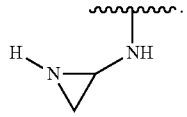

In certain embodiments, $R^D$ is of the formula:

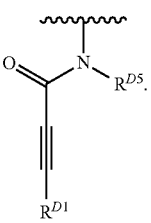

In certain embodiments, $R^D$ is of the formula:

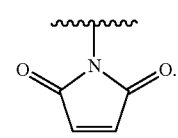

In certain embodiments, $R^D$ is of the formula:

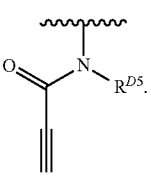

In certain embodiments, $R^D$ is of the formula:

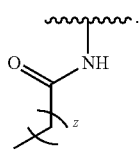

In certain embodiments, $R^D$ is of the formula:

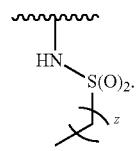

In certain embodiments, $R^D$ is of the formula:

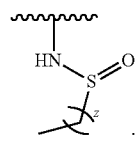

In certain embodiments, $R^D$ is of the formula:

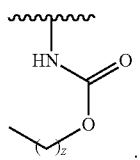

In certain embodiments, $R^D$ is of the formula:

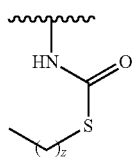

In certain embodiments, $R^D$ is of the formula:

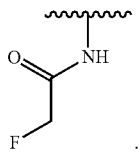

In certain embodiments, $R^D$ is of the formula:

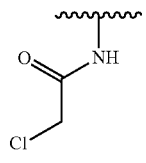

In certain embodiments, $R^D$ is of the formula:

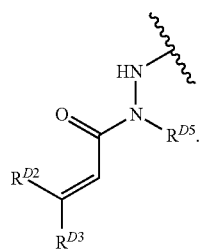

In certain embodiments, $R^D$ is of the formula:

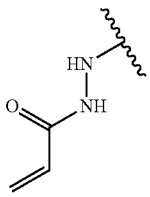

Various combinations of certain embodiments of Formula (I) are further contemplated herein.

For example, in certain embodiments, a compound of Formula (I) is a compound of Formula (I-a) or (I-b):

(I-a)

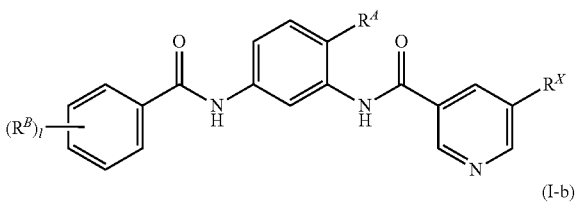

(I-b)

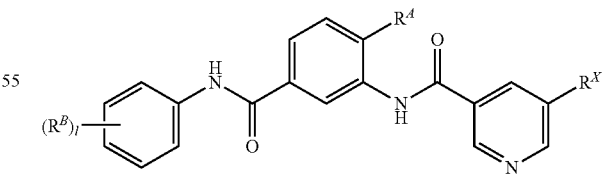

wherein $R^X$, $R^A$, $R^B$, and l are defined herein. In certain embodiments $R^A$ is substituted or unsubstituted $C_{1-6}$ alkyl. In certain embodiments, $R^A$ is methyl. In certain embodiments, l is 1. In certain embodiments, l is 1; and $R^B$ is meta to the point of attachment of the amide linker. In certain embodiments, l is 2. In certain embodiments, l is 2; and the two $R^B$ groups are meta to the point of attachment of the amide linker. In certain embodiments, l is 2; one $R^B$ group is meta to the point of attachment of the amide linker; and the second $R^B$ group is para to the point of attachment of the amide linker. In certain embodiments, one $R^B$ group is substituted or unsubstituted $C_{1-6}$alkyl. In certain embodiments, one $R^B$ group is $C_{1-6}$alkyl substituted with one —CN group. In certain embodiments, one $R^B$ group is

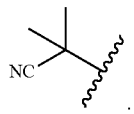

In certain embodiments, one $R^B$ group is substituted or unsubstituted —CH$_2$-(piperazinyl). In certain embodiments, one $R^B$ group is

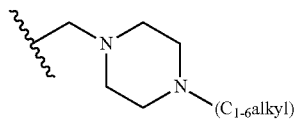

where the alkyl is optionally substituted. In certain embodiments, one $R^B$ group is

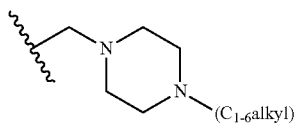

where the alkyl is unsubstituted. In certain embodiments, one $R^B$ group is

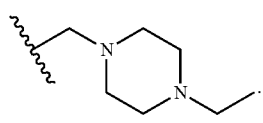 [SMILES: *CN1CCN(CC)CC1]

In certain embodiments, one $R^B$ group is haloalkyl. In certain embodiments, one $R^B$ group is —CF$_3$. In certain embodiments, one $R^B$ group is substituted or unsubstituted imidazoyl. In certain embodiments, one $R^B$ group is

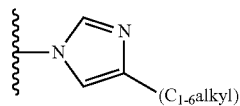

where the alkyl is optionally substituted. In certain embodiments, one $R^B$ group is

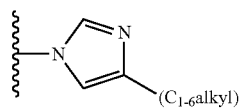

where the alkyl is unsubstituted. In certain embodiments, one $R^B$ group is

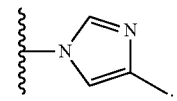

In certain embodiments, one $R^B$ group is substituted or unsubstituted piperazinyl. In certain embodiments, one $R^B$ group is

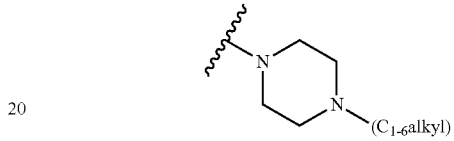

where there alkyl is optionally substituted. In certain embodiments, one $R^B$ group is

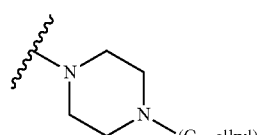

where there alkyl is unsubstituted. In certain embodiments, one $R^B$ group is

In certain embodiments, one $R^B$ group is substituted or unsubstituted morpholine. In certain embodiments, two $R^B$ groups are substituted or unsubstituted morpholine. In certain embodiments, $R^X$ is substituted or unsubstituted heteroaryl. In certain embodiments, $R^X$ is substituted or unsubstituted thiophene. In certain embodiments, $R^X$ is substituted or unsubstituted isoxazole. In certain embodiments, $R^X$ is substituted or unsubstituted pyrazole.

In certain embodiments, a compound of Formula (I-a) is a compound of Formula (I-a1), (I-a2), or (I-a3):

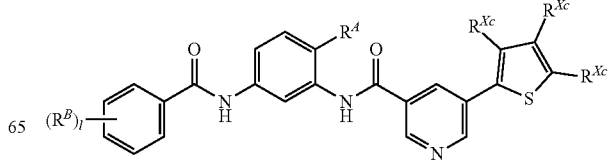

(I-a1)

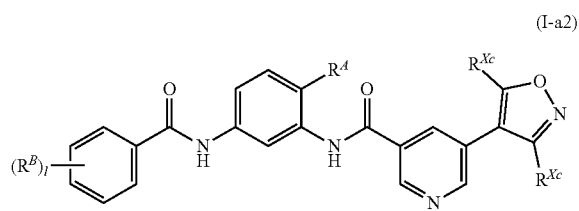
(I-a2)

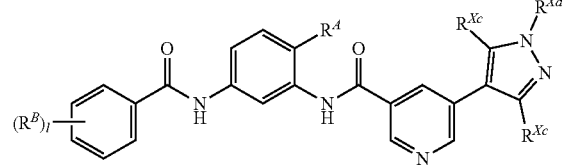
(I-a3)

wherein $R^{Xa}$, $R^{Xc}$, $R^A$, $R^B$, and l are defined herein. In certain embodiments $R^A$ is substituted or unsubstituted $C_{1-6}$ alkyl. In certain embodiments, $R^A$ is methyl. In certain embodiments, l is 1. In certain embodiments, l is 1; and $R^B$ is meta to the point of attachment of the amide linker. In certain embodiments, l is 2. In certain embodiments, l is 2; and the two $R^B$ groups are meta to the point of attachment of the amide linker. In certain embodiments, l is 2; one $R^B$ group is meta to the point of attachment of the amide linker; and the second $R^B$ group is para to the point of attachment of the amide linker. In certain embodiments, one $R^B$ group is substituted or unsubstituted $C_{1-6}$alkyl. In certain embodiments, one $R^B$ group is $C_{1-6}$alkyl substituted with one —CN group. In certain embodiments, one R group is

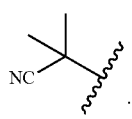 [SMILES: *C(C)(C)C#N]

In certain embodiments, one $R^B$ group is substituted or unsubstituted —CH$_2$-(piperazinyl). In certain embodiments, one $R^B$ group is

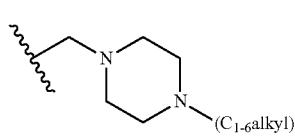

where the alkyl is optionally substituted. In certain embodiments, one $R^B$ group is

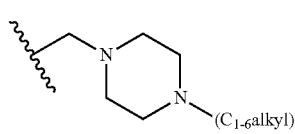

where the alkyl is unsubstituted. In certain embodiments, one $R^B$ group is

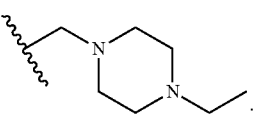 [SMILES: *CN1CCN(CC)CC1]

In certain embodiments, one $R^B$ group is haloalkyl. In certain embodiments, one $R^B$ group is —CF$_3$. In certain embodiments, one $R^B$ group is substituted or unsubstituted imidazoyl. In certain embodiments, one $R^B$ group is

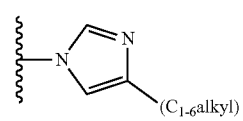

where the alkyl is optionally substituted. In certain embodiments, one $R^B$ group is

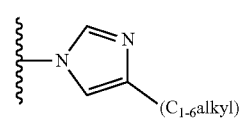

where the alkyl is unsubstituted. In certain embodiments, one $R^B$ group is

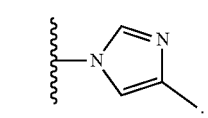 [SMILES: *n1cnc(C)c1]

In certain embodiments, one $R^B$ group is substituted or unsubstituted piperazinyl. In certain embodiments, one $R^B$ group is

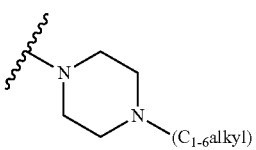

where there alkyl is optionally substituted. In certain embodiments, one $R^B$ group is

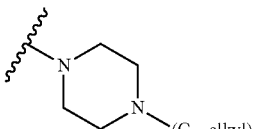

where there alkyl is unsubstituted. In certain embodiments, one $R^B$ group is

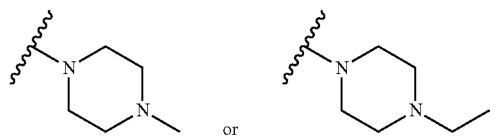 or 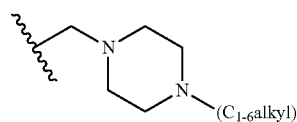

In certain embodiments, one $R^B$ group is substituted or unsubstituted morpholine. In certain embodiments, two $R^B$ groups are substituted or unsubstituted morpholine. In certain embodiments, all instances of $R^{Xc}$ are hydrogen. In certain embodiments, $R^{Xa}$ is substituted or unsubstituted $C_{1-6}$alkyl. In certain embodiments, $R^{Xa}$ is methyl or ethyl.

In certain embodiments, a compound of Formula (I-b) is a compound of Formula (I-b1), (I-b2), or (I-b3):

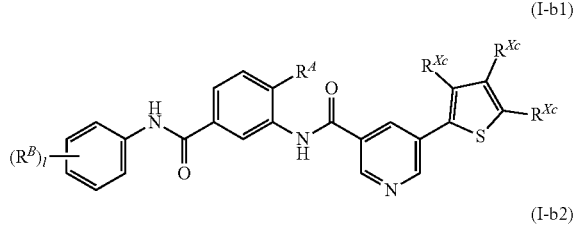

(I-b1)

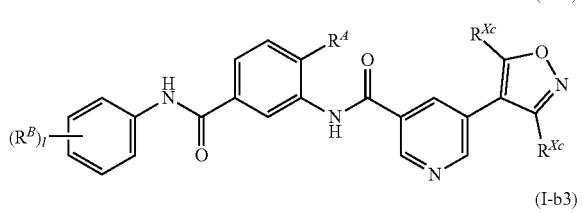

(I-b2)

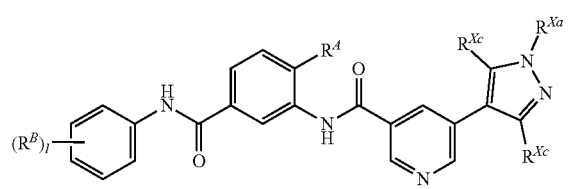

(I-b3)

wherein $R^{Xa}$, $R^{Xc}$, $R^A$, $R^B$, and l are defined herein. In certain embodiments $R^A$ is substituted or unsubstituted $C_{1-6}$ alkyl. In certain embodiments, $R^A$ is methyl. In certain embodiments, l is 1. In certain embodiments, l is 1; and $R^B$ is meta to the point of attachment of the amide linker. In certain embodiments, l is 2. In certain embodiments, l is 2; and the two $R^B$ groups are meta to the point of attachment of the amide linker. In certain embodiments, l is 2; one $R^B$ group is meta to the point of attachment of the amide linker; and the second $R^B$ group is para to the point of attachment of the amide linker. In certain embodiments, one $R^B$ group is substituted or unsubstituted $C_{1-6}$alkyl. In certain embodiments, one $R^B$ group is $C_{1-6}$alkyl substituted with one —CN group. In certain embodiments, one $R^B$ group is

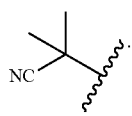

In certain embodiments, one $R^B$ group is substituted or unsubstituted —CH$_2$-(piperazinyl). In certain embodiments, one $R^B$ group is

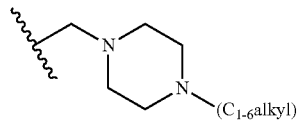

where the alkyl is optionally substituted. In certain embodiments, one $R^B$ group is

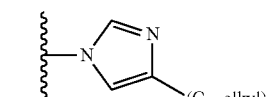

where the alkyl is unsubstituted. In certain embodiments, one $R^B$ group is

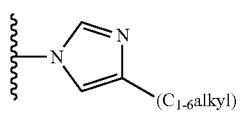

In certain embodiments, one $R^B$ group is haloalkyl. In certain embodiments, one $R^B$ group is —CF$_3$. In certain embodiments, one $R^B$ group is substituted or unsubstituted imidazoyl. In certain embodiments, one $R^B$ group is where the alkyl is optionally substituted. In certain embodiments, one $R^B$ group is where the alkyl is unsubstituted. In certain embodiments, one $R^B$ group is

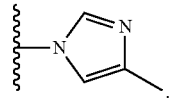

In certain embodiments, one $R^B$ group is substituted or unsubstituted piperazinyl. In certain embodiments, one $R^B$ group is

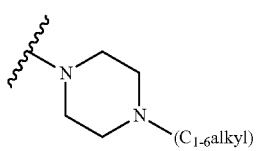

where there alkyl is optionally substituted. In certain embodiments, one R$^B$ group is

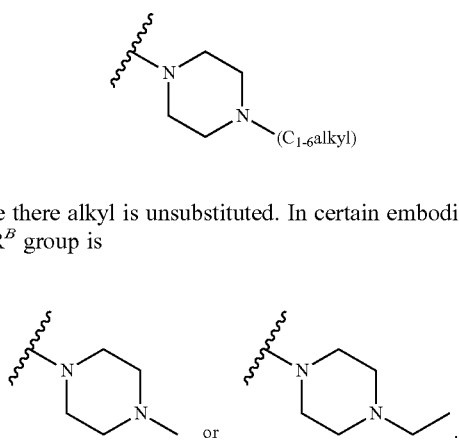

where there alkyl is unsubstituted. In certain embodiments, one R$^B$ group is

In certain embodiments, one R$^B$ group is substituted or unsubstituted morpholine. In certain embodiments, two R$^B$ groups are substituted or unsubstituted morpholine. In certain embodiments, all instances of R$^{Xc}$ are hydrogen. In certain embodiments, R$^{Xa}$ is substituted or unsubstituted C$_{1-6}$alkyl. In certain embodiments, R$^{Xa}$ is methyl or ethyl.

In certain embodiments, a compound of Formula (I-a) is a compound of Formula (I-a4)-(I-a12):

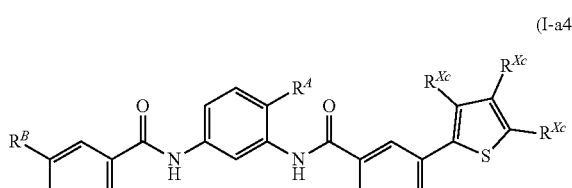

(I-a4)

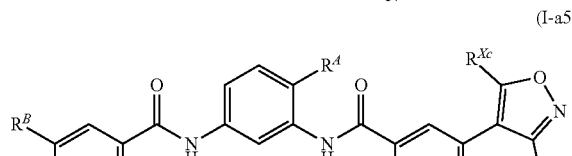

(I-a5)

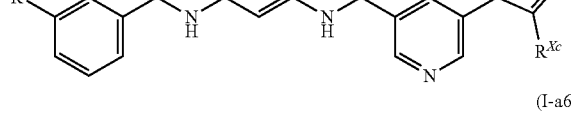

(I-a6)

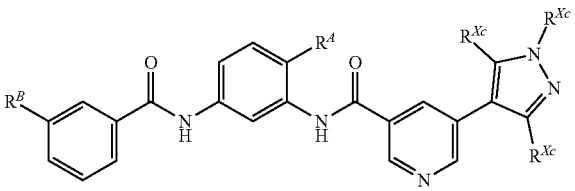

(I-a7)

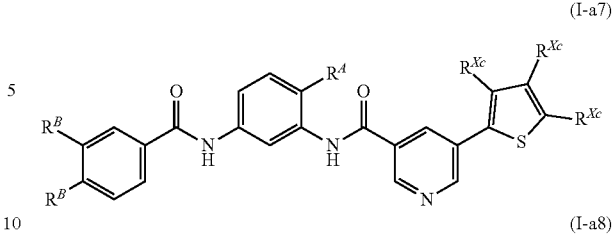

(I-a8)

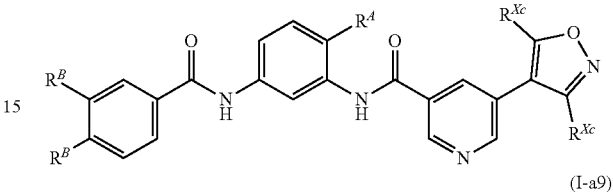

(I-a9)

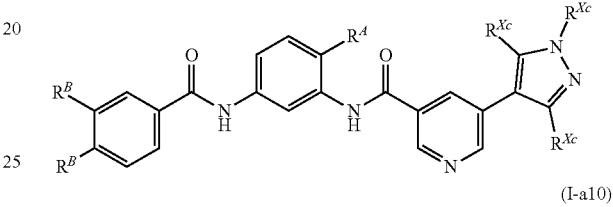

(I-a10)

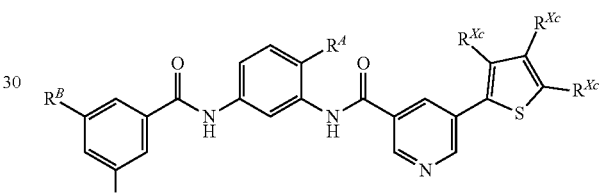

(I-a11)

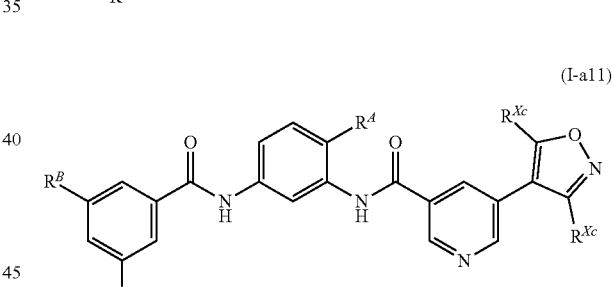

(I-a12)

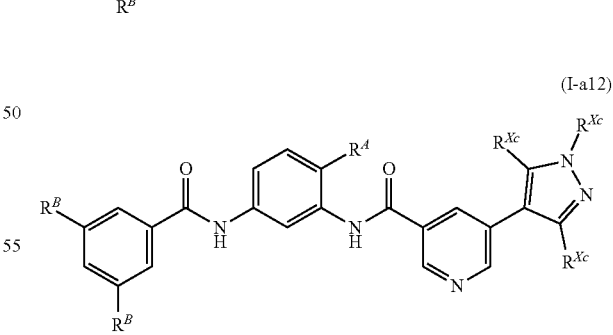

wherein R$^{Xa}$, R$^{Xc}$, R$^A$, and R$^B$ are defined herein. In certain embodiments R$^A$ is substituted or unsubstituted C$_{1-6}$ alkyl. In certain embodiments, R$^A$ is methyl. In certain embodiments, one R$^B$ group is substituted or unsubstituted C$_{1-6}$alkyl. In certain embodiments, one R$^B$ group is C$_{1-6}$alkyl substituted with one —CN group. In certain embodiments, one R$^B$ group is

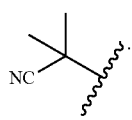

In certain embodiments, one $R^B$ group is substituted or unsubstituted —CH$_2$-(piperazinyl). In certain embodiments, one $R^B$ group is

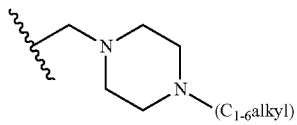

where the alkyl is optionally substituted. In certain embodiments, one $R^B$ group is

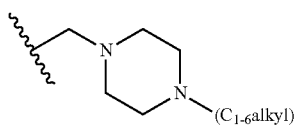

where the alkyl is unsubstituted. In certain embodiments, one $R^B$ group is

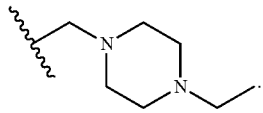 [SMILES: *CN1CCN(CC)CC1]

In certain embodiments, one $R^B$ group is haloalkyl. In certain embodiments, one $R^B$ group is —CF$_3$. In certain embodiments, one $R^B$ group is substituted or unsubstituted imidazoyl. In certain embodiments, one $R^B$ group is

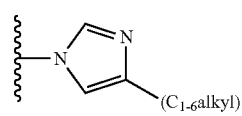

where the alkyl is optionally substituted. In certain embodiments, one $R^B$ group is

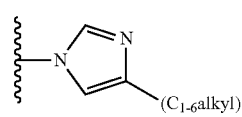

where the alkyl is unsubstituted. In certain embodiments, one $R^B$ group is

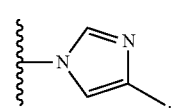

In certain embodiments, one $R^B$ group is substituted or unsubstituted piperazinyl. In certain embodiments, one $R^B$ group is

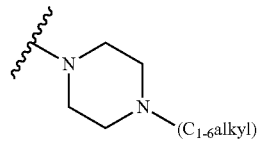

where there alkyl is optionally substituted. In certain embodiments, one $R^B$ group is

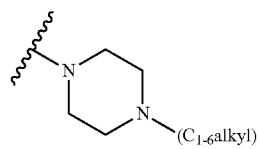

where there alkyl is unsubstituted. In certain embodiments, one $R^B$ group is

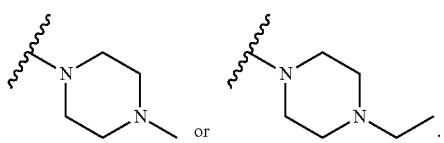

In certain embodiments, one $R^B$ group is substituted or unsubstituted morpholine. In certain embodiments, two $R^B$ groups are substituted or unsubstituted morpholine. In certain embodiments, all instances of $R^{Xc}$ are hydrogen. In certain embodiments, $R^{Xa}$ is substituted or unsubstituted C$_{1-6}$alkyl. In certain embodiments, $R^{Xa}$ is methyl or ethyl.

In certain embodiments, a compound of Formula (I-b) is a compound of Formula (I-b4)-(I-b12):

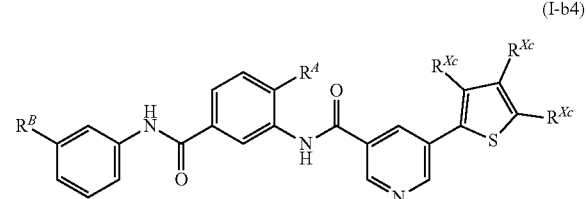

(I-b4)

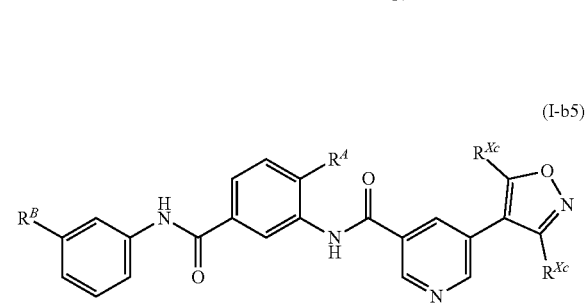

(I-b5)

-continued (I-b6)
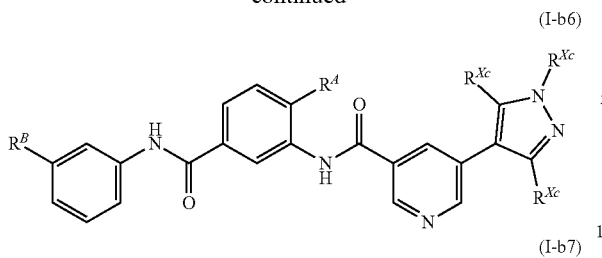

(I-b7)
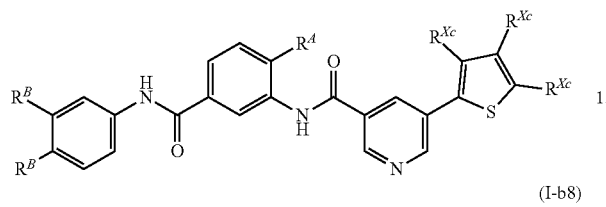

(I-b8)
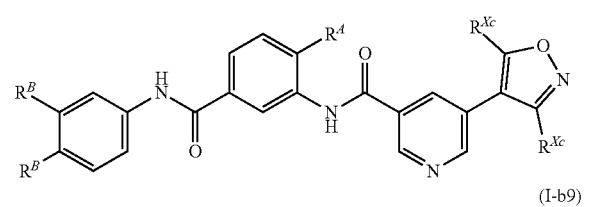

(I-b9)
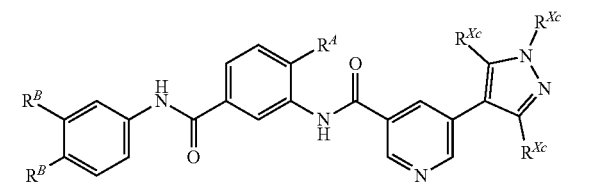

(I-b10)
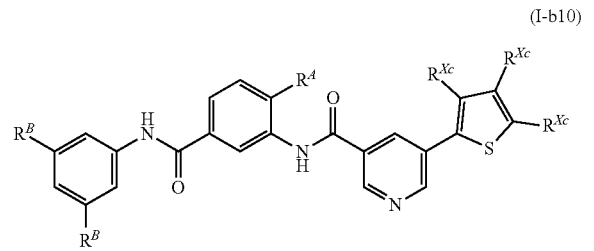

(I-b11)
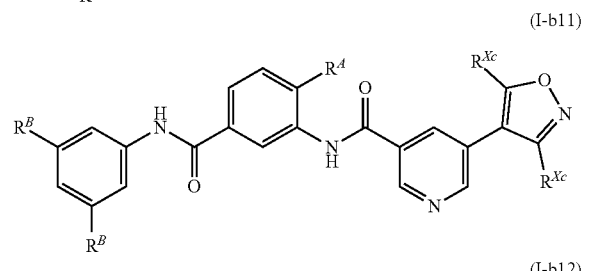

(I-b12)
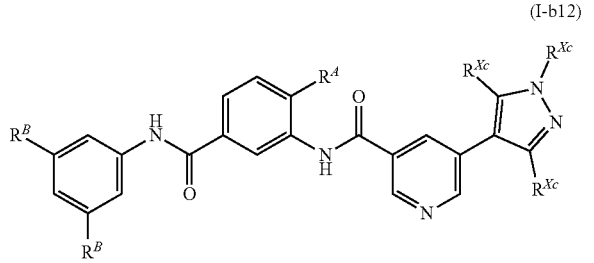

wherein $R^{Xa}$, $R^{Xc}$, $R^A$, and $R^B$ are defined herein. In certain embodiments $R^A$ is substituted or unsubstituted $C_{1-6}$ alkyl. In certain embodiments, $R^A$ is methyl. In certain embodiments, one $R^B$ group is substituted or unsubstituted $C_{1-6}$alkyl. In certain embodiments, one $R^B$ group is $C_{1-6}$alkyl substituted with one —CN group. In certain embodiments, one $R^B$ group is

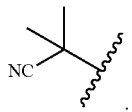

In certain embodiments, one $R^B$ group is substituted or unsubstituted —CH$_2$-(piperazinyl). In certain embodiments, one $R^B$ group is

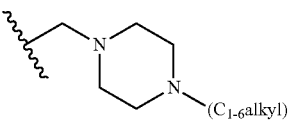

where the alkyl is optionally substituted. In certain embodiments, one $R^B$ group is

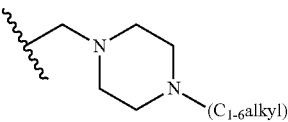

where the alkyl is unsubstituted. In certain embodiments, one $R^B$ group is

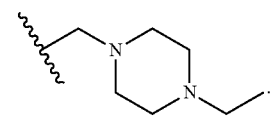 [SMILES: *CN1CCN(CC)CC1]

In certain embodiments, one $R^B$ group is haloalkyl. In certain embodiments, one $R^B$ group is —CF$_3$. In certain embodiments, one $R^B$ group is substituted or unsubstituted imidazoyl. In certain embodiments, one $R^B$ group is

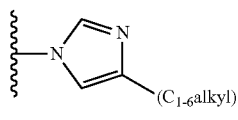

where the alkyl is optionally substituted. In certain embodiments, one $R^B$ group is

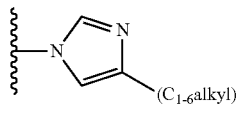

where the alkyl is unsubstituted. In certain embodiments, one $R^B$ group is

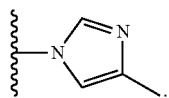 [SMILES: *n1cnc(C)c1]

In certain embodiments, one $R^B$ group is substituted or unsubstituted piperazinyl. In certain embodiments, one $R^B$ group is

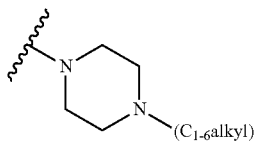

where there alkyl is optionally substituted. In certain embodiments, one $R^B$ group is

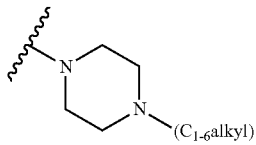

where there alkyl is unsubstituted. In certain embodiments, one $R^B$ group is or

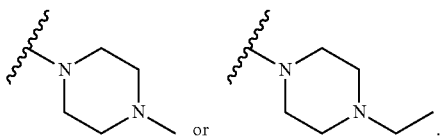

In certain embodiments, one $R^B$ group is substituted or unsubstituted morpholine. In certain embodiments, two $R^B$ groups are substituted or unsubstituted morpholine. In certain embodiments, all instances of $R^{Xc}$ are hydrogen. In certain embodiments, $R^{Xa}$ is substituted or unsubstituted $C_{1-6}$alkyl. In certain embodiments, $R^{Xa}$ is methyl or ethyl.

In another aspect, provided are compounds of Formula (V):

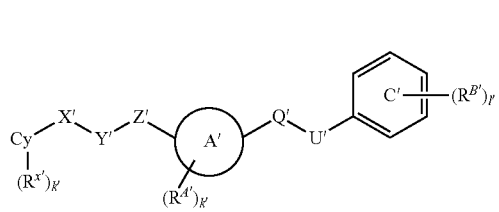

and pharmaceutically acceptable salts, solvates, hydrates, polymorphs, co-crystals, tautomers, stereoisomers, isotopically labeled derivatives, and prodrugs thereof; wherein:

each instance of each instance of $R^{A\prime}$, $R^{B\prime}$, and $R^{X\prime}$ are independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{A1\prime}$, $-N(R^{A1\prime})_2$, $-SR^{A1\prime}$, $-CN$, $-C(=O)R^{A1\prime}$, $-C(=O)OR^{A1\prime}$, $-C(=O)SR^{A1\prime}$, $-C(=O)N(R^{A1\prime})_2$, $-C(=S)R^{A1\prime}$, $-C(=S)OR^{A1\prime}$, $-C(=S)SR^{A1\prime}$, $-C(=S)N(R^{A1\prime})_2$, $-C(=NR^{A1\prime})R^{A1}$, $-C(=NR^{A1\prime})OR^{A1\prime}$, $-C(=NR^{A1\prime})SR^{A1\prime}$, $-C(=NR^{A1\prime})N(R^{A1\prime})_2$, $-NO_2$, $-N_3$, $-N(R^{A1\prime})_3{}^+X^{\prime-}$, wherein $X^{\prime-}$ is a counterion, $-N(OR^{A1\prime})R^{A1\prime}$, $-NR^{A1\prime}C(=O)R^{A1\prime}$, $-NR^{A1\prime}C(=O)OR^{A1}$, $-NR^{A1\prime}C(=O)SR^{A1\prime}$, $-NR^{A1\prime}C(=O)N(R^{A1\prime})_2$, $-NR^{A1\prime}C(=S)R^{A\prime}$, $-NR^{A1\prime}C(=S)OR^{A1\prime}$, $-NR^{A1\prime}C(=S)SR^{A1\prime}$, $-NR^{A1\prime}C(=S)N(R^{A1\prime})_2$, $-NR^{A1\prime}C(=NR^{A1\prime})R^{A1\prime}$, $-NR^{A1\prime}C(=NR^{A1\prime})OR^{A1\prime}$, $-NR^{A1\prime}C(=NR^{A1\prime})SR^{A1\prime}$, $-NR^{A1\prime}C(=NR^{A1\prime})N(R^{A1\prime})_2$, $-NR^{A1\prime}S(=O)_2R^{A1\prime}$, $-NR^{A1\prime}S(=O)_2OR^{A1\prime}$, $-NR^{A1\prime}S(=O)_2SR^{A1\prime}$, $-NR^{A1\prime}S(=O)_2N(R^{A1\prime})_2$, $-NR^{A1\prime}S(=O)R^{A1\prime}$, $-NR^{A1\prime}S(=O)OR^{A1\prime}$, $-NR^{A1\prime}S(=O)SR^{A1\prime}$, $-NR^{A1\prime}S(=O)N(R^{A1\prime})_2$, $-NR^{A1\prime}P(=O)$, $-NR^{A1\prime}P(=O)_2$, $-NR^{A1\prime}P(=O)(R^{A1\prime})_2$, $-NR^{A1\prime}P(=O)R^{A1\prime}(OR^{A1\prime})$, $-NR^{A1\prime}P(=O)(OR^{A1\prime})_2$, $-OC(=O)R^{A1\prime}$, $-OC(=O)OR^{A1\prime}$, $-OC(=O)SR^{A1\prime}$, $-OC(=O)N(R^{A1\prime})_2$, $-OC(=NR^{A1\prime})R^{A1\prime}$, $-OC(=NR^{A1\prime})OR^{A1\prime}$, $-OC(=NR^{A1\prime})N(R^{A1\prime})_2$, $-OC(=S)R^{A1\prime}$, $-OC(=S)OR^{A1\prime}$, $-OC(=S)SR^{A1\prime}$, $-OC(=S)N(R^{A1\prime})_2$, $-ON(R^{A1\prime})_2$, $-OS(=O)R^{A1\prime}$, $-OS(=O)OR^{A1\prime}$, $-OS(=O)SR^{A1\prime}$, $-OS(=O)N(R^{A1\prime})_2$, $-OS(=O)_2R^{A1\prime}$, $-OS(=O)_2OR^{A1\prime}$, $-OS(=O)_2SR^{A1\prime}$, $-OS(=O)_2N(R^{A1\prime})_2$, $-OP(=O)_2$, $-OP(=O)(R^{A1\prime})_2$, $-OP(=O)R^{A1\prime}(OR^{A1\prime})$, $-OP(=O)(OR^{A1\prime})_2$, $-OP(=O)$, $-OP(R^{A1\prime})_2$, $-OPR^{A1\prime}(OR^{A1})$, $-OP(OR^{A1\prime})_2$, $-OSi(R^{A1\prime})_3$, $-OSi(R^{A1\prime})_2OR^{A1\prime}$, $-OSi(R^{A1\prime})(OR^{A1\prime})_2$, $-OSi(OR^{A1\prime})_3$, $-SSR^{A1\prime}$, $-S(=O)R^{A1\prime}$, $-S(=O)OR^{A1\prime}$, $-S(=O)N(R^{A1\prime})_2$, $-S(=O)_2R^{A1\prime}$, $-S(=O)_2OR^{A1\prime}$, $-S(=O)_2N(R^{A1\prime}-)^2$, $-SC(=O)R^{A1\prime}$, $-SC(=O)OR^{A1\prime}$, $-SC(=O)SR^{A1\prime}$, $-SC(=O)N(R^{A1\prime})_2$, $-SC(=S)R^{A1\prime}$, $-SC(=S)OR^{A1\prime}$, $-SC(=S)SR^{A1\prime}$, $-SC(=S)N(R^{A1\prime})_2$, $-P(R^{A1\prime})_2$, $-PR^{A1\prime}(OR^{A1\prime})$, $-P(OR^{A1\prime})_2$, $-P(=O)$, $-P(=O)(R^{A1\prime})_2$, $-P(=O)(OR^{A1\prime})_2$, $-P(=O)R^{A1\prime}(OR^{A1\prime})$, $-P(=O)_2$, $-B(R^{A1\prime})_2$, $-B(OR^{A1\prime})_2$, $-BR^{A1\prime}(OR^{A1\prime})$, $-Si(R^{A1\prime})_3$, $-Si(R^{A1\prime})_2OR^{A1\prime}$, $-SiR^{A1\prime}(OR^{A1\prime})_2$, and $-Si(OR^{A1\prime})_3$, two $R^{A\prime}$ or $R^{B\prime}$ groups are joined to form an optionally substituted carbocyclic, optionally substituted heterocyclic, optionally substituted aryl, or optionally substituted heteroaryl ring, or $R^{A\prime}$ or $R^{B\prime}$ forms an optional 5 to 8 membered ring with any one of X', Y', Z', Q', U', or Cy; wherein each occurrence of $R^{A1\prime}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A1\prime}$ groups are joined to form an optionally substituted heterocyclic ring;

k' and l' are each independently 0, 1, 2, 3, 4, or 5;

X', Y', Z' are each independently $-CH_2$, $-CHR^{A\prime}$, $-CH$, $-C(R^{A\prime})_2$, $-C$, $-N$, $-NR^{A\prime}$, $-O$, $-S$ or $-C=O$, or bond and may optionally form a 5 to 8 membered ring with $R^{A\prime}$ or $R^{B\prime}$;

Q' and U' are each independently $-NR^{A\prime}$, $-O$, $-C=O$, $-NR^{A\prime}CO$, or bond;

Ring A' is an optionally substituted aryl, or optionally substituted heteroaryl ring Ring C' is an optionally substituted aryl ring; and Cy is an optionally substituted aryl ring, optionally substituted heteroaryl ring, bond, or hydrogen.

Compounds of Formula (V) include an aryl group for Ring A' optionally substituted with one or more $R^{A\prime}$ groups.

In certain embodiments, when Ring A' is naphthyl, the invention provides compounds of Formula (V-a):

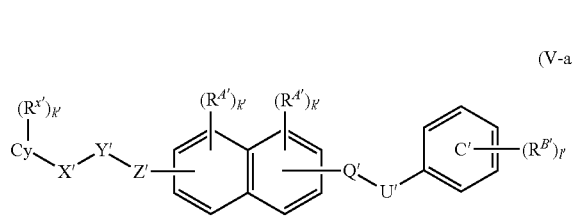
(V-a)

wherein Ring C', Cy, Q', U', X', Y', Z', $R^{A'}$, $R^{B'}$, $R^{X'}$, k', and l' are as defined herein.

Compounds of Formula (V) include an aryl group for Ring A' optionally substituted with one or more $R^{A'}$ groups. In certain embodiments, Ring A' is naphthyl, the invention provides compounds of Formula (V-b):

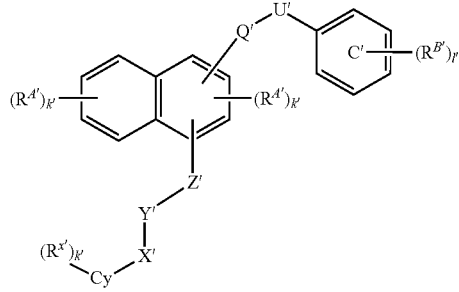
(V-b)

wherein Ring C', Cy, Q', U', X', Y', Z', $R^{A'}$, $R^{B'}$, $R^{X'}$, k', and l' are as defined herein.

Compounds of Formula (V) include an aryl group for Ring A' optionally substituted with one or more $R^{A'}$ groups. In certain embodiments, when Ring A' is phenyl, the invention provides compounds of Formula (V-c):

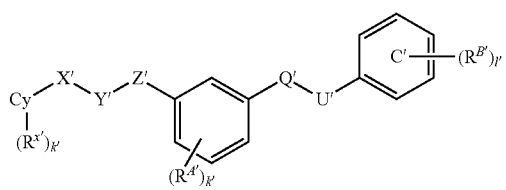
(V-c)

wherein Ring C', Cy, Q', U', X', Y', Z', $R^{A'}$, $R^{B'}$, $R^{X'}$, k', and l' are as defined herein.

Compounds of Formula (V) include an aryl group for Ring A' optionally substituted with one or more $R^{A'}$ groups. In certain embodiments, when Ring A' is phenyl, the invention provides compounds of Formula (V-d):

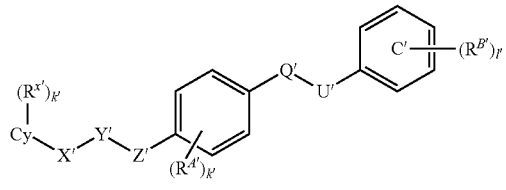
(V-d)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is pyrrolopyrimidine, the invention provides compounds of Formula (V-e):

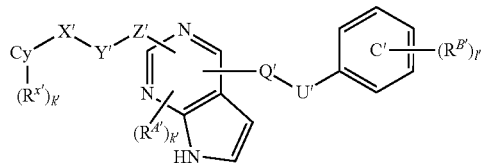
(V-e)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is a pyrimidine, the invention provides compounds of Formula (V-$e^A$):

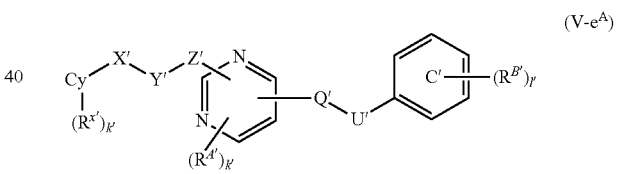
(V-$e^A$)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is a 1H-pyrazolo[3,4-d]pyrimidin-4-amine, the invention provides compounds of Formula (V-$e^B$):

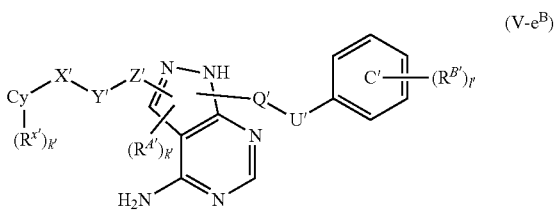
(V-$e^B$)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is a furo[2,3-c]pyridin-7-amine, the invention provides compounds of Formula (V-e$^C$):

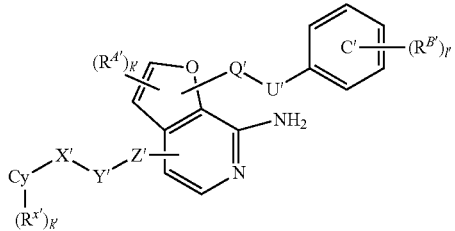

(V-e$^C$)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is a quinazoline, the invention provides compounds of Formula (V-e$^D$):

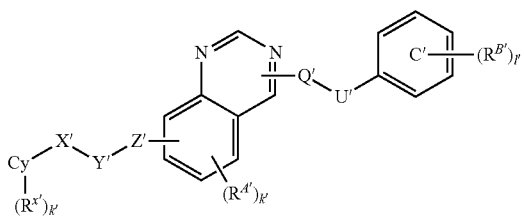

(V-e$^D$)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is phenyl, and at least one $R^{A'}$ group links to Cy forming an optional 5 to 8 membered ring, the invention provides compounds of Formula (V-f):

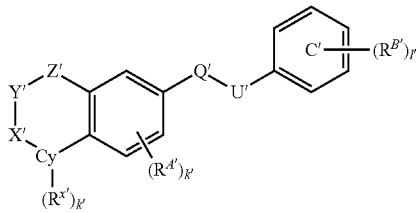

(V-f)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is phenyl, and at least one $R^{A'}$ group links to Cy forming an optional 5 to 8 membered ring, the invention provides compounds of Formula (V-g):

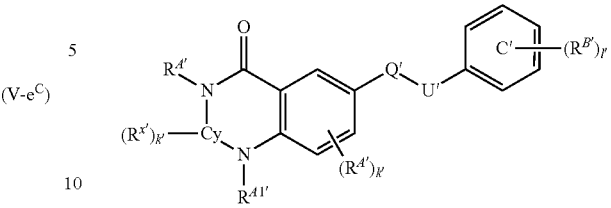

(V-g)

wherein Ring C', Cy, Q', U', X', Y', Z', $R^{A'}$, $R^{B'}$, $R^{X'}$, k', and l' are as defined herein.

In some embodiments, the subject is administered a compound of Formula (III):

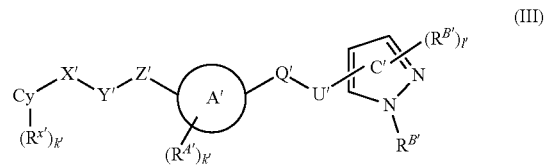

(III)

and pharmaceutically acceptable salts, solvates, hydrates, polymorphs, co-crystals, tautomers, stereoisomers, isotopically labeled derivatives, and prodrugs thereof;
wherein:
each instance of each instance of $R^{A'}$, $R^{B'}$, and $R^{X'}$ are independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1'}$, —N(R$^{A1'}$)$_2$, —SR$^{A1'}$, —CN, —C(=O)R$^{A1'}$, —C(=O)OR$^{A1'}$, —C(=O)SR$^{A1'}$, —C(=O)N(R$^{A1'}$)$_2$, —C(=S)R$^{A1'}$, —C(=S)OR$^{A1'}$, —C(=S)SR$^{A1'}$, —C(=S)N(R$^{A1'}$)$_2$, —C(=NR$^{A1'}$)R$^{A1}$, —C(=NR$^{A1'}$)OR$^{A1'}$, —C(=NR$^{A1'}$)SR$^{A1'}$, —C(=NR$^{A1'}$)N(R$^{A1'}$)$_2$, —NO$_2$, —N$_3$, —N(R$^{A1'}$)$_3$$^+$X'$^-$, wherein X'$^-$ is a counterion, —N(OR$^{A1'}$)R$^{A1'}$, —NR$^{A1'}$C(=O)R$^{A1'}$, —NR$^{A1'}$C(=O)OR$^{A1'}$, —NR$^{A1'}$C(=O)SR$^{A1'}$, —NR$^{A1'}$C(=O)N(R$^{A1'}$)$_2$, —NR$^{A1'}$C(=S)R$^{A1'}$, —NR$^{A1'}$C(=S)OR$^{A1'}$, —NR$^{A1'}$C(=S)SR$^{A1'}$, —NR$^{A1'}$C(=S)N(R$^{A1'}$)$_2$, —NR$^{A1'}$C(=NR$^{A1'}$)R$^{A1'}$, —NR$^{A1'}$C(=NR$^{A1'}$)OR$^{A1'}$, —NR$^{A1'}$C(=NR$^{A1'}$)SR$^{A1'}$, —NR$^{A1'}$C(=NR$^{A1'}$)N(R$^{A1'}$)$_2$, —NR$^{A1'}$S(=O)$_2$R$^{A1'}$, —NR$^{A1'}$S(=O)$_2$OR$^{A1'}$, —NR$^{A1'}$S(=O)SR$^{A1'}$, —NR$^{A1'}$S(=O)$_2$N(R$^{A1'}$)$_2$, —NR$^{A1'}$S(=O)R$^{A1'}$, —NR$^{A1'}$S(=O)OR$^{A1'}$, —NR$^{A1'}$S(=O)SR$^{A1'}$, —NR$^{A1'}$S(=O)N(R$^{A1'}$)$_2$, —NR$^{A1'}$P(=O), —NR$^{A1'}$P(=O)$_2$, —NR$^{A1'}$P(=O)(R$^{A1'}$)$_2$, —NR$^{A1'}$P(=O)R$^{A1'}$(OR$^{A1'}$), —NR$^{A1'}$P(=O)(OR$^{A1'}$)$_2$, —OC(=O)R$^{A1'}$, —OC(=O)OR$^{A1'}$, —OC(=O)SR$^{A1'}$, —OC(=O)N(R$^{A1'}$)$_2$, —OC(=NR$^{A1'}$)R$^{A1'}$, —OC(=NR$^{A1'}$)OR$^{A1'}$, —OC(=NR$^{A1'}$)N(R$^{A1'}$)$_2$, —OC(=S)R$^{A1'}$, —OC(=S)OR$^{A1'}$, —OC(=S)SR$^{A1'}$, —OC(=S)N(R$^{A1'}$)$_2$, —ON(R$^{A1'}$)$_2$, —OS(=O)R$^{A1'}$, —OS(=O)OR$^{A1'}$, —OS(=O)SR$^{A1'}$, —OS(=O)N(R$^{A1'}$)$_2$, —OS(=O)$_2$R$^{A1'}$, —OS(=O)$_2$OR$^{A1'}$, —OS(=O)$_2$SR$^{A1'}$, —OS(=O)$_2$N(R$^{A1'}$)$_2$, —OP(=O)$_2$, —OP(=O)(R$^{A1'}$)$_2$, —OP(=O)R$^{A1'}$(OR$^{A1}$), —OP(=O)(OR$^{A1'}$)$_2$, —OP(=O), —OP(R$^{A1'}$)$_2$, —OPR$^{A1'}$(OR$^{A1}$), —OP(OR$^{A1'}$)$_2$, —OSi(R$^{A1'}$)$_3$, —OSi(R$^{A1'}$)$_2$OR$^{A1'}$, —OSi(R$^{A1'}$)(OR$^{A1'}$)$_2$, —OSi(OR$^{A1'}$)$_3$, —SSR$^{A1'}$, —S(=O)R$^{A1'}$, —S(=O)OR$^{A1'}$, —S(=O)N(R$^{A1'}$)$_2$, —S(=O)$_2$R$^{A1'}$, —S(=O)$_2$OR$^{A1'}$, —S(=O)$_2$N(R$^{A1'}$)$^2$, —SC(=O)R$^{A1'}$, —SC(=O)OR$^{A1'}$, —SC(=O)SR$^{A1'}$, —SC(=O)N(R$^{A1'}$)$_2$, —SC(=S)R$^{A1'}$, —SC(=S)OR$^{A1'}$, —SC(=S)SR$^{A1'}$, —SC(=S)N(R$^{A1'}$)$_2$, —P(R$^{A1'}$)$_2$, —PR$^{A1'}$(OR$^{A1'}$), —P(OR$^{A1'}$)$_2$, —P(=O), —P(=O)(R$^{A1'}$)$_2$, —P(=O)(OR$^{A1'}$)$_2$, —P(=O)R$^{A1'}$(OR$^{A1'}$), —P(=O)$_2$, —B(R$^{A1'}$)$_2$, —B(OR$^{A1'}$)$_2$, —BR$^{A1'}$(OR$^{A1'}$), —Si(R$^{A'}$)$_3$, —Si(R$^{A1'}$)$_2$OR$^{A1'}$, —SiR$^{A1'}$(OR$^{A1'}$)$_2$, and —Si(OR$^{A1'}$)$_3$, two R$^{A'}$ or R$^{B'}$ groups are joined to form an optionally substituted carbocyclic, optionally substituted heterocyclic, optionally substituted aryl, or optionally substituted heteroaryl ring, or R$^{A'}$ or R$^{B'}$ forms an optional 5 to 8 membered ring with any one of X', Y', Z', Q', U', or Cy; wherein each occurrence of R$^{A1'}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{A1'}$ groups are joined to form an optionally substituted heterocyclic ring;

k' and l' are each independently 0, 1, 2, 3, 4, or 5;

X', Y', Z' are each independently —CH$_2$, —CHR$^{A'}$, —CH, —C(R$^{A'}$)$_2$, —C, —N, —NR$^{A'}$, —O, —S or —C=O, or bond and may optionally form a 5 to 8 membered ring with R$^{A'}$ or R$^{B'}$;

Q' and U' are each independently —NR$^{A'}$, —O, —C=O, —NR$^{A'}$CO, or bond;

Ring A' is an optionally substituted aryl, or optionally substituted heteroaryl ring Ring C' is an optionally substituted aryl ring; and Cy is an optionally substituted aryl ring, optionally substituted heteroaryl ring, bond, or hydrogen.

In another aspect, provided herein are compound of Formula (II):

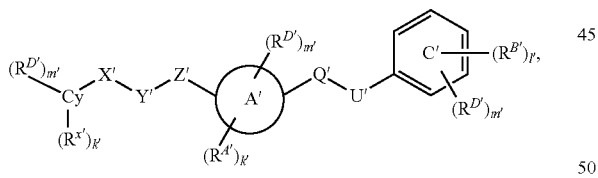

(II)

and pharmaceutically acceptable salts, solvates, hydrates, polymorphs, co-crystals, tautomers, stereoisomers, isotopically labeled derivatives, and prodrugs thereof; wherein: each instance of R$^{D'}$ is independently an optional electrophilic moiety that can be attached to Cy, Ring A', or Ring C';

each instance of m' is independently 0 or 1; and

Ring A', Ring C', Cy, Q', U', X', Y', Z', R$^{A'}$, R$^{B'}$, R$^{X'}$, k', and l' are as defined herein.

In certain embodiments, R$^{D'}$ is an optional electrophilic moiety that can be attached to Cy, Ring A', or Ring C'; and m' is 0 or 1. In compounds of Formula (II), R$^{D'}$ is an optional electrophilic moiety that can be attached to Cy, Ring A', or Ring C'. In certain embodiments, R$^{D'}$ is any one of Formulae (i-1)-(i-17):

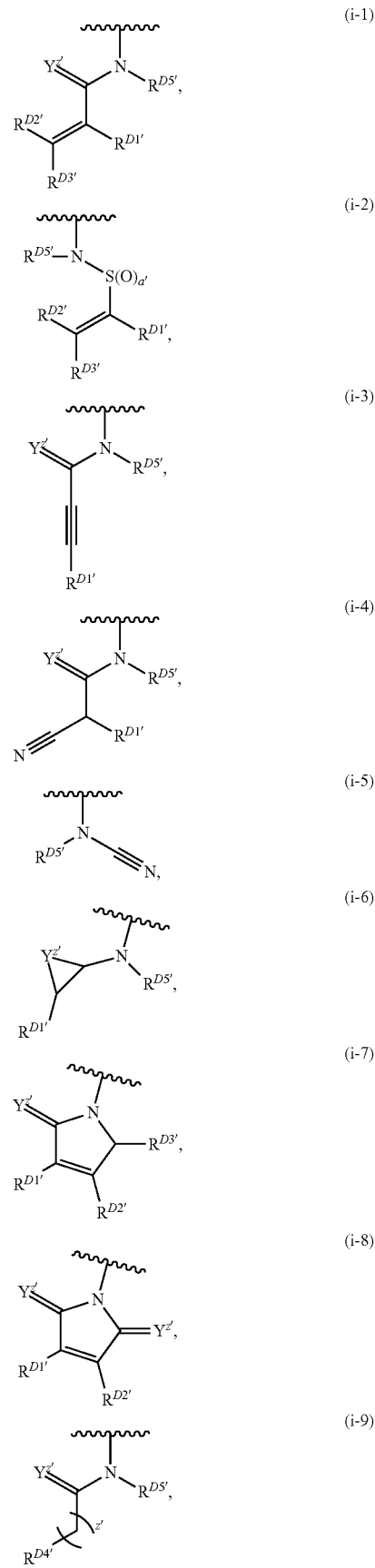

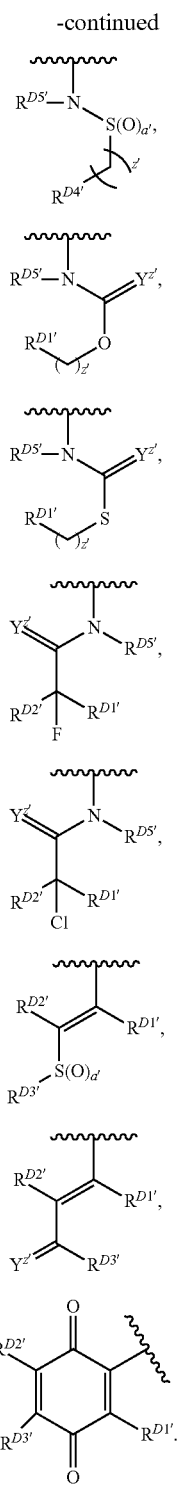

$R^{D1'}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D1a'}$, —N(R$^{D1a'}$)$_2$, —SR$^{D1a'}$, —CH$_2$OR$^{D1a'}$, —CH$_2$N(R$^{D1a'}$)$_2$, —CH$_2$SR$^{D1a'}$, —C(=O)R$^{D1a'}$, —C(=O)OR$^{D1a'}$, —C(=O)SR$^{D1a'}$, —C(=O)N(R$^{D1a'}$)$_2$, —C(=S)R$^{D1a'}$, —C(=S)OR$^{D1a'}$, —C(=S)SR$^{D1a'}$, —C(=S)N(R$^{D1a'}$)$_2$, —C(=NR$^{D1a'}$)R$^{D1a'}$, —C(=NR$^{D1a'}$)OR$^{D1a'}$, —C(=NR$^{D1a'}$)SR$^{D1a'}$, and —C(=NR$^{D1a'}$)N(R$^{D1a'}$)$_2$, wherein each occurrence of R$^{D1a'}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D1a'}$ groups are joined to form an optionally substituted heterocyclic ring;

R$^{D2'}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D2a'}$, —N(R$^{D2a'}$)$_2$, —SR$^{D2a'}$, —CH$_2$OR$^{D2a'}$, —CH$_2$N(R$^{D2a'}$)$_2$, —CH$_2$SR$^{D2a'}$, —C(=O)R$^{D2a'}$, —C(=O)OR$^{D2a'}$, —C(=O)SR$^{D2a'}$, —C(=O)N(R$^{D2a'}$)$_2$, —C(=S)R$^{D2a'}$, —C(=S)OR$^{D2a'}$, —C(=S)SR$^{D2a'}$, —C(=S)N(R$^{D2a'}$)$_2$, —C(=NR$^{D2a'}$)R$^{D2a'}$, —C(=NR$^{D2a'}$)OR$^{D2a'}$, —C(=NR$^{D2a'}$)SR$^{D2a'}$, and —C(=NR$^{D2a'}$)N(R$^{D2a'}$)$_2$, wherein each occurrence of R$^{D2a'}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D2a'}$ groups are joined to form an optionally substituted heterocyclic ring;

R$^{D3'}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D3a'}$, —N(R$^{D3a'}$)$_2$, —SR$^{D3a'}$, —CH$_2$OR$^{D3a'}$, —CH$_2$N(R$^{D3a'}$)$_2$, —CH$_2$SR$^{D3a'}$, —C(=O)R$^{D3a'}$, —C(=O)OR$^{D3a'}$, —C(=O)SR$^{D3a'}$, —C(=O)N(R$^{D3a'}$)$_2$, —C(=S)R$^{D3a'}$, —C(=S)OR$^{D3a'}$, —C(=S)SR$^{D3a'}$, —C(=S)N(R$^{D3a'}$)$_2$, —C(=NR$^{D3a'}$)R$^{D3a'}$, —C(=NR$^{D3a'}$)OR$^{D3a'}$, —C(=NR$^{D3a'}$)SR$^{D3a'}$, and —C(=NR$^{D3a'}$)N(R$^{D3a'}$)$_2$, wherein each occurrence of R$^{D3a'}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D3a'}$ groups are joined to form an optionally substituted heterocyclic ring;

optionally R$^{D1'}$ and R$^{D3'}$, or R$^{D2'}$ and R$^{D3'}$, or R$^{D1'}$ and R$^{D2'}$ are joined to form an optionally substituted carbocyclic or optionally substituted heterocyclic ring;

R$^{D4'}$ is a leaving group;

R$^{D5'}$ is hydrogen, C$_{1-6}$ alkyl, or a nitrogen protecting group;

Y$^{z'}$ is —O, —S, or —NR$^{D6'}$, wherein R$^{D6'}$ is hydrogen, C$_{1-6}$ alkyl, or a nitrogen protecting group;

a' is 1 or 2; and z' is 0, 1, 2, 3, 4, 5, or 6.

Compounds of Formula (II) include an aryl group for Ring A' optionally substituted with one or more R$^{A'}$ groups. In certain embodiments, when Ring A' is naphthyl, the invention provides compounds of Formula (II-a):

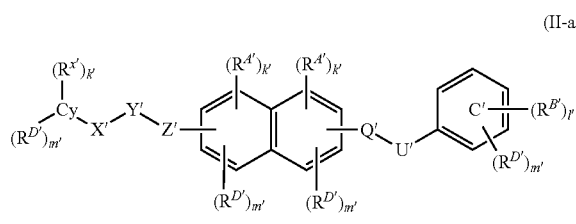

(II-a)

wherein Ring C', Cy, Q', U', X', Y', Z', $R^{A'}$, $R^{B'}$, $R^{D'}$, $R^{X'}$, k', l', and m' are as defined herein.

Compounds of Formula (II) include an aryl group for Ring A' optionally substituted with one or more $R^{A'}$ groups. In certain embodiments, when Ring A' is naphthyl, the invention provides compounds of Formula (II-b):

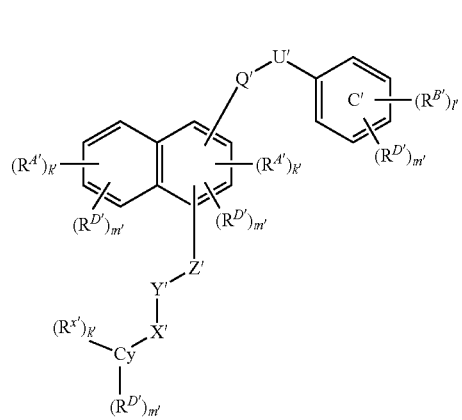

(II-b)

wherein Ring C', Cy, Q', U', X', Y', Z', $R^{A'}$, $R^{B'}$, $R^{D'}$, $R^{X'}$, k', l', and m' are as defined herein.

Compounds of Formula (II) include an aryl group for Ring A' optionally substituted with one or more $R^{A'}$ groups. In certain embodiments, when Ring A' is phenyl, the invention provides compounds of Formula (II-c):

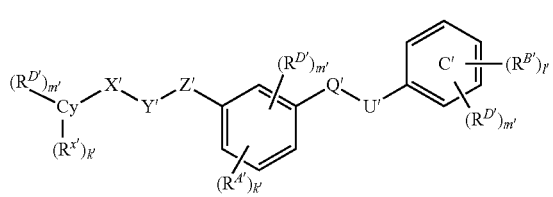

(II-c)

wherein Ring C', Cy, Q', U', X', Y', Z', $R^{A'}$, $R^{B'}$, $R^{D'}$, $R^{X'}$, k', l', and m' are as defined herein.

Compounds of Formula (II) include an aryl group for Ring A' optionally substituted with one or more $R^{A'}$ groups. In certain embodiments, when Ring A' is phenyl, the invention provides compounds of Formula (II-d):

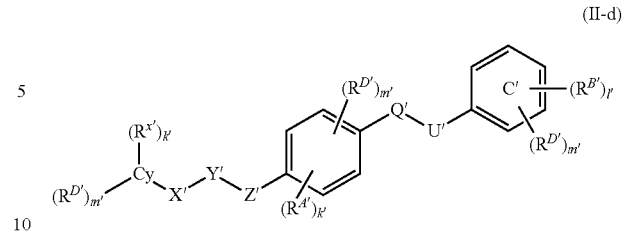

(II-d)

wherein Ring C', Cy, Q', U', X', Y', Z', $R^{A'}$, $R^{B'}$, $R^{D'}$, $R^{X'}$, k', l', and m' are as defined herein.

Compounds of Formula (II) include an heteroaryl group for Ring A' optionally substituted with one or more $R^{A'}$ groups. In certain embodiments, when Ring A' is pyrrolopyrimidine, the invention provides compounds of Formula (II-e):

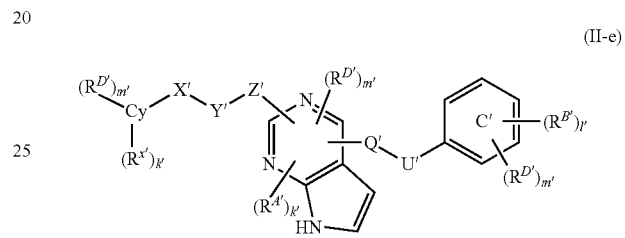

(II-e)

wherein Ring C', Cy, Q', U', X', Y', Z', $R^{A'}$, $R^{B'}$, $R^{D'}$, $R^{X'}$, k', l', and m' are as defined herein.

Compounds of Formula (II) include an heteroaryl group for Ring A' optionally substituted with one or more $R^{A'}$ groups. In certain embodiments, when Ring A' is pyrimidine, the invention provides compounds of Formula (II-e$^A$):

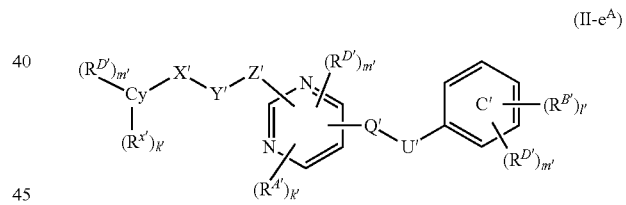

(II-e$^A$)

wherein Ring C', Cy, Q', U', X', Y', Z', $R^{A'}$, $R^{B'}$, $R^{D'}$, $R^{X'}$, k', l', and m' are as defined herein.

Compounds of Formula (II) include an heteroaryl group for Ring A' optionally substituted with one or more $R^{A'}$ groups. In certain embodiments, when Ring A' is pyrimidine, the invention provides compounds of Formula (II-e$^B$):

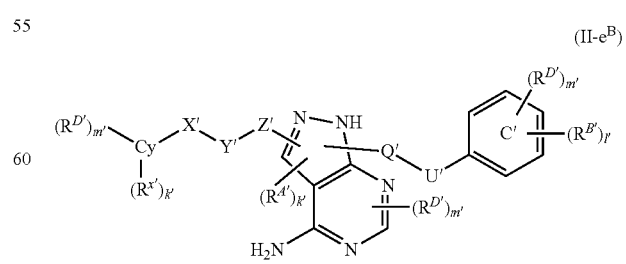

(II-e$^B$)

wherein Ring C', Cy, Q', U', X', Y', Z', $R^{A'}$, $R^{B'}$, $R^{D'}$, $R^{X'}$, k', l', and m' are as defined herein.

Compounds of Formula (II) include an heteroaryl group for Ring A' optionally substituted with one or more R$^{A'}$ groups. In certain embodiments, when Ring A' is a furo[2,3-c]pyridin-7-amine, the invention provides compounds of Formula (II-e$^C$):

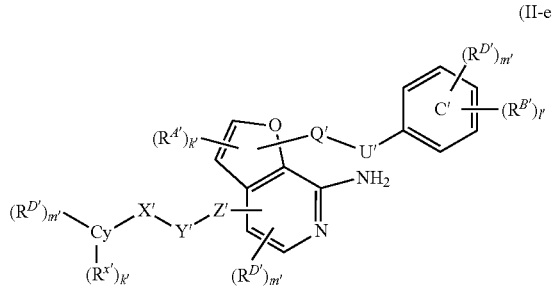

(II-e$^C$)

wherein Ring C', Cy, Q', U', X', Y', Z', R$^{A'}$, R$^{B'}$, R$^{X'}$, k', and l' are as defined herein.

Compounds of Formula (II) include an heteroaryl group for Ring A' optionally substituted with one or more R$^{A'}$ groups. In certain embodiments, when Ring A' is a quinazoline, the invention provides compounds of Formula (II-e$^D$):

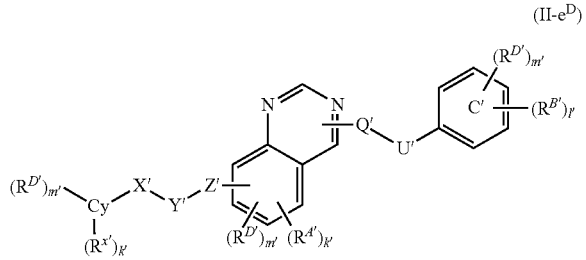

(II-e$^D$)

wherein Ring C', Cy, Q', U', X', Y', Z', R$^{A'}$, R$^{B'}$, R$^{X'}$, k', and l' are as defined herein.

Compounds of Formula (II) include an heteroaryl group for Ring A' optionally substituted with one or more R$^{A'}$ groups. In certain embodiments, when Ring A' is phenyl, and at least one R$^{A'}$ group links to Cy forming an optional 5 to 8 membered ring, the invention provides compounds of Formula (II-f):

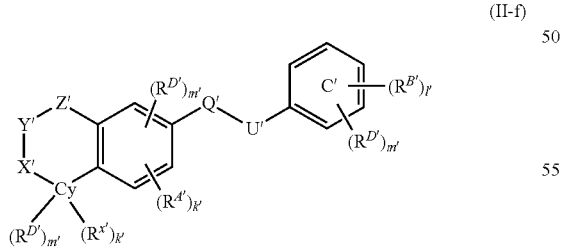

(II-f)

wherein Ring C', Cy, Q', U', X', Y', Z', R$^{A'}$, R$^{B'}$, R$^{D'}$, R$^{X'}$, k', l', and m' are as defined herein.

Compounds of Formula (II) include an heteroaryl group for Ring A' optionally substituted with one or more R$^{A'}$ groups. In certain embodiments, when Ring A' is phenyl, and at least one R$^{A'}$ group links to Cy forming an optional 5 to 8 membered ring, the invention provides compounds of Formula (II-g):

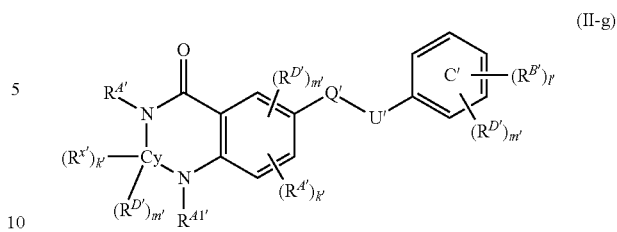

(II-g)

wherein Ring C', Cy, Q', U', X', Y', Z', R$^{A'}$, R$^{B'}$, R$^{D'}$, R$^{X'}$, k', l', and m' are as defined herein.

In another aspect, provided herein are compounds of Formula (IV):

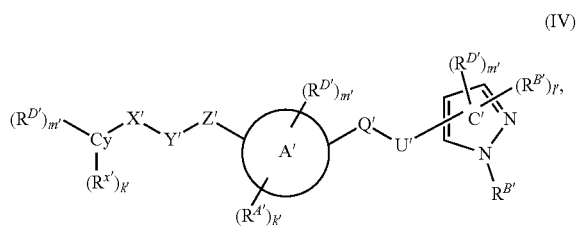

(IV)

and pharmaceutically acceptable salts, solvates, hydrates, polymorphs, co-crystals, tautomers, stereoisomers, isotopically labeled derivatives, and prodrugs thereof; wherein:

each instance of R$^{D'}$ is independently an optional electrophilic moiety that can be attached to Cy, Ring A', or Ring C';

each instance of m' is independently 0 or 1; and

Ring A', Ring C', Cy, Q', U', X', Y', Z', R$^{A'}$, R$^{B'}$, R$^{X'}$, k', and l' are as defined herein.

In certain embodiments, R$^{D'}$ is an optional electrophilic moiety that can be attached to Cy, Ring A', or Ring C'; and m' is 0 or 1. In compounds of Formula (IV), R$^{D'}$ is an optional electrophilic moiety that can be attached to Cy, Ring A', or Ring C'. In certain embodiments, R$^{D'}$ is any one of Formulae (i-1)-(i-17):

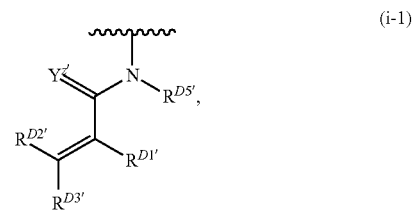

(i-1)

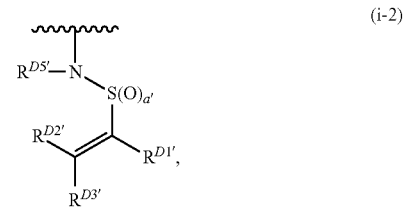

(i-2)

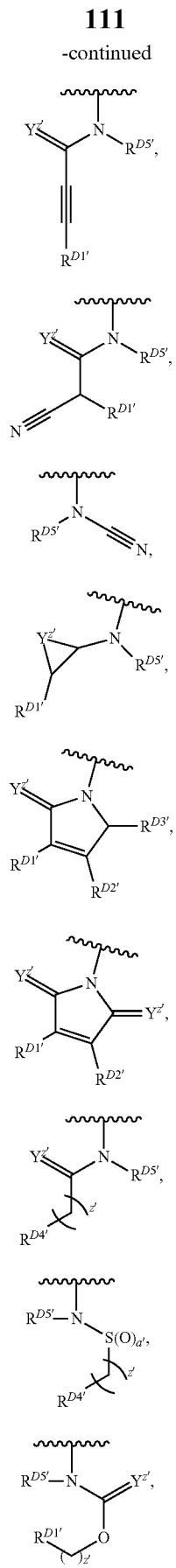
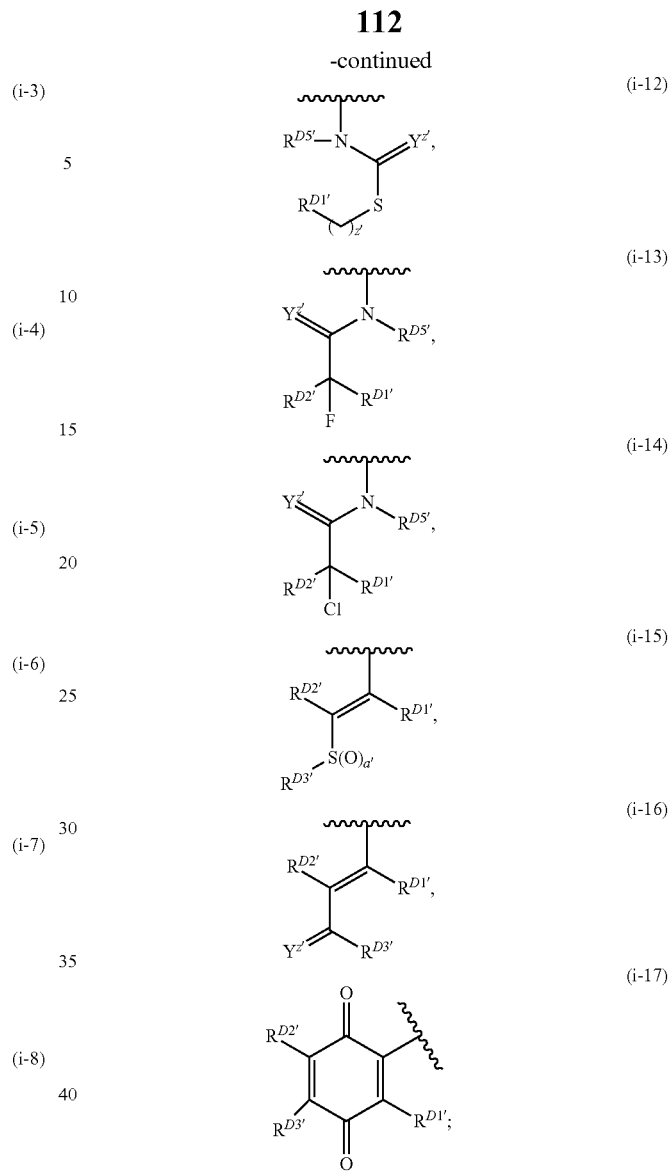

$R^{D1'}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D1a'}$, —N(R$^{D1a'}$)$_2$, —SR$^{D1a'}$, —CH$_2$OR$^{D1a'}$, —CH$_2$N(R$^{D1a'}$)$_2$, —CH$_2$SR$^{D1a'}$, —C(=O)R$^{D1a'}$, —C(=O)OR$^{D1a'}$, —C(=O)SR$^{D1a'}$, —C(=O)N(R$^{D1a'}$)$_2$, —C(=S)R$^{D1a'}$, —C(=S)OR$^{D1a'}$, —C(=S)SR$^{D1a'}$, —C(=S)N(R$^{D1a'}$)$_2$, —C(=NR$^{D1a'}$)R$^{D1a'}$, —C(=NR$^{D1a'}$)OR$^{D1a'}$, —C(=NR$^{D1a'}$)SR$^{D1a'}$, and —C(=NR$^{D1a'}$)N(R$^{D1a'}$)$_2$, wherein each occurrence of R$^{D1a'}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D1a'}$ groups are joined to form an optionally substituted heterocyclic ring;

$R^{D2'}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D2a'}$, —N(R$^{D2a'}$)$_2$, —SR$^{D2a'}$, —CH$_2$OR$^{D2a'}$, —CH$_2$N(R$^{D2a'}$)$_2$, —CH$_2$SR$^{D2a'}$, —C(=O)R$^{D2a'}$, —C(=O)OR$^{D2a'}$, —C(=O)SR$^{D2a'}$, —C(=O)N(R$^{D2a'}$)$_2$, —C(=S)R$^{D2a'}$, —C(=S)OR$^{D2a'}$, —C(=S)SR$^{D2a'}$, —C(=S)N(R$^{D2a'}$)$_2$, —C(=NR$^{D2a'}$)R$^{D2a'}$, —C(=NR$^{D2a'}$)OR$^{D2a'}$, —C(=NR$^{D2a'}$)SR$^{D2a'}$, and —C(=NR$^{D2a'}$)N(R$^{D2a'}$)$_2$, wherein each occurrence of R$^{D2a'}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D2a'}$ groups are joined to form an optionally substituted heterocyclic ring;

R$^{D3'}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D3a'}$, —N(R$^{D3a'}$)$_2$, —SR$^{D3a'}$, —CH$_2$OR$^{D3a'}$, —CH$_2$N(R$^{D3a'}$)$_2$, —CH$_2$SR$^{D3a'}$, —C(=O)R$^{D3a'}$, —C(=O)OR$^{D3a'}$, —C(=O)SR$^{D3a'}$, —C(=O)N(R$^{D3a'}$)$_2$, —C(=S)R$^{D3a'}$, —C(=S)OR$^{D3a'}$, —C(=S)SR$^{D3a'}$, —C(=S)N(R$^{D3a'}$)$_2$, —C(=NR$^{D3a'}$)R$^{D3a'}$, —C(=NR$^{D3a'}$)OR$^{D3a'}$, —C(=NR$^{D3a'}$)SR$^{D3a'}$, and —C(=NR$^{D3a'}$)N(R$^{D3a'}$)$_2$, wherein each occurrence of R$^{D3a'}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D3a'}$ groups are joined to form an optionally substituted heterocyclic ring;

optionally R$^{D1'}$ and R$^{D3'}$, or R$^{D2'}$ and R$^{D3'}$, or R$^{D1'}$ and R$^{D2'}$ are joined to form an optionally substituted carbocyclic or optionally substituted heterocyclic ring;

R$^{D4'}$ is a leaving group;

R$^{D5'}$ is hydrogen, C$_{1-6}$ alkyl, or a nitrogen protecting group;

Y$^{Z'}$ is —O, —S, or —NR$^{D6'}$, wherein R$^{D6'}$ is hydrogen, C$_{1-6}$ alkyl, or a nitrogen protecting group;

a' is 1 or 2; and z' is 0, 1, 2, 3, 4, 5, or 6.

In compounds of Formula (II) and (IV), R$^{D'}$ is a substituent on Ring A', Ring C', or Cy. In certain embodiments, R$^{D'}$ comprises a Michael acceptor moiety. This Michael acceptor moiety may react with a cysteine or other nucleophilic residue to allow covalent attachment of the compound to the target. In certain embodiments, the covalent attachment is irreversible. In other embodiments, the covalent attachment is reversible. In certain embodiments, R$^{D'}$ is of Formula (i-1). In certain embodiments, R$^{D'}$ is of Formula (i-2). In certain embodiments, R$^{D'}$ is of Formula (i-3). In certain embodiments, R$^{D'}$ is of Formula (i-4). In certain embodiments, R$^{D'}$ is of Formula (i-5). In certain embodiments, R$^{D'}$ is of Formula (i-6). In certain embodiments, R$^{D'}$ is of Formula (i-7). In certain embodiments, R$^{D'}$ is of Formula (i-8). In certain embodiments, R$^{D'}$ is of Formula (i-9). In certain embodiments, R$^{D'}$ is of Formula (i-10). In certain embodiments, R$^{D'}$ is of Formula (i-11). In certain embodiments, R$^{D'}$ is of Formula (i-12). In certain embodiments, R$^{D'}$ is of Formula (i-13). In certain embodiments, R$^{D'}$ is of Formula (i-14). In certain embodiments, R$^{D'}$ is of Formula (i-15). In certain embodiments, R$^{D'}$ is of Formula (i-16). In certain embodiments, R$^{D'}$ is of Formula (i-17).

In compounds of Formula (II) and (IV), R$^{D'}$ may include a substituent R$^{D1'}$. In certain embodiments, R$^{D1'}$ is H. In certain embodiments, R$^{D1'}$ is halogen. In certain embodiments, R$^{D1'}$ is F. In certain embodiments, R$^{D1'}$ is Cl. In certain embodiments, R$^{D1'}$ is Br. In certain embodiments, R$^{D1'}$ is I (iodine). In certain embodiments, R$^{D1'}$ is substituted acyl. In certain embodiments, R$^{D1'}$ is unsubstituted acyl. In certain embodiments, R$^{D1'}$ is acetyl. In certain embodiments, R$^{D1'}$ is substituted alkyl. In certain embodiments, R$^{D1'}$ is unsubstituted alkyl. In certain embodiments, R$^{D1'}$ is C$_{1-6}$ alkyl. In certain embodiments, R$^{D1'}$ is methyl. In certain embodiments, R$^{D1'}$ is ethyl. In certain embodiments, R$^{D1'}$ is propyl. In certain embodiments, R$^{D1'}$ is butyl. In certain embodiments, R$^{D1'}$ is substituted alkenyl. In certain embodiments, R$^{D1'}$ is unsubstituted alkenyl. In certain embodiments, R$^{D1'}$ is substituted alkynyl. In certain embodiments, R$^{D1'}$ is unsubstituted alkynyl. In certain embodiments, R$^{D1'}$ is substituted carbocyclyl. In certain embodiments, R$^{D1'}$ is unsubstituted carbocyclyl. In certain embodiments, R$^{D1'}$ is substituted heterocyclyl. In certain embodiments, R$^{D1'}$ is unsubstituted heterocyclyl. In certain embodiments, R$^{D1'}$ is substituted aryl. In certain embodiments, R$^{D1'}$ is unsubstituted aryl. In certain embodiments, R$^{D1'}$ is substituted phenyl. In certain embodiments, R$^{D1'}$ is unsubstituted phenyl. In certain embodiments, R$^{D1'}$ is substituted heteroaryl. In certain embodiments, R$^{D1'}$ is unsubstituted heteroaryl. In certain embodiments, R$^{D1'}$ is substituted pyridyl. In certain embodiments, R$^{D1'}$ is unsubstituted pyridyl. In certain embodiments, R$^{D1'}$ is —CN. In certain embodiments, R$^{D1'}$ is —NO$_2$. In certain embodiments, R$^{D1'}$ is —OR$^{D1a'}$. In certain embodiments, R$^{D1'}$ is —N(R$^{D1a'}$)$_2$. In certain embodiments, R$^{D1'}$ is —SR$^{D1a'}$. In certain embodiments, R$^{D1'}$ is —CH$_2$OR$^{D1a'}$. In certain embodiments, R$^{D1'}$ is —CH$_2$N(R$^{D1a'}$)$_2$. In certain embodiments, R$^{D1'}$ is —CH$_2$SR$^{D1a'}$.

In certain embodiments, at least one R$^{D1a'}$ is H. In certain embodiments, at least one R$^{D1a'}$ is substituted acyl. In certain embodiments, at least one R$^{D1a'}$ is unsubstituted acyl. In certain embodiments, at least one R$^{D1a'}$ is acetyl. In certain embodiments, at least one R$^{D1a'}$ is substituted alkyl. In certain embodiments, at least one R$^{D1a'}$ is unsubstituted alkyl. In certain embodiments, at least one R$^{D1a'}$ is C$_{1-6}$ alkyl. In certain embodiments, at least one R$^{D1a'}$ is methyl. In certain embodiments, at least one R$^{D1a'}$ is ethyl. In certain embodiments, at least one R$^{D1a'}$ is propyl. In certain embodiments, at least one R$^{D1a'}$ is butyl. In certain embodiments, at least one R$^{D1a'}$ is substituted alkenyl. In certain embodiments, at least one R$^{D1a'}$ is unsubstituted alkenyl. In certain embodiments, at least one R$^{D1a'}$ is substituted alkynyl. In certain embodiments, at least one R$^{D1a'}$ is unsubstituted alkynyl. In certain embodiments, at least one R$^{D1a'}$ is substituted carbocyclyl. In certain embodiments, at least one R$^{D1a'}$ is unsubstituted carbocyclyl. In certain embodiments, at least one R$^{D1a'}$ is substituted heterocyclyl. In certain embodiments, at least one R$^{D1a'}$ is unsubstituted heterocyclyl. In certain embodiments, at least one R$^{D1a'}$ is substituted aryl. In certain embodiments, at least one R$^{D1a'}$ is unsubstituted aryl. In certain embodiments, at least one R$^{D1a'}$ is substituted phenyl. In certain embodiments, at least one R$^{D1a'}$ is unsubstituted phenyl. In certain embodiments, at least one R$^{D1a'}$ is substituted heteroaryl. In certain embodiments, at least one R$^{D1a'}$ is unsubstituted heteroaryl. In certain embodiments, at least one R$^{D1a'}$ is substituted pyridyl. In certain embodiments, at least one R$^{D1a'}$ is unsubstituted pyridyl. In certain embodiments, at least one R$^{D1a'}$ is a nitrogen protecting group when attached to a nitrogen atom. In certain embodiments, at least one R$^{D1a'}$ is Bn, BOC, Cbz, Fmoc, trifluoroacetyl, triphenylmethyl, or Ts when attached to a nitrogen atom. In certain embodiments, $R^{D1a'}$ is an oxygen protecting group when attached to an oxygen atom. In certain embodiments, $R^{D1a'}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1a'}$ is a sulfur protecting group when attached to a sulfur atom. In certain embodiments, $R^{D1a'}$ is acetamidomethyl, t-Bu, 3-nitro-2-pyridine sulfenyl, 2-pyridine-sulfenyl, or triphenylmethyl when attached to a sulfur atom. In certain embodiments, two $R^{D1a'}$ groups are joined to form a substituted heterocyclic ring. In certain embodiments, two $R^{D1a'}$ groups are joined to form an unsubstituted heterocyclic ring.

In compounds of Formula (II) and (IV), $R^{D'}$ may include a substituent $R^{D2'}$. In certain embodiments, $R^{D2'}$ is H. In certain embodiments, $R^{D2'}$ is halogen. In certain embodiments, $R^{D2'}$ is F. In certain embodiments, $R^{D2'}$ is Cl. In certain embodiments, $R^{D2'}$ is Br. In certain embodiments, $R^{D2'}$ is I (iodine). In certain embodiments, $R^{D2'}$ is substituted acyl. In certain embodiments, $R^{D2'}$ is unsubstituted acyl. In certain embodiments, $R^{D2'}$ is acetyl. In certain embodiments, $R^{D2'}$ is substituted alkyl. In certain embodiments, $R^{D2'}$ is unsubstituted alkyl. In certain embodiments, $R^{D2'}$ is $C_{1-6}$ alkyl. In certain embodiments, $R^{D2'}$ is methyl. In certain embodiments, $R^{D2'}$ is ethyl. In certain embodiments, $R^{D2'}$ is propyl. In certain embodiments, $R^{D2'}$ is butyl. In certain embodiments, $R^{D2'}$ is substituted alkenyl. In certain embodiments, $R^{D2'}$ is unsubstituted alkenyl. In certain embodiments, $R^{D2'}$ is substituted alkynyl. In certain embodiments, $R^{D2'}$ is unsubstituted alkynyl. In certain embodiments, $R^{D2'}$ is substituted carbocyclyl. In certain embodiments, $R^{D2'}$ is unsubstituted carbocyclyl. In certain embodiments, $R^{D2'}$ is substituted heterocyclyl. In certain embodiments, $R^{D2'}$ is unsubstituted heterocyclyl. In certain embodiments, $R^{D2'}$ is substituted aryl. In certain embodiments, $R^{D2'}$ is unsubstituted aryl. In certain embodiments, $R^{D2'}$ is substituted phenyl. In certain embodiments, $R^{D2'}$ is unsubstituted phenyl. In certain embodiments, $R^{D2'}$ is substituted heteroaryl. In certain embodiments, $R^{D2'}$ is unsubstituted heteroaryl. In certain embodiments, $R^{D2'}$ is substituted pyridyl. In certain embodiments, $R^{D2'}$ is unsubstituted pyridyl. In certain embodiments, $R^{D2'}$ is —CN. In certain embodiments, $R^{D2'}$ is —NO$_2$. In certain embodiments, $R^{D2'}$ is —OR$^{D2a'}$. In certain embodiments, $R^{D2'}$ is —N(R$^{D2a'}$)$_2$. In certain embodiments, $R^{D2'}$ is —SR$^{D2a'}$. In certain embodiments, $R^{D2'}$ is —CH$_2$OR$^{D2a'}$ In certain embodiments, $R^{D2'}$ is —CH$_2$N(R$^{D2a'}$)$_2$. In certain embodiments, $R^{D2'}$ is —CH$_2$SR$^{D2a'}$.

In certain embodiments, at least one $R^{D2a'}$ is H. In certain embodiments, at least one $R^{D2a'}$ is substituted acyl. In certain embodiments, at least one $R^{D2a'}$ is unsubstituted acyl. In certain embodiments, at least one $R^{D2a'}$ is acetyl. In certain embodiments, at least one $R^{D2a'}$ is substituted alkyl. In certain embodiments, at least one $R^{D2a'}$ is unsubstituted alkyl. In certain embodiments, at least one $R^{D2a'}$ is $C_{1-6}$ alkyl. In certain embodiments, at least one $R^{D2a'}$ is methyl. In certain embodiments, at least one $R^{D2a'}$ is ethyl. In certain embodiments, at least one $R^{D2a'}$ is propyl. In certain embodiments, at least one $R^{D2a'}$ is butyl. In certain embodiments, at least one $R^{D2a'}$ is substituted alkenyl. In certain embodiments, at least one $R^{D2a'}$ is unsubstituted alkenyl. In certain embodiments, at least one $R^{D2a'}$ is substituted alkynyl. In certain embodiments, at least one $R^{D2a'}$ is unsubstituted alkynyl. In certain embodiments, at least one $R^{D2a'}$ is substituted carbocyclyl. In certain embodiments, at least one $R^{D2a'}$ is unsubstituted carbocyclyl. In certain embodiments, at least one $R^{D2a'}$ is substituted heterocyclyl. In certain embodiments, at least one $R^{D2a'}$ is unsubstituted heterocyclyl. In certain embodiments, at least one $R^{D2a'}$ is substituted aryl. In certain embodiments, at least one $R^{D2a'}$ is unsubstituted aryl. In certain embodiments, at least one $R^{D2a'}$ is substituted phenyl. In certain embodiments, at least one $R^{D2a'}$ is unsubstituted phenyl. In certain embodiments, at least one $R^{D2a'}$ is substituted heteroaryl. In certain embodiments, at least one $R^{D2a'}$ is unsubstituted heteroaryl. In certain embodiments, at least one $R^{D2a'}$ is substituted pyridyl. In certain embodiments, at least one $R^{D2a'}$ is unsubstituted pyridyl. In certain embodiments, at least one $R^{D2a'}$ is a nitrogen protecting group when attached to a nitrogen atom. In certain embodiments, at least one $R^{D2a'}$ is Bn, BOC, Cbz, Fmoc, trifluoroacetyl, triphenylmethyl, or Ts when attached to a nitrogen atom. In certain embodiments, $R^{D2a'}$ is an oxygen protecting group when attached to an oxygen atom. In certain embodiments, $R^{D2a'}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D2a'}$ is a sulfur protecting group when attached to a sulfur atom. In certain embodiments, $R^{D2a'}$ is acetamidomethyl, t-Bu, 3-nitro-2-pyridine sulfenyl, 2-pyridine-sulfenyl, or triphenylmethyl when attached to a sulfur atom. In certain embodiments, two $R^{D2a'}$ groups are joined to form a substituted heterocyclic ring. In certain embodiments, two $R^{D2a'}$ groups are joined to form an unsubstituted heterocyclic ring.

In compounds of Formula (II) and (IV), $R^{D'}$ may include a substituent $R^{D3'}$. In certain embodiments, $R^{D3'}$ is H. In certain embodiments, $R^{D3'}$ is halogen. In certain embodiments, $R^{D3'}$ is F. In certain embodiments, $R^{D3'}$ is Cl. In certain embodiments, $R^{D3'}$ is Br. In certain embodiments, $R^{D3'}$ is I (iodine). In certain embodiments, $R^{D3'}$ is substituted acyl. In certain embodiments, $R^{D3'}$ is unsubstituted acyl. In certain embodiments, $R^{D3'}$ is acetyl. In certain embodiments, $R^{D3'}$ is substituted alkyl. In certain embodiments, $R^{D3'}$ is unsubstituted alkyl. In certain embodiments, $R^{D3'}$ is $C_{1-6}$ alkyl. In certain embodiments, $R^{D3'}$ is methyl. In certain embodiments, $R^{D3'}$ is ethyl. In certain embodiments, $R^{D3'}$ is propyl. In certain embodiments, $R^{D3'}$ is butyl. In certain embodiments, $R^{D3'}$ is substituted alkenyl. In certain embodiments, $R^{D3'}$ is unsubstituted alkenyl. In certain embodiments, $R^{D3'}$ is substituted alkynyl. In certain embodiments, $R^{D3'}$ is unsubstituted alkynyl. In certain embodiments, $R^{D3'}$ is substituted carbocyclyl. In certain embodiments, $R^{D3'}$ is unsubstituted carbocyclyl. In certain embodiments, $R^{D3'}$ is substituted heterocyclyl. In certain embodiments, $R^{D3'}$ is unsubstituted heterocyclyl. In certain embodiments, $R^{D3'}$ is substituted aryl. In certain embodiments, $R^{D3'}$ is unsubstituted aryl. In certain embodiments, $R^{D3'}$ is substituted phenyl. In certain embodiments, $R^{D3'}$ is unsubstituted phenyl. In certain embodiments, $R^{D3'}$ is substituted heteroaryl. In certain embodiments, $R^{D3'}$ is unsubstituted heteroaryl. In certain embodiments, $R^{D3'}$ is substituted pyridyl. In certain embodiments, $R^{D3'}$ is unsubstituted pyridyl. In certain embodiments, $R^{D3'}$ is —CN. In certain embodiments, $R^{D3'}$ is —NO$_2$. In certain embodiments, $R^{D3'}$ is —OR$^{D3a'}$. In certain embodiments, $R^{D3'}$ is —N(R$^{D3a'}$)$_2$. In certain embodiments, $R^{D3'}$ is —SR$^{D3a'}$. In certain embodiments, $R^{D3'}$ is —CH$_2$OR$^{D3a}$, In certain embodiments, $R^{D3'}$ is —CH$_2$N(R$^{D3a'}$)$_2$. In certain embodiments, $R^{D3'}$ is —CH$_2$SR$^{D3a'}$.

In certain embodiments, at least one $R^{D3a'}$ is H. In certain embodiments, at least one $R^{D3a'}$ is substituted acyl. In certain embodiments, at least one $R^{D3a'}$ is unsubstituted acyl. In certain embodiments, at least one $R^{D3a'}$ is acetyl. In certain embodiments, at least one $R^{D3a\prime}$ is substituted alkyl. In certain embodiments, at least one $R^{D3a\prime}$ is unsubstituted alkyl. In certain embodiments, at least one $R^{D3a\prime}$ is $C_{1-6}$ alkyl. In certain embodiments, at least one $R^{D3a\prime}$ is methyl. In certain embodiments, at least one $R^{D3a\prime}$ is ethyl. In certain embodiments, at least one $R^{D3a\prime}$ is propyl. In certain embodiments, at least one $R^{D3a\prime}$ is butyl. In certain embodiments, at least one $R^{D3a\prime}$ is substituted alkenyl. In certain embodiments, at least one $R^{D3a\prime}$ is unsubstituted alkenyl. In certain embodiments, at least one $R^{D3a\prime}$ is substituted alkynyl. In certain embodiments, at least one $R^{D3a\prime}$ is unsubstituted alkynyl. In certain embodiments, at least one $R^{D3a\prime}$ is substituted carbocyclyl. In certain embodiments, at least one $R^{D3a\prime}$ is unsubstituted carbocyclyl. In certain embodiments, at least one $R^{D3a\prime}$ is substituted heterocyclyl. In certain embodiments, at least one $R^{D3a\prime}$ is unsubstituted heterocyclyl. In certain embodiments, at least one $R^{D3a\prime}$ is substituted aryl. In certain embodiments, at least one $R^{D3a\prime}$ is unsubstituted aryl. In certain embodiments, at least one $R^{D3a\prime}$ is substituted phenyl. In certain embodiments, at least one $R^{D3a\prime}$ is unsubstituted phenyl. In certain embodiments, at least one $R^{D3a\prime}$ is substituted heteroaryl. In certain embodiments, at least one $R^{D3a\prime}$ is unsubstituted heteroaryl. In certain embodiments, at least one $R^{D3a\prime}$ is substituted pyridyl. In certain embodiments, at least one $R^{D3a\prime}$ is unsubstituted pyridyl. In certain embodiments, at least one $R^{D3a\prime}$ is a nitrogen protecting group when attached to a nitrogen atom. In certain embodiments, at least one $R^{D3a\prime}$ is Bn, BOC, Cbz, Fmoc, trifluoroacetyl, triphenylmethyl, or Ts when attached to a nitrogen atom. In certain embodiments, $R^{D3a\prime}$ is an oxygen protecting group when attached to an oxygen atom. In certain embodiments, $R^{D3a\prime}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D3a\prime}$ is a sulfur protecting group when attached to a sulfur atom. In certain embodiments, $R^{D3a\prime}$ is acetamidomethyl, t-Bu, 3-nitro-2-pyridine sulfenyl, 2-pyridine-sulfenyl, or triphenylmethyl when attached to a sulfur atom. In certain embodiments, two $R^{D3a\prime}$ groups are joined to form a substituted heterocyclic ring. In certain embodiments, two $R^{D3a\prime}$ groups are joined to form an unsubstituted heterocyclic ring.

In compounds of Formula (II) and (IV), $R^{D\prime}$ may include a substituent $R^{D4\prime}$. In certain embodiments, $R^{D4\prime}$ is a leaving group. In certain embodiments, $R^{D4\prime}$ is halogen. In certain embodiments, $R^{D4\prime}$ is F. In certain embodiments, $R^{D4\prime}$ is Cl. In certain embodiments, $R^{\prime\prime\prime}$ is Br. In certain embodiments, $R^{D4\prime}$ is I (iodine). In certain embodiments, $R^{D4\prime}$ is —OS$(=O)_w R^{D4a\prime}$. In certain embodiments, w' is 1. In certain embodiments, w' is 2. In certain embodiments, $R^{D4\prime}$ is —OMs. In certain embodiments, $R^{D4\prime}$ is —OTf. In certain embodiments, $R^{D4\prime}$ is —OTs. In certain embodiments, $R^{D4\prime}$ is —OBs. In certain embodiments, $R^{D4\prime}$ is 2-nitrobenzenesulfonyloxy. In certain embodiments, $R^{D4\prime}$ is —$OR^{D4a\prime}$. In certain embodiments, $R^{D4\prime}$ is —OMe. In certain embodiments, $R^{D4\prime}$ is —$OCF_3$. In certain embodiments, $R^{D4\prime}$ is —OPh. In certain embodiments, $R^{D4\prime}$ is —OC(=O)$R^{D4a\prime}$. In certain embodiments, $R^{D4\prime}$ is —OC(=O)Me. In certain embodiments, $R^{D4\prime}$ is —OC(=O)$CF_3$. In certain embodiments, $R^{D4\prime}$ is —OC(=O)Ph. In certain embodiments, $R^{D4\prime}$ is —OC(=O)Cl. In certain embodiments, $R^{D4\prime}$ is —OC(=O)$OR^{D4a\prime}$. In certain embodiments, $R^{D4\prime}$ is —OC(=O)OMe. In certain embodiments, $R^{D4\prime}$ is —OC(=O)O(t-Bu).

In certain embodiments, $R^{D4a\prime}$ is substituted alkyl. In certain embodiments, $R^{D4a\prime}$ is unsubstituted alkyl. In certain embodiments, $R^{D4a\prime}$ is $C_{1-6}$ alkyl. In certain embodiments, $R^{D4a\prime}$ is methyl. In certain embodiments, $R^{D4a\prime}$ is ethyl. In certain embodiments, $R^{D4a\prime}$ is propyl. In certain embodiments, $R^{D4a\prime}$ is butyl. In certain embodiments, $R^{D4a\prime}$ is substituted alkenyl. In certain embodiments, $R^{D4a\prime}$ is unsubstituted alkenyl. In certain embodiments, $R^{D4a\prime}$ is vinyl. In certain embodiments, $R^{D4a\prime}$ is substituted alkynyl. In certain embodiments, $R^{D4a\prime}$ is unsubstituted alkynyl. In certain embodiments, $R^{D4a\prime}$ is ethynyl. In certain embodiments, $R^{D4a\prime}$ is substituted carbocyclyl. In certain embodiments, $R^{D4a\prime}$ is unsubstituted carbocyclyl. In certain embodiments, $R^{D4a\prime}$ is substituted heterocyclyl. In certain embodiments, $R^{D4a\prime}$ is unsubstituted heterocyclyl. In certain embodiments, $R^{D4a\prime}$ is substituted aryl. In certain embodiments, $R^{D4a\prime}$ is unsubstituted aryl. In certain embodiments, $R^{D4a\prime}$ is substituted phenyl. In certain embodiments, $R^{D4a\prime}$ is unsubstituted phenyl. In certain embodiments, $R^{D4a\prime}$ is substituted heteroaryl. In certain embodiments, $R^{D4a\prime}$ is unsubstituted heteroaryl. In certain embodiments, $R^{D4a\prime}$ is substituted pyridyl. In certain embodiments, $R^{D4a\prime}$ is unsubstituted pyridyl.

In compounds of Formula (II) and (IV), $R^{D\prime}$ may include a substituent $R^{D5\prime}$. In certain embodiments, $R^{D5\prime}$ is H. In certain embodiments, $R^{D5\prime}$ is substituted alkyl. In certain embodiments, $R^{D5\prime}$ is unsubstituted alkyl. In certain embodiments, $R^{D5\prime}$ is $C_{1-6}$ alkyl. In certain embodiments, $R^{D5\prime}$ is methyl. In certain embodiments, $R^{D5\prime}$ is ethyl. In certain embodiments, $R^{D5\prime}$ is propyl. In certain embodiments, $R^{D5\prime}$ is butyl. In certain embodiments, $R^{D5\prime}$ is a nitrogen protecting group. In certain embodiments, $R^{D5\prime}$ is Bn, BOC, Cbz, Fmoc, trifluoroacetyl, triphenylmethyl, or Ts.

In certain embodiments, $R^{D1\prime}$ and $R^{D2\prime}$ are each hydrogen. In certain embodiments, $R^{D1\prime}$ and $R^{D3\prime}$ are each hydrogen. In certain embodiments, $R^{D2\prime}$ and $R^{D3\prime}$ are each hydrogen. In certain embodiments, $R^{D1\prime}$, $R^{D2\prime}$, and $R^{D3\prime}$ are each hydrogen. In certain embodiments, $R^{D1\prime}$, $R^{D2\prime}$, and $R^{D3\prime}$, and $R^{D5\prime}$ are each hydrogen.

In certain embodiments, a' is 1. In certain embodiments, a' is 2.

In certain embodiments, z' is 0. In certain embodiments, z' is 1. In certain embodiments, z' is 2. In certain embodiments, z' is 3. In certain embodiments, z' is 4. In certain embodiments, z' is 5. In certain embodiments, z' is 6.

In certain embodiments, $Y^{Z\prime}$ is —O—. In certain embodiments, $Y^{Z\prime}$ is =O. In certain embodiments, $Y^{Z\prime}$ is —S—. In certain embodiments, $Y^{Z\prime}$ is =S. In certain embodiments, $Y^{Z\prime}$ is —$NR^{D6\prime}$—, wherein $R^{D6\prime}$ is hydrogen, $C_{1-6}$ alkyl, or a nitrogen protecting group. In certain embodiments, $Y^{Z\prime}$ is —NH—. In certain embodiments, $Y^{Z\prime}$ is —$NCH_3$—. In certain embodiments, $Y^{Z\prime}$ is —N(BOC)—. In certain embodiments, $Y^{Z\prime}$ is —N(Fmoc)-. In certain embodiments, $Y^{Z\prime}$ is —N(Cbz)-. In certain embodiments, $Y^{Z\prime}$ is —N(Bn)-. In certain embodiments, $Y^{Z\prime}$ is =$NR^{D6\prime}$, wherein $R^{D6\prime}$ is hydrogen, $C_{1-6}$ alkyl, or a nitrogen protecting group. In certain embodiments, $Y^{Z\prime}$ is =NH. In certain embodiments, $Y^{Z\prime}$ is =$NCH_3$. In certain embodiments, $Y^{Z\prime}$ is =NTs. In certain embodiments, $Y^{Z\prime}$ is =NBn. In certain embodiments, $Y^{Z\prime}$ is =$NCH(Ph)_2$.

In certain embodiments, $R^{D\prime}$ is of the formula:

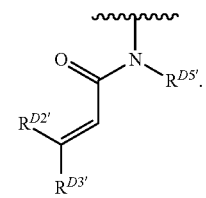

In certain embodiments, $R^{D'}$ is of the formula:

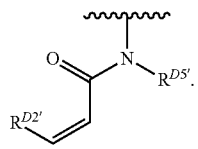

In certain embodiments, $R^{D'}$ is of the formula:

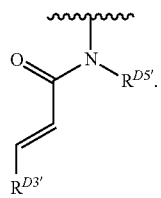

In certain embodiments, $R^{D'}$ is of the formula:

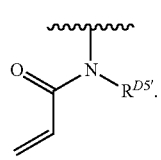

In certain embodiments, $R^{D'}$ is of the formula:

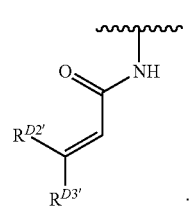

In certain embodiments, $R^{D'}$ is of the formula:

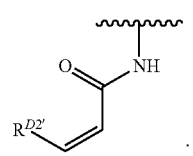

In certain embodiments, $R^{D'}$ is of the formula:

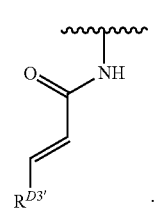

In certain embodiments, $R^{D'}$ is of the formula:

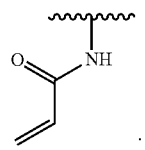

In certain embodiments, $R^{D'}$ is of the formula:

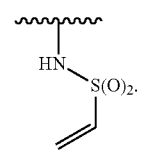

In certain embodiments, $R^{D'}$ is of the formula:

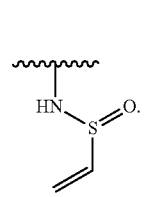

In certain embodiments, $R^{D'}$ is of the formula:

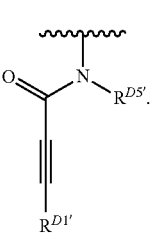

In certain embodiments, $R^{D'}$ is of the formula:

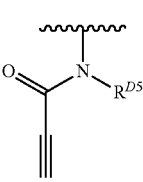

In certain embodiments, $R^{D'}$ is of the formula:

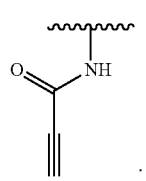

certain embodiments, $R^{D'}$ is of the formula:

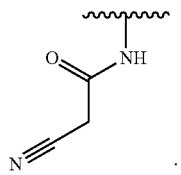

In certain embodiments, $R^{D'}$ is of the formula:

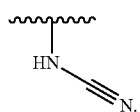

In certain embodiments, $R^{D'}$ is of the formula:

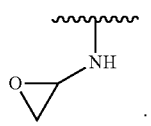 [SMILES: *NC1CO1]

In certain embodiments, $R^{D'}$ is of the formula:

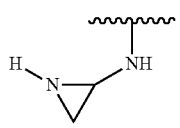

In certain embodiments, $R^{D'}$ is of the formula:

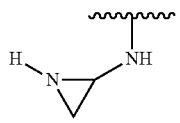

In certain embodiments, $R^{D'}$ is of the formula:

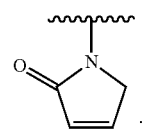

In certain embodiments, $R^{D'}$ is of the formula:

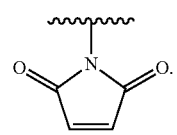 [SMILES: *N1C(=O)C=CC1=O]

In certain embodiments, $R^{D'}$ is of the formula:

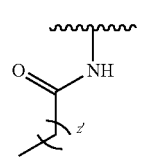

In certain embodiments, $R^{D'}$ is of the formula:

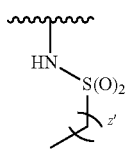

In certain embodiments, $R^{D'}$ is of the formula:

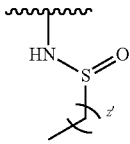

In certain embodiments, $R^{D'}$ is of the formula:

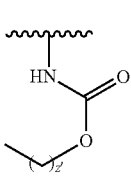

In certain embodiments, $R^{D'}$ is of the formula:

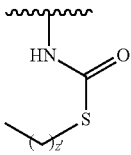

In certain embodiments, $R^{D'}$ is of the formula:

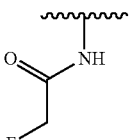

In certain embodiments, $R^{D'}$ is of the formula:

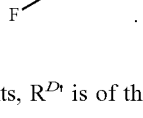

In certain embodiments, $R^{D'}$ is of the formula:

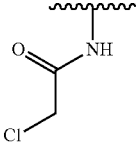

Compounds of any one of Formulae (II) to (V) include an aryl Ring A' optionally substituted with one or more $R^{A'}$ groups. In certain embodiments, k' is 0. In certain embodiments, Ring A' is of the formula:

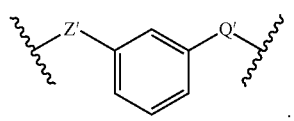

In certain embodiments, Ring A' is of the formula:

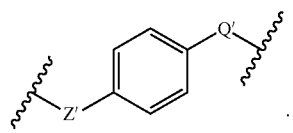

In certain embodiments, k' is 1. In certain embodiments, Ring A' is of the formula:

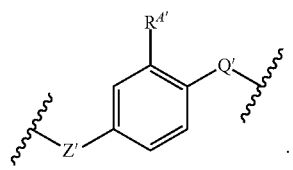

In certain embodiments, Ring A' is of the formula:

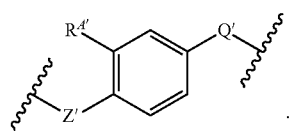

In certain embodiments, Ring A' is of the formula:

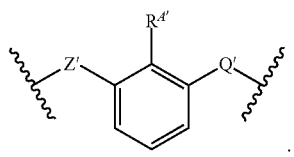

In certain embodiments, Ring A' is of the formula:

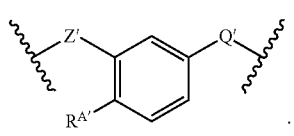

In certain embodiments, Ring A' is of the formula:

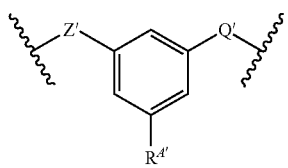

In certain embodiments, Ring A' is of the formula:

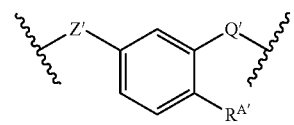

In certain embodiments, k' is 2. In certain embodiments, Ring A' is of the formula:

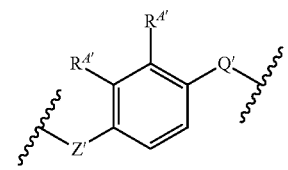

In certain embodiments, Ring A' is of the formula:

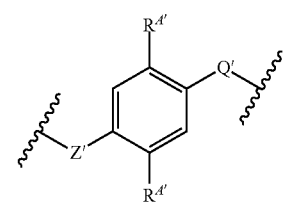

In certain embodiments, Ring A' is of the formula:

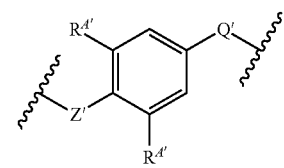

In certain embodiments, Ring A' is of the formula:

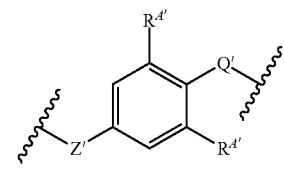

In certain embodiments, Ring A' is of the formula:

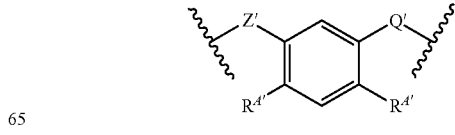

In certain embodiments, Ring A' is of the formula:

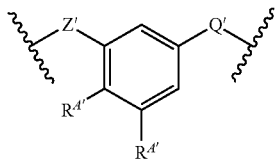

In certain embodiments, Ring A' is of the formula:

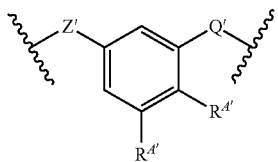

In certain embodiments, Ring A' is of the formula:

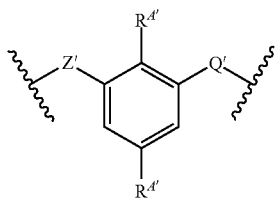

In certain embodiments, Ring A' is of the formula:

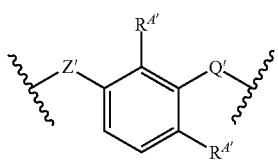

In certain embodiments, Ring A' is of the formula:

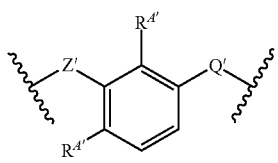

In certain embodiments, k' is 3. In certain embodiments, Ring A' is of the formula:

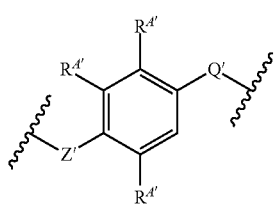

In certain embodiments, Ring A' is of the formula:

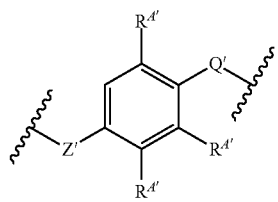

In certain embodiments, Ring A' is of the formula:

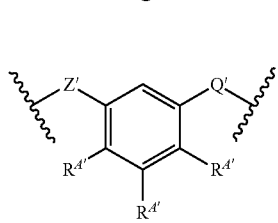

In certain embodiments, Ring A' is of the formula:

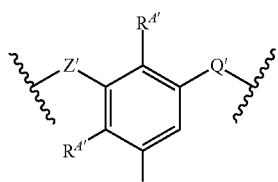

In certain embodiments, Ring A' is of the formula:

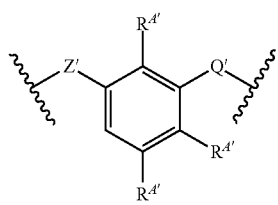

In certain embodiments, Ring A' is of the formula:

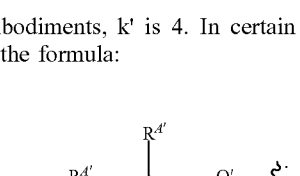

In certain embodiments, k' is 4. In certain embodiments, Ring A' is of the formula:

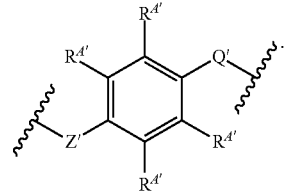

In certain embodiments, Ring A' is of the formula:

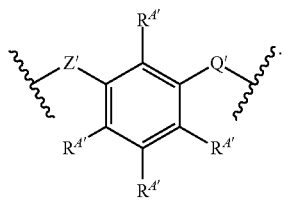

Compounds of any one of Formulae (II) to (V) include an aryl Ring A' optionally substituted with one or more $R^{A'}$ groups. In certain embodiments, X', Y', and Z' are bonds, and Cy is hydrogen. In certain embodiments, k' is 0. In certain embodiments, Ring A' is of the formula:

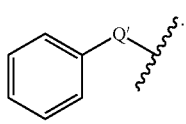

In certain embodiments, k' is 1. In certain embodiments, Ring A' is of the formula:

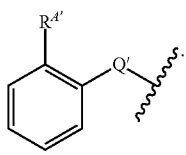

In certain embodiments, Ring A' is of the formula:

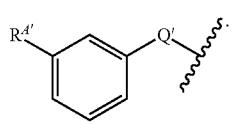

In certain embodiments, Ring A' is of the formula:

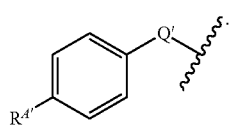

In certain embodiments, k' is 2. In certain embodiments, Ring A' is of the formula:

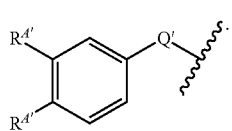

In certain embodiments, Ring A' is of the formula:

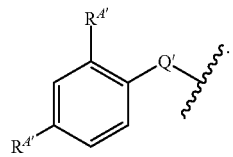

In certain embodiments, Ring A' is of the formula:

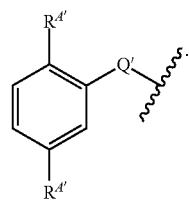

In certain embodiments, Ring A' is of the formula:

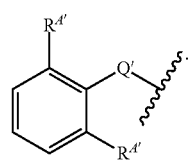

In certain embodiments, Ring A' is of the formula:

(image)

In certain embodiments, Ring A' is of the formula:

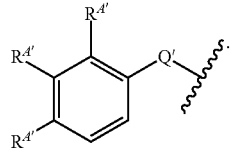

In certain embodiments, Ring A' is of the formula:

(image)

In certain embodiments, Ring A' is of the formula:

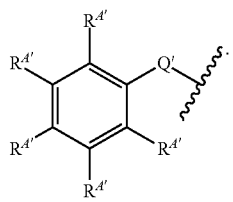

In compounds of any one of Formulae (II) to (V), Ring A' may be substituted with one or more $R^{A'}$ groups. In certain embodiments, at least one $R^{A'}$ is H. In certain embodiments, at least two $R^{A'}$ groups are H. In certain embodiments, at least three $R^{A'}$ groups are H. In certain embodiments, at least four $R^{A'}$ groups are H. In certain embodiments, at least one $R^{A'}$ is halogen. In certain embodiments, at least one $R^{A'}$ is F. In certain embodiments, at least one $R^{A'}$ is Cl. In certain embodiments, at least one $R^{A'}$ is Br. In certain embodiments, at least one $R^{A'}$ is I (iodine). In certain embodiments, at least one $R^{A'}$ is substituted acyl. In certain embodiments, at least one $R^{A'}$ is —C(=O)N($R^{A'}$)$_2$. In certain embodiments, at least one $R^{A'}$ is —C(=O)NHR$^{A1'}$. In certain embodiments, at least one $R^{A'}$ is —C(=O)NH(C$_{1-6}$ alkyl). In certain embodiments, at least one $R^{A'}$ is —C(=O)NHMe. In certain embodiments, at least one $R^{A'}$ is —C(=O)NH$_2$. In certain embodiments, at least one $R^{A'}$ is unsubstituted acyl. In certain embodiments, at least one $R^{A'}$ is acetyl. In certain embodiments, at least one $R^{A'}$ is substituted alkyl. In certain embodiments, at least one $R^{A'}$ is substituted methyl. In certain embodiments, at least one $R^{A'}$ is unsubstituted alkyl. In certain embodiments, at least one $R^{A'}$ is $C_{1-6}$ alkyl. In certain embodiments, at least one $R^{A'}$ is methyl. In certain embodiments, at least one $R^{A'}$ is ethyl. In certain embodiments, at least one $R^{A'}$ is propyl. In certain embodiments, at least one $R^{A'}$ is butyl. In certain embodiments, at least one $R^{A'}$ is substituted alkenyl. In certain embodiments, at least one $R^{A'}$ is unsubstituted alkenyl. In certain embodiments, at least one $R^{A'}$ is substituted alkynyl. In certain embodiments, at least one $R^{A'}$ is unsubstituted alkynyl. In certain embodiments, at least one $R^{A'}$ is substituted carbocyclyl. In certain embodiments, at least one $R^{A'}$ is unsubstituted carbocyclyl. In certain embodiments, at least one $R^{A'}$ is substituted heterocyclyl. In certain embodiments, at least one $R^{A'}$ is unsubstituted heterocyclyl. In certain embodiments, at least one $R^{A'}$ is

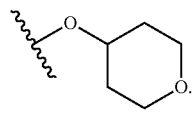

In certain embodiments, at least one $R^{A'}$ is substituted aryl. In certain embodiments, at least one $R^{A'}$ is unsubstituted aryl. In certain embodiments, at least one $R^{A'}$ is substituted phenyl. In certain embodiments, at least one $R^{A'}$ is unsubstituted phenyl. In certain embodiments, at least one $R^{A'}$ is substituted heteroaryl. In certain embodiments, at least one $R^{A'}$ is unsubstituted heteroaryl. In certain embodiments, at least one $R^{A'}$ is substituted pyridyl. In certain embodiments, at least one $R^{A'}$ is unsubstituted pyridyl. In certain embodiments, at least one $R^{A'}$ is —OR$^{A1'}$. In certain embodiments, at least one $R^{A'}$ is —O(C$_{1-6}$ alkyl). In certain embodiments, at least one $R^{A'}$ is —OMe. In certain embodiments, at least one $R^{A'}$ is —OH. In certain embodiments, at least one $R^{A'}$ is —N(R$^{A1'}$)$_2$. In certain embodiments, at least one $R^{A'}$ is —NH$_2$. In certain embodiments, at least one $R^{A'}$ is —SR$^{A1'}$. In certain embodiments, at least one $R^{A'}$ is —SH. In certain embodiments, at least one $R^{A'}$ is —NR$^{A1'}$C(=O)N(R$^{A'}$)$_2$. In certain embodiments, at least one $R^{A'}$ is —NHC(=O)N(R$^{A'}$)$_2$. In certain embodiments, at least one $R^{A'}$ is —NHC(=O)NHR$^{A1'}$. In certain embodiments, at least one $R^{A'}$ is —NHC(=O)NH(C$_{1-6}$ alkyl). In certain embodiments, at least one $R^{A'}$ is —NHC(=O)NHMe. In certain embodiments, at least one $R^{A'}$ is —NHC(=O)NH$_2$. In certain embodiments, at least one $R^{A'}$ is —NR$^{A1'}$C(=O)NHR$^{A1'}$. In certain embodiments, at least one $R^{A'}$ is —NR$^{A1'}$C(=O)NH$_2$. In certain embodiments, at least one $R^{A'}$ is —NR$^{A1'}$S(=O)$_2$R$^{A1'}$. In certain embodiments, at least one $R^{A'}$ is —NHS(=O)$_2$R$^{A1'}$. In certain embodiments, at least one $R^{A'}$ is —NHS(=O)$_2$(C$_{1-6}$ alkyl). In certain embodiments, at least one $R^{A'}$ is —NHS(=O)$_2$Me. In certain embodiments, at least one $R^{A'}$ is —S(=O)$_2$N(R$^{A1}$)$_2$. In certain embodiments, at least one $R^{A'}$ is —S(=O)$_2$N(R$^{A1'}$)$_2$. In certain embodiments, at least one $R^{A'}$ is —S(=O)$_2$N(C$_{1-6}$ alkyl)$_2$. In certain embodiments, at least one $R^{A'}$ is —S(=O)$_2$NH(C$_{1-6}$ alkyl). In certain embodiments, at least one $R^{A'}$ is —S(=O)$_2$NH(t-Bu). In certain embodiments, at least one $R^{A'}$ is —S(=O)$_2$NH$_2$.

In compounds of any one of Formulae (II) to (V), Ring C' may be substituted with one or more $R^{B'}$ groups. In certain embodiments, at least one $R^{B'}$ is H. In certain embodiments, at least two $R^{B'}$ groups are H. In certain embodiments, at least three $R^{B'}$ groups are H. In certain embodiments, at least four $R^{B'}$ groups are H. In certain embodiments, at least one $R^{B'}$ is halogen. In certain embodiments, at least one $R^{B'}$ is F. In certain embodiments, at least one $R^{B'}$ is Cl. In certain embodiments, at least one $R^{B'}$ is Br. In certain embodiments, at least one $R^{B'}$ is I (iodine). In certain embodiments, at least one $R^{B'}$ is substituted acyl. In certain embodiments, at least one $R^{B'}$ is —C(=O)N(R$^{A1}$)$_2$. In certain embodiments, at least one $R^{B'}$ is —C(=O)NHR$^{A1'}$. In certain embodiments, at least one $R^{B'}$ is —C(=O)NH(C$_{1-6}$ alkyl). In certain embodiments, at least one $R^{B'}$ is —C(=O)NHMe. In certain embodiments, at least one $R^{B'}$ is —C(=O)NH$_2$. In certain embodiments, at least one $R^{B'}$ is unsubstituted acyl. In certain embodiments, at least one $R^{B'}$ is acetyl. In certain embodiments, at least one $R^{B'}$ is substituted alkyl. In certain embodiments, at least one $R^{B'}$ is substituted methyl. In certain embodiments, at least one $R^{B'}$ is unsubstituted alkyl. In certain embodiments, at least one $R^{B'}$ is $C_{1-6}$ alkyl. In certain embodiments, at least one $R^{B'}$ is methyl. In certain embodiments, at least one $R^{B'}$ is ethyl. In certain embodiments, at least one $R^{B'}$ is propyl. In certain embodiments, at least one $R^{B'}$ is butyl. In certain embodiments, at least one $R^{B'}$ is —CF$_3$. In certain embodiments, at least one $R^{B'}$ is substituted alkenyl. In certain embodiments, at least one $R^{B'}$ is unsubstituted alkenyl. In certain embodiments, at least one $R^{B'}$ is substituted alkynyl. In certain embodiments, at least one $R^{B'}$ is unsubstituted alkynyl. In certain embodiments, at least one $R^{B'}$ is substituted carbocyclyl. In certain embodiments, at least one $R^{B'}$ is unsubstituted carbocyclyl. In certain embodiments, at least one $R^{B'}$ is substituted heterocyclyl. In certain embodiments, at least one $R^{B'}$ is unsubstituted heterocyclyl. In certain embodiments, at least one $R^{B'}$ is substituted aryl. In certain embodiments, at least one $R^{B'}$ is unsubstituted aryl. In certain embodiments, at least one $R^{B'}$ is substituted phenyl. In certain embodiments, at least one $R^{B'}$ is unsubstituted phenyl. In certain embodiments, at least one $R^{B'}$ is substituted heteroaryl. In certain embodiments, at least one $R^{B'}$ is unsubstituted heteroaryl. In certain embodiments, at least one $R^{B'}$ is substituted pyridyl. In certain embodiments, at least one $R^{B'}$ is unsubstituted pyridyl. In certain embodiments, at least one $R^{B'}$ is —$O^{A1}$. In certain embodiments, at least one $R^{B'}$ is —$O(C_{1-6}$ alkyl). In certain embodiments, at least one $R^{B'}$ is —OMe. In certain embodiments, at least one $R^{B'}$ is —OH. In certain embodiments, at least one $R^{B'}$ is —$N(R^{A1})_2$. In certain embodiments, at least one $R^{B'}$ is —$NH_2$. In certain embodiments, at least one $R^{B'}$ is —$SR^{A1'}$. In certain embodiments, at least one $R^{B'}$ is —SH. In certain embodiments, at least one $R^{B'}$ is —$NR^{A1'}C(=O)N(R^{A1})_2$. In certain embodiments, at least one $R^{B'}$ is —$NHC(=O)N(R^{A1'})_2$. In certain embodiments, at least one $R^{B'}$ is —$NHC(=O)NHR^{A1'}$. In certain embodiments, at least one $R^{B'}$ is —$NHC(=O)NH(C_{1-6}$ alkyl). In certain embodiments, at least one $R^{B'}$ is —$NHC(=O)NHMe$. In certain embodiments, at least one $R^{B'}$ is —$NHC(=O)NH_2$. In certain embodiments, at least one $R^{B'}$ is —$NR^{A1'}C(=O)NHR^{A1'}$. In certain embodiments, at least one $R^{B'}$ is —$NR^{A1'}C(=O)NH_2$. In certain embodiments, at least one $R^{B'}$ is —$NR^{A1'}S(=O)_2R^{A1}$. In certain embodiments, at least one $R^{B'}$ is —$NHS(=O)_2R^{A1'}$. In certain embodiments, at least one $R^{B'}$ is —$NHS(=O)_2(C_{1-6}$ alkyl). In certain embodiments, at least one $R^{B'}$ is —$NHS(=O)_2Me$. In certain embodiments, at least one $R^{B'}$ is —$S(=O)_2N(R^{A1'})_2$. In certain embodiments, at least one $R^{B'}$ is —$S(=O)_2N(R^{A1'})_2$. In certain embodiments, at least one $R^{B'}$ is —$S(=O)_2N(C_{1-6}$ alkyl)$_2$. In certain embodiments, at least one $R^{B'}$ is —$S(=O)_2NH(C_{1-6}$ alkyl). In certain embodiments, at least one $R^{B'}$ is —$S(=O)_2NH(t\text{-Bu})$. In certain embodiments, at least one $R^{B'}$ is —$S(=O)_2NH_2$. In certain embodiments, at least one $R^{B'}$ is substituted imidazole. In certain embodiments, at least one $R^{B'}$ is substituted piperidine. In certain embodiments, at least one $R^{B'}$ substituted piperizine. In certain embodiments, at least one $R^{B'}$ substituted pyrrolidine. In certain embodiments, at least one $R^{B'}$ is substituted morpholine. In certain embodiments, at least one $R^{B'}$ is substituted diazapane. In certain embodiments, at least one $R^{B'}$ is

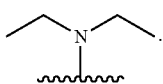

In certain embodiments, at least one $R^{B'}$ is

In certain embodiments, at least one $R^{B'}$ is

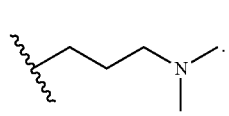 [SMILES: *CCCN(C)C]

In certain embodiments, at least one $R^{B'}$ is

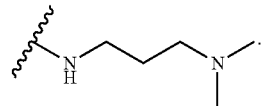 [SMILES: *NCCCN(C)C]

In certain embodiments, at least one $R^{B'}$ is

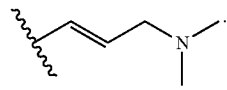 [SMILES: */C=C/CN(C)C]

In certain embodiments, at least one $R^{B}$ is

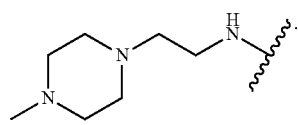 [SMILES: *NCCN1CCN(C)CC1]

In certain embodiments, at least one $R^{B'}$ is

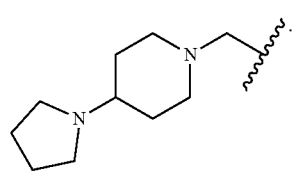 [SMILES: *CN1CCC(N2CCCC2)CC1]

In certain embodiments, at least one $R^{B'}$ is

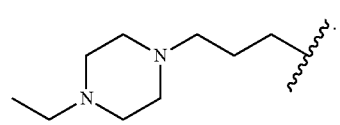 [SMILES: *CCCN1CCN(CC)CC1]

In certain embodiments, at least one $R^{B'}$ is

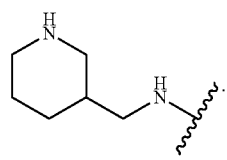 [SMILES: *NCC1CCCNC1]

In certain embodiments, at least one $R^{B'}$ is

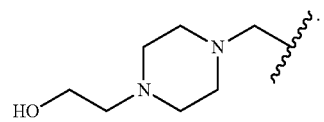 [SMILES: *CN1CCN(CCO)CC1]

In certain embodiments, at least one $R^{B'}$ is

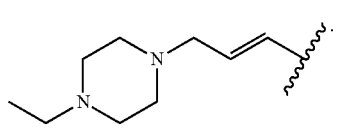 [SMILES: */C=C/CN1CCN(CC)CC1]

In certain embodiments, at least one $R^{B'}$ is

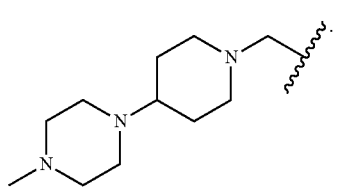 [SMILES: *CN1CCC(N2CCN(C)CC2)CC1]

In certain embodiments, at least one $R^{B'}$ is

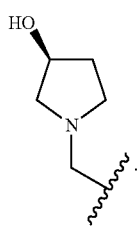

In certain embodiments, at least one $R^{B'}$ is

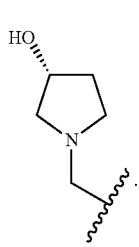

In certain embodiments, at least one $R^{B'}$ is

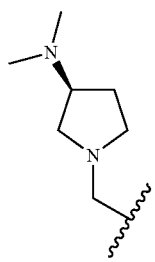

In certain embodiments, at least one $R^{B'}$ is

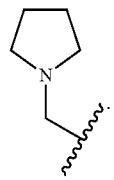

In certain embodiments, at least one $R^{B'}$ is

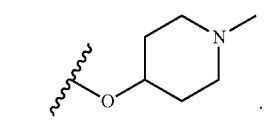 [SMILES: *OC1CCN(C)CC1]

In certain embodiments, at least one $R^{B'}$ is

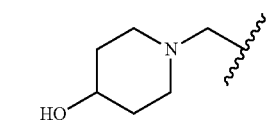

In certain embodiments, at least one $R^{B'}$ is

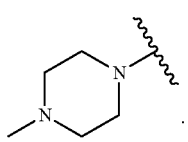 [SMILES: *N1CCN(C)CC1]

In certain embodiments, at least one $R^{B'}$ is

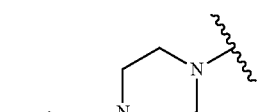

In certain embodiments, at least one $R^{B'}$ is

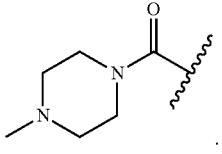 [SMILES: *C(=O)N1CCN(C)CC1]

In certain embodiments, at least one $R^{B'}$ is

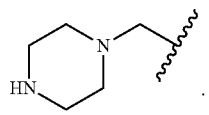

In certain embodiments, at least one $R^{B'}$ is

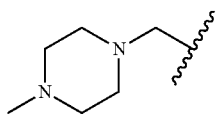

In certain embodiments, at least one $R^{B'}$ is

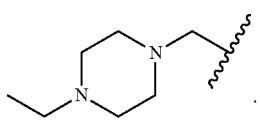 [SMILES: *CN1CCN(CC)CC1]

In certain embodiments, at least one $R^{B'}$ is

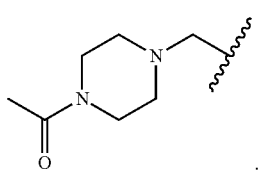 [SMILES: *CN1CCN(C(C)=O)CC1]

In certain embodiments, at least one $R^{B'}$ is

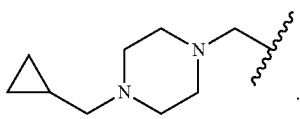 [SMILES: *CN1CCN(CC2CC2)CC1]

In certain embodiments, at least one $R^{B'}$ is

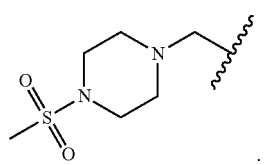 [SMILES: *CN1CCN(S(C)(=O)=O)CC1]

In certain embodiments, at least one $R^{B}$ is

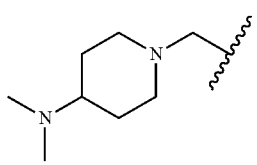

In certain embodiments, at least one $R^{B'}$ is

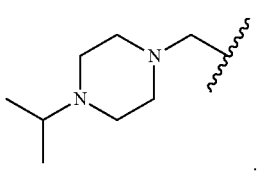 [SMILES: *CN1CCN(C(C)C)CC1]

In certain embodiments, at least one $R^{B'}$ is

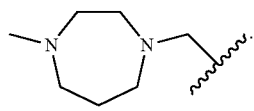 [SMILES: *CN1CCCN(C)CC1]

In certain embodiments, at least one $R^{B'}$ is

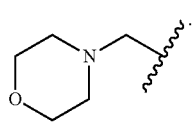 [SMILES: *CN1CCOCC1]

In certain embodiments, at least one $R^{B'}$ is

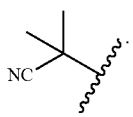 [SMILES: *C(C)(C)C#N]

In certain embodiments, at least one $R^{B'}$ is

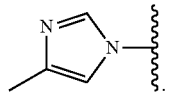

In certain embodiments, at least one $R^{B'}$ is

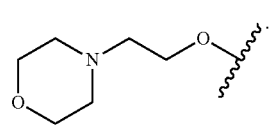 [SMILES: *OCCN1CCOCC1]

In certain embodiments, at least one $R^{B'}$ is

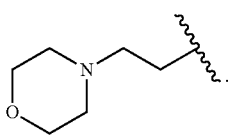 [SMILES: *CCN1CCOCC1]

In certain embodiments, at least one $R^{B'}$ is

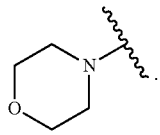 [SMILES: *N1CCOCC1]

In certain embodiments, at least one $R^{B'}$ is

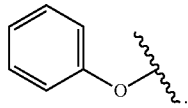 [SMILES: *Oc1ccccc1]

In certain embodiments, at least one $R^{B'}$ is

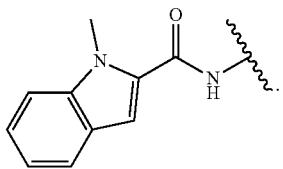 [SMILES: *NC(=O)c1cc2ccccc2n1C]

In certain embodiments, at least one $R^{B'}$ is

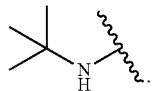

In certain embodiments, at least one $R^{B'}$ is

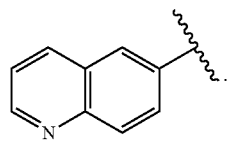 [SMILES: *c1ccc2ncccc2c1]

In certain embodiments, two $R^{B'}$ groups are joined to form a 1,3 dioxolane. In certain embodiments, two $R^{B'}$ groups are joined to form a 1,3 dioxolane which is fused to aryl Ring C', together comprising an optionally substituted benzodioxolane. In certain embodiments, two $R^{B'}$ groups are joined to form a 1,2,3-thiadiazole. In certain embodiments, two $R^{B'}$ groups are joined to form a 1,2,3-thiadiazole which is fused to aryl Ring C', together comprising an optionally substituted benzo[d][1,2,3]thiadiazole.

In certain embodiments, at least one $R^{A1'}$ is H. In certain embodiments, at least one $R^{A1'}$ is substituted acyl. In certain embodiments, at least one $R^{A1'}$ is unsubstituted acyl. In certain embodiments, at least one $R^{A1'}$ is acetyl. In certain embodiments, at least one $R^{A1'}$ is substituted alkyl. In certain embodiments, at least one $R^{A1'}$ is unsubstituted alkyl. In certain embodiments, at least one $R^{A1'}$ is $C_{1-6}$ alkyl. In certain embodiments, at least one $R^{A1'}$ is methyl. In certain embodiments, at least one $R^{A1'}$ is ethyl. In certain embodiments, at least one $R^{A1'}$ is propyl. In certain embodiments, at least one $R^{A1'}$ is butyl. In certain embodiments, at least one $R^{A1'}$ is substituted alkenyl. In certain embodiments, at least one $R^{A1'}$ is unsubstituted alkenyl. In certain embodiments, at least one $R^{A1'}$ is substituted alkynyl. In certain embodiments, at least one $R^{A1'}$ is unsubstituted alkynyl. In certain embodiments, at least one $R^{A1'}$ is substituted carbocyclyl. In certain embodiments, at least one $R^{A1'}$ is unsubstituted carbocyclyl. In certain embodiments, at least one $R^{A1'}$ is substituted heterocyclyl. In certain embodiments, at least one $R^{A1'}$ is unsubstituted heterocyclyl. In certain embodiments, at least one $R^{A1'}$ is substituted aryl. In certain embodiments, at least one $R^{A1'}$ is unsubstituted aryl. In certain embodiments, at least one $R^{A1'}$ is substituted phenyl. In certain embodiments, at least one $R^{A1'}$ is unsubstituted phenyl. In certain embodiments, at least one $R^{A1'}$ is substituted heteroaryl. In certain embodiments, at least one $R^{A1'}$ is unsubstituted heteroaryl. In certain embodiments, at least one $R^{A1'}$ is substituted pyridyl. In certain embodiments, at least one $R^{A1'}$ is unsubstituted pyridyl. In certain embodiments, at least one $R^{A1'}$ is a nitrogen protecting group when attached to a nitrogen atom. In certain embodiments, at least one $R^{A1'}$ is Bn, BOC, Cbz, Fmoc, trifluoroacetyl, triphenylmethyl, or Ts when attached to a nitrogen atom. In certain embodiments, $R^{A1'}$ is an oxygen protecting group when attached to an oxygen atom. In certain embodiments, $R^{A1'}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1'}$ is a sulfur protecting group when attached to a sulfur atom. In certain embodiments, $R^{A1'}$ is acetamidomethyl, t-Bu, 3-nitro-2-pyridine sulfenyl, 2-pyridine-sulfenyl, or triphenylmethyl when attached to a sulfur atom.

In compounds of any one of Formulae (II) to (V), two $R^{A1'}$ groups may be joined to form an optionally substituted carbocyclic, optionally substituted heterocyclic, optionally substituted aryl, or optionally substituted heteroaryl ring. In certain embodiments, two $R^{A1'}$ groups are joined to form a substituted carbocyclic ring. In certain embodiments, two $R^{A1'}$ groups are joined to form an unsubstituted carbocyclic ring. In certain embodiments, two $R^{A1'}$ groups are joined to form a substituted heterocyclic ring. In certain embodiments, two $R^{A1'}$ groups are joined to form an unsubstituted heterocyclic ring. In certain embodiments, two $R^{A1'}$ groups are joined to form a substituted aryl ring. In certain embodiments, two $R^{A1'}$ groups are joined to form an unsubstituted aryl ring. In certain embodiments, two $R^{A1'}$ groups are joined to form a substituted phenyl ring. In certain embodiments, two $R^{A1'}$ groups are joined to form an unsubstituted phenyl ring. In certain embodiments, two $R^{A1'}$ groups are joined to form a substituted heteroaryl ring. In certain embodiments, two $R^{A1'}$ groups are joined to form an unsubstituted heteroaryl ring.

In certain embodiments, $R^{A'}$ is —$OR^{A1'}$ and k' is 1. In certain embodiments, $R^{A'}$ is —$O(C_{1-6}$ alkyl) and k' is 1. In certain embodiments, $R^{A'}$ is —OMe and k' is 1. In certain embodiments, $R^{A'}$ is —OH and k' is 1.

In certain embodiments, $R^{A'}$ is substituted $C_{1-6}$ alkyl; and k' is 1. In certain embodiments, $R^{A'}$ is unsubstituted $C_{1-6}$ alkyl; and k' is 1. In certain embodiments, $R^{A'}$ is methyl; and k' is 1. In certain embodiments, $R^{A'}$ is —$CF_3$; and k' is 1. In certain embodiments, $R^{A'}$ is ethyl; and k' is 1. In certain embodiments, $R^{A'}$ is propyl; and k' is 1. In certain embodiments, $R^{A'}$ is butyl; and k' is 1. In certain embodiments, $R^{A'}$ is propyl; and k' is 1. In certain embodiments, $R^{A'}$ is butyl; and k' is 1.

In certain embodiments, $R^{A'}$ is halogen; and k' is 1. In certain embodiments, $R^{A'}$ is F; and k' is 1. In certain embodiments, $R^{A'}$ is Cl; and k' is 1. In certain embodiments, $R^{A'}$ is Br; and k' is 1. In certain embodiments, $R^{A'}$ is I (iodine); and k' is 1.

In certain embodiments, one instance of $R^{A'}$ is halogen, another instance of $R^{A'}$ is substituted $C_{1-6}$ alkyl; and k' is 2. In certain embodiments, one instance of $R^{A'}$ is F, another instance of $R^{A'}$ is substituted $C_{1-6}$ alkyl; and k' is 2. In certain embodiments, one instance of $R^{A'}$ is Cl, another instance of $R^{A'}$ is substituted $C_{1-6}$ alkyl; and k' is 2. In certain embodiments, one instance of $R^{A'}$ is halogen, another instance of $R^{A'}$ is unsubstituted $C_{1-6}$ alkyl; and k' is 2. In certain embodiments, one instance of $R^{A'}$ is F, another instance of $R^{A'}$ is unsubstituted $C_{1-6}$ alkyl; and k' is 2. In certain embodiments, one instance of $R^{A'}$ is Cl, another instance of $R^{A'}$ is unsubstituted $C_{1-6}$ alkyl; and k' is 2. In certain embodiments, one instance of $R^{A'}$ is halogen, another instance of $R^{A'}$ is methyl; and k' is 2. In certain embodiments, one instance of $R^{A'}$ is F, another instance of $R^{A'}$ is methyl; and k' is 2. In certain embodiments, one instance of $R^{A'}$ is Cl, another instance of $R^{A'}$ is methyl; and k' is 2. In certain embodiments, one instance of $R^{A'}$ is halogen, another instance of $R^{A'}$ is —$CF_3$; and k' is 2. In certain embodiments, one instance of $R^{A'}$ is F, another instance of $R^{A'}$ is —$CF_3$; and k' is 2. In certain embodiments, one instance of $R^{A'}$ is Cl, another instance of $R^{A'}$ is —$CF_3$; and k' is 2.

In compounds of any one of Formulae (II) to (V), linker X', Y', and Z' are divalent linker moieties. In certain embodiments, X' is a bond. In certain embodiments, X' is a single bond. In certain embodiments, X' is —$CH_2$. In certain embodiments, X' is —$CHR^{A'}$. In certain embodiments, X' is —CH. In certain embodiments, X' is —$C(R^{A'})_2$. In certain embodiments, X' is —C. In certain embodiments, X' is —N. In certain embodiments, X' is —$NR^{A'}$. In certain embodiments, X' is —O. In certain embodiments, X' is —C=O. In certain embodiments, X' is —O. In certain embodiments, X' is —S. In certain embodiments, X' may optionally form a 5 to 8 membered ring with $R^{A'}$ or $R^{B'}$. In certain embodiments, Y' is a bond. In certain embodiments, Y' is a single bond. In certain embodiments, Y' is —$CH_2$. In certain embodiments, Y' is —$CHR^{A'}$. In certain embodiments, Y' is —CH. In certain embodiments, Y' is —$C(R^{A'})_2$. In certain embodiments, Y' is —C. In certain embodiments, Y' is —N. In certain embodiments, Y' is —$NR^{A'}$. In certain embodiments, Y' is —O. In certain embodiments, Y' is —C=O. In certain embodiments, Y' is —S. In certain embodiments, Y' may optionally form a 5 to 8 membered ring with $R^{A'}$ or $R^{B'}$. In certain embodiments, Z' is a bond. In certain embodiments, Z' is a single bond. In certain embodiments, Z' is —$CH_2$. In certain embodiments, Z' is —$CHR^{A'}$. In certain embodiments, Z' is —CH. In certain embodiments, Z' is —$C(R^{A'})_2$. In certain embodiments, Z' is —C. In certain embodiments, Z' is —N. In certain embodiments, Z' is —$NR^{A'}$. In certain embodiments, Z' is —O. In certain embodiments, Z' is —C=O. In certain embodiments, Z' is —S. In certain embodiments, Z' may optionally form a 5 to 8 membered ring with $R^{A'}$ or $R^{B'}$.

In compounds of any one of Formulae (II) to (V), linker X', Y', and Z' can be taken together to represent specific linking groups. In certain embodiments, X', Y', and Z' together represent In certain embodiments, X', Y', and Z' together represent

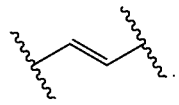 [SMILES: */C=C/*]

In certain embodiments, X', Y', and Z' together represent

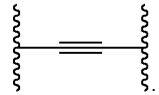

In certain embodiments, X', Y', and Z' together represent

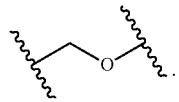

In certain embodiments, X', Y', and Z' together represent

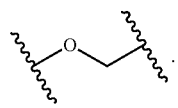 [SMILES: *CO*]

In certain embodiments, X', Y', and Z' together represent

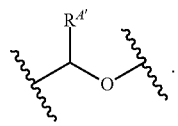

In certain embodiments, X', Y', and Z' together represent

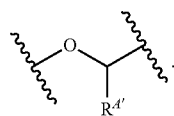

In certain embodiments, X', Y', and Z' together represent

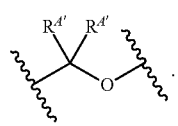

In certain embodiments, X', Y', and Z' together represent

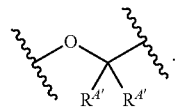

In certain embodiments, X', Y', and Z' together represent

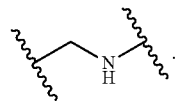 [SMILES: *CN*]

In certain embodiments, X', Y', and Z' together represent

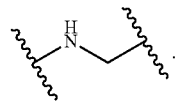 [SMILES: *CN*]

In certain embodiments, X', Y', and Z' together represent

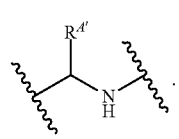

In certain embodiments, X', Y', and Z' together represent

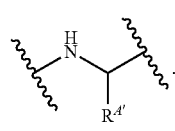

In certain embodiments, X', Y', and Z' together represent

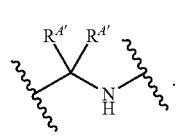

In certain embodiments, X', Y', and Z' together represent

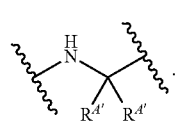

In certain embodiments, X', Y', and Z' together represent

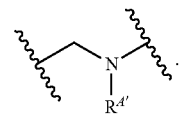

In certain embodiments, X', Y', and Z' together represent

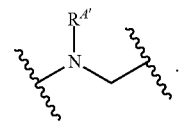

In certain embodiments, X', Y', and Z' together represent

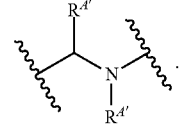

In certain embodiments, X', Y', and Z' together represent

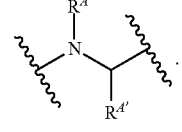

In certain embodiments, X', Y', and Z' together represent

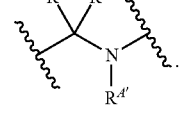

In certain embodiments, X', Y', and Z' together represent

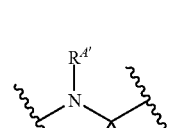

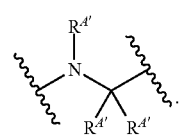

In certain embodiments, X', Y', and Z' together represent

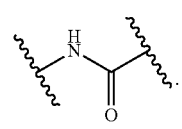 [SMILES: *NC(*)=O]

In certain embodiments, X', Y', and Z' together represent

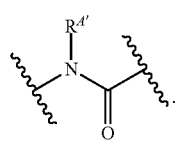

In certain embodiments, X', Y', and Z' together represent

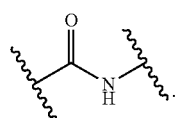

In certain embodiments, X', Y', and Z' together represent

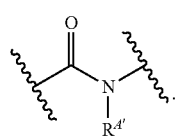

In certain embodiments, X', Y', and Z' together represent

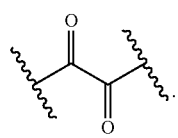 [SMILES: *C(=O)C(*)=O]

In certain embodiments, X', Y', and Z' together represent

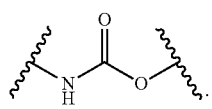

In certain embodiments, X', Y', and Z' together represent

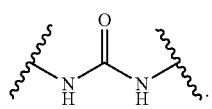 [SMILES: *NC(=O)N*]

In certain embodiments, X', Y', and Z' together represent

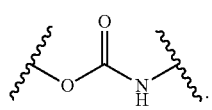 [SMILES: *NC(=O)O*]

In certain embodiments, X', Y', and Z' together represent

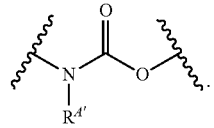

In certain embodiments, X', Y', and Z' together represent

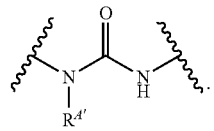

In certain embodiments, X', Y', and Z' together represent

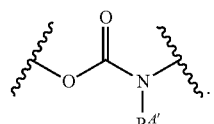

In certain embodiments, X', Y', and Z' together represent

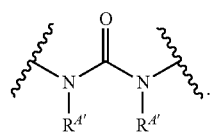

In certain embodiments, X', Y', and Z' together represent

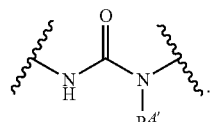

In certain embodiments, X', Y', and Z' together represent

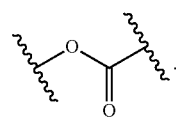 [SMILES: *OC(*)=O]

In certain embodiments, X', Y', and Z' together represent

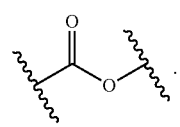 [SMILES: *OC(*)=O]

In certain embodiments, X', Y', and Z' together represent a single bond.

In compounds of any one of Formulae (II) to (V), linker Q' and U' are divalent linker moieties. In certain embodiments, Q' is —NR$^{A'}$. In certain embodiments, Q' is —NH. In certain embodiments, Q' is —C=O. In certain embodiments, Q' is —NR$^{A'}$CO. In certain embodiments, Q' is a bond. In certain embodiments, X' may optionally form a 5 to 8 membered ring with R$^{A'}$ or R$^{B'}$. In certain embodiments, U' is —NR$^{A'}$. In certain embodiments, U' is —NH. In certain embodiments, U' is —C=O. In certain embodiments, U' is —NR$^{A'}$CO. In certain embodiments, U' is a bond. In certain embodiments, U' may optionally form a 5 to 8 membered ring with R$^{A'}$ or R$^{B'}$.

In compounds of any one of Formulae (II) to (V), linker Q' and U' can be taken together to represent specific linking groups. In certain embodiments, Q' and U' together represent

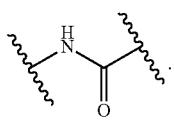

In certain embodiments, Q' and U' together represent

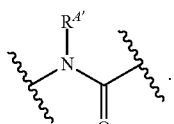

In certain embodiments, Q' and U' together represent

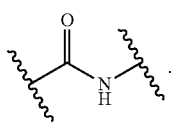 [SMILES: *NC(*)=O]

In certain embodiments, Q' and U' together represent

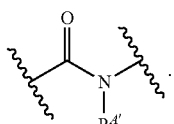

In certain embodiments, Q' and U' together represent

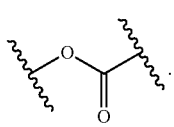

In certain embodiments, Q' and U' together represent

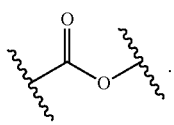

In certain embodiments, Q' and U' together represent

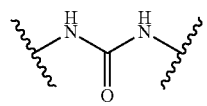

In certain embodiments, Q' and U' together represent

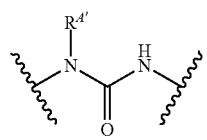

In certain embodiments, Q' and U' together represent

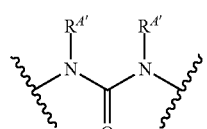

In certain embodiments, Q' and U' together represent

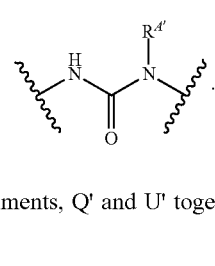

In certain embodiments, Q' and U' together represent

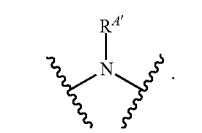

In certain embodiments, Q' and U' together represent

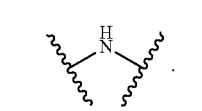

Cy of any one of Formulae (II) to (V) may be an optionally substituted aryl ring. In certain embodiments, Ring Cy is a substituted aryl ring. In certain embodiments, Cy is an unsubstituted aryl ring. In certain embodiments, Cy is a monocyclic aryl ring. In certain embodiments, Cy is substituted phenyl. In certain embodiments, Cy is unsubstituted phenyl. In certain embodiments, Cy is a bicyclic aryl ring. In certain embodiments, Cy is substituted naphthyl. In certain embodiments, Cy is unsubstituted naphthyl. In certain embodiments, Cy is an optionally substituted aryl ring fused with one or more optionally substituted carbocyclic, optionally substituted heterocyclic, optionally substituted aryl, or optionally substituted heteroaryl groups wherein the point of attachment is on the aryl ring.

Cy of any one of Formulae (II) to (V) may also be an optionally substituted heteroaryl ring. In certain embodiments, Cy is a substituted heteroaryl ring. In certain embodiments, Cy is an unsubstituted heteroaryl ring. In certain embodiments, Cy is a monocyclic heteroaryl ring. In certain embodiments, Cy is a 5-membered monocyclic heteroaryl ring. In certain embodiments, Cy is a 5-membered monocyclic heteroaryl ring with one heteroatom selected from the group consisting of S, N, and O. In certain embodiments, Cy is a 5-membered monocyclic heteroaryl ring with two heteroatoms selected from the group consisting of S, N, and O. In certain embodiments, Cy is a 5-membered monocyclic heteroaryl ring with three heteroatoms selected from the group consisting of S, N, and O. In certain embodiments, Cy is substituted pyrrolyl. In certain embodiments, Cy is unsubstituted pyrrolyl. In certain embodiments, Cy is substituted furanyl. In certain embodiments, Cy is unsubstituted furanyl. In certain embodiments, Cy is substituted thienyl. In certain embodiments, Cy is unsubstituted thienyl. In certain embodiments, Cy is substituted pyrazolyl. In certain embodiments, Cy is unsubstituted pyrazolyl. In certain embodiments, Cy is substituted imidazolyl. In certain embodiments, Cy is unsubstituted imidazolyl. In certain embodiments, Cy is substituted oxazolyl. In certain embodiments, Cy is unsubstituted oxazolyl. In certain embodiments, Cy is substituted isoxazolyl. In certain embodiments, Cy is unsubstituted isoxazolyl. In certain embodiments, Cy is substituted thiazolyl. In certain embodiments, Cy is unsubstituted thiazolyl. In certain embodiments, Cy is substituted isothiazolyl. In certain embodiments, Cy is unsubstituted isothiazolyl. In certain embodiments, Cy is substituted triazolyl. In certain embodiments, Cy is unsubstituted triazolyl. In certain embodiments, Cy is substituted oxadiazolyl. In certain embodiments, Cy is unsubstituted oxadiazolyl. In certain embodiments, Cy is substituted thiadiazolyl. In certain embodiments, Cy is unsubstituted thiadiazolyl. In certain embodiments, Cy is a 6-membered monocyclic heteroaryl ring. In certain embodiments, Cy is a 6-membered monocyclic heteroaryl ring with one heteroatom selected from the group consisting of S, N, and O. In certain embodiments, Cy is a 6-membered monocyclic heteroaryl ring with two heteroatoms selected from the group consisting of S, N, and O. In certain embodiments, Cy is a 6-membered monocyclic heteroaryl ring with three heteroatoms selected from the group consisting of S, N, and O. In certain embodiments, Cy is substituted pyridyl. In certain embodiments, Cy is unsubstituted pyridyl. In certain embodiments, Cy is substituted pyridazinyl. In certain embodiments, Cy is unsubstituted pyridazinyl. In certain embodiments, Cy is substituted pyrimidinyl. In certain embodiments, Cy is unsubstituted pyrimidinyl. In certain embodiments, Cy is substituted pyrazinyl. In certain embodiments, Cy is unsubstituted pyrazinyl. In certain embodiments, Cy is substituted triazinyl. In certain embodiments, Cy is unsubstituted triazinyl. In certain embodiments, Cy is an optionally substituted heteroaryl ring fused with one or more optionally substituted carbocyclic, optionally substituted heterocyclic, optionally substituted aryl, or optionally substituted heteroaryl groups wherein the point of attachment is on any one of the heteroaryl ring, or carbocyclic, heterocyclic, aryl, or heteroaryl groups, as valency permits. In certain embodiments, Cy is a bicyclic heteroaryl ring. In certain embodiments, Cy is an optionally substituted heteroaryl ring fused with an optionally substituted phenyl ring. In certain embodiments, Cy is substituted indolyl. In certain embodiments, Cy is unsubstituted indolyl. In certain embodiments, Cy is substituted isoindolyl. In certain embodiments, Cy is unsubstituted isoindolyl. In certain embodiments, Cy is substituted indazolyl. In certain embodiments, Cy is unsubstituted indazolyl. In certain embodiments, Cy is substituted benzothienyl. In certain embodiments, Cy is unsubstituted benzothienyl. In certain embodiments, Cy is substituted isobenzothienyl. In certain embodiments, Cy is unsubstituted isobenzothienyl. In certain embodiments, Cy is substituted benzofuranyl. In certain embodiments, Cy is unsubstituted benzofuranyl. In certain embodiments, Cy is substituted benzoisofuranyl. In certain embodiments, Cy is unsubstituted benzoisofuranyl. In certain embodiments, Cy is substituted benzimidazolyl. In certain embodiments, Cy is unsubstituted benzimidazolyl. In certain embodiments, Cy is substituted benzoxazolyl. In certain embodiments, Cy is unsubstituted benzoxazolyl. In certain embodiments, Cy is substituted benzisoxazolyl. In certain embodiments, Cy is unsubstituted benzisoxazolyl. In certain embodiments, Cy is substituted benzothiazolyl. In certain embodiments, Cy is unsubstituted benzothiazolyl. In certain embodiments, Cy is substituted benzisothiazolyl. In certain embodiments, Cy is unsubstituted benzisothiazolyl. In certain embodiments, Cy is substituted benzotriazolyl. In certain embodiments, Cy is unsubstituted benzotriazolyl. In certain embodiments, Cy is substituted benzoxadiazolyl. In certain embodiments, Cy is unsubstituted benzoxadiazolyl. In certain embodiments, Cy is substituted quinolinyl. In certain embodiments, Cy is unsubstituted quinolinyl. In certain embodiments, Cy is substituted isoquinolinyl. In certain embodiments, Cy is unsubstituted isoquinolinyl. In certain embodiments, Cy is substituted cinnolinyl. In certain embodiments, Cy is unsubstituted cinnolinyl. In certain embodiments, Cy is substituted quinoxalinyl. In certain embodiments, Cy is unsubstituted quinoxalinyl. In certain embodiments, Cy is substituted phthalazinyl. In certain embodiments, Cy is unsubstituted phthalazinyl. In certain embodiments, Cy is substituted quinazolinyl. In certain embodiments, Cy is unsubstituted quinazolinyl. In certain embodiments, Cy is

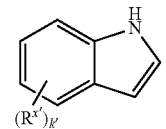

wherein X' may link to any freely valent position. In certain embodiments, Cy is

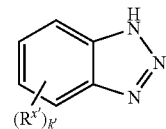

wherein X' may link to any freely valent position. In certain embodiments, Cy is

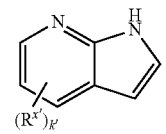

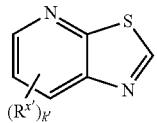

wherein X' may link to any freely valent position. In certain embodiments, Cy is

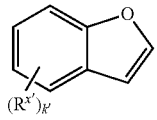

wherein X' may link to any freely valent position. In certain embodiments, Cy is

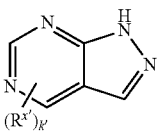

wherein X' may link to any freely valent position. In certain embodiments, Cy is

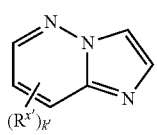

wherein X' may link to any freely valent position. In certain embodiments, Cy is

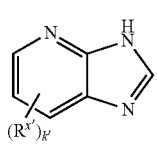

wherein X' may link to any freely valent position. In certain embodiments, Cy is

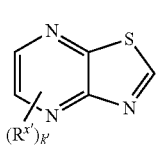

wherein X' may link to any freely valent position. In certain embodiments, Cy is

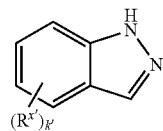

wherein X' may link to any freely valent position. In certain embodiments, Cy is

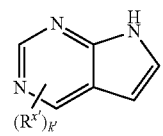

wherein X' may link to any freely valent position. In certain embodiments, Cy is

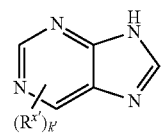

wherein X' may link to any freely valent position. In certain embodiments, Cy is

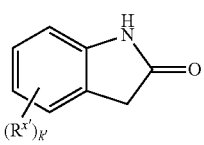

wherein X' may link to any freely valent position. In certain embodiments, Cy is

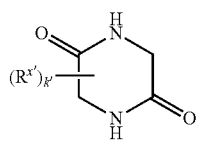

wherein X' may link to any freely valent position. In certain embodiments, Cy is

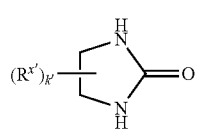

wherein X' may link to any freely valent position. In certain embodiments, Cy is

151

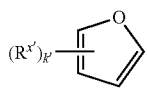

wherein X' may link to any freely valent position. In certain embodiments, Cy is

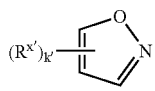

wherein X' may link to any freely valent position. In certain embodiments, Cy is

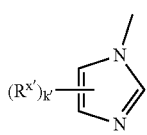

wherein X' may link to any freely valent position. In certain embodiments, Cy is

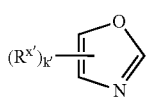

wherein X' may link to any freely valent position. In certain embodiments, Cy is

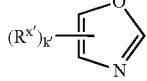

wherein X' may link to any freely valent position. In certain embodiments, Cy is

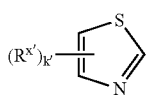

wherein X' may link to any freely valent position. In certain embodiments, Cy is

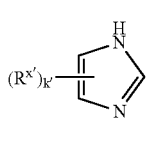

wherein X' may link to any freely valent position. In certain embodiments, Cy is

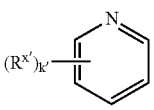

wherein X' may link to any freely valent position. In certain embodiments, Cy is

152

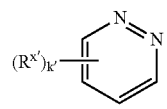

wherein X' may link to any freely valent position. In certain embodiments, Cy is

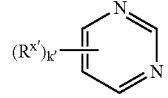

wherein X' may link to any freely valent position. In certain embodiments, Cy is

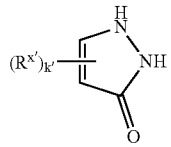

wherein X' may link to any freely valent position. In certain embodiments, Cy is

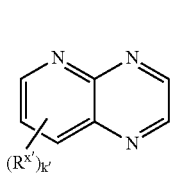

wherein X' may link to any freely valent position. In certain embodiments, Cy is

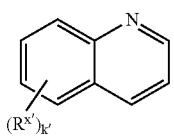

wherein X' may link to any freely valent position. In certain embodiments, Cy is

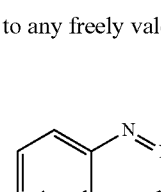

wherein X' may link to any freely valent position. In certain embodiments, Cy is

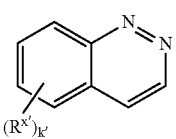

wherein X' may link to any freely valent position. In certain embodiments, Cy is

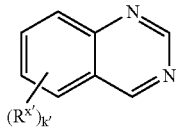

wherein X' may link to any freely valent position. In certain embodiments, Cy is

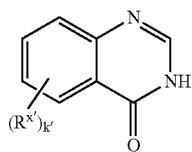

wherein X' may link to any freely valent position. In certain embodiments, Cy is

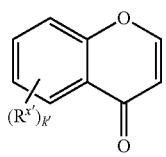

wherein X' may link to any freely valent position. In certain embodiments, Cy is

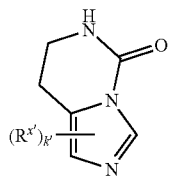

wherein X' may link to any freely valent position. In certain embodiments, Cy is

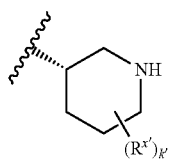

wherein X' may link to any freely valent position. In certain embodiments, Cy is

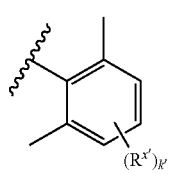

wherein X' may link to any freely valent position.

In compounds of any one of Formulae (II) to (V), Cy may be substituted with one or more $R^{X\prime}$ groups. In certain embodiments, at least one $R^{X\prime}$ is H. In certain embodiments, at least two $R^{X\prime}$ groups are H. In certain embodiments, at least three $R^{X\prime}$ groups are H. In certain embodiments, at least four $R^{X\prime}$ groups are H. In certain embodiments, at least one $R^{X\prime}$ is halogen. In certain embodiments, at least one $R^{X\prime}$ is F. In certain embodiments, at least one $R^{X\prime}$ is Cl. In certain embodiments, at least one $R^{X\prime}$ is Br. In certain embodiments, at least one $R^{X\prime}$ is I (iodine). In certain embodiments, at least one $R^{X\prime}$ is substituted acyl. In certain embodiments, at least one $R^{X\prime}$ is —C(=O)N($R^{A1\prime}$)$_2$. In certain embodiments, at least one $R^{X\prime}$ is —C(=O)NH$R^{A1\prime}$. In certain embodiments, at least one $R^{X\prime}$ is —C(=O)NH(C$_{1-6}$ alkyl). In certain embodiments, at least one $R^{X\prime}$ is —C(=O)NHMe. In certain embodiments, at least one $R^{X\prime}$ is —C(=O)NH$_2$. In certain embodiments, at least one $R^{X\prime}$ is unsubstituted acyl. In certain embodiments, at least one $R^{X\prime}$ is acetyl. In certain embodiments, at least one $R^{X\prime}$ is substituted alkyl. In certain embodiments, at least one $R^{X\prime}$ is substituted methyl. In certain embodiments, at least one $R^{X\prime}$ is unsubstituted alkyl. In certain embodiments, at least one $R^{X\prime}$ is C$_{1-6}$ alkyl. In certain embodiments, at least one $R^{X\prime}$ is methyl. In certain embodiments, at least one $R^{X\prime}$ is ethyl. In certain embodiments, at least one $R^{X\prime}$ is propyl. In certain embodiments, at least one $R^{X\prime}$ is butyl. In certain embodiments, at least one $R^{X\prime}$ is substituted alkenyl. In certain embodiments, at least one $R^{X\prime}$ is unsubstituted alkenyl. In certain embodiments, at least one $R^{X\prime}$ is substituted alkynyl. In certain embodiments, at least one $R^{X\prime}$ is unsubstituted alkynyl. In certain embodiments, at least one $R^{X\prime}$ is substituted carbocyclyl. In certain embodiments, at least one $R^{X\prime}$ is unsubstituted carbocyclyl. In certain embodiments, at least one $R^{X\prime}$ is substituted heterocyclyl. In certain embodiments, at least one $R^{X\prime}$ is unsubstituted heterocyclyl. In certain embodiments, at least one $R^{X\prime}$ is substituted aryl. In certain embodiments, at least one $R^{X\prime}$ is unsubstituted aryl. In certain embodiments, at least one $R^{X\prime}$ is substituted phenyl. In certain embodiments, at least one $R^{X\prime}$ is unsubstituted phenyl. In certain embodiments, at least one $R^{X\prime}$ is substituted heteroaryl. In certain embodiments, at least one $R^{X\prime}$ is unsubstituted heteroaryl. In certain embodiments, at least one $R^{X\prime}$ is substituted pyridyl. In certain embodiments, at least one $R^{X\prime}$ is unsubstituted pyridyl. In certain embodiments, at least one $R^{X\prime}$ is —O$R^{A1\prime}$. In certain embodiments, at least one $R^{X\prime}$ is —O(C$_{1-6}$ alkyl). In certain embodiments, at least one $R^{X\prime}$ is —OMe. In certain embodiments, at least one $R^{X\prime}$ is —OH. In certain embodiments, at least one $R^{X\prime}$ is —N($R^{A1\prime}$)$_2$. In certain embodiments, at least one $R^{X\prime}$ is —NH$_2$. In certain embodiments, at least one $R^{X\prime}$ is —S$R^{A1\prime}$. In certain embodiments, at least one $R^{X\prime}$ is —SH. In certain embodiments, at least one $R^{X\prime}$ is —N$R^{A1\prime}$C(=O)N($R^{A1\prime}$)$_2$. In certain embodiments, at least one $R^{X\prime}$ is —NHC(=O)N($R^{A1\prime}$)$_2$. In certain embodiments, at least one $R^{X\prime}$ is —NHC(=O)NH$R^{A1\prime}$. In certain embodiments, at least one $R^{X\prime}$ is —NHC(=O)NH(C$_{1-6}$ alkyl). In certain embodiments, at least one $R^{X\prime}$ is —NHC(=O)NHMe. In certain embodiments, at least one $R^{X\prime}$ is —NHC(=O)NH$_2$. In certain embodiments, at least one $R^{X\prime}$ is —N$R^{A\prime}$C(=O)NH$R^{A\prime}$. In certain embodiments, at least one $R^{X\prime}$ is —N$R^{A1\prime}$C(=O)NH$_2$. In certain embodiments, at least one $R^{X\prime}$ is —N$R^{A1\prime}$S(=O)$_2$$R^{A1}$. In certain embodiments, at least one $R^{X\prime}$ is —NHS(=O)$_2$$R^{A1}$. In certain embodiments, at least one $R^{X\prime}$ is —NHS(=O)$_2$(C$_{1-6}$ alkyl). In certain embodiments, at least one $R^{X\prime}$ is —NHS(=O)$_2$Me. In certain embodiments, at least one $R^{X\prime}$ is —S(=O)$_2$N($R^{A1\prime}$)$_2$. In certain embodiments, at least one $R^{X\prime}$ is —S(=O)$_2$N(R$^{A1'}$)$_2$. In certain embodiments, at least one R$^{X_1}$ is —S(=O)$_2$N(C$_{1-6}$ alkyl)$_2$. In certain embodiments, at least one R$^{X_1}$ is —S(=O)$_2$NH(C$_{1-6}$ alkyl). In certain embodiments, at least one R$^{X_1}$ is —S(=O)$_2$NH(t-Bu). In certain embodiments, at least one R$^{X_1}$ is —S(=O)$_2$NH$_2$. In certain embodiments, at least one R$^{X_1}$ is

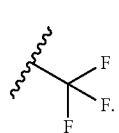 [SMILES: *C(F)(F)F]

In certain embodiments, at least one R$^{X_1}$ is

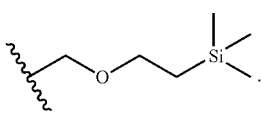 [SMILES: *COCC[Si](C)(C)C]

In certain embodiments, at least one R$^{X_1}$ is

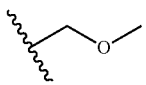

In certain embodiments, at least one R$^{X_1}$ is

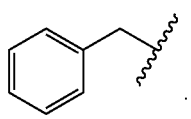 [SMILES: *Cc1ccccc1]

In certain embodiments, at least one R$^{X_1}$ is

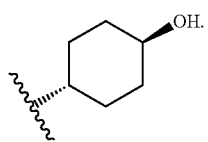 [SMILES: *[C@H]1CC[C@H](O)CC1]

In certain embodiments, at least one R$^{X_1}$ is

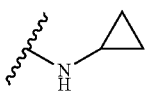

In certain embodiments, at least one R$^{X_1}$ is

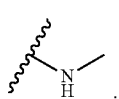

In certain embodiments, at least one R$^{X_1}$ is

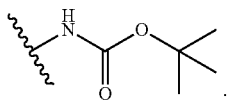 [SMILES: *NC(=O)OC(C)(C)C]

In certain embodiments, at least one R$^{X_1}$ is

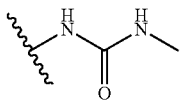

In certain embodiments, at least one R$^{X_1}$ is

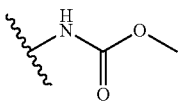

In certain embodiments, at least one R$^{X_1}$ is

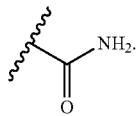

In certain embodiments, at least one R$^{X_1}$ is

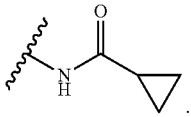

In certain embodiments, at least one R$^{X_1}$ is

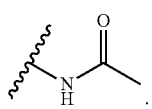

In certain embodiments, at least one R$^{X_1}$ is

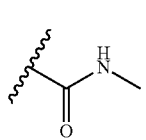

In certain embodiments, at least one R$^{X_1}$ is

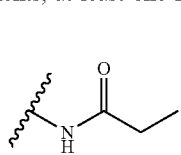

In certain embodiments, at least one $R^{X_1}$ is

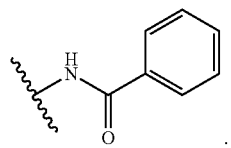

In certain embodiments, at least one $R^{X_1}$ is

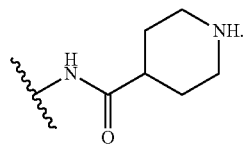 [SMILES: *NC(=O)C1CCNCC1]

In certain embodiments, at least one $R^{X_1}$ is

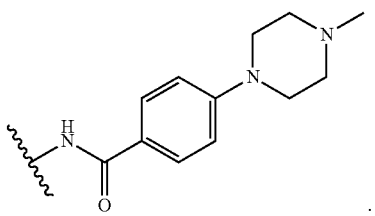 [SMILES: *NC(=O)c1ccc(N2CCN(C)CC2)cc1]

In certain embodiments, at least one $R^{X_1}$ is

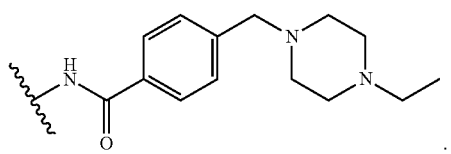 [SMILES: *NC(=O)c1ccc(CN2CCN(CC)CC2)cc1]

In certain embodiments, at least one $R^{X_1}$ is

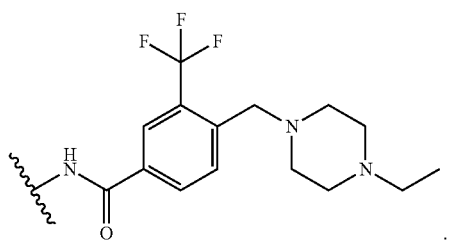 [SMILES: *NC(=O)c1ccc(CN2CCN(CC)CC2)c(C(F)(F)F)c1]

In certain embodiments, at least one $R^{X_1}$ is

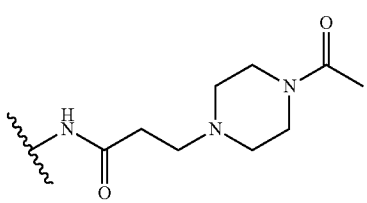

In certain embodiments, at least one $R^{X_1}$ is

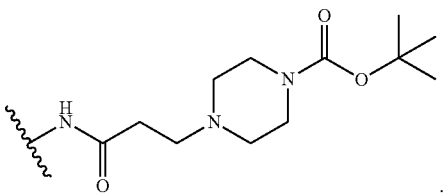 [SMILES: *NC(=O)CCN1CCN(C(=O)OC(C)(C)C)CC1]

In certain embodiments, at least one $R^{X_1}$ is

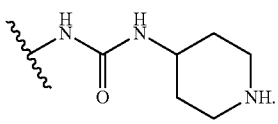 [SMILES: *NC(=O)NC1CCNCC1]

In certain embodiments, at least one $R^{X_1}$ is

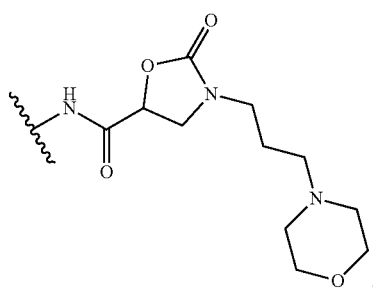

In certain embodiments, at least one $R^{X_1}$ is

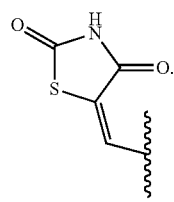 [SMILES: */C=C1/SC(=O)NC1=O]

In certain embodiments, at least one $R^{X_1}$ is

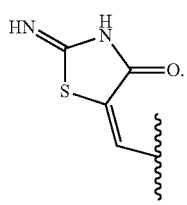 [SMILES: */C=C1/SC(=N)NC1=O]

In certain embodiments, at least one $R^{X_1}$ is

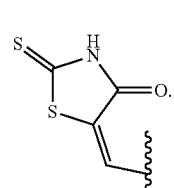

In certain embodiments, at least one $R^{X_1}$

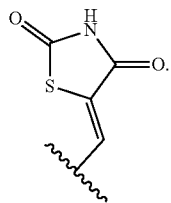 [SMILES: */C=C1\SC(=O)NC1=O]

In certain embodiments, at least one $R^{X_1}$ is

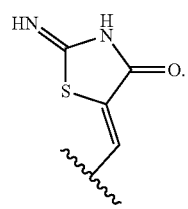 [SMILES: */C=C1\SC(=N)NC1=O]

In certain embodiments, at least one $R^{X_1}$ is

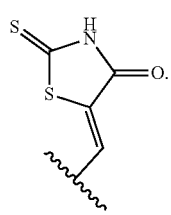 [SMILES: */C=C1\SC(=S)NC1=O]

In certain embodiments, at least one $R^{X_1}$ is

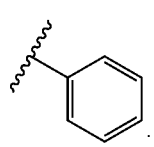 [SMILES: *c1ccccc1]

In certain embodiments, at least one $R^{X_1}$ is

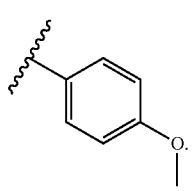 [SMILES: *c1ccc(OC)cc1]

In certain embodiments, at least one $R^{X_1}$ is

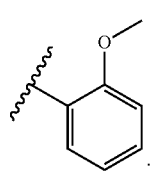 [SMILES: *c1ccccc1OC]

In certain embodiments, at least one $R^{X_1}$ is

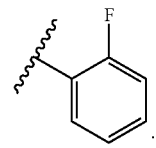 [SMILES: *c1ccccc1F]

In certain embodiments, at least one $R^{X_1}$ is

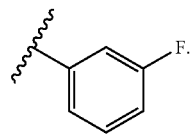 [SMILES: *c1cccc(F)c1]

In certain embodiments, at least one $R^{X_1}$ is

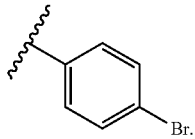 [SMILES: *c1ccc(Br)cc1]

In certain embodiments, at least one $R^{X_1}$ is

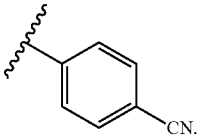 [SMILES: *c1ccc(C#N)cc1]

In certain embodiments, at least one $R^{X_1}$ is

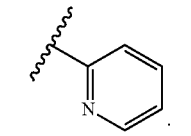 [SMILES: *c1ccccn1]

In certain embodiments, at least one $R^{X_1}$ is

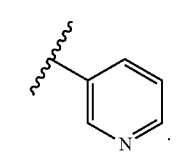 [SMILES: *c1cccnc1]

In certain embodiments at least one $R^{X_1}$ is

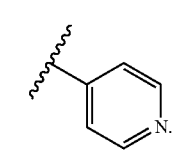 [SMILES: *c1ccncc1]

In certain embodiments, at least one $R^{X_1}$ is

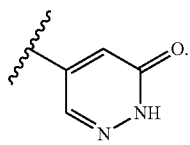

In certain embodiments, at least one $R^{X_1}$ is

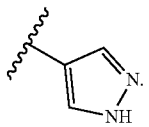

In certain embodiments, at least one $R^{X_1}$ is

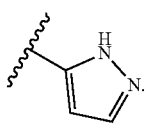 [SMILES: *c1ccn[nH]1]

In certain embodiments, at least one $R^{X_1}$ is

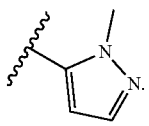 [SMILES: *c1ccnn1C]

In certain embodiments, at least one $R^{X_1}$ is

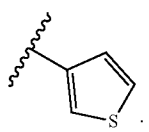

In certain embodiments, at least one $R^{X_1}$ is

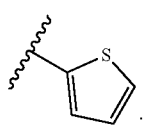

In certain embodiments, at least one $R^{X_1}$ is

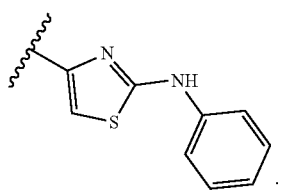 [SMILES: *c1csc(Nc2ccccc2)n1]

In certain embodiments, at least one $R^{X_1}$ is

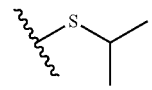

In certain embodiments, at least one $R^{X_1}$ is

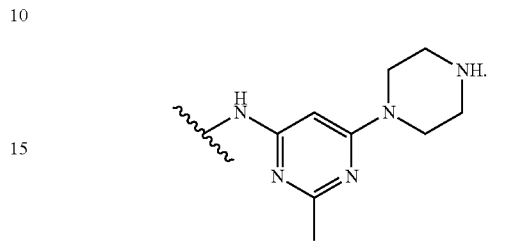

In certain embodiments, at least one $R^{X_1}$ is

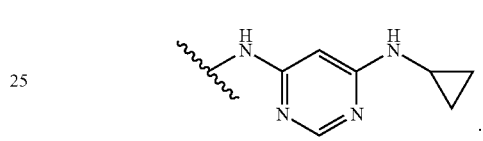

In certain embodiments, at least one $R^{X_1}$ is

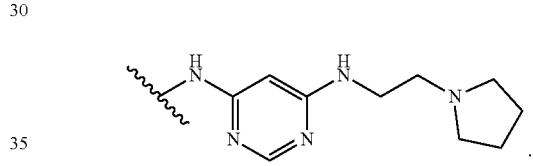

In certain embodiments, at least one $R^{X_1}$ is

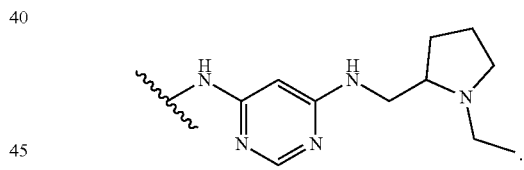

In certain embodiments, at least one $R^{X_1}$ is

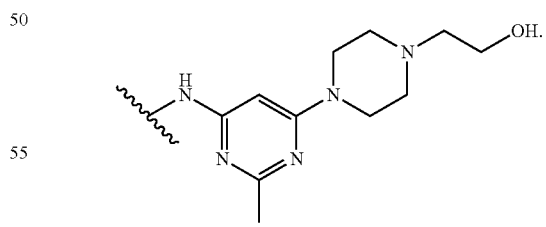

In certain embodiments, at least one $R^{X_1}$ is

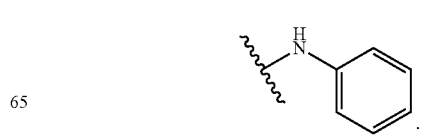

In certain embodiments, at least one $R^{X_1}$ is

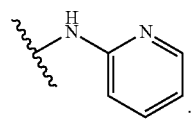

In certain embodiments, at least one $R^{X_1}$ is

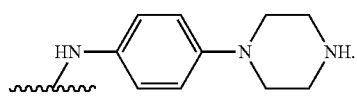

In certain embodiments, at least one $R^{X_1}$ is

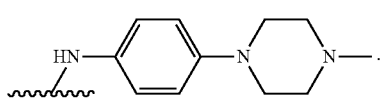

In certain embodiments, at least one $R^{X_1}$ is

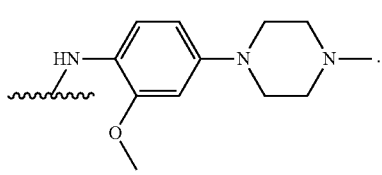 [SMILES: *Nc1ccc(N2CCN(C)CC2)cc1OC]

In certain embodiments, at least one $R^{X_1}$ is

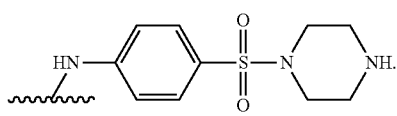 [SMILES: *Nc1ccc(S(=O)(=O)N2CCNCC2)cc1]

In certain embodiments, at least one $R^{X_1}$ is

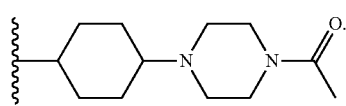

In certain embodiments, at least one $R^{X_1}$ is

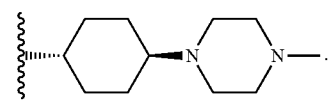

In certain embodiments, at least one $R^{X_1}$ is

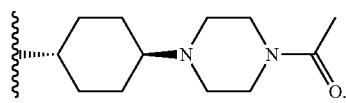

In certain embodiments, at least one $R^{X_1}$ is

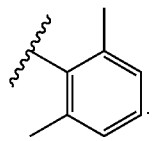 [SMILES: *c1c(C)cccc1C]

In certain embodiments, at least one $R^{X_1}$ is

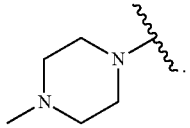 [SMILES: *N1CCN(C)CC1]

In certain embodiment, a compound of the invention is a compound of Formula (I), or a pharmaceutically acceptable salt, solvate, hydrate, polymorph, co-crystal, tautomer, stereoisomer, isotopically labeled derivative, or prodrug thereof. In certain embodiment, a compound of the invention is a compound of Formula (I), or a pharmaceutically acceptable salt thereof. In certain embodiment, a compound of the invention is a compound of Formula (II), or a pharmaceutically acceptable salt, solvate, hydrate, polymorph, co-crystal, tautomer, stereoisomer, isotopically labeled derivative, or prodrug thereof. In certain embodiment, a compound of the invention is a compound of Formula (II), or a pharmaceutically acceptable salt thereof. In certain embodiment, a compound of the invention is a compound of Formula (III), or a pharmaceutically acceptable salt, solvate, hydrate, polymorph, co-crystal, tautomer, stereoisomer, isotopically labeled derivative, or prodrug thereof. In certain embodiment, a compound of the invention is a compound of Formula (III), or a pharmaceutically acceptable salt thereof. In certain embodiment, a compound of the invention is a compound of Formula (IV), or a pharmaceutically acceptable salt, solvate, hydrate, polymorph, co-crystal, tautomer, stereoisomer, isotopically labeled derivative, or prodrug thereof. In certain embodiment, a compound of the invention is a compound of Formula (IV), or a pharmaceutically acceptable salt thereof. In certain embodiment, a compound of the invention is a compound of Formula (V), or a pharmaceutically acceptable salt, solvate, hydrate, polymorph, co-crystal, tautomer, stereoisomer, isotopically labeled derivative, or prodrug thereof. In certain embodiment, a compound of the invention is a compound of Formula (V), or a pharmaceutically acceptable salt thereof.

In certain embodiments, compounds of the present invention include those which:
  exhibit kinase inhibitory activity,
  exhibit the ability to inhibit transforming growth factor b-activated kinase-1 (TAK1), hemopoietic cell kinase (HCK) or both TAK1 and HCK,
  exhibit the ability to inhibit hematopoietic progenitor kinase 1 (HPK1, also known as mitogen-activated protein kinase kinase kinase kinase 1 or MAP4K1),
  exhibit the ability to inhibit Bruton's tyrosine kinase (BTK), v-src sarcoma (Schmidt-Ruppin A-2) viral oncogene homolog (SRC) family of kinases or both BTK and SRC,
  exhibit cytotoxic or growth inhibitory effect on WM cell lines maintained in vitro or in animal studies using a scientifically acceptable cancer cell xenograft model; and/or exhibit a therapeutic profile (e.g., optimum safety and curative effect) that is superior to existing chemotherapeutic agents.

As used herein "kinase" refers to a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation and proliferation. There are estimated to be about 2,000 distinct protein kinases in the human body and although each of these phosphorylates particular protein/peptide substrates, they all bind the same second substrate ATP in a highly conserved pocket. About 50% of the known oncogene products are protein tyrosine kinases PTKs and their kinase activity has been shown to lead to cell transformation.

In certain embodiments, the kinase to be inhibited is involved in the myeloid differentiation primary response gene (88) (MYD88) signaling pathway. For example, the kinase is Transforming growth factor b-activated kinase-1 (TAK1) TAK1 or Hemopoietic cell kinase (HCK). In certain embodiments, the compound of the invention inhibits TAK1, HCK, or both TAK1 and HCK.

Myeloid differentiation primary response gene (88) (MYD88) L265P is a widely expressed somatic mutation in WM patients that supports NF-NFκB signaling through stimulation of BTK, IRAK1/4, TAK1. MYD88 is an adaptor molecule for Toll-like receptors (TLR) with the exception of TLR-3 and interleukin-1 receptor (IL-1R) signaling. Following TLR or IL-1R stimulation, MYD88 is recruited to the activated receptor complex as a homodimer which then complexes with interleukin-1 receptor-associated kinase 4 (IRAK4) and activates IRAK1 and IRAK2. Tumor necrosis factor receptor associated factor 6 (TRAF6) is then activated by IRAK1 leading to NFκB activation via IκBα phosphorylation and TAK1 activation.

Transforming growth factor b-activated kinase-1 (TAK1; also known as MAP3K7) is a member of the serine/threonine protein kinase family. This kinase mediates the signaling transduction induced by TGF beta and morphogenetic protein (BMP), and controls a variety of cell functions including transcription regulation and apoptosis. TAK1 knockout is embryonic lethal to mice. Conditional knockdown of TAK1 in adult mice results in systemic inflammation, spenomegaly, degeneration in heart, kidneys and liver and increased proliferation and differentiation of myeloid progenitor cells. TAK1 is located downstream of Myd88, Bruton's tyrosine kinase (BTK), and interleukin-1 receptor-associated kinase (IRAK), and is being investigated for its role in innate immunity, inflammatory response, and Ras-dependent cancers.

Hemopoietic cell kinase (HCK) is a non-receptor tyrosine-protein kinase found in hematopoietic cells and is known to interact with Bruton's tyrosine kinase (BTK) upon activation by B cell receptors (Proc Natl Acad Sci USA. 1994 August 16; 91(17): 8152-8155). HCK transmits signals from cell surface receptors and plays an important role in the regulation of innate immune responses, including neutrophil, monocyte, macrophage and mast cell functions, phagocytosis, cell survival and proliferation, cell adhesion and migration. It acts downstream of receptors that bind the Fc region of immunoglobulins, such as FCGR1A and FCGR2A, but also CSF3R, PLAUR, the receptors for IFNG, IL2, IL6 and IL8, and integrins, such as ITGB1 and ITGB2. During the phagocytic process, it mediates mobilization of secretory lysosomes, degranulation, and activation of NADPH oxidase to bring about the respiratory burst. It also plays a role in the release of inflammatory molecules, promotes reorganization of the actin cytoskeleton and actin polymerization, and formation of podosomes and cell protrusions.

Hematopoietic progenitor kinase 1 (HPK1) is a hematopoietic cell-restricted member of the Ste20 serine/threonine kinase super family. HPK1 is also known as mitogen-activated protein kinase kinase kinase kinase 1 (MAP4K1). HPK1 is a tissue-specific upstream activator of the MEKK/JNK/SAPK signaling pathway. HPK1 diminishes T cell receptor (TCR) signaling activity and T cell proliferation by phosphorylating the adaptor protein SLP-76. Cytosolic HPK1 is recruited to the TCR complex, and its kinase activity is induced upon the engagement of the TCR. Overexpression of HPK1 suppresses TCR-induced activation of AP-1-dependent gene transcription in a kinase-dependent manner, suggesting that the kinase activity of HPK1 is required to inhibit the Erk MAPK pathway. This blockage of the Erk MAPK pathway is thought to be the inhibitory mechanism that negatively regulates TCR-induced IL-2 gene transcription (*Immunol. Res.* 2012, 54(1-3), 262-65). In certain embodiments, the compounds of the invention, such as the compounds of Formula (I) (e.g., compounds of Formula (I-1)-(I-9)) and compounds of any one of Formulae (II) to (V), inhibit HPK1.

In certain embodiments, the compounds of the invention are selective inhibitors of TAK1, HCK, or HPK1. The term "selective inhibitor" as used herein is understood to mean that in contrast to many kinase inhibitors of the prior art, the compounds do not act on a variety of kinases but act specifically on TAK1, HCK, or HPK1. In certain embodiments, the compounds of the invention inhibit one or more kinases in addition to TAK1, HCK, or HPK1 such as BTK or the SRC family of kinases. In certain embodiments of the invention, the specificity of the inhibitors is given by the $IC_{50}$ value. In some embodiments, a the $IC_{50}$ value for a selective inhibitor is <100 µM for TAK1, HCK, or HPK1, but >100 µM for other kinases.

The $IC_{50}$ value is defined as the concentration of inhibitor required to inhibit 50% of the kinase activity. In certain embodiments, the compounds of of the invention may exhibit $IC_{50}$ values <100 µM. In certain other embodiments, the compounds exhibit $IC_{50}$ values <50 µM. In certain other embodiments, the compounds exhibit $IC_{50}$ values <40 µM. In certain other embodiments, the compounds exhibit $IC_{50}$ values <30 µM. In certain other embodiments, the compounds exhibit $IC_{50}$ values <20 µM. In certain other embodiments, the compounds exhibit $IC_{50}$ values <10 µM. In certain other embodiments, the compounds exhibit $IC_{50}$ values <7.5 µM. In certain embodiments, the compounds exhibit $IC_{50}$ values <5 µM. In certain other embodiments, the compounds exhibit $IC_{50}$ values <2.5 µM. In certain embodiments, the compounds exhibit $IC_{50}$ values <1 µM. In certain other embodiments, the compounds exhibit $IC_{50}$ values <0.75 µM. In certain embodiments, the compounds exhibit $IC_{50}$ values <0.5 µM. In certain embodiments, the compounds exhibit $IC_{50}$ values <0.25 µM. In certain embodiments, the compounds exhibit $IC_{50}$ values <0.1 µM. In certain other embodiments, the compounds exhibit $IC_{50}$ values <75 nM. In certain other embodiments, the compounds exhibit $IC_{50}$ values <50 nM. In certain other embodiments, the compounds exhibit $IC_{50}$ values <25 nM. In certain other embodiments, the compounds exhibit $IC_{50}$ values <10 nM. In other embodiments, the compounds exhibit $IC_{50}$ values <7.5 nM. In other embodiments, the compounds exhibit $IC_{50}$ values <5 nM.

In certain embodiments, the compounds of the invention (e.g., the compounds of Formula (I) and compounds of any one of Formulae (II) to (V)) inhibit HCK selectively. A non-limiting example of a selective HCK inhibitor is:

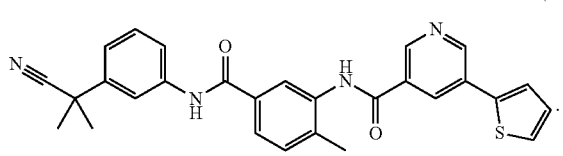

(I-6)

In some embodiments, this selective HCK inhibitor has an $IC_{50}$ value <50 nM.

In certain embodiments, the compounds of the invention (e.g., the compounds of Formula (I) and compounds of any one of Formulae (II) to (V)) inhibit both TAK1 and HCK. In certain embodiments, the compounds of the invention (e.g., the compounds of Formula (I) and compounds of any one of Formulae (II) to (V)) inhibit HPK1 selectively.

Also, provided are methods to treat B cell neoplasms using compounds of the invention in combination with inhibitors of Bruton's tyrosine kinase (BTK), interleukin-1 receptor-associated kinase 1 (IRAK1), interleukin-1 receptor-associated kinase 4 (IRAK4), bone marrow on X chromosome kinase (BMX), phosphoinositide 3-kinase (PI3K), transforming growth factor b-activated kinase-1 (TAK1), and/or a Src family kinase. In certain embodiments, one or more compounds of the invention are used in combination with an inhibitor of the phosphoinositide 3-kinase delta isoform (PI3Kδ). In certain embodiments, combinations of 2, 3, 4, 5, 6, 7, 8, 9, 10, or more of the agents described herein are used for treating WM. In certain embodiments, the agents described herein are used in combination with inhibitors of Bruton's tyrosine kinase (BTK), interleukin-1 receptor-associated kinase 1 (IRAK1), interleukin-1 receptor-associated kinase 4 (IRAK4), bone marrow on X chromosome kinase (BMX), phosphoinositide 3-kinase (PI3K), transforming growth factor b-activated kinase-1 (TAK1), and/or a Src family kinase.

Bruton's tyrosine kinase (BTK) is a key signaling enzyme expressed in all hematopoietic cells types except T lymphocytes and natural killer cells. BTK plays an essential role in the B cell signaling pathway linking cell surface B cell receptor BCR stimulation to downstream intracellular responses. BTK is a key regulator of B cell development activation signaling and survival (Kurosaki, *Curr. Op. Imm.*, 2000, 276-281; Schaeffer and Schwartzberg, *Curr. Op. Imm.*, 2000, 282-288). In addition BTK plays a role in a number of other hematopoietic cell signaling pathways, e.g., Toll like receptor (TLR) and cytokine receptor-mediated TNF-α production in macrophages, IgE receptor (FcepsilonRI) signaling in mast cells, inhibition of Fas/APO-1 apoptotic signaling in B-lineage lymphoid cells, and collagen stimulated platelet aggregation. See e.g., C. A. Jeffries, et al., *J. Biol. Chem.*, 2003, 278, 26258-26264; N. J. Horwood, et al., *J. Exp. Med.*, 2003, 197, 1603-1611; Iwaki et al., *J. Biol. Chem.*, 2005, 280(48), 40261-40270; Vassilev et al., *J. Biol. Chem.*, 1999, 274(3),1646-1656; and Quek et al., *Curr. Biol.*, 1998, 8(20),1137-1140. Activated Btk interacts with MyD88 and TRIF, promoting the activation of MyD88-dependent and TRIF-dependent pathways (*Nature Immunology*, 2011, 12, 416-424).

BTK inhibitors are well-known in the art, and include, for example, ibrutinib and benzonaphthyridinones (see U.S. provisional patent application U.S. Ser. No. 61/716,273, filed Oct. 19, 2012). Additional non-limiting examples of BTK inhibitors are disclosed in WO 1999/054286, WO 2013/010380, WO 2009/137596, WO 2011/029043, WO 2010/056875, WO 2000/056737, and WO 2013/067277.

IRAK1 and 4 are serine/threonine-protein kinases that play a critical role in initiating innate immune response against foreign pathogens. They are involved in Toll-like receptor (TLR) and IL-1R signaling pathways, and are rapidly recruited by MYD88 to the receptor-signaling complex upon TLR activation. Association with MYD88 leads to IRAK1 phosphorylation by IRAK4 and subsequent autophosphorylation and kinase activation of IRAK1 (*Immunity*, 1997, 7(6), 837-47). IRAK4−/− mice have abolished cellular responses to various IL-1 and TLR ligands and are severely impaired in their response to viral and bacterial challenges. IRAK1−/− mice show a similar but partial response.

IRAK1 and IRAK4 inhibitors are well-known in the art, and include, for example, those disclosed in WO 2003/030902, WO 2012/007375, G. M. Buckely et al., *Biorg. Med. Chem. Lett.*, 2008, 18, 3211-3214, and G. M. Buckely et al., *Biorg. Med. Chem. Lett.*, 2008, 18, 3656-3660, WO2013/074986, and U.S. provisional patent application, U.S. Ser. No. 61/727,640, filed Nov. 16, 2012.

In certain embodiments, the IRAK4 inhibitor is

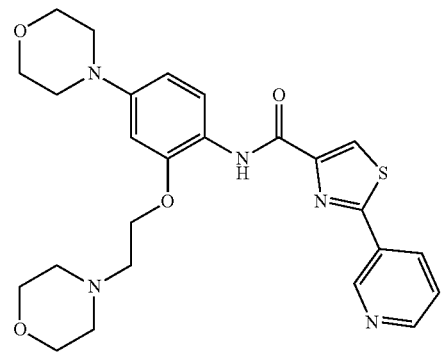

JH-IV-96-01
IRAK4 IC50 = 20 nm or its analogs.

"Bone Marrow on X chromosome" kinase (BMX, also termed ETK) is a non-receptor tyrosine kinase and is activated downstream of phosphatidylinositol-3 kinase (PI-3K) and v-src sarcoma (Schmidt-Ruppin A-2) viral oncogene homolog (SRC), but its substrates are unknown. Positional scanning peptide library screening revealed a marked preference for a priming phosphotyrosine (pY) in the −1 position. Potential substrates include multiple tyrosine kinases with kinase domain pYpY sites required for full activity. BMX has been found to phosphorylate residue Y577 of focal adhesion kinase (FAK) subsequent to Y576 phosphorylation by SRC. In addition, BMX loss by RNA interference and mouse embryonic fibroblasts (MEFs) from Bmx negative (Bmx⁻) mice displayed impaired FAK signaling. Insulin receptor (IR) phosphorylation similarly was decreased by BMX loss, as was hepatic IR phosphorylation in Bmx⁻ mice. However, glucose tolerance was increased, reflecting a marked compensatory decrease in the activity of the AKT phosphatase PHLPP. These findings reveal a mechanism through which BMX functions as a central regulator of multiple kinase pathways.

BMX inhibitors are well-known in the art, and include, for example, those disclosed in U.S. Ser. No. 61/716,273 and 61/717,345, the contents of both of which are incorporated herein by reference. In certain embodiments, the BMX inhibitor is of formula:

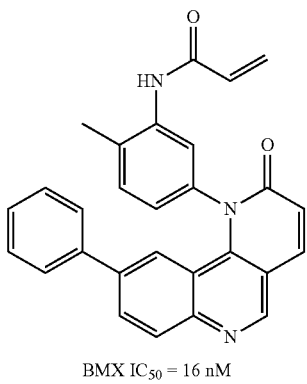 [SMILES: C=CC(=O)Nc1cc(-n2c(=O)ccc3cnc4ccc(-c5ccccc5)cc4c32)ccc1C]

BMX IC$_{50}$ = 16 nM or an analog thereof.

Phosphatidylinositol 3-kinases (PI3-kinases or PI3Ks) are a family of enzymes involved in cellular functions such as cell growth, proliferation, differentiation, motility, survival and intracellular trafficking, which in turn are involved in cancer. PI3Ks are a family of related intracellular signal transducer enzymes capable of phosphorylating the 3 position hydroxyl group of the inositol ring of phosphatidylinositol (PtdIns). Phosphatidylinositol 3-kinase is composed of an 85 kDa regulatory subunit and a 110 kDa catalytic subunit. The protein encoded by PI3KCA gene represents the catalytic subunit, which uses ATP to phosphorylate phosphatidylinositols (PtdIns), PtdIns4P and PtdIns(4,5)P2. Of particular interest is the PI3K delta isoform, which is expressed in white blood cells and is mainly involved in the signaling, development, and survival of B cells.

PI3K inhibitors are well-known in the art, and include, for example, those disclosed in International PCT PublicationsWO 2013/088404, WO 2012/068096, and WO 2013/052699, which are incorporated herein by reference.

In certain embodiments, the PI3K inhibitor is of formula:

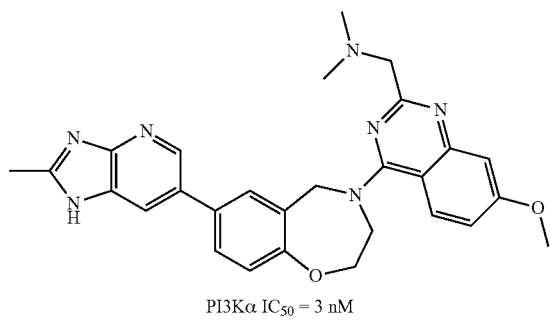

PI3Kα IC$_{50}$ = 3 nM or an analog thereof.

Compounds of the invention may be combined with other kinase inhibitors to treat WM or other B cell neoplasms. In certain embodiments, a compound of the invention is administered with an inhibitor of Bruton's tyrosine kinase (BTK) to treat WM or other B cell neoplasm. In certain embodiments, a compound of of the invention is administered with an inhibitor of interleukin-1 receptor-associated kinase 1 (IRAK1) to treat WM or other B cell neoplasm. In certain embodiments, a of the invention is administered with an inhibitor of phosphoinositide 3-kinase (PI3K) to treat WM or other B cell neoplasm. In certain embodiments, a compound of of the invention is administered with an inhibitor of the phosphoinositide 3-kinase delta isoform (PI3Kδ) to treat WM or other B cell neoplasm. In certain embodiments, a compound of of the invention is administered with two of any inhibitors of BTK, IRAK1, or PI3K to treat WM or other B cell neoplasm. In certain embodiments, a compound of the invention is administered with more than two of any inhibitors of BTK, IRAK1, or PI3K to treat WM or other B cell neoplasm.

The BTK inhibitors, the IRAK1 inhibitors, the IRAK4 inhibitors, and/or the PI3K inhibitors can be administered to the subject simultaneously or sequentially.

A "subject" or "patient" to which administration is contemplated includes, any animal. In some embodiments, a subject includes but is not limited to, humans, commercially relevant mammals such as cattle, pigs, horses, sheep, goats, cats, and/or dogs), birds (e.g., commercially relevant birds such as chickens, ducks, geese, and/or turkeys) and experimental animals (e.g., mice, rats, non-human primates). A subject in need of treatment is a subject identified as having a B cell neoplasm, i.e., the subject has been diagnosed by a physician (e.g., using methods well known in the art) as having a B cell neoplasm. In certain embodiments, the subject in need of treatment is a subject suspected of having or developing a B cell neoplasm, such as a subject presenting one or more symptoms indicative of a B cell neoplasm. The term "subject in need of treatment" further includes people who once had a B cell neoplasm but whose signs and/or symptoms have been ameliorated (ie., their cancer is in remission). The one or more symptoms or clinical features of B cell neoplasms include, but are not limited to, asymptomatic localized or generalized peripheral lymphadenopathy, plasmacytic difference, bone marrow involvement, autoimmune thrombocytopenia, peripheral blood villous lymphocytes, end organ damage (hypercalcemia, renal insufficiency, bone lesions), recurrent infections, elevated creatine, hyperuricemia, and hypoalbunemia.

In certain embodiments, the subject is diagnosed as having Waldenström's macroglobulinemia (WM). The subject may present one or more signs, symptoms, or clinical features of WM including anemia, hyper-viscosity, neuropathy, coagulopathies, splenomegaly, hepatomegaly, adenopathy, and an IgM serum paraprotein. In certain embodiments, the subject is diagnosed as having WM on the basis that the subject has a mutation at position 38182641 of chromosome 3p22.2. In some embodiments, the mutation results in a single nucleotide change from T to C in the MYD88 gene. In some embodiments, the mutation results in an amino acid change from leucine to proline at position 265 in the MYD88 gene. The mutation may be detected in a biological sample obtained from the subject using any suitable method known in the art, including but not limited to, direct sequencing of nucleic acid molecules, HPLC analysis, DNA chip technologies, and mass spectroscopy. Non-limiting examples of the biological sample include bone marrow, lymph node, spleen, or blood.

The terms "administer," "administering," or "administration," as used herein refers to implanting, absorbing, ingesting, injecting, or inhaling an inventive compound, or a pharmaceutical composition thereof.

As used herein, the terms "treatment," "treat," and "treating" refer to reversing, alleviating, delaying the onset of, or inhibiting the progress of a B cell neoplasm. In certain embodiments, treatment may be administered after one or more signs or symptoms have developed or have been observed. In other embodiments, treatment may be administered in the absence of signs or symptoms of the B cell neoplasm. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

An "effective amount" of compounds of the invention refers to an amount sufficient to elicit the desired biological response, i.e., treating the B cell neoplasm. As will be appreciated by those of ordinary skill in this art, the effective amount of compounds of the invention may vary depending on such factors as the desired biological endpoint, the pharmacokinetics of the compound, the condition being treated, the mode of administration, and the age and health of the subject. An effective amount includes, but is not limited to, that amount necessary to slow, reduce, inhibit, ameliorate or reverse one or more signs and/or symptoms associated with a B cell neoplasm. In the treatment of Waldenström's macroglobulinemia, this may refer to a reduction in the levels of IgM serum paraprotein, reduction in anemia, reduction in hyper-viscosity, reduction in neuropathy, reduction in coagulopathies, reduction in splenomegaly, reduction in hepatomegaly, and reduction in adenopathy.

An effective amount of a compound may vary from about 0.001 mg/kg to about 1000 mg/kg in one or more dose administrations, for one or several days (depending on the mode of administration). In certain embodiments, the effective amount varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, from about 1.0 mg/kg to about 100 mg/kg, and from about 10.0 mg/kg to about 150 mg/kg.

One or more additional pharmaceutical agents, such as anti-cancer agents (e.g., chemotherapeutics), anti-inflammatory agents, steroids, immunosuppressants, radiation therapy, or other agents, can be used in combination with the compounds of the invention in the treatment of a B cell neoplasm. The one or more additional pharmaceutical agents can be administered to the subject simultaneously or sequentially.

Exemplary chemotherapeutic agents include alkylating agents such as nitrogen mustards, ethylenimines, methylmelamines, alkyl sulfonates, nitrosuoureas, and triazenes; antimetabolites such as folic acid analogs, pyrimidine analogs, in particular fluorouracil and cytosine arabinoside, and purine analogs; natural products such as *vinca* alkaloids epi-podophyllotoxins, antibiotics, enzymes, and biological response modifiers; and miscellaneous products such as platinum coordination complexes, anthracenedione, substituted urea such as hydroxyurea, methyl hydrazine derivatives, and adrenocorticoid suppressant.

Exemplary chemotherapeutic agents also include anthracycline antibiotics, actinomycin D, plicamycin, puromycin, gramicidin D, paclitaxel, colchicine, cytochalasin B, emetine, maytansine, amsacrine, cisplatin, carboplatin, mitomycin, altretamine, cyclophosphamide, lomustine, and carmustine.

In yet another aspect, the present invention provides pharmaceutical compositions comprising an effective amount of a compound of the invention, and pharmaceutically acceptable salts, solvates, hydrates, polymorphs, co-crystals, tautomers, stereoisomers, isotopically labeled derivatives, and prodrugs, and optionally a pharmaceutically acceptable excipient, for use in the treatment of a B cell neoplasm. In certain embodiments, provided by the invention are the compounds of the invention, and pharmaceutically acceptable salts and compositions thereof, for use in the treatment of a B cell neoplasm. In certain embodiments, the effective amount is a therapeutically effective amount. In certain embodiments, the therapeutically effective amount is an amount useful for the treatment and/or prevention of a B cell neoplasm. In certain embodiments, the B cell neoplasm is, but is not limited to, Hodgkin's lymphomas and most non-Hodgkins lymphomas, such as, diffuse large B cell lymphoma, Follicular lymphoma, Mucosa-Associated Lymphatic Tissue lymphoma (MALT), small cell lymphocytic lymphoma (overlaps with Chronic lymphocytic leukemia), Mantle cell lymphoma (MCL), Burkitt lymphoma, Mediastinal large B cell lymphoma, Waldenström's macroglobulinemia, Nodal marginal zone B cell lymphoma (NMZL), Splenic marginal zone lymphoma (SMZL), Intravascular large B-cell lymphoma, Primary effusion lymphoma and Lymphomatoid granulomatosis. An effective amount of a compound may vary from about 0.001 mg/kg to about 1000 mg/kg in one or more dose administrations, for one or several days (depending on the mode of administration). In certain embodiments, the effective amount varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

Pharmaceutical compositions described herein can be prepared by any method known in the art of pharmacology. In general, such preparatory methods include the steps of bringing a compound of the invention (the "active ingredient") into association with a carrier or excipient, and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

The pharmaceutical preparations of the present invention may include or be diluted into a pharmaceutically acceptable carrier. The term "pharmaceutically acceptable carrier" as used herein means one or more compatible fillers, diluents or other such substances, which are suitable for administration to a human or other mammal, such as a dog, cat, rat, mouse, or horse. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral, subcutaneous, intravenous, intramuscular, etc. formulations can be found in *Remington's Pharmaceutical Sciences*, Mack Publishing Company, Easton, Pa.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compound of of the invention is administered at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The present invention is further illustrated by the following Example, which in no way should be construed as further limiting. The entire contents of all of the references (including literature references, issued patents, published patent applications, and co pending patent applications) cited throughout this application are hereby expressly incorporated by reference.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Preparation of the Compounds

Preparation of I-1

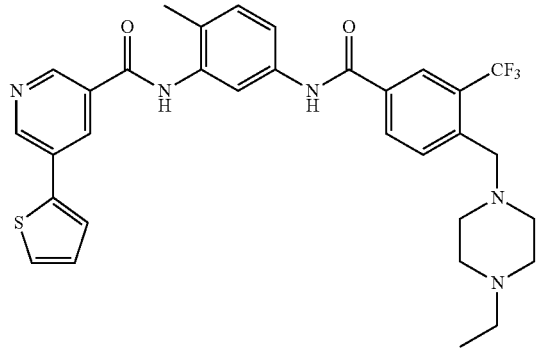

N-(5-(4-((4-ethylpiperazin-1-yl)methyl)-3-(trifluoromethyl)benzamido)-2-methylphenyl)-5-(thiophen-2-yl)nicotinamide (I-1)

To a solution of 5-(thiophen-2-yl)nicotinic acid (205 mg, 1.0 mmol), DMAP (147 mg, 1.2 mmol), HATU (456 mg, 1.2 mmol) and iPr$_2$NEt (440 uL, 2.5 mmol) in CH$_2$Cl$_2$ (5 mL) was added N-(3-amino-4-methylphenyl)-4-((4-ethylpiperazin-1-yl)methyl)-3-(trifluoromethyl)benzamide (420 mg, 1.0 mmol) and the resulting mixture was stirred at room temperature for 24 hours. The solution was filtered to remove solids, concentrated and purified by reverse phase HPLC to afford 485 mg (80%) of title compound as a white solid.

Preparation of I-3

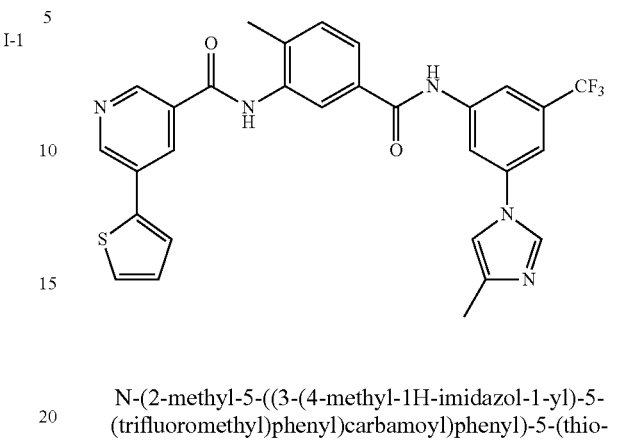

N-(2-methyl-5-((3-(4-methyl-1H-imidazol-1-yl)-5-(trifluoromethyl)phenyl)carbamoyl)phenyl)-5-(thiophen-2-yl)nicotinamide (I-3)

To a solution of 5-(thiophen-2-yl)nicotinic acid (205 mg, 1.0 mmol), DMAP (147 mg, 1.2 mmol), HATU (456 mg, 1.2 mmol) and iPr$_2$NEt (440 uL, 2.5 mmol) in CH$_2$Cl$_2$ (5 mL) was added 3-amino-4-methyl-N-(3-(4-methyl-1H-imidazol-1-yl)-5-(trifluoromethyl)phenyl)benzamide (375 mg, 1.0 mmol) and the resulting mixture was stirred at room temperature for 24 hours. The solution was filtered to remove solids, concentrated and purified by reverse phase HPLC to afford 425 mg (76%) of title compound as a white solid.

Compounds I-2, I1-4, I1-5, I-6 and I-7 were prepared similarly to I-3.

Characterization data for all final compounds is in the table below.

| ID # | Structure | Name | $^1$H NMR and or MS (m/z) |
|---|---|---|---|
| I-1 | 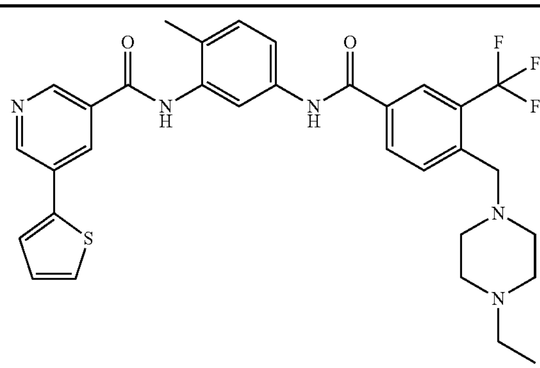 | N-(5-(4-((4-ethylpiperazin-1-yl)methyl)-3-(trifluoromethyl) benzamido)-2-methylpheny0-5-(thiophen-2-yl)nicotinamide | $^1$H NMR (600 MHz, TFA salt, DMSO) δ 10.57 (s, 1H), 10.33 (s, 1H), 9.50 (br, 1H), 9.17 (s,1H), 9.10 (s, 1H), 8.59 (s, 1H), 8.37 (s, 1H), 8.32 (d, J = 8.4 Hz, 1H), 7.99 (d, J = 8.4 Hz, 1H), 7.94 (s, 1H), 7.84 (d, J = 3.6 Hz, 1H), 7.79 (d, J = 4.8, 1H), 7.68 (d, J = 3.6 Hz, 1H), 7.36 (d, J = 8.4 Hz, 1H), 7.31 (dd, J = 5.4, 3.6 Hz, 1H), 3.80 (s, 2H), 3.38 (m, 2H), 3.14 (q, J = 7.2 Hz, 1H), 3.01 (m, 2H), 2.94 (m, 2H), 2.45 (m, 2H), 2.25 (s, 3H), 1.22 (t, J = 7.2 Hz, 3H). MS (ESI) m/z 608 (M + H)$^+$. |
| I-2 | 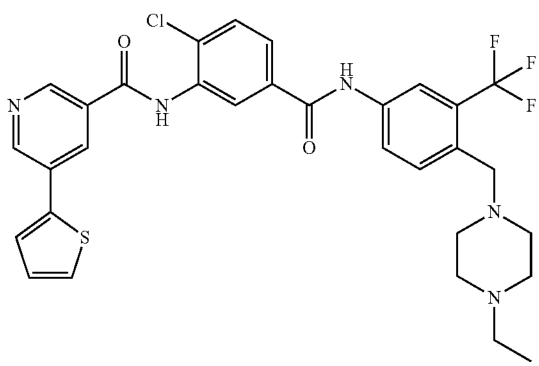 [SMILES: CCN1CCN(Cc2ccc(NC(=O)c3ccc(Cl)c(NC(=O)c4cncc(-c5cccs5)c4)c3)cc2C(F)(F)F)CC1] | N-(2-chloro-5-((4-((4-ethylpiperazin-1-yl)methyl)-3-(trifluoromethyl)phenyl) carbamoyl)phenyl)-5-(thiophen-2-yl)nicotinamide | $^1$H NMR (600 MHz, TFA salt, DMSO) δ 10.65 (s, 1H), 10.64 (s, 1H), 9.54 (br, 1H), 9.13 (s, 1H), 9.04 (s, 1H), 8.54 (s, 1H), 8.22 (s, 1H), 8. 21 (s, 1H), 8.10 (d, J = 8.4 Hz, 1H), 7.95 (d, J = 8.4 Hz, 1H), 7.79 (d, J = 8.4 Hz, 1H), 7.78 (d, J = 3.6 Hz, 1H), 7.73 (d, J = 4.8, 1H), 7.72 (d, J = 8.4 Hz, 1H), 7.24 (dd, J = 4.8, 3.6 Hz, 1H), 3.68 (s, 2H), 3.44 (m, 2H), 3.12 (m, 2H), 2.98 (m, 2H), 2.92 (m, 2H), 2.41 (m, 2H), 1.20 (t, J = 7.2 Hz, 3H). MS (ESI) m/z 628 (M + H)$^+$. |

-continued

| ID # | Structure | Name | ¹H NMR and or MS (m/z) |
|---|---|---|---|
| I-3 | 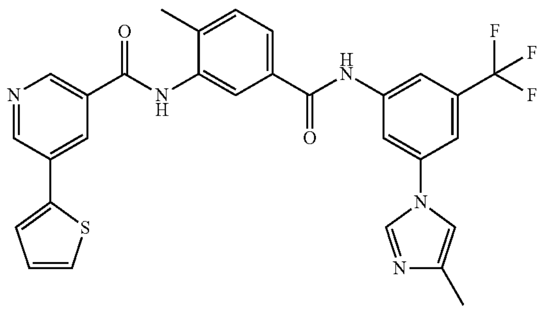 [SMILES: Cc1cn(-c2cc(NC(=O)c3ccc(C)c(NC(=O)c4cncc(-c5cccs5)c4)c3)cc(C(F)(F)F)c2)cn1] | N-(2-methyl-5-((3-(4-methyl-1H-imidazol-1-yl)-5-(trifluoromethyl)phenyl)carbamoyl)phenyl)-5-(thiophen-2-yl)nicotinamide | ¹H NMR (600 MHz, TFA salt, DMSO) δ 10.82 (s, 1H), 10.38 (s, 1H), 9.45 (br, 1H), 9.12 (s,1H), 9.05 (s, 1H), 8.55 (s, 1H), 8.52 (s, 1H), 8.23 (s, 1H), 8.07 (s, 1H), 7.98 (s, 1H), 7.88 (d, J = 8.4 Hz, 1H), 7.77 (d, J = 3.6 Hz, 1H), 7.72 (d, J = 4.8 Hz, 1H), 7.52 (d, J = 8.4, 1H), 7.24 (dd, J = 4.8, 3.6 Hz, 1H), 2.36 (s, 3H), 2.33 (s, 3H). MS (ESI) m/z 562 (M + H)⁺. |
| I-4 | 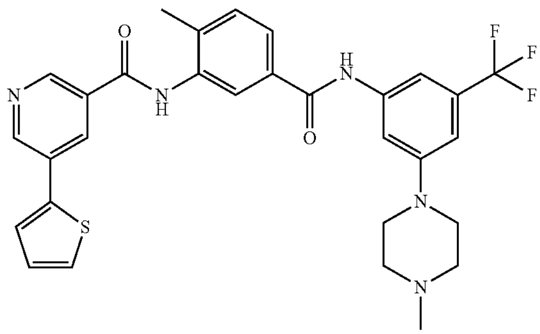 [SMILES: Cc1ccc(C(=O)Nc2cc(N3CCN(C)CC3)cc(C(F)(F)F)c2)cc1NC(=O)c1cncc(-c2cccs2)c1] | N-(2-methyl-5-((3-(4-methylpiperazin-1-yl)-5-(trifluoromethyl)phenyl)carbamoyl)phenyl)-5-(thiophen-2-yl)nicotinamide | ¹H NMR (600 MHz, TFA salt, DMSO) δ 10.38 (s, 1H), 10.37 (s, 1H), 9.87 (br, 1H), 9.11 (s,1H), 9.04 (s, 1H), 8.53 (s, 1H), 8.02 (s, 1H), 7.84 (d, J = 7.8 Hz, 1H), 7.77 (d, J = 3.6 Hz, 1H), 7.70-7.75 (m, 3H), 7.48 (d, J = 8.4 Hz, 1H), 7.24 (dd, J = 4.8, 3.6 Hz, 1H), 7.06 (s, 1H), 3.91 (m, 2H), 3.54 (m, 2H), 3.16 (m, 2H), 3.05 (m, 2H), 2.86 (s, 3H), 2.35 (s, 3H). MS (ESI) m/z 580 (M + H)⁺. |
| I-5 | 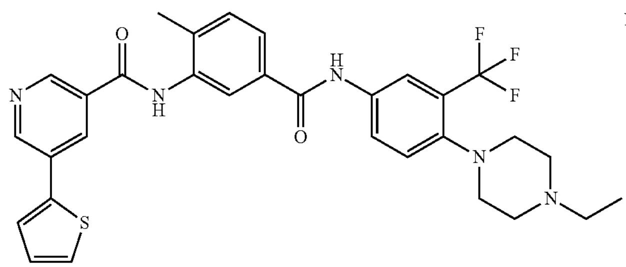 [SMILES: CCN1CCN(c2ccc(NC(=O)c3ccc(C)c(NC(=O)c4cncc(-c5cccs5)c4)c3)cc2C(F)(F)F)CC1] | N-(5-((4-(4-ethylpiperazin-1-yl)-3-(trifluoromethyl)phenyl)carbamoyl)-2-methylphenyl)-5-(thiophen-2-yl)nicotinamide | ¹H NMR (600 MHz, TFA salt, DMSO) δ 10.43 (s, 1H), 10.32 (s, 1H), 9.43 (br, 1H), 9.06 (s,1H), 8.99 (s, 1H), 8.47 (s, 1H), 8.13 (s, 1H), 8.08 (d, J = 8.4 Hz, 1H), 7.97 (s, 1H), 7.79 (d, J = 7.8 Hz, 1H), 7.72 (d, J = 4.8 Hz, 1H), 7.67 (d, J = 4.8 Hz, 1H), 7.52 (d, J = 8.4 Hz, 1H), 7.52 (d, J = 7.8 Hz, 1H), 7.18 (dd, J = 4.8, 4.8 Hz, 1H), 3.51 (m, 4H), 3.18 (m, 2H), 3.00 (m, 4H), 2.29 (s, 3H), 1.18 (t, J = 7.2 Hz, 3H). MS (ESI) m/z 594 (M + H)⁺. |
| I-6 | 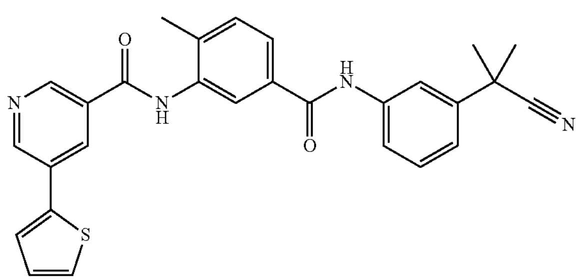 [SMILES: Cc1ccc(C(=O)Nc2cccc(C(C)(C)C#N)c2)cc1NC(=O)c1cncc(-c2cccs2)c1] | N-(5-((3-(2-cyanopropan-2-yl)phenyl)carbamoyl)-2-methylphenyl)-5-(thiophen-2-yl)nicotinamide | ¹H NMR (600 MHz, TFA salt, DMSO) δ 10.32 (s, 1H), 10.28 (s, 1H), 9.06 (s,1H), 9.00 (s, 1H), 8.49 (s, 1H), 7.96 (s, 1H), 7.89 (s, 1H), 7.81 (s, 1H), 7.80 (d, J = 8.4 Hz, 1H), 7.72 (d, J = 3.6 Hz, 1H), 7.67 (d, J = 4.8 Hz, 1H), 7.42 (d, J = 8.4 Hz, 1H), 7.18 (m, 2H), 2.29 (s, 3H), 1.63 (s, 6H). MS (ESI) m/z 481 (M + H)⁺. |
| I-7 | 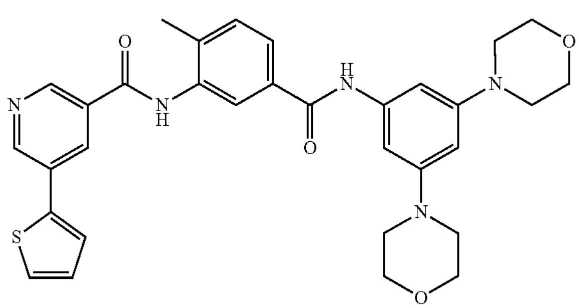 [SMILES: Cc1ccc(C(=O)Nc2cc(N3CCOCC3)cc(N3CCOCC3)c2)cc1NC(=O)c1cncc(-c2cccs2)c1] | N-(5-((3,5-dimorpholinophenyl)carbamoyl)-2-methylphenyl)-5-(thiophen-2-yl)nicotinamide | ¹H NMR (600 MHz, TFA salt, DMSO) δ 10.30 (s, 1H), 9.89 (s, 1H), 9.06 (s, 1H), 8.99 (s, 1H), 8.48 (s, 1H), 7.93 (s, 1H), 7.75 (d, J = 7.8 Hz, 1H), 7.72 (d, J = 3.6 Hz, 1H), 7.64 (d, J = 4.8 Hz, 1H), 7.39 (d, J = 8.4 Hz, 1H), 7.18 (dd, J = 4.8, 3.6 Hz, 1H), 6.96 (s, 2H), 6.26 (s, 1H), 3.67 (m, 8H), 3.04 (m, 8H), 2.28 (s, 3H). MS (ESI) m/z 584 (M + H)⁺. |

Example 2. Biological Assays of the Compounds

In Vitro Activity Assays

The in vitro activity of the compounds described herein in inhibiting TAK1, HCK, and other kinases were obtained using an Invitrogen Select Screening assay as known in the art. The $IC_{50}$ values determined from this assay are shown below.

Cell Proliferation Analysis

CellTiter-Glo® Luminescent cell viability assay (Promega) was used to assess cell survival following treatment with the compounds described. Cells were seeded into 384 well plates with the EL406 Combination Washer Dispenser (BioTek Instruments, Inc.), and the compounds were injected into the cells culture media with the JANUS Automated Workstation (PerkinElmer Inc.). Cells were treated with a series diluted inhibitors (20~0.04 µM) for 72 hours at 37° C. Luminescent measurement is performed using the 2104 Envision® Multilabel Reader (PerkinElmer Inc.).

Apoptosis Analysis for Primary Patient Bone Marrow Tumor Cells

WM cells were treated with and without the compounds described herein. Cells were incubated at 37° C. with 0.01~4 uM of the compounds described herein. Apoptosis analysis was performed using Annexin V/Propidium iodide staining with the Apoptosis Detection Kit I (BD Pharmingen). 1×106/well cells were treated in 24 well plates for ~24 hours with inhibitors or corresponding controls. A minimum of 10,000 events were acquired using a BD™ FACSCanto II flow cytometer and analyzed with BD FACS DIVA Software.

Results

A number of compounds described herein show inhibitory activity against TAK1, HCK, BTK and other kinases. Shown in Table 1 and 1a are exemplary in vitro $IC_{50}$ data of these compounds. Table 2 and 2a shows the in vitro $EC_{50}$ values of these compounds.

TABLE 1

| Structure | Compound ID | BTK $IC_{50}$ (nM) | HCK $IC_{50}$ (nM) Inv | TAK1 $IC_{50}$ (nM) | GCK $IC_{50}$ (nM) |
|---|---|---|---|---|---|
| 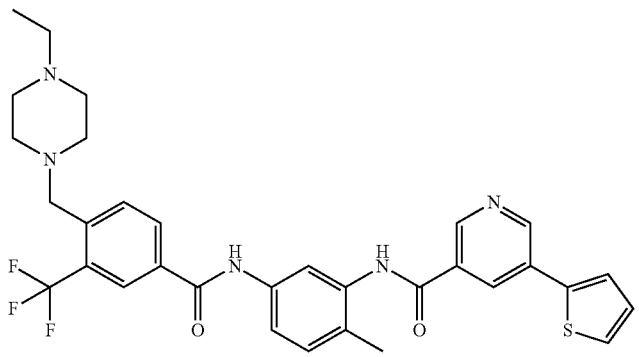 [SMILES: CCN1CCN(Cc2ccc(C(=O)Nc3ccc(C)c(NC(=O)c4cncc(-c5cccs5)c4)c3)cc2C(F)(F)F)CC1] | (I-1) | 22.9 | 7.4 | 8210 | — |
| 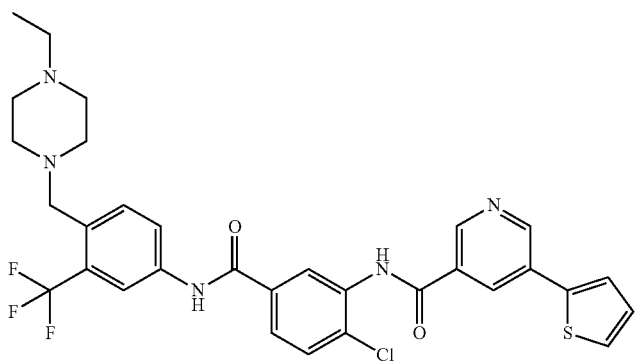 [SMILES: CCN1CCN(Cc2ccc(NC(=O)c3ccc(Cl)c(NC(=O)c4cncc(-c5cccs5)c4)c3)cc2C(F)(F)F)CC1] | (I-2) | — | — | — | — |
| 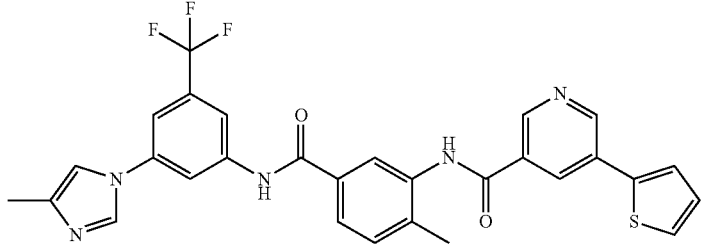 [SMILES: Cc1cn(-c2cc(NC(=O)c3ccc(C)c(NC(=O)c4cncc(-c5cccs5)c4)c3)cc(C(F)(F)F)c2)cn1] | (I-3) | 196 | 62.2 | — | — |

TABLE 1-continued
| Structure | Compound ID | BTK IC$_{50}$ (nM) | HCK IC$_{50}$ (nM) Inv | TAK1 IC$_{50}$ (nM) | GCK IC$_{50}$ (nM) |
|---|---|---|---|---|---|
| 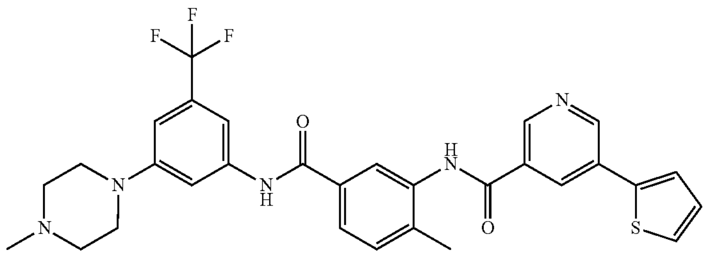 [SMILES: Cc1ccc(C(=O)Nc2cc(N3CCN(C)CC3)cc(C(F)(F)F)c2)cc1NC(=O)c1cncc(-c2cccs2)c1] | (I-4) | 459 | 22.8 | — | — |
| 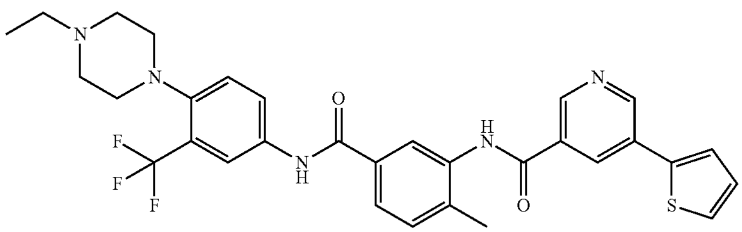 [SMILES: CCN1CCN(c2ccc(NC(=O)c3ccc(C)c(NC(=O)c4cncc(-c5cccs5)c4)c3)cc2C(F)(F)F)CC1] | (I-5) | 3910 | 117 | >10000 | — |
| 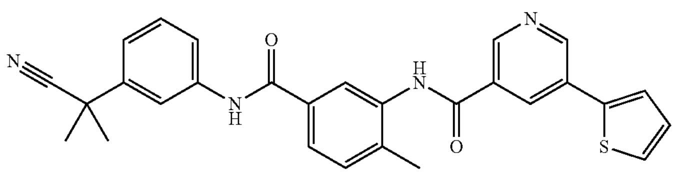 [SMILES: Cc1ccc(C(=O)Nc2cccc(C(C)(C)C#N)c2)cc1NC(=O)c1cncc(-c2cccs2)c1] | (I-6) | 1150 | 29.9 | >3330 | — |
| 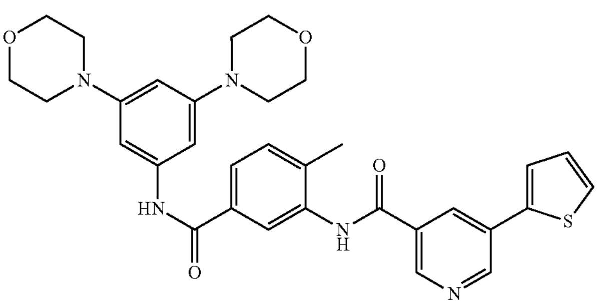 [SMILES: Cc1ccc(C(=O)Nc2cc(N3CCOCC3)cc(N3CCOCC3)c2)cc1NC(=O)c1cncc(-c2cccs2)c1] | (I-7) | 3420 | 56.5 | — | — |
TABLE 1a
| Structure | Compound ID | BTK IC$_{50}$ (nM) | HCK IC$_{50}$ (nM) Inv | TAK1 IC$_{50}$ (nM) |
|---|---|---|---|---|
| 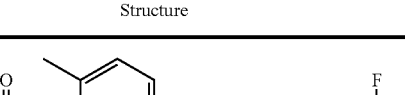 | (I-8) | 69.7 | 5.33 | — |

TABLE 1a-continued

| Structure | Compound ID | BTK IC$_{50}$ (nM) | HCK IC$_{50}$ (nM) Inv | TAK1 IC$_{50}$ (nM) |
|---|---|---|---|---|
| [structure] | (I-9) | 25.3 | 2.43 | — |

TABLE 2

| Compound ID | BCWM.1 EC$_{50}$ (nM) | MWCL-1 EC$_{50}$ (nM) | RPCIWM-1 EC$_{50}$ (nM) | OCI-Ly3 EC$_{50}$ (nM) | Ramos EC$_{50}$ (nM) | OCI-Ly19 EC$_{50}$ (nM) | Mec1 EC$_{50}$ (nM) |
|---|---|---|---|---|---|---|---|
| (I-1) | 38 | 459 | — | 2900 | 4150 | 552 | — |
| (I-2) | 12 | 16 | 110 | 161 | 60 | 52 | — |
| (I-3) | 141 | 355 | 725 | 411 | 555 | 508 | — |
| (I-4) | — | — | — | — | — | — | — |
| (I-5) | 365 | 1090 | 0.02 | 2160 | 989 | 1560 | — |
| (I-6) | — | — | — | — | — | — | — |
| (I-7) | 180 | 1760 | 4800 | 3540 | 2380 | 2970 | — |

TABLE 2a

| Compound ID | BCWM.1 EC$_{50}$ (nM) | MWCL-1 EC$_{50}$ (nM) | TMD8 EC$_{50}$ (nM) | OCI-Ly7 EC$_{50}$ (nM) | OCI-Ly3 EC$_{50}$ (nM) | Ramos EC$_{50}$ (nM) | OCI-Ly19 EC$_{50}$ (nM) |
|---|---|---|---|---|---|---|---|
| (I-8) | 2.7 | 15 | — | — | 76 | 329 | 56 |
|  | <1 | <1 |  |  | 356 |  |  |
| (I-9) | 542 | 294 | — | — | 5300 | 7470 | 2650 |
|  | 305 | 281 |  |  | 356 |  |  |

Kinative

The kinase selectivity of I-6 was evaluated using a chemical proteomic approach named KiNativ which detects 260 kinases in A375 cells (ActivX Biosciences). To probe the intracellular targets of the compounds, A375 cells were incubated with the inhibitor at 1 µM final concentration and then looked for protection of labeling by an ATP-biotin probe that non-specifically labels conserved lysines on kinases and other nucleotide-dependent enzymes.

Results

Table 3 shows that compound I-6 inhibits a number of kinases at 1 µM, including Abl (>90%), FYN (55.7%), LYN (87.6%), and ZAK (>95%).

TABLE 3

| Kinase | Reference | Description | Sequence | SEQ ID NO: | Labeling Site | Compound I-6 (1 µM) |
|---|---|---|---|---|---|---|
| ABL, ARG | UniRef100_P00519 | Proto-oncogene tyrosine-protein kinase ABL1 [Homo sapiens (Human)] | LMTGDTYTAHAGAK FPIK | 1 | Activation Loop | >90 |
| ACK | UniRef100_Q07912 | Activated CDC42 kinase 1 [Homo sapiens (Human)] | TVSVAVKCLKPDVLS QPEAMDDFIR | 2 | Lys1 | −1.2 |
| AMPKa1, AMPKa2 | UniRef100_Q13131 | 5'-AMP-activated protein kinase catalytic subunit alpha-1 [Homo sapiens (Human)] | VAVKILNR | 3 | Lys1 | 15.3 |

TABLE 3-continued

| Kinase | Reference | Description | Sequence | SEQ ID NO: Labeling Site | Compound I-6 (1 μM) |
|---|---|---|---|---|---|
| ATR | UniRef100_Q13535 | Serine/threonine-protein kinase ATR [Homo sapiens (Human)] | FYIMMCKPK | 4 ATP | 26.2 |
| AurA | UniRef100_O14965 | Serine/threonine-protein kinase 6 [Homo sapiens (Human)] | DIKPENLLLGSAGELK | 5 Lys2 | −21.6 |
| AurB | UniRef100_Q96GD4 | Serine/threonine-protein kinase 12 [Homo sapiens (Human)] | SHFIVALKVLFK | 6 Lys1 | −94 |
| BARK1 | UniRef100_P25098 | Beta-adrenergic receptor kinase 1 n = 1 Tax = Homo sapiens RepID = ARBK1_HUMAN | DLKPANILLDEHGHVR | 7 Lys2 | −1.2 |
| BLK | UniRef100_P51451 | Tyrosine-protein kinase BLK n = 2 Tax = Homo sapiens RepID = BLK_HUMAN | IIDSEYTAQEGAKFPIK | 8 Activation Loop | 68.8 |
| BRAF | UniRef100_P15056 | B-Raf proto-oncogene serine/threonine-protein kinase [Homo sapiens (Human)] | DLKSNNIFLHEDLTVK | 9 Lys2 | −20.3 |
| BTK | UniRef100_Q06187 | Tyrosine-protein kinase BTK [Homo sapiens] | GQYDVAIKMIK | 10 Lys1 | 7.8 |
| BTK | UniRef100_Q06187 | Tyrosine-protein kinase BTK [Homo sapiens] | YVLDDEYTSSVGSKFPVR | 11 Activation Loop | −12.5 |
| CaMK1d | UniRef100_Q8IU85 | Calcium/calmodulin-dependent protein kinase type 1D [Homo sapiens (Human)] | LFAVKCIPK | 12 Lys1 | −17.8 |
| CaMK2a, CaMK2b, CaMK2d, CaMK2g | UniRef100_Q9UQM7 | Calcium/calmodulin-dependent protein kinase type II alpha chain [Homo sapiens (Human)] | DLKPENLLLASK | 13 Lys2 | 0.7 |
| CaMK2d | UniRef100_Q13557 | Calcium/calmodulin-dependent protein kinase type II delta chain n = 2 Tax = Euarchontoglires RepID = KCC2D_HUMAN | IPTGQEYAAKIINTKK | 14 Lys1 | −1.1 |
| CaMK4 | UniRef100_Q16566 | Calcium/calmodulin-dependent protein kinase type IV [Homo sapiens (Human)] | DLKPENLLYATPAPDAPLK | 15 Lys2 | 20.7 |
| CDC2 | UniRef100_P06493 | Cell division control protein 2 homolog [Homo sapiens (Human)] | DLKPQNLLIDDKGTIK | 16 Lys2 | −7.9 |
| CDK11, CDK8 | UniRef100_P49336 | Cell division protein kinase 8 [Homo sapiens (Human)] | DLKPANILVMGEGPER | 17 Lys2 | 20.7 |
| CDK2 | UniRef100_P24941 | Cell division protein kinase 2 [Homo sapiens (Human)] | DLKPQNLLINTEGAIK | 18 Lys2 | 8.6 |
| CDK5 | UniRef100_Q00535 | Cell division protein kinase 5 [Homo sapiens (Human)] | DLKPQNLLINR | 19 Lys2 | 9.3 |
| CDK7 | UniRef100_P50613 | Cell division protein kinase 7 [Homo sapiens (Human)] | DLKPNNLLLDENGVLK | 20 Lys2 | −6.8 |
| CHK2 | UniRef100_O96017 | Serine/threonine-protein kinase Chk2 [Homo sapiens (Human)] | VAIKIISK | 21 Lys1 | 4.7 |
| CK1a | UniRef100_P48729 | Casein kinase I isoform alpha [Homo sapiens (Human)] | DIKPDNFLMGIGR | 22 Lys2 | 25.1 |
| CK1g1 | UniRef100_Q9HCP0 | Casein kinase I isoform gamma-1 [Homo sapiens (Human)] | DVKPENFLIGR | 23 Lys2 | 14.4 |
| CK1g2 | UniRef100_P78368 | Casein kinase I isoform gamma-2 [Homo sapiens (Human)] | DVKPENFLVGRPGTK | 24 Lys2 | 10.8 |
| CSK | UniRef100_P41240 | Tyrosine-protein kinase CSK [Homo sapiens (Human)] | VSDFGLTKEASSTQDTGKLPVK | 25 Activation Loop | 23.3 |

TABLE 3-continued

| Kinase | Reference | Description | Sequence | SEQ ID NO: | Labeling Site | Compound I-6 (1 µM) |
|---|---|---|---|---|---|---|
| DNAPK | UniRef100_P78527 | DNA-dependent protein kinase catalytic subunit [Homo sapiens (Human)] | EHPFLVKGGEDLR | 26 | ATP | 4.6 |
| eEF2K | UniRef100_O00418 | Elongation factor 2 kinase [Homo sapiens (Human)] | YIKYNSNSGFVR | 27 | ATP | 12 |
| Erk1 | UniRef100_P27361 | Mitogen-activated protein kinase 3 [Homo sapiens (Human)] | DLKPSNLLINTTCDLK | 28 | Lys2 | −3 |
| Erk2 | UniRef100_P28482 | Mitogen-activated protein kinase 1 [Homo sapiens] | DLKPSNLLLNTTCDLK | 29 | Lys2 | −11 |
| FER | UniRef100_P16591 | Proto-oncogene tyrosine-protein kinase FER n = 2 Tax = Homo sapiens RepID = FER_HUMAN | TSVAVKTCKEDLPQELK | 30 | Lys1 | −9.6 |
| FGR | UniRef100_P09769 | Proto-oncogene tyrosine-protein kinase FOR [Homo sapiens (Human)] | LIKDDEYNPCQGSKFPIK | 31 | Activation Loop | 3.5 |
| FRAP | UniRef100_P42345 | FKBP12-rapamycin complex-associated protein [Homo sapiens (Human)] | IQSIAPSLPQRVITSKQRPR | 32 | ATP | −8.8 |
| FYN, SRC, YES | UniRef100_P06241 | Proto-oncogene tyrosine-protein kinase Fyn n = 2 Tax = Homo sapiens RepID = FYN_HUMAN | QGAKFPIKWTAPEAALYGR | 33 | Activation Loop | 55.7 |
| GCK | UniRef100_Q12851 | Mitogen-activated protein kinase kinase kinase kinase 2 n = 1 Tax = Homo sapiens RepID = M4K2_HUMAN | DIKGANLLLTLQGDVK | 34 | Lys2 | 21.9 |
| GSK3A | UniRef100_P49840 | Glycogen synthase kinase-3 alpha [Homo sapiens (Human)] | DIKPQNLLVDPDTAVLK | 35 | Lys2 | 17.3 |
| GSK3B | UniRef100_P49841 | Glycogen synthase kinase-3 beta n = 2 Tax = Homo sapiens RepID = GSK3B_HUMAN | DIKPQNLLLDPDTAVLK | 36 | Lys2 | 15.9 |
| HPK1 | UniRef100_Q92918 | Mitogen-activated protein kinase kinase kinase kinase 1 [Homo sapiens (Human)] | DKVSGDLVALKMVK | 37 | Lys1 | 7.5 |
| IKKe | UniRef100_Q14164 | Inhibitor of nuclear factor kappa-B kinase epsilon subunit [Homo sapiens (Human)] | SGELVAVKVFNTTSYLRPR | 38 | Lys1 | 3.8 |
| IKKe, TBK1 | UniRef100_Q14164 | Inhibitor of nuclear factor kappa-B kinase epsilon subunit [Homo sapiens (Human)] | DIKPGNIMR | 39 | Lys2 | 24.8 |
| ILK | UniRef100_Q13418 | Integrin-linked protein kinase 1 [Homo sapiens (Human)] | ISMADVKFSFQCPGR | 40 | Protein Kinase Domain | 17.2 |
| IRAK4 | UniRef100_Q9NWZ3 | Interleukin-1 receptor-associated kinase 4 [Homo sapiens (Human)] | DIKSANILLDEAFTAK | 41 | Lys2 | −1.4 |
| JAK1 | UniRef100_P23458 | Tyrosine-protein kinase JAK1 n = 1 Tax = Homo sapiens RepID = JAK1_HUMAN | QLASALSYLEDKDLVHGNVCTKNLLLAR | 42 | Protein Kinase Domain | 16.6 |
| JAK1 domain2 | UniRef100_P23458 | Tyrosine-protein kinase JAK1 n = 1 Tax = Homo sapiens RepID = JAK1_HUMAN | YDPEGDNTGEQVAVKSLKPESGGNHIADLKK | 43 | Lys1 | 3.3 |
| JNK1, JNK2, JNK3 | UniRef100_P45983 | Mitogen-activated protein kinase 8 [Homo sapiens (Human)] | DLKPSNIVVK | 44 | Lys2 | 11.7 |

TABLE 3-continued

| Kinase | Reference | Description | Sequence | SEQ ID NO:Labeling Site | Compound I-6 (1 μM) |
|---|---|---|---|---|---|
| KHS1 | UniRef100_Q9Y4K4 | Mitogen-activated protein kinase kinase kinase kinase 5 [Homo sapiens (Human)] | NVHTGELAAVKIIK | 45 Lys1 | -21.8 |
| LCK | UniRef100_P06239 | Proto-oncogene tyrosine-protein kinase LCK n = 2 Tax = Homo sapiens RepID = LCK_HUMAN | EGAKFPIKWTAPEAI NYGTFTIK | 46 Activation Loop | 82.1 |
| LKB1 | UniRef100_Q15831 | Serine/threonine-protein kinase 11 [Homo sapiens (Human)] | DIKPGNLLLTTGGTLK | 47 Lys2 | 4.9 |
| LOK | UniRef100_O94804 | Serine/threonine-protein kinase 10 [Homo sapiens (Human)] | DLKAGNVLMTLEGDIR | 48 Lys2 | 23.9 |
| LYN | UniRef100_P07948 | Tyrosine-protein kinase Lyn n = 1 Tax = Homo sapiens RepID = LYN_HUMAN | VAVKTLKPGTMSVQ AFLEEANLMK | 49 Lys1 | 87.6 |
| LYN | UniRef100_P07948 | Tyrosine-protein kinase Lyn n = 1 Tax = Homo sapiens RepID = LYN_HUMAN | EGAKFPIKWTAPEAI NFGCFTIK | 50 Activation Loop | 68.5 |
| MAP2K1 | UniRef100_Q02750 | Dual specificity mitogen-activated protein kinase kinase 1 n = 4 Tax = Eutheria RepID = MP2K1_HUMAN | IMHRDVKPSNILVNSR | 51 Lys2 | 10.8 |
| MAP2K1, MAP2K2 | UniRef100_Q02750 | Dual specificity mitogen-activated protein kinase kinase 1 n = 4 Tax = Eutheria RepID = MP2K1_HUMAN | DVKPSNILVNSR | 52 Lys2 | 4.1 |
| MAP2K3 | UniRef100_P46734 | Dual specificity mitogen-activated protein kinase kinase 3 [Homo sapiens (Human)] | DVKPSNVLINK | 53 Lys2 | 4.9 |
| MAP2K4 | UniRef100_P45985 | Dual specificity mitogen-activated protein kinase kinase 4 [Homo sapiens (Human)] | DIKPSNILLDR | 54 Lys2 | -14.6 |
| MAP2K5 | UniRef100_Q13163 | Dual specificity mitogen-activated protein kinase kinase 5 n = 1 Tax = Homo sapiens RepID = MP2K5_HUMAN | DVKPSNMLVNTR | 55 Lys2 | 28.7 |
| MAP2K6 | UniRef100_P52564 | Dual specificity mitogen-activated protein kinase kinase 6 [Homo sapiens (Human)] | DVKPSNVLINALGQVK | 56 Lys2 | 9.4 |
| MAP2K7 | UniRef100_O14733 | Dual specificity mitogen-activated protein kinase kinase 7 [Homo sapiens (Human)] | DVKPSNILLDER | 57 Lys2 | -3 |
| MAP3K1 | UniRef100_Q13233 | Mitogen-activated protein kinase kinase kinase 1 n = 1 Tax = Homo sapiens RepID = M3K1_HUMAN | DVKGANLLIDSTGQR | 58 Lys2 | 9.8 |
| MAP3K2, MAP3K3 | UniRef100_Q9Y2U5 | Mitogen-activated protein kinase kinase kinase 2 n = 3 Tax = Homo sapiens RepID = M3K2_HUMAN | DIKGANILR | 59 Lys2 | -15.3 |
| MAP3K4 | UniRef100_Q9Y6R4 | Mitogen-activated protein kinase kinase kinase 4 [Homo sapiens (Human)] | DIKGANIFLTSSGLIK | 60 Lys2 | 6.5 |
| MAP3K5 | UniRef100_Q99683 | Mitogen-activated protein kinase kinase kinase 5 [Homo sapiens (Human)] | DIKGDNVLINTYSGV LK | 61 Lys2 | 16.2 |
| MARK1, MARK2 | UniRef100_Q7KZI7 | Serine/threonine-protein kinase MARK2 [Homo sapiens (Human)] | EVAVKIIDK | 62 Lys1 | -4.9 |
| MARK2, MARK3 | UniRef100_P27448 | MAP/microtubule affinity-regulating kinase 3 [Homo sapiens (Human)] | DLKAENLLLDADMNIK | 63 Lys2 | 17.2 |

TABLE 3-continued

| Kinase | Reference | Description | Sequence | SEQ ID NO: Labeling Site | Compound I-6 (1 µM) |
|---|---|---|---|---|---|
| MARK3 | UniRef100_P27448 | MAP/microtubule affinity-regulating kinase 3 [Homo sapiens (Human)] | EVAIKIIDKTQLNPTSLQK | 64 Lys1 | -2.2 |
| MAST3 | UniRef100_O60307 | Microtubule-associated serine/threonine-protein kinase 3 [Homo sapiens (Human)] | DLKPDNLLITSLGHIK | 65 Lys2 | 18.9 |
| MASTL | UniRef100_Q96GX5 | Microtubule-associated serine/threonine-protein kinase-like [Homo sapiens (Human)] | LYAVKVVK | 66 Lys1 | -3.7 |
| MST1 | UniRef100_Q13043 | Serine/threonine-protein kinase 4 [Homo sapiens (Human)] | ETGQIVAIKQVPVESDLQEIIK | 67 Lys1 | -26.3 |
| MST2 | UniRef100_Q13188 | Serine/threonine-protein kinase 3 [Homo sapiens (Human)] | ESGQVVAIKQVPVESDLQEIIK | 68 Lys1 | -6.1 |
| MST3 | UniRef100_Q9Y6E0 | Serine/threonine-protein kinase 24 [Homo sapiens (Human)] | DIKAANVLLSEHGEVK | 69 Lys2 | -0.4 |
| MST4, YSK1 | UniRef100_O00506 | Serine/threonine-protein kinase 25 [Homo sapiens (Human)] | DIKAANVLLSEQGDVK | 70 Lys2 | 22 |
| NDR1 | UniRef100_Q15208 | Serine/threonine-protein kinase 38 [Homo sapiens (Human)] | DTGHVYAMKILR | 71 Lys1 | -10.5 |
| NDR2 | UniRef100_Q9Y2H1 | Serine/threonine-protein kinase 38-like [Homo sapiens (Human)] | DIKPDNLLLDAK | 72 Lys2 | -12.5 |
| NEK3 | UniRef100_P51956 | Serine/threonine-protein kinase Nek3 [Homo sapiens (Human)] | SKNIFLTQNGK | 73 Activation Loop | 10 |
| NEK6, NEK7 | UniRef100_Q9HC98 | Serine/threonine-protein kinase Nek6 [Homo sapiens (Human)] | DIKPANVFITATGVVK | 74 Lys2 | -3.7 |
| NEK7 | UniRef100_Q8TDX7 | Serine/threonine-protein kinase Nek7 [Homo sapiens (Human)] | AACLLDGVPVALKK | 75 Lys1 | 10.7 |
| NEK9 | UniRef100_Q8TD19 | Serine/threonine-protein kinase Nek9 n = 1 Tax = Homo sapiens RepID = NEK9_HUMAN | DIKTLNIFLTK | 76 Lys2 | -0.3 |
| p38a | UniRef100_Q16539 | Mitogen-activated protein kinase 14 n = 3 Tax = Eutheria RepID = MK14_HUMAN | QELNKTIWEVPER | 77 Protein Kinase Domain | 85.1 |
| p38d, p38g | UniRef100_P53778 | Mitogen-activated protein kinase 12 [Homo sapiens (Human)] | DLKPGNLAVNEDCELK | 78 Lys2 | 17.8 |
| p70S6K | UniRef100_P23443 | Ribosomal protein S6 kinase 1 (EC 2.7.1.37) (S6K) (S6K1) (70 kDa ribosomal protein S6 kinase 1) (p70 S6 kinase alpha) (p70(S6K)-alpha) [Homo sapiens (Human)] | DLKPENIMLNHQGHVK | 79 Lys2 | 7.4 |
| PFTAIRE1 | UniRef100_O94921 | Serine/threonine-protein kinase PFTAIRE-1 n = 1 Tax = Homo sapiens RepID = PFTK1_HUMAN | LVALKVIR | 80 Lys1 | -31.3 |
| PI4KB | UniRef100_Q9UBF8 | Phosphatidylinositol 4-kinase beta n = 2 Tax = Homo sapiens RepID = PI4KB_HUMAN | VPHTQAVVLNSKDK | 81 ATP | -15.1 |
| PIK3C3 | UniRef100_Q8NEB9 | Phosphatidylinositol 3-kinase catalytic subunit type 3 [Homo sapiens (Human)] | TEDGGKYPVIFKHGDDLR | 82 ATP | -23.1 |
| PIK3CB | UniRef100_P42338 | Phosphatidylinositol-4,5-bisphosphate 3-kinase catalytic subunit beta isoform [Homo sapiens (Human)] | VFGEDSVGVIFKNGDDLR | 83 ATP | 2.8 |
| PIK3CD | UniRef100_O00329 | Phosphatidylinositol-4,5-bisphosphate 3-kinase catalytic | VNWLAHNVSKDNRQ | 84 ATP | -6.8 |

TABLE 3-continued

| Kinase | Reference | Description | Sequence | SEG ID NO: Labeling Site | Compound I-6 (1 μM) |
|---|---|---|---|---|---|
| | | subunit delta isoform [Homo sapiens (Human)] | | | |
| PIP4K2A | UniRef100_P48426 | Phosphatidylinositol-4-phosphate 5-kinase type II alpha (EC 2.7.1.68) (1-phosphatidylinositol-4-phosphate 5-kinase 2-alpha) (PtdIns(4)P-5-kinase isoform 2-alpha) (PIP5KII-alpha) (Diphosphoinositide kinase 2-alpha) (PtdIns(4)P-5-kinase B isoform) (PIP5K1 | AKELPTLKDNDFINE GQK | 85 ATP | 12.8 |
| PIP4K2C | UniRef100_Q8TBX8 | Phosphatidylinositol-5-phosphate 4-kinase type-2 gamma n = 1 Tax = Homo sapiens RepID = PI42C_HUMAN | TLVIKEVSSEDIADM HSNLSNYHQYIVK | 86 ATP | 12.3 |
| PIP5K3 | UniRef100_Q9Y2I7 | FYVE finger-containing phosphoinositide kinase (EC 2.7.1.68) (1-phosphatidylinositol-4-phosphate 5-kinase) (Phosphatidylinositol-3-phosphate 5-kinase type III) (PIP5K) (PtdIns(4)P-5-kinase) [Homo sapiens (Human)] | GGKSGAAFYATEDD RFILK | 87 ATP | 17.8 |
| PITSLRE | UniRef100_P21127 | PITSLRE serine/threonine-protein kinase CDC2L1 [Homo sapiens (Human)] | DLKTSNLLLSHAGILK | 88 Lys2 | 1.9 |
| PKCi | UniRef100_P41743 | Protein kinase C iota type [Homo sapiens (Human)] | DLKLDNVLLDSEGHIK | 89 Lys2 | -17.5 |
| PKD1, PKD2 | UniRef100_Q15139 | Serine/threonine-protein kinase D1 n = 1 Tax = Homo sapiens RepID = KPCD1_HUMAN | NIVHCDLKPENVLLA SADPFPQVK | 90 Lys2 | -2.5 |
| PKD2 | UniRef100_Q9BZL6 | Protein kinase D2 [Homo sapiens (Human)] | DVAVKVIDK | 91 Lys1 | -17.8 |
| PKD3 | UniRef100_O94806 | Protein kinase D3 [Homo sapiens (Human)] | NIVHCDLKPENVLLA SAEPFPQVK | 92 Lys2 | -4.5 |
| PKN1 | UniRef100_Q16512 | Protein kinase N1 [Homo sapiens (Human)] | VLLSEFRPSGELFAI KALK | 93 Lys1 | -35.2 |
| PKR | UniRef100_P19525 | Interferon-induced, double-stranded RNA-activated protein kinase [Homo sapiens (Human)] | DLKPSNIFLVDTK | 94 Lys2 | 3.2 |
| PLK1 | UniRef100_P53350 | Serine/threonine-protein kinase PLK1 [Homo sapiens (Human)] | CFEISDADTKEVFAG KIVPK | 95 Lys1 | -5.4 |
| PYK2 | UniRef100_Q14289 | Protein tyrosine kinase 2 beta [Homo sapiens (Human)] | YIEDEDYYKASVTR | 96 Activation Loop | 5.4 |
| ROCK1, ROCK2 | UniRef100_O75116 | Rho-associated protein kinase 2 [Homo sapiens (Human)] | DVKPDNMLLDK | 97 Lys2 | 12.7 |
| RSK1 domain1 | UniRef100_Q15418 | Ribosomal protein S6 kinase alpha 1 [Homo sapiens (Human)] | DLKPENILLDEEGHIK LTDFGLSKEAIDHEK | 98 Lys2 | 33.3 |
| RSK1 domain2 | UniRef100_Q15418 | Ribosomal protein S6 kinase alpha 1 [Homo sapiens (Human)] | DLKPSNILYVDESGN PECLR | 99 Lys2 | -22.9 |
| RSK2 domain1 | UniRef100_P51812 | Ribosomal protein S6 kinase alpha 3 [Homo sapiens (Human)] | DLKPENILLDEEGHIK LTDFGLSKESIDHEK | 100 Lys2 | 5 |
| RSK2 domain2 | UniRef100_P51812 | Ribosomal protein S6 kinase alpha 3 [Homo sapiens (Human)] | DLKPSNILYVDESGN PESIR | 101 Lys2 | -15.8 |
| SGK3 | UniRef100_Q96BR1 | Serine/threonine-protein kinase Sgk3 [Homo sapiens (Human)] | FYAVKVLQK | 102 Lys1 | -7.2 |

TABLE 3-continued

| Kinase | Reference | Description | Sequence | SEQ ID NO:Labeling Site | Compound I-6 (1 µM) |
|---|---|---|---|---|---|
| SLK | UniRef100_Q9H2G2 | CTCL tumor antigen se20-9 [Homo sapiens (Human)] | DLKAGNILFTLDGDIK | 103 Lys2 | -19.5 |
| STLK5 | UniRef100_Q7RTN6 | STE20-related adaptor protein [Homo sapiens (Human)] | YSVKVLPWLSPEVL QQNLQGYDAK | 104 Activation Loop | -17.8 |
| STLK6 | UniRef100_Q9C0K7 | Serine/threonine-protein kinase ALS2CR2 [Homo sapiens (Human)] | SIKASHILISGDGLVT LSGLSHLHSLVK | 105 Lys2 | 44.8 |
| SYK | UniRef100_P43405 | Tyrosine-protein kinase SYK [Homo sapiens (Human)] | ISDFGLSKALR | 106 Activation Loop | -7.9 |
| SYK | UniRef100_P43405 | Tyrosine-protein kinase SYK [Homo sapiens (Human)] | TVAVKILK | 107 Lys1 | -38.5 |
| TAO1, TAO3 | UniRef100_Q9H2K8 | Serine/threonine-protein kinase TAO3 [Homo sapiens (Human)] | DIKAGNILLTEPGQVK | 108 Lys2 | 11.9 |
| TAO2 | UniRef100_Q9UL54 | Serine/threonine-protein kinase TAO2 n = 2 Tax = Homo sapiens RepID = TAOK2_HUMAN | DVKAGNILLSEPGLVK | 109 Lys2 | 33.4 |
| TEC | UniRef100_P42680 | Tyrosine-protein kinase Tec n = 2 Tax = Homo sapiens RepID = TEC_HUMAN | YVLDDQYTSSSGAK FPVK | 110 Activation Loop | -28.9 |
| TLK1 | UniRef100_Q9UKI8 | Serine/threonine-protein kinase tousled-like 1 [Homo sapiens (Human)] | YLNEIKPPIIHYDLKP GNILLVDGTACGEIK | 111 Lys2 | 3.9 |
| TLK2 | UniRef100_Q86UE8 | Serine/threonine-protein kinase tousled-like 2 [Homo sapiens (Human)] | YLNEIKPPIIHYDLKP GNILLVNGTACGEIK | 112 Lys2 | -18.8 |
| ULK3 | UniRef100_Q6PHR2 | Unc-51-like kinase 3 [Homo sapiens (Human)] | EVVAIKCVAK | 113 Lys1 | -21.5 |
| ZAK | UniRef100_Q9NYL2 | Mitogen-activated protein kinase kinase kinase MLT [Homo sapiens (Human)] | WISQDKEVAVKK | 114 Lys1 | >95 |
| ZAP70 | UniRef100_P43403 | Tyrosine-protein kinase ZAP-70 [Homo sapiens (Human)] | ISDFGLSKALGADDS YYTAR | 115 Activation Loop | 7.5 |
| ZC1/HGK, ZC2/TNIK, ZC3/MINK | UniRef100_O95819 | Mitogen-activated protein kinase kinase kinase kinase 4 [Homo sapiens (Human)] | DIKGQNVLLTENAEVK | 116 Lys2 | 27 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

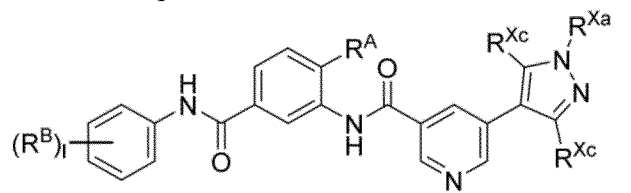

What is claimed is:

1. A compound of the formula:

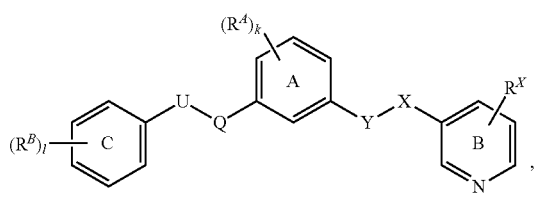

or a pharmaceutically acceptable salt, solvate, hydrate, polymorph, co-crystal, tautomer, stereoisomer, isotopically labeled derivative, or prodrug thereof;
wherein:
  each instance of $R^A$ is independently hydrogen, halogen, optionally substituted alkyl, optionally substituted carbocyclyl, $OR^{A1}$, $N(R^{A1})_2$, —CN, —C(=O) $R^{A1}$, —C(=O)O$R^{A1}$, —C(=O)N$(R^{A1})_2$, —NO$_2$, —N$R^{A1}$C(=O)$R^{A1}$, —N$R^{A1}$C(=O)O$R^{A1}$, —N$R^{A1}$S(=O)$_2R^{A1}$, —S(=O)$_2R^{A1}$, or —S(=O)$_2$N$(R^{A1})_2$;
  each instance of $R^B$ is independently hydrogen, halogen, optionally substituted alkyl, optionally substituted carbocyclyl, optionally substituted heterocyclyl, optionally substituted aryl, optionally substituted heteroaryl, —O$R^{A1}$, —N$(R^{A1})_2$, —CN, —C(=O)$R^{A1}$, —C(=O)O$R^{A1}$, —C(=O)N$(R^{A1})_2$, —NO$_2$, —N$R^{A1}$C(=O)$R^{A1}$, —N$R^{A1}$C(=O)O$R^{A1}$, —N$R^{A1}$S(=O)$_2R^{A1}$, —S(=O)$_2R^{A1}$, or —S(=O)$_2$N$(R^{A1})_2$;
  each instance of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A1}$ groups are joined to form an optionally substituted heterocyclic ring;

$R^X$ is selected from the group consisting of optionally substituted carbocyclyl, optionally substituted heterocyclyl, optionally substituted aryl, optionally substituted bicyclic heteroaryl, optionally substituted pyrrolyl, optionally substituted furanyl, optionally substituted imidazolyl, optionally substituted pyrazolyl, optionally substituted oxazolyl, optionally substituted isoxazolyl, optionally substituted thiazolyl, optionally substituted isothiazolyl, optionally substituted triazolyl, optionally substituted oxadiazolyl, optionally substituted thiadiazolyl, optionally substituted tetrazolyl, and optionally substituted 6-membered monocyclic heteroaryl;

k is 0, 1, 2, 3, or 4;

l is 1, 2, 3, 4, or 5; and

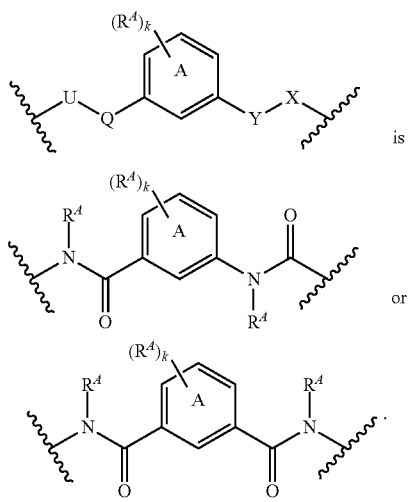

2. The compound of claim 1, wherein the compound is of Formula:

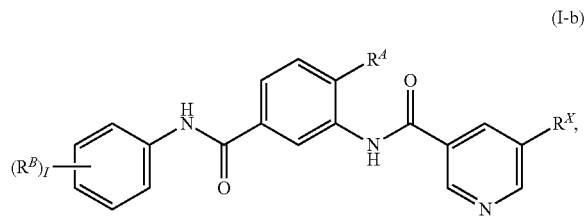

or a pharmaceutically acceptable salt, solvate, hydrate, polymorph, co-crystal, tautomer, stereoisomer, isotopically labeled derivative, or prodrug thereof.

3. The compound of claim 2, wherein the compound is of the formula:

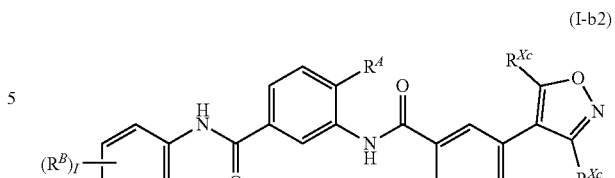

or

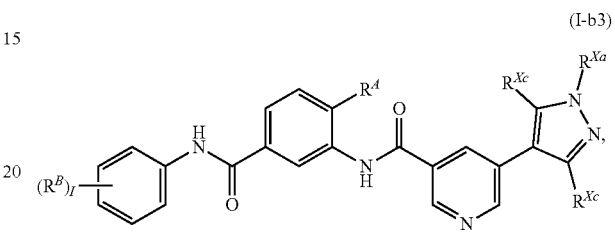

or a pharmaceutically acceptable salt, solvate, hydrate, polymorph, co-crystal, tautomer, stereoisomer, isotopically labeled derivative, or prodrug thereof, wherein:

$R^{Xa}$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{A1}$, —C(=O)O$R^{A1}$, —C(=O)N($R^{A1}$)$_2$, —S(=O)$R^{A1}$, —S(=O)N($R^{A1}$)$_2$, —S(=O)$_2$$R^{A1}$, —S(=O)$_2$O$R^{A1}$, —S(=O)$_2$N($R^{A1}$)$_2$, and a nitrogen protecting group; and each instance of $R^{Xc}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —O$R^{A1}$, —N($R^{A1}$)$_2$, —S$R^{A1}$, —CN, —C(=O)$R^{A1}$, —C(=O)O$R^{A1}$, —C(=O)N($R^{A1}$)$_2$, —NO$_2$, —N$_3$, —N$R^{A1}$C(=O)$R^{A1}$, —N$R^{A1}$C(=O)O$R^{A1}$, —N$R^{A1}$C(=O)N($R^{A1}$)$_2$, —N$R^{A1}$S(=O)$_2$$R^{A1}$, —N$R^{A1}$S(=O)$R^{A1}$, —OC(=O)$R^{A1}$, —OC(=O)O$R^{A1}$, —OC(=O)N($R^{A1}$)$_2$, —S(=O)$R^{A1}$, —S(=O)N($R^{A1}$)$_2$, —S(=O)$_2$$R^{A1}$, and —S(=O)$_2$N($R^{A1}$)$_2$.

4. The compound of claim 1, or a pharmaceutically acceptable salt, solvate, hydrate, polymorph, co-crystal, tautomer, stereoisomer, isotopically labeled derivative, or prodrug thereof, wherein at least one instance of $R^A$ is substituted or unsubstituted, $C_{1-6}$ alkyl or halogen.

5. The compound of claim 1, or a pharmaceutically acceptable salt, solvate, hydrate, polymorph, co-crystal, tautomer, stereoisomer, isotopically labeled derivative, or prodrug thereof, wherein l is 1 or 2.

6. The compound of claim 1, or a pharmaceutically acceptable salt, solvate, hydrate, polymorph, co-crystal, tautomer, stereoisomer, isotopically labeled derivative, or prodrug thereof, wherein at least one $R^B$ group is substituted or unsubstituted, $C_{1-6}$ alkyl.

7. The compound of claim 1, or a pharmaceutically acceptable salt, solvate, hydrate, polymorph, co-crystal, tautomer, stereoisomer, isotopically labeled derivative, or prodrug thereof, wherein one $R^B$ group is substituted or unsubstituted —$CH_2$-(piperazinyl).

8. The compound of claim 1, or a pharmaceutically acceptable salt, solvate, hydrate, polymorph, co-crystal, tautomer, stereoisomer, isotopically labeled derivative, or prodrug thereof, wherein one $R^B$ group is haloalkyl.

9. The compound of claim 1, or a pharmaceutically acceptable salt, solvate, hydrate, polymorph, co-crystal, tautomer, stereoisomer, isotopically labeled derivative, or prodrug thereof, wherein one $R^B$ group is substituted or unsubstituted imidazoyl, substituted or unsubstituted piperazinyl, or substituted or unsubstituted morpholinyl.

10. The compound of claim 1, wherein the compound is of the formula:

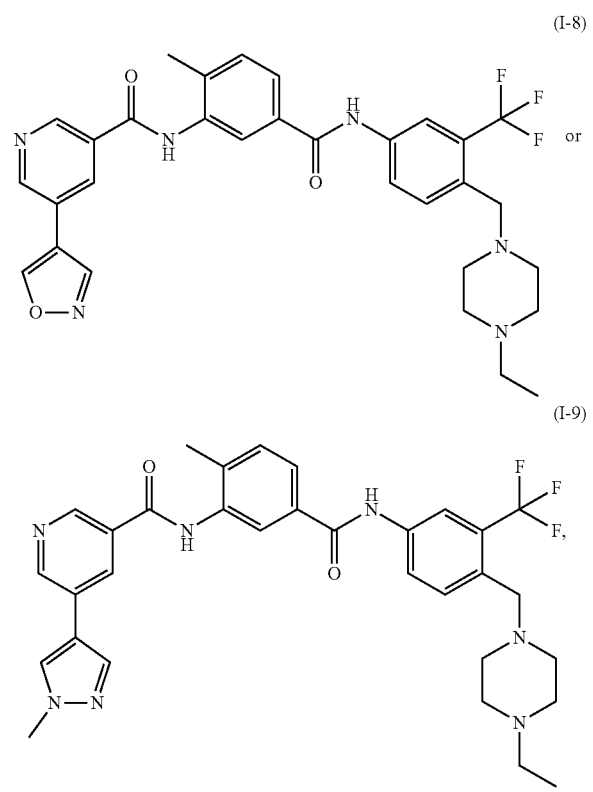

or a pharmaceutically acceptable salt, solvate, hydrate, polymorph, co-crystal, tautomer, stereoisomer, isotopically labeled derivative, or prodrug thereof.

11. A pharmaceutical composition comprising a compound of claim 1, or a pharmaceutically acceptable salt, solvate, hydrate, polymorph, co-crystal, tautomer, stereoisomer, isotopically labeled derivative, or prodrug thereof, and optionally a pharmaceutically acceptable excipient.

12. A method of treating a non-Hodgkin's lymphoma in a subject comprising administering an effective amount of a compound of claim 1, or a pharmaceutically acceptable salt, solvate, hydrate, polymorph, co-crystal, tautomer, stereoisomer, isotopically labeled derivative, or prodrug thereof to the subject.

13. A kit comprising a container, a compound of claim 1, or a pharmaceutically acceptable salt, solvate, hydrate, polymorph, co-crystal, tautomer, stereoisomer, isotopically labeled derivative, or prodrug thereof, and instructions for use in a subject.

14. The compound of claim 1, or a pharmaceutically acceptable salt, solvate, hydrate, polymorph, co-crystal, tautomer, stereoisomer, isotopically labeled derivative, or prodrug thereof, wherein at least one instance of $R^A$ is —$CH_3$ or Cl.

15. The compound of claim 1, or a pharmaceutically acceptable salt, solvate, hydrate, polymorph, co-crystal, tautomer, stereoisomer, isotopically labeled derivative, or prodrug thereof, wherein at least one $R^B$ group is optionally substituted heterocyclyl, optionally substituted —($CH_2$)(heterocyclyl), optionally substituted —($CH_2$)$_2$(heterocyclyl), or optionally substituted —($CH_2$)$_3$(heterocyclyl).

16. The compound of claim 1, or a pharmaceutically acceptable salt, solvate, hydrate, polymorph, co-crystal, tautomer, stereoisomer, isotopically labeled derivative, or prodrug thereof, wherein at least one $R^B$ group is optionally substituted heteroaryl.

17. The compound of claim 1, or a pharmaceutically acceptable salt, solvate, hydrate, polymorph, co-crystal, tautomer, stereoisomer, isotopically labeled derivative, or prodrug thereof, wherein $R^X$ is optionally substituted pyrrolyl, optionally substituted furanyl, optionally substituted imidazolyl, optionally substituted pyrazolyl, optionally substituted oxazolyl, optionally substituted isoxazolyl, optionally substituted thiazolyl, optionally substituted isothiazolyl, optionally substituted triazolyl, optionally substituted oxadiazolyl, optionally substituted thiadiazolyl, or optionally substituted tetrazolyl.

18. The compound of claim 1, or a pharmaceutically acceptable salt, solvate, hydrate, polymorph, co-crystal, tautomer, stereoisomer, isotopically labeled derivative, or prodrug thereof, wherein

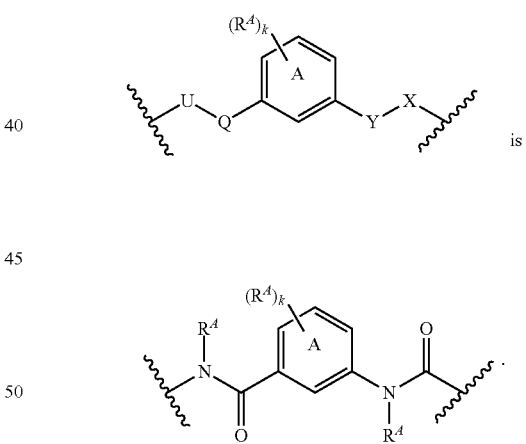

is

19. The compound of claim 1, or a pharmaceutically acceptable salt, solvate, hydrate, polymorph, co-crystal, tautomer, stereoisomer, isotopically labeled derivative, or prodrug thereof, wherein

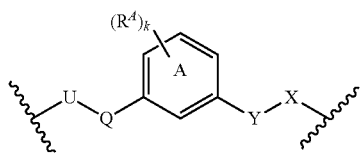

is

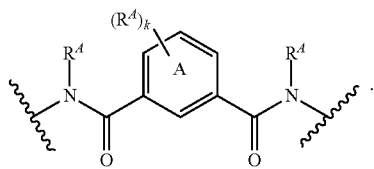

20. The compound of claim 3, wherein the compound is of Formula:

(I-b5)
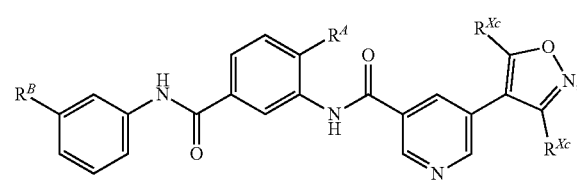

(I-b6)
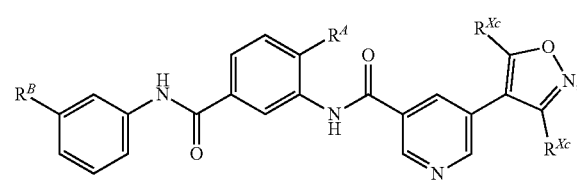

(I-b8)
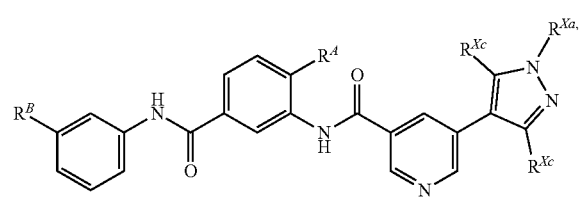

(I-b9)
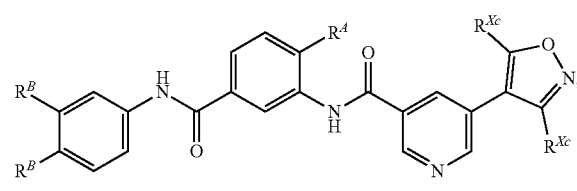

(I-b11)
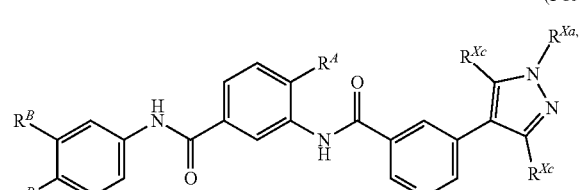

or (I-b12)
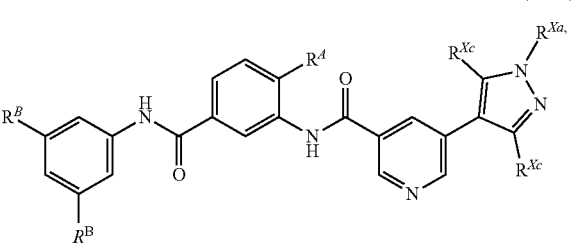

or a pharmaceutically acceptable salt, solvate, hydrate, polymorph, co-crystal, tautomer, stereoisomer, isotopically labeled derivative, or prodrug thereof.

21. The compound of claim 1, or a pharmaceutically acceptable salt thereof.

22. The compound of claim 10, or a pharmaceutically acceptable salt thereof.

23. A compound of the formula:

(I-2)
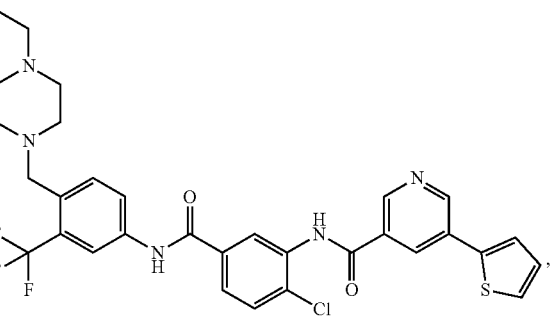

(I-3)
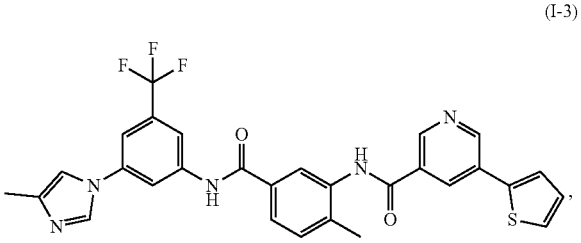

(I-4)
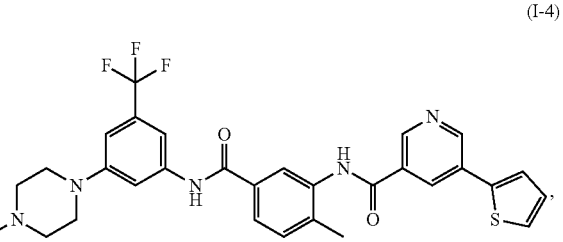

(I-5)
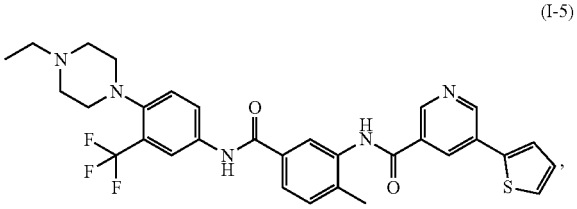

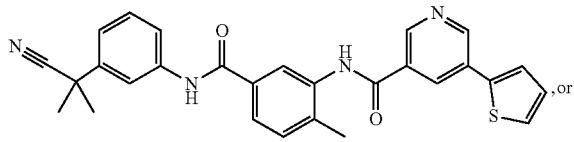
(I-6)

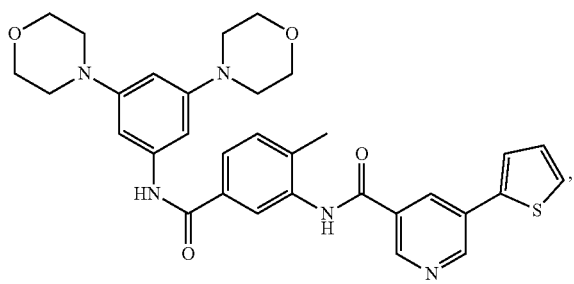
(I-7)

or a pharmaceutically acceptable salt, solvate, hydrate, polymorph, co-crystal, tautomer, stereoisomer, isotopically labeled derivative, or prodrug thereof.

24. A pharmaceutical composition comprising a compound of claim 23, or a pharmaceutically acceptable salt, solvate, hydrate, polymorph, co-crystal, tautomer, stereoisomer, isotopically labeled derivative, or prodrug thereof, and optionally a pharmaceutically acceptable excipient.

25. A method of treating a non-Hodgkin's lymphoma in a subject comprising administering an effective amount of a compound of claim 23, or a pharmaceutically acceptable salt, solvate, hydrate, polymorph, co-crystal, tautomer, stereoisomer, isotopically labeled derivative, or prodrug thereof, to the subject.

26. A kit comprising a container, a compound of claim 23, or a pharmaceutically acceptable salt, solvate, hydrate, polymorph, co-crystal, tautomer, stereoisomer, isotopically labeled derivative, or prodrug thereof, and instructions for use in a subject.

27. The compound of claim 23, or a pharmaceutically acceptable salt thereof.

28. The method of claim 12, wherein the non-Hodgkin's lymphoma is Waldenström's macroglobulinemia.

29. The method of claim 12, wherein the compound is of the formula:

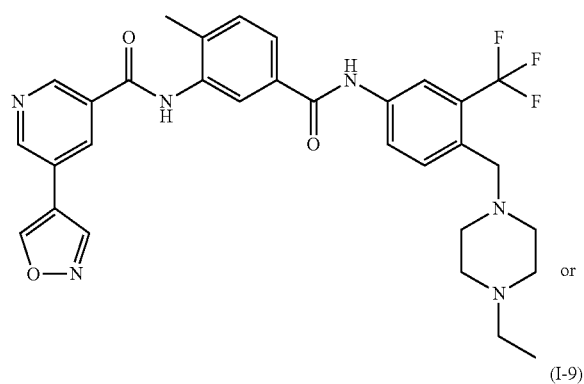
(I-8)

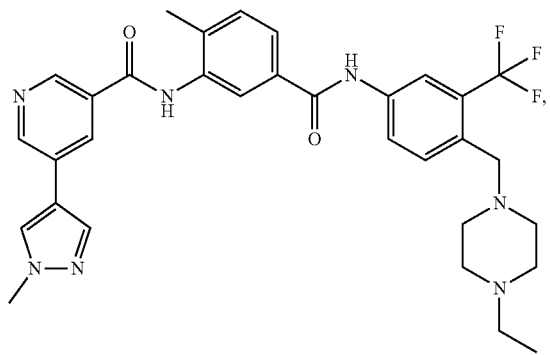
(I-9)

or a pharmaceutically acceptable salt, solvate, hydrate, polymorph, co-crystal, tautomer, stereoisomer, isotopically labeled derivative, or prodrug thereof.

30. The method of claim 25, wherein the non-Hodgkin's lymphoma is Waldenström's macroglobulinemia.

* * * * *

UNITED STATES PATENT AND TRADEMARK OFFICE
CERTIFICATE OF CORRECTION

| | |
|---|---|
| PATENT NO. | : 10,597,387 B2 |
| APPLICATION NO. | : 15/904143 |
| DATED | : March 24, 2020 |
| INVENTOR(S) | : Steven P. Treon et al. |

Page 1 of 2

It is certified that error appears in the above-identified patent and that said Letters Patent is hereby corrected as shown below:

On the Title Page

Item (57) In the Abstract, please change the first sentence:
"The present invention provides compounds of any one of Formulae (I) to (V) (e.g., compounds of any one of Formulae (I-1) to (I-9)), and methods for treating Waldenström's macroglobulinemia (WM) and other B cell neoplams in a subject using the compounds."
To:
-- The present invention provides compounds of any one of Formulae (I) to (V) (e.g., compounds of any one of Formulae (I-1) to (I-9)), and methods for treating Waldenström's macroglobulinemia (WM) and other B cell neoplasms in a subject using the compounds. --

In the Claims

In Claim 2, at Column 233, Lines 52-60, formula:

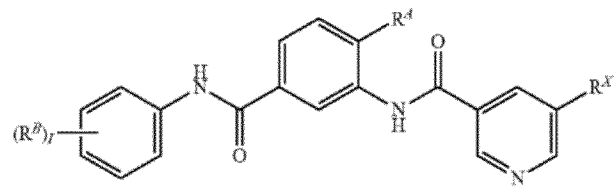

Should be replaced with the formula:

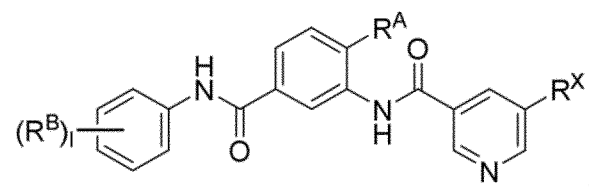

.

Signed and Sealed this
Twenty-eighth Day of July, 2020

Andrei Iancu
*Director of the United States Patent and Trademark Office*

CERTIFICATE OF CORRECTION (continued)
U.S. Pat. No. 10,597,387 B2

In Claim 3, at Column 234, Lines 1-10, the formula:

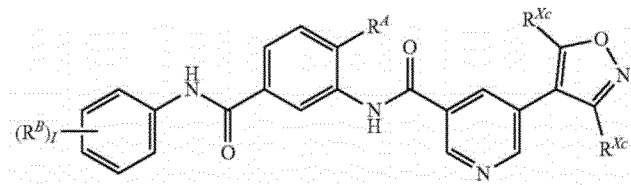

Should be replaced with the formula:

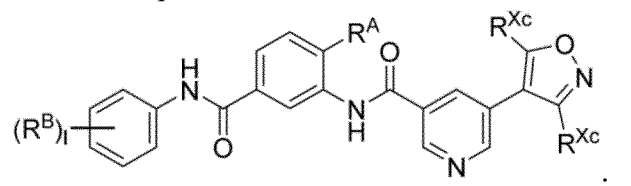

In Claim 3, at Column 234, Lines 15-23, the formula:

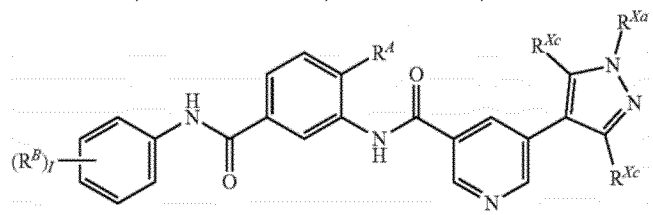

Should be replaced with the formula: